United States Patent
Bednarek et al.

(10) Patent No.: US 12,371,464 B2
(45) Date of Patent: Jul. 29, 2025

(54) POLYPEPTIDES AND USES THEREOF

(71) Applicant: MEDIMMUNE LIMITED, Cambridge (GB)

(72) Inventors: Maria Aleksandra Bednarek, Cambridge (GB); Sivaneswary Genapathy, Cambridge (GB)

(73) Assignee: MedImmune Limited, Cambridge (GB)

( * ) Notice: Subject to any disclaimer, the term of this patent is extended or adjusted under 35 U.S.C. 154(b) by 55 days.

(21) Appl. No.: 17/551,701

(22) Filed: Dec. 15, 2021

(65) Prior Publication Data

US 2022/0204580 A1 Jun. 30, 2022

Related U.S. Application Data

(60) Provisional application No. 63/125,996, filed on Dec. 16, 2020.

(51) Int. Cl.
| | |
|---|---|
| *C07K 14/575* | (2006.01) |
| *A61K 38/00* | (2006.01) |
| *A61P 3/00* | (2006.01) |
| *A61P 3/04* | (2006.01) |
| *A61P 3/10* | (2006.01) |

(52) U.S. Cl.
CPC .............. *C07K 14/575* (2013.01); *A61P 3/00* (2018.01); *A61P 3/04* (2018.01); *A61P 3/10* (2018.01); *A61K 38/00* (2013.01); *C07K 2319/31* (2013.01)

(58) Field of Classification Search
CPC ..... C07K 14/575; C07K 2319/31; A61P 3/00; A61P 3/04; A61P 3/10; A61P 3/08; A61K 38/00
See application file for complete search history.

(56) References Cited

U.S. PATENT DOCUMENTS

| | | | | |
|---|---|---|---|---|
| 2010/0222269 A1* | 9/2010 | Schaffer | ............ | A61P 3/00 530/324 |
| 2011/0105394 A1* | 5/2011 | Schaffer | ............ | A61P 9/12 514/6.9 |
| 2016/0318987 A1* | 11/2016 | Revell | ............ | A61K 9/0053 |

FOREIGN PATENT DOCUMENTS

| | | |
|---|---|---|
| WO | 2007/104789 A2 | 9/2007 |
| WO | 2009/034119 A1 | 3/2009 |
| WO | 2010/046357 A1 | 4/2010 |
| WO | 2013/059336 A1 | 4/2013 |
| WO | 2016/083499 A1 | 6/2016 |
| WO | 2020/225781 A1 | 11/2020 |
| WO | WO-2022129254 A1 | 6/2022 |

OTHER PUBLICATIONS

International Search Report and Written Opinion for International Application No. PCT/EP2021/086034, European Patent Office, Netherlands, mailed on May 18, 2022, 16 pages.
Kruger, O.F., et al., "Pramlintide for the treatment of insulin-requiring diabetes mellitus: rationale and review of clinical data," Drugs 64(13):1419-32, Springer, Germany (Jul. 2004).
Pullman, J., et al., "Pramlintide is used in the management of insulin-using patients with type 2 and type 1 diabetes," Vasc Health Risk Manag 2(3):203-212, Dove Medical Press, United Kingdom (Sep. 2006).
Roth, J.D., et al., "GLP-1 Rand amylin agonism in metabolic disease: complementary mechanisms and future opportunities," Br J Pharmacol 166(1):121-136, British Pharmacological Society, United Kingdom (May 2012).

* cited by examiner

*Primary Examiner* — Melissa L Fisher
*Assistant Examiner* — Joseph Fischer
(74) *Attorney, Agent, or Firm* — Sterne, Kessler, Goldstein & Fox P.L.L.C.

(57) ABSTRACT

Disclosed are polypeptides which are pramlintide analogues and uses thereof. In particular, the present invention relates to polypeptides of SEQ ID NO 2 which are pramlintide analogues conjugated to half-life extending moieties such as albumin binding moieties and uses thereof.

7 Claims, No Drawings

Specification includes a Sequence Listing.

SEQUENCE LISTING

```
<160> NUMBER OF SEQ ID NOS: 311

<210> SEQ ID NO 1
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues

<400> SEQUENCE: 1
```

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Pro Thr Asn Val
            20                  25                  30

Gly Ser Asn Thr Tyr
        35

```
<210> SEQ ID NO 2
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys (albumin binding moiety), or absent
<220> FEATURE:
<221> NAME/KEY: MOD_RES
<222> LOCATION: (2)..(2)
<223> OTHER INFORMATION: Gly or absent
<220> FEATURE:
<221> NAME/KEY: MOD_RES
<222> LOCATION: (3)..(3)
<223> OTHER INFORMATION: Gly or absent
<220> FEATURE:
<221> NAME/KEY: MOD_RES
<222> LOCATION: (4)..(4)
<223> OTHER INFORMATION: Gly, Lys (albumin binding moiety), or absent
<220> FEATURE:
<221> NAME/KEY: MOD_RES
<222> LOCATION: (5)..(5)
<223> OTHER INFORMATION: Lys, Lys (albumin binding moiety), or absent
<220> FEATURE:
<221> NAME/KEY: MOD_RES
<222> LOCATION: (8)..(8)
<223> OTHER INFORMATION: Thr, Ile, Ala
<220> FEATURE:
<221> NAME/KEY: MOD_RES
<222> LOCATION: (18)..(18)
<223> OTHER INFORMATION: Asn, His, Glu, 2,4-diaminobutanoic acid (Dab),
      alpha methyl amino acid
<220> FEATURE:
<221> NAME/KEY: MOD_RES
<222> LOCATION: (19)..(19)
<223> OTHER INFORMATION: Phe or Trp
<220> FEATURE:
<221> NAME/KEY: MOD_RES
<222> LOCATION: (20)..(20)
<223> OTHER INFORMATION: Leu or D-Leu
<220> FEATURE:
<221> NAME/KEY: MOD_RES
<222> LOCATION: (21)..(21)
<223> OTHER INFORMATION: Val, Ser, Glu, Arg, (2S,4R)-4-
      hydroxypyrrolidine-2-carboxylic acid (Hyp), Dab, alpha methyl
      amino acid
<220> FEATURE:
<221> NAME/KEY: MOD_RES
<222> LOCATION: (24)..(24)
<223> OTHER INFORMATION: Ser, Ile, Pro, alpha methyl amino acid
<220> FEATURE:
<221> NAME/KEY: MOD_RES
<222> LOCATION: (25)..(25)
<223> OTHER INFORMATION: Asn, Dab, His, Pro, Ser, Arg, Lys,
      Gly, Glu, Ala, Hyp , alpha methyl amino acid
<220> FEATURE:
<221> NAME/KEY: MOD_RES
<222> LOCATION: (26)..(26)
<223> OTHER INFORMATION: Asn, His, Hyp, Dab, alpha methyl amino acid
<220> FEATURE:
<221> NAME/KEY: MOD_RES
<222> LOCATION: (27)..(27)
<223> OTHER INFORMATION: Phe, Hyp, alpha methyl amino acid
<220> FEATURE:
<221> NAME/KEY: MOD_RES
```

```
<222> LOCATION: (28)..(28)
<223> OTHER INFORMATION: Gly, Pro, Hyp, alpha methyl amino acid
<220> FEATURE:
<221> NAME/KEY: MOD_RES
<222> LOCATION: (29)..(29)
<223> OTHER INFORMATION: Pro, Ala, Hyp, alpha methyl amino acid
<220> FEATURE:
<221> NAME/KEY: MOD_RES
<222> LOCATION: (30)..(30)
<223> OTHER INFORMATION: Ile, D-Ile, Arg, Hyp, alpha methyl amino acid
<220> FEATURE:
<221> NAME/KEY: MOD_RES
<222> LOCATION: (31)..(31)
<223> OTHER INFORMATION: Leu, D-Leu, Hyp, alpha methyl amino acid
<220> FEATURE:
<221> NAME/KEY: MOD_RES
<222> LOCATION: (32)..(32)
<223> OTHER INFORMATION: Pro, D-Pro, Ser, Hyp, alpha methyl amino acid
<220> FEATURE:
<221> NAME/KEY: MOD_RES
<222> LOCATION: (33)..(33)
<223> OTHER INFORMATION: Pro, Hyp, alpha methyl amino acid
<220> FEATURE:
<221> NAME/KEY: MOD_RES
<222> LOCATION: (35)..(35)
<223> OTHER INFORMATION: Asn, Glu, His, Arg, Pro, Dab,
      alpha methyl amino acid
<220> FEATURE:
<221> NAME/KEY: MOD_RES
<222> LOCATION: (36)..(36)
<223> OTHER INFORMATION: Val, Hyp, Dab, alpha methyl amino acid
<220> FEATURE:
<221> NAME/KEY: MOD_RES
<222> LOCATION: (37)..(37)
<223> OTHER INFORMATION: Gly, Pro, Hyp, alpha methyl amino acid
<220> FEATURE:
<221> NAME/KEY: MOD_RES
<222> LOCATION: (38)..(38)
<223> OTHER INFORMATION: Ser, Pro, His, Hyp, alpha methyl amino acid
<220> FEATURE:
<221> NAME/KEY: MOD_RES
<222> LOCATION: (39)..(39)
<223> OTHER INFORMATION: Asn, Pro, Arg, Glu, Dab, Hyp,
      alpha methyl amino acid
<220> FEATURE:
<221> NAME/KEY: MOD_RES
<222> LOCATION: (40)..(40)
<223> OTHER INFORMATION: Thr, Hyp, alpha methyl amino acid
<220> FEATURE:
<221> NAME/KEY: MOD_RES
<222> LOCATION: (41)..(41)
<223> OTHER INFORMATION: Tyr, Pro, Hyp, alpha methyl amino acid
<220> FEATURE:
<221> NAME/KEY: SITE
<222> LOCATION: (1)..(41)
<223> OTHER INFORMATION: Variant residues given in the sequence have no
      preference with respect to those in the annotations
      for variant positions

<400> SEQUENCE: 2

Xaa Xaa Xaa Xaa Xaa Cys Asn Xaa Ala Thr Cys Ala Thr Gln Arg Leu
1               5                   10                  15

Ala Xaa Xaa Xaa Xaa His Ser Xaa Xaa Xaa Xaa Xaa Xaa Xaa Xaa
            20                  25                  30

Xaa Thr Xaa Xaa Xaa Xaa Xaa Xaa Xaa
        35                  40

<210> SEQ ID NO 3
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<221> NAME/KEY: MOD_RES
<222> LOCATION: (1)..(1)
<223> OTHER INFORMATION: C18diacid-gamma-Glu
<220> FEATURE:
<221> NAME/KEY: SITE
<222> LOCATION: (3)..(8)
<223> OTHER INFORMATION: Disulphide bridge between Cys residues

<400> SEQUENCE: 3

Xaa Lys Cys Asn Thr Ala Thr Cys Ala Thr Gln Arg Leu Ala Asn Phe
 1               5                  10                  15

Leu Val His Ser Ser Asn Asn Phe Gly Pro Ile Leu Pro Pro Thr Asn
             20                  25                  30

Val Gly Ser Asn Thr Tyr
         35

<210> SEQ ID NO 4
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: C18diacid-gamma-Glu
<220> FEATURE:
<221> NAME/KEY: MOD_RES
<222> LOCATION: (2)..(2)
<223> OTHER INFORMATION: gamma-Glu
<220> FEATURE:
<221> NAME/KEY: SITE
<222> LOCATION: (7)..(12)
<223> OTHER INFORMATION: Disulphide bridge between Cys residues

<400> SEQUENCE: 4

Xaa Xaa Gly Gly Gly Lys Cys Asn Thr Ala Thr Cys Ala Thr Gln Arg
 1               5                  10                  15

Leu Ala Asn Phe Leu Val His Ser Ser Asn Asn Phe Gly Pro Ile Leu
             20                  25                  30

Pro Pro Thr Asn Val Gly Ser Asn Thr Tyr
         35                  40

<210> SEQ ID NO 5
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-gamma-Glu-C18diacid
<220> FEATURE:
<221> NAME/KEY: SITE
<222> LOCATION: (2)..(7)
<223> OTHER INFORMATION: Disulphide bridge between Cys residues

<400> SEQUENCE: 5

Xaa Cys Asn Thr Ala Thr Cys Ala Thr Gln Arg Leu Ala Asn Phe Leu
 1               5                  10                  15

Val His Ser Ser Asn Asn Phe Gly Pro Ile Leu Pro Pro Thr Asn Val
             20                  25                  30

Gly Ser Asn Thr Tyr
         35
```

<210> SEQ ID NO 6
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to O2Oc-O2Oc-gamma-Glu-C18diacid
<220> FEATURE:
<221> NAME/KEY: SITE
<222> LOCATION: (2)..(7)
<223> OTHER INFORMATION: Disulphide bridge between Cys residues

<400> SEQUENCE: 6

Xaa Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Pro Thr Asn Val
            20                  25                  30

Gly Ser Asn Thr Tyr
        35

<210> SEQ ID NO 7
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to O2Oc-O2Oc-gamma-Glu-C18diacid
<220> FEATURE:
<221> NAME/KEY: SITE
<222> LOCATION: (6)..(11)
<223> OTHER INFORMATION: Disulphide bridge between Cys residues

<400> SEQUENCE: 7

Xaa Gly Gly Gly Lys Cys Asn Thr Ala Thr Cys Ala Thr Gln Arg Leu
1               5                   10                  15

Ala Asn Phe Leu Val His Ser Ser Asn Asn Phe Gly Pro Ile Leu Pro
            20                  25                  30

Pro Thr Asn Val Gly Ser Asn Thr Tyr
        35                  40

<210> SEQ ID NO 8
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)

<223> OTHER INFORMATION: 2,4-diaminobutanoic acid

<400> SEQUENCE: 8

Xaa Cys Asn Thr Ala Thr Cys Ala Thr Gln Arg Leu Ala Asn Phe Leu
1               5                   10                  15

Val His Ser Ser Xaa Asn Phe Pro Ala Ile Leu Ser Pro Thr Asn Val
            20                  25                  30

Gly Ser Asn Thr Tyr
            35

<210> SEQ ID NO 9
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid

<400> SEQUENCE: 9

Xaa Cys Asn Thr Ala Thr Cys Ala Thr Gln Arg Leu Ala Asn Phe Leu
1               5                   10                  15

Val His Ser Ser Xaa Asn Phe Pro Ala Ile Leu Ser Pro Thr Asn Val
            20                  25                  30

Gly Ser Asn Thr Tyr
            35

<210> SEQ ID NO 10
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: C18diacid-gamma-Glu
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (23)..(23)
<223> OTHER INFORMATION: (S)-2-amino-2-methyl-3-phenylpropanoic acid

<400> SEQUENCE: 10

Xaa Cys Asn Thr Ala Thr Cys Ala Thr Gln Arg Leu Ala Glu Phe Leu
1               5                   10                  15

Arg His Ser Ser Asn Asn Xaa Gly Pro Ile Leu Pro Pro Thr Asn Val
            20                  25                  30

Gly Ser Asn Thr Tyr
            35

```
<210> SEQ ID NO 11
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (23)..(23)
<223> OTHER INFORMATION: (S)-2-amino-2-methyl-3-phenylpropanoic acid

<400> SEQUENCE: 11

Xaa Cys Asn Thr Ala Thr Cys Ala Thr Gln Arg Leu Ala Glu Phe Leu
1               5                   10                  15

Arg His Ser Ser Asn Asn Xaa Gly Pro Ile Leu Pro Pro Thr Asn Val
            20                  25                  30

Gly Ser Asn Thr Tyr
            35

<210> SEQ ID NO 12
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (24)..(24)
<223> OTHER INFORMATION: (S)-2-amino-2-methyl-3-phenylpropanoic acid

<400> SEQUENCE: 12

Xaa Lys Cys Asn Thr Ala Thr Cys Ala Thr Gln Arg Leu Ala Glu Phe
1               5                   10                  15

Leu Arg His Ser Ser Asn Asn Xaa Gly Pro Ile Leu Pro Pro Thr Asn
            20                  25                  30

Val Gly Ser Asn Thr Tyr
            35

<210> SEQ ID NO 13
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-gamma-Glu-C18diacid
<220> FEATURE:
```

```
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (23)..(23)
<223> OTHER INFORMATION: (S)-2-amino-2-methyl-3-phenylpropanoic acid

<400> SEQUENCE: 13

Xaa Cys Asn Thr Ala Thr Cys Ala Thr Gln Arg Leu Ala Asn Phe Leu
1               5                   10                  15

Val His Ser Ser Asn Asn Xaa Gly Pro Ile Leu Pro Pro Thr Asn Val
            20                  25                  30

Gly Ser Asn Thr Tyr
        35

<210> SEQ ID NO 14
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (24)..(24)
<223> OTHER INFORMATION: (S)-2-amino-2-methyl-3-phenylpropanoic acid

<400> SEQUENCE: 14

Xaa Lys Cys Asn Thr Ala Thr Cys Ala Thr Gln Arg Leu Ala Asn Phe
1               5                   10                  15

Leu Val His Ser Ser Asn Asn Xaa Gly Pro Ile Leu Pro Pro Thr Asn
            20                  25                  30

Val Gly Ser Asn Thr Tyr
        35

<210> SEQ ID NO 15
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (24)..(24)
<223> OTHER INFORMATION: (S)-2-amino-2-methyl-3-phenylpropanoic acid

<400> SEQUENCE: 15

Xaa Lys Cys Asn Thr Ala Thr Cys Ala Thr Gln Arg Leu Ala Asn Phe
1               5                   10                  15
```

Leu Arg His Ser Ser Asn Asn Xaa Gly Pro Ile Leu Pro Pro Thr Glu
            20                  25                  30

Val Gly Ser Asn Thr Tyr
        35

<210> SEQ ID NO 16
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (23)..(23)
<223> OTHER INFORMATION: (S)-2-amino-2-methyl-3-phenylpropanoic acid

<400> SEQUENCE: 16

Xaa Cys Asn Thr Ala Thr Cys Ala Thr Gln Arg Leu Ala Asn Phe Leu
1               5                   10                  15

Arg His Ser Ser Asn Asn Xaa Gly Pro Ile Leu Pro Pro Thr Glu Val
            20                  25                  30

Gly Ser Asn Thr Tyr
        35

<210> SEQ ID NO 17
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to O2Oc-O2Oc-gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (23)..(23)
<223> OTHER INFORMATION: (S)-2-amino-2-methyl-3-phenylpropanoic acid

<400> SEQUENCE: 17

Xaa Cys Asn Thr Ala Thr Cys Ala Thr Gln Arg Leu Ala Asn Phe Leu
1               5                   10                  15

Arg His Ser Ser Asn Asn Xaa Gly Pro Ile Leu Pro Pro Thr Glu Val
            20                  25                  30

Gly Ser Asn Thr Tyr
        35

<210> SEQ ID NO 18
<211> LENGTH: 37
<212> TYPE: PRT
<213> ORGANISM: Artificial Sequence
<220> FEATURE:
<223> OTHER INFORMATION: Description of Artificial Sequence: Synthetic

```
                                polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (23)..(23)
<223> OTHER INFORMATION: (S)-2-amino-2-methyl-3-phenylpropanoic acid

<400> SEQUENCE: 18

Xaa Cys Asn Thr Ala Thr Cys Ala Thr Gln Arg Leu Ala Asn Phe Leu
1               5                   10                  15

Arg His Ser Ser Asn Asn Xaa Gly Pro Ile Leu Pro Pro Thr Glu Val
            20                  25                  30

Gly Ser Asn Thr Tyr
            35

<210> SEQ ID NO 19
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (23)..(23)
<223> OTHER INFORMATION: (S)-2-amino-2-methyl-3-phenylpropanoic acid

<400> SEQUENCE: 19

Xaa Cys Asn Thr Ala Thr Cys Ala Thr Gln Arg Leu Ala Asn Phe Leu
1               5                   10                  15

Arg His Ser Ser Asn Asn Xaa Gly Pro Ile Leu Pro Pro Thr Asn Val
            20                  25                  30

Gly Ser Asn Thr Tyr
            35

<210> SEQ ID NO 20
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (23)..(23)
```

<223> OTHER INFORMATION: (S)-2-amino-2-methyl-3-phenylpropanoic acid

<400> SEQUENCE: 20

Xaa Cys Asn Thr Ala Thr Cys Ala Thr Gln Arg Leu Ala Asn Phe Leu
1               5                   10                  15

Arg His Ser Ser Asn Asn Xaa Gly Pro Ile Leu Pro Pro Thr Asn Val
            20                  25                  30

Gly Ser Asn Thr Tyr
            35

<210> SEQ ID NO 21
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (23)..(23)
<223> OTHER INFORMATION: (S)-2-amino-2-methyl-3-phenylpropanoic acid

<400> SEQUENCE: 21

Xaa Cys Asn Thr Ala Thr Cys Ala Thr Gln Arg Leu Ala Asn Phe Leu
1               5                   10                  15

Val His Ser Ser Asn Asn Xaa Gly Pro Ile Leu Pro Pro Thr Asn Val
            20                  25                  30

Gly Ser Arg Thr Tyr
            35

<210> SEQ ID NO 22
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (20)..(20)
<223> OTHER INFORMATION: (S)-2-amino-3-hydroxy-2-methylpropanoic acid

<400> SEQUENCE: 22

Xaa Cys Asn Thr Ala Thr Cys Ala Thr Gln Arg Leu Ala Asn Phe Leu
1               5                   10                  15

Val His Ser Xaa Asn Asn Phe Gly Pro Ile Leu Pro Pro Thr Asn Val
            20                  25                  30

Gly Ser Asn Thr Tyr
            35

```
<210> SEQ ID NO 23
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (23)..(23)
<223> OTHER INFORMATION: (S)-2-amino-2-methyl-3-phenylpropanoic acid

<400> SEQUENCE: 23

Xaa Cys Asn Thr Ala Thr Cys Ala Thr Gln Arg Leu Ala Asn Phe Leu
1               5                   10                  15

Val His Ser Ser Asn Asn Xaa Gly Pro Ile Leu Pro Pro Thr Glu Val
            20                  25                  30

Gly Ser Asn Thr Tyr
        35

<210> SEQ ID NO 24
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (23)..(23)
<223> OTHER INFORMATION: (S)-2-amino-2-methyl-3-phenylpropanoic acid

<400> SEQUENCE: 24

Xaa Cys Asn Thr Ala Thr Cys Ala Thr Gln Arg Leu Ala Asn Phe Leu
1               5                   10                  15

Val His Ser Ser Asn Asn Xaa Gly Pro Ile Leu Pro Pro Thr Arg Val
            20                  25                  30

Gly Ser Asn Thr Tyr
        35

<210> SEQ ID NO 25
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
```

```
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (23)..(23)
<223> OTHER INFORMATION: (S)-2-amino-2-methyl-3-phenylpropanoic acid

<400> SEQUENCE: 25

Xaa Cys Asn Thr Ala Thr Cys Ala Thr Gln Arg Leu Ala Asn Phe Leu
1               5                   10                  15

Val His Ser Ser Asn Asn Xaa Gly Pro Ile Leu Pro Pro Thr Arg Val
            20                  25                  30

Gly Ser Asn Thr Tyr
            35

<210> SEQ ID NO 26
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid
<220> FEATURE:
<221> NAME/KEY: MOD_RES
<222> LOCATION: (23)..(23)
<223> OTHER INFORMATION: (S)-2-amino-2-methyl-3-phenylpropanoic acid

<400> SEQUENCE: 26

Xaa Cys Asn Thr Ala Thr Cys Ala Thr Gln Arg Leu Ala Asn Phe Leu
1               5                   10                  15

Xaa His Ser Ser Asn Asn Xaa Gly Pro Ile Leu Pro Pro Thr Asn Val
            20                  25                  30

Gly Ser Asn Thr Tyr
            35

<210> SEQ ID NO 27
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2,4-diaminobutanoic acid
```

```
<400> SEQUENCE: 27

Xaa Cys Asn Ile Ala Thr Cys Ala Thr Gln Arg Leu Ala Asn Phe Leu
1               5                   10                  15

Val His Ser Ser Xaa Asn Phe Gly Pro Ile Leu Pro Pro Thr Asn Val
            20                  25                  30

Gly Ser Arg Thr Tyr
            35

<210> SEQ ID NO 28
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (22)..(22)
<223> OTHER INFORMATION: 2,4-diaminobutanoic acid

<400> SEQUENCE: 28

Xaa Lys Cys Asn Thr Ala Thr Cys Ala Thr Gln Arg Leu Ala Asn Phe
1               5                   10                  15

Leu Val His Ser Ser Xaa Asn Phe Gly Pro Ile Leu Pro Pro Thr Glu
                20                  25                  30

Val Gly Ser Asn Thr Tyr
                35

<210> SEQ ID NO 29
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (22)..(22)
<223> OTHER INFORMATION: 2,4-diaminobutanoic acid

<400> SEQUENCE: 29

Xaa Lys Cys Asn Thr Ala Thr Cys Ala Thr Gln Arg Leu Ala Asn Phe
1               5                   10                  15

Leu Val His Ser Ser Xaa Asn Phe Gly Pro Ile Leu Pro Pro Thr Asn
                20                  25                  30

Val Gly Ser Asn Thr Tyr
                35

<210> SEQ ID NO 30
```

```
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (18)..(18)
<223> OTHER INFORMATION: 2-amino-2-methylpropanoic acid
<220> FEATURE:
<221> NAME/KEY: MOD_RES
<222> LOCATION: (22)..(22)
<223> OTHER INFORMATION: 2,4-diaminobutanoic acid

<400> SEQUENCE: 30

Xaa Lys Cys Asn Thr Ala Thr Cys Ala Thr Gln Arg Leu Ala Asn Phe
1               5                   10                  15

Leu Xaa His Ser Ser Xaa Asn Phe Gly Pro Ile Leu Pro Pro Thr Glu
            20                  25                  30

Val Gly Ser Asn Thr Tyr
            35

<210> SEQ ID NO 31
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (22)..(22)
<223> OTHER INFORMATION: 2,4-diaminobutanoic acid
<220> FEATURE:
<221> NAME/KEY: MOD_RES
<222> LOCATION: (26)..(26)
<223> OTHER INFORMATION: 2-amino-2-methylpropanoic acid

<400> SEQUENCE: 31

Xaa Lys Cys Asn Thr Ala Thr Cys Ala Thr Gln Arg Leu Ala Asn Phe
1               5                   10                  15

Leu Val His Ser Ser Xaa Asn Phe Gly Xaa Ile Leu Pro Pro Thr Asn
            20                  25                  30

Val Gly Ser Asn Thr Tyr
            35

<210> SEQ ID NO 32
<211> LENGTH: 38
<212> TYPE: PRT
<213> ORGANISM: Artificial Sequence
<220> FEATURE:
<223> OTHER INFORMATION: Description of Artificial Sequence: Synthetic
```

-continued

```
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (15)..(15)
<223> OTHER INFORMATION: 2,4-diaminobutanoic acid
<220> FEATURE:
<221> NAME/KEY: MOD_RES
<222> LOCATION: (24)..(24)
<223> OTHER INFORMATION: (S)-2-amino-2-methyl-3-phenylpropanoic acid

<400> SEQUENCE: 32

Xaa Lys Cys Asn Thr Ala Thr Cys Ala Thr Gln Arg Leu Ala Xaa Phe
1               5                   10                  15

Leu Val His Ser Ser Asn Asn Xaa Gly Pro Ile Leu Pro Pro Thr Glu
            20                  25                  30

Val Gly Ser Asn Thr Tyr
        35

<210> SEQ ID NO 33
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (15)..(15)
<223> OTHER INFORMATION: 2,4-diaminobutanoic acid

<400> SEQUENCE: 33

Xaa Lys Cys Asn Thr Ala Thr Cys Ala Thr Gln Arg Leu Ala Xaa Phe
1               5                   10                  15

Leu Val His Ser Ser Asn Asn Phe Gly Pro Ile Leu Pro Pro Thr Asn
            20                  25                  30

Val Gly Ser Asn Thr Tyr
        35

<210> SEQ ID NO 34
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
```

<223> OTHER INFORMATION: Disulphide bridge between Cys residues
<220> FEATURE:
<221> NAME/KEY: MOD_RES
<222> LOCATION: (15)..(15)
<223> OTHER INFORMATION: 2,4-diaminobutanoic acid

<400> SEQUENCE: 34

Xaa Lys Cys Asn Thr Ala Thr Cys Ala Thr Gln Arg Leu Ala Xaa Phe
1               5                   10                  15

Leu Val His Ser Ser Asn Asn Phe Gly Pro Ile Leu Pro Pro Thr Glu
            20                  25                  30

Val Gly Ser Asn Thr Tyr
        35

<210> SEQ ID NO 35
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (22)..(22)
<223> OTHER INFORMATION: 2-amino-2-methylpropanoic acid

<400> SEQUENCE: 35

Xaa Lys Cys Asn Thr Ala Thr Cys Ala Thr Gln Arg Leu Ala Asn Phe
1               5                   10                  15

Leu Val His Ser Ser Xaa Asn Phe Gly Pro Ile Leu Pro Pro Thr Asn
            20                  25                  30

Val Gly Ser Asn Thr Tyr
        35

<210> SEQ ID NO 36
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (18)..(18)
<223> OTHER INFORMATION: 2-amino-2-methylpropanoic acid
<220> FEATURE:
<221> NAME/KEY: MOD_RES
<222> LOCATION: (22)..(22)
<223> OTHER INFORMATION: 2-amino-2-methylpropanoic acid

<400> SEQUENCE: 36

Xaa Lys Cys Asn Thr Ala Thr Cys Ala Thr Gln Arg Leu Ala Asn Phe

```
                1               5                  10                 15
Leu Xaa His Ser Ser Xaa Asn Phe Gly Pro Ile Leu Pro Pro Thr Asn
            20                  25                 30

Val Gly Ser Asn Thr Tyr
            35

<210> SEQ ID NO 37
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (22)..(22)
<223> OTHER INFORMATION: 2-amino-2-methylpropanoic acid

<400> SEQUENCE: 37

Xaa Lys Cys Asn Thr Ala Thr Cys Ala Thr Gln Arg Leu Ala Asn Phe
1               5                   10                  15

Leu Ser His Ser Ser Xaa Asn Phe Gly Pro Ile Leu Pro Pro Thr Asn
            20                  25                  30

Val Gly Ser Asn Thr Tyr
            35

<210> SEQ ID NO 38
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (22)..(22)
<223> OTHER INFORMATION: 2-amino-2-methylpropanoic acid

<400> SEQUENCE: 38

Xaa Lys Cys Asn Thr Ala Thr Cys Ala Thr Gln Arg Leu Ala Glu Phe
1               5                   10                  15

Leu Val His Ser Ser Xaa Asn Phe Gly Pro Ile Leu Pro Pro Thr Asn
            20                  25                  30

Val Gly Ser Asn Thr Tyr
            35

<210> SEQ ID NO 39
<211> LENGTH: 38
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (22)..(22)
<223> OTHER INFORMATION: 2-amino-2-methylpropanoic acid

<400> SEQUENCE: 39

Xaa Lys Cys Asn Thr Ala Thr Cys Ala Thr Gln Arg Leu Ala Asn Phe
1               5                   10                  15

Leu Glu His Ser Ser Xaa Asn Phe Gly Pro Ile Leu Pro Pro Thr Asn
            20                  25                  30

Val Gly Ser Asn Thr Tyr
        35

<210> SEQ ID NO 40
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (22)..(22)
<223> OTHER INFORMATION: 2-amino-2-methylpropanoic acid

<400> SEQUENCE: 40

Xaa Lys Cys Asn Thr Ala Thr Cys Ala Thr Gln Arg Leu Ala Asn Phe
1               5                   10                  15

Leu Val His Ser Ser Xaa Asn Phe Gly Pro Ile Leu Pro Pro Thr His
            20                  25                  30

Val Gly Ser Asn Thr Tyr
        35

<210> SEQ ID NO 41
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
```

```
<221> NAME/KEY: MOD_RES
<222> LOCATION: (22)..(22)
<223> OTHER INFORMATION: 2-amino-2-methylpropanoic acid

<400> SEQUENCE: 41

Xaa Lys Cys Asn Thr Ala Thr Cys Ala Thr Gln Arg Leu Ala Asn Phe
1               5                   10                  15

Leu Val His Ser Ser Xaa Asn Phe Gly Pro Ile Leu Pro Pro Thr Glu
            20                  25                  30

Val Gly Ser Asn Thr Tyr
        35

<210> SEQ ID NO 42
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (22)..(22)
<223> OTHER INFORMATION: 2-amino-2-methylpropanoic acid

<400> SEQUENCE: 42

Xaa Lys Cys Asn Thr Ala Thr Cys Ala Thr Gln Arg Leu Ala Asn Phe
1               5                   10                  15

Leu Val His Ser Ser Xaa Asn Phe Gly Pro Ile Leu Pro Pro Thr Asn
            20                  25                  30

Val Gly Ser Glu Thr Tyr
        35

<210> SEQ ID NO 43
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (22)..(22)
<223> OTHER INFORMATION: 2-amino-2-methylpropanoic acid

<400> SEQUENCE: 43

Xaa Lys Cys Asn Thr Ala Thr Cys Ala Thr Gln Arg Leu Ala Asn Phe
1               5                   10                  15

Leu Arg His Ser Ser Xaa Asn Phe Gly Pro Ile Leu Pro Pro Thr Glu
            20                  25                  30

Val Gly Ser Asn Thr Tyr
```

<210> SEQ ID NO 44
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid

<400> SEQUENCE: 44

Xaa Cys Asn Thr Ala Thr Cys Ala Thr Gln Arg Leu Ala Asn Phe Leu
1               5                   10                  15

Arg His Ser Ser Xaa Asn Phe Gly Pro Ile Leu Pro Pro Thr Glu Val
            20                  25                  30

Gly Ser Asn Thr Tyr
            35

<210> SEQ ID NO 45
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to O2Oc-O2Oc-gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid

<400> SEQUENCE: 45

Xaa Cys Asn Thr Ala Thr Cys Ala Thr Gln Arg Leu Ala Asn Phe Leu
1               5                   10                  15

Arg His Ser Ser Xaa Asn Phe Gly Pro Ile Leu Pro Pro Thr Glu Val
            20                  25                  30

Gly Ser Asn Thr Tyr
            35

<210> SEQ ID NO 46
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)

<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (22)..(22)
<223> OTHER INFORMATION: 2-amino-2-methylpropanoic acid

<400> SEQUENCE: 46

Xaa Lys Cys Asn Thr Ala Thr Cys Ala Thr Gln Arg Leu Ala His Phe
1               5                   10                  15

Leu Val His Ser Ser Xaa Asn Phe Gly Pro Ile Leu Pro Pro Thr Asn
            20                  25                  30

Val Gly Ser Asn Thr Tyr
        35

<210> SEQ ID NO 47
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (22)..(22)
<223> OTHER INFORMATION: 2-amino-2-methylpropanoic acid

<400> SEQUENCE: 47

Xaa Lys Cys Asn Thr Ala Thr Cys Ala Thr Gln Arg Leu Ala His Phe
1               5                   10                  15

Leu Val His Ser Ser Xaa Asn Phe Gly Pro Ile Leu Pro Pro Thr Asn
            20                  25                  30

Val Gly Ser Glu Thr Tyr
        35

<210> SEQ ID NO 48
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid

<400> SEQUENCE: 48

Xaa Cys Asn Thr Ala Thr Cys Ala Thr Gln Arg Leu Ala Asn Phe Leu
1               5                   10                  15

Arg His Ser Ser Xaa Asn Phe Gly Pro Ile Leu Pro Pro Thr Asn Val
            20                  25                  30

Gly Ser Asn Thr Tyr
        35

<210> SEQ ID NO 49
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid

<400> SEQUENCE: 49

Xaa Cys Asn Thr Ala Thr Cys Ala Thr Gln Arg Leu Ala Asn Phe Leu
1               5                   10                  15

Val His Ser Ser Xaa Asn Phe Gly Pro Ile Leu Pro Pro Thr Glu Val
            20                  25                  30

Gly Ser Asn Thr Tyr
        35

<210> SEQ ID NO 50
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid

<400> SEQUENCE: 50

Xaa Cys Asn Thr Ala Thr Cys Ala Thr Gln Arg Leu Ala Asn Phe Leu
1               5                   10                  15

Arg His Ser Ser Xaa Asn Phe Gly Pro Ile Leu Pro Pro Thr Glu Val
            20                  25                  30

Gly Ser Asn Thr Tyr
        35

<210> SEQ ID NO 51
<211> LENGTH: 38
<212> TYPE: PRT

```
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (22)..(22)
<223> OTHER INFORMATION: 2-amino-2-methylpropanoic acid

<400> SEQUENCE: 51

Xaa Lys Cys Asn Thr Ala Thr Cys Ala Thr Gln Arg Leu Ala Asn Phe
1               5                   10                  15

Leu Ser His Ser Ser Xaa Asn Phe Gly Pro Ile Leu Pro Pro Thr His
            20                  25                  30

Val Gly Ser Asn Thr Tyr
            35

<210> SEQ ID NO 52
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (22)..(22)
<223> OTHER INFORMATION: 2-amino-2-methylpropanoic acid

<400> SEQUENCE: 52

Xaa Lys Cys Asn Thr Ala Thr Cys Ala Thr Gln Arg Leu Ala Asn Phe
1               5                   10                  15

Leu Ser His Ser Ser Xaa Asn Phe Gly Pro Ile Leu Pro Pro Thr Arg
            20                  25                  30

Val Gly Ser Asn Thr Tyr
            35

<210> SEQ ID NO 53
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
```

```
<220> FEATURE:
<221> NAME/KEY: MOD_RES
<222> LOCATION: (22)..(22)
<223> OTHER INFORMATION: 2-amino-2-methylpropanoic acid

<400> SEQUENCE: 53

Xaa Lys Cys Asn Thr Ala Thr Cys Ala Thr Gln Arg Leu Ala Asn Phe
1               5                   10                  15

Leu Ser His Ser Ser Xaa Asn Phe Gly Pro Ile Leu Pro Pro Thr Pro
            20                  25                  30

Val Gly Ser Asn Thr Tyr
            35

<210> SEQ ID NO 54
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (22)..(22)
<223> OTHER INFORMATION: 2-amino-2-methylpropanoic acid

<400> SEQUENCE: 54

Xaa Lys Cys Asn Thr Ala Thr Cys Ala Thr Gln Arg Leu Ala Asn Phe
1               5                   10                  15

Leu Ser His Ser Ser Xaa Asn Phe Gly Pro Ile Leu Pro Pro Thr Asn
            20                  25                  30

Val Pro Ser Asn Thr Tyr
            35

<210> SEQ ID NO 55
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (22)..(22)
<223> OTHER INFORMATION: 2-amino-2-methylpropanoic acid

<400> SEQUENCE: 55

Xaa Lys Cys Asn Thr Ala Thr Cys Ala Thr Gln Arg Leu Ala Asn Phe
1               5                   10                  15

Leu Ser His Ser Ser Xaa Asn Phe Gly Pro Ile Leu Pro Pro Thr Asn
            20                  25                  30
```

Val Gly Ser Pro Thr Tyr
        35

<210> SEQ ID NO 56
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid

<400> SEQUENCE: 56

Xaa Cys Asn Thr Ala Thr Cys Ala Thr Gln Arg Leu Ala Asn Phe Leu
1               5                   10                  15

Val His Ser Ser Xaa Asn Phe Gly Pro Ile Leu Pro Pro Thr Asn Val
            20                  25                  30

Gly Ser Asn Thr Tyr
        35

<210> SEQ ID NO 57
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (22)..(22)
<223> OTHER INFORMATION: 2-amino-2-methylpropanoic acid

<400> SEQUENCE: 57

Xaa Lys Cys Asn Thr Ala Thr Cys Ala Thr Gln Arg Leu Ala Asn Phe
1               5                   10                  15

Leu Val His Ser Ser Xaa Asn Phe Gly Pro Ile Leu Pro Pro Thr Asn
            20                  25                  30

Val Gly Ser Asn Thr Tyr
        35

<210> SEQ ID NO 58
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES

```
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (22)..(22)
<223> OTHER INFORMATION: 2-amino-2-methylpropanoic acid

<400> SEQUENCE: 58

Xaa Lys Cys Asn Thr Ala Thr Cys Ala Thr Gln Arg Leu Ala Asn Phe
1               5                   10                  15

Leu Val His Ser Ser Xaa Asn Phe Gly Pro Ile Leu Pro Pro Thr Asn
            20                  25                  30

Val Gly Ser Asn Thr Pro
        35

<210> SEQ ID NO 59
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid
<220> FEATURE:
<221> NAME/KEY: MOD_RES
<222> LOCATION: (27)..(27)
<223> OTHER INFORMATION: D-Leu

<400> SEQUENCE: 59

Xaa Cys Asn Thr Ala Thr Cys Ala Thr Gln Arg Leu Ala Asn Phe Leu
1               5                   10                  15

Val His Ser Ser Xaa Asn Phe Gly Pro Ile Xaa Pro Pro Thr Asn Val
            20                  25                  30

Gly Ser Asn Thr Tyr
        35

<210> SEQ ID NO 60
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
```

-continued

```
<222> LOCATION: (21)..(21)
<223> OTHER INFORMATION: 2-amino-2-methylpropanoic acid
<220> FEATURE:
<221> NAME/KEY: MOD_RES
<222> LOCATION: (28)..(28)
<223> OTHER INFORMATION: D-Pro

<400> SEQUENCE: 60

Xaa Cys Asn Thr Ala Thr Cys Ala Thr Gln Arg Leu Ala Asn Phe Leu
1               5                   10                  15

Val His Ser Ser Xaa Asn Phe Gly Pro Ile Leu Xaa Pro Thr Asn Val
            20                  25                  30

Gly Ser Asn Thr Tyr
        35

<210> SEQ ID NO 61
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid
<220> FEATURE:
<221> NAME/KEY: MOD_RES
<222> LOCATION: (26)..(26)
<223> OTHER INFORMATION: D-Ile

<400> SEQUENCE: 61

Xaa Cys Asn Thr Ala Thr Cys Ala Thr Gln Arg Leu Ala Asn Phe Leu
1               5                   10                  15

Val His Ser Ser Xaa Asn Phe Gly Pro Xaa Leu Pro Pro Thr Asn Val
            20                  25                  30

Gly Ser Asn Thr Tyr
        35

<210> SEQ ID NO 62
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (16)..(16)
<223> OTHER INFORMATION: D-Leu
<220> FEATURE:
<221> NAME/KEY: MOD_RES
<222> LOCATION: (21)..(21)
```

<223> OTHER INFORMATION: 2-amino-2-methylpropanoic acid

<400> SEQUENCE: 62

Xaa Cys Asn Thr Ala Thr Cys Ala Thr Gln Arg Leu Ala Asn Phe Xaa
1               5                   10                  15

Val His Ser Ser Xaa Asn Phe Gly Pro Ile Leu Pro Pro Thr Asn Val
            20                  25                  30

Gly Ser Asn Thr Tyr
        35

<210> SEQ ID NO 63
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid

<400> SEQUENCE: 63

Xaa Cys Asn Thr Ala Thr Cys Ala Thr Gln Arg Leu Ala Asn Phe Leu
1               5                   10                  15

Val His Ser Ser Xaa Asn Phe Gly Pro Ile Leu Pro Pro Thr Arg Val
            20                  25                  30

Gly Ser Asn Thr Tyr
        35

<210> SEQ ID NO 64
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid

<400> SEQUENCE: 64

Xaa Cys Asn Thr Ala Thr Cys Ala Thr Gln Arg Leu Ala Asn Phe Leu
1               5                   10                  15

Val His Ser Ser Xaa Asn Phe Gly Pro Ile Leu Pro Pro Thr Asn Val
            20                  25                  30

Gly Ser Arg Thr Tyr
        35

```
<210> SEQ ID NO 65
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (22)..(22)
<223> OTHER INFORMATION: 2-amino-2-methylpropanoic acid

<400> SEQUENCE: 65

Xaa Lys Cys Asn Thr Ala Thr Cys Ala Thr Gln Arg Leu Ala Asn Phe
1               5                   10                  15

Leu Arg His Ser Ser Xaa Asn Phe Gly Pro Ile Leu Pro Pro Thr Asn
            20                  25                  30

Val Gly Ser Asn Thr Tyr
            35

<210> SEQ ID NO 66
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (22)..(22)
<223> OTHER INFORMATION: 2-amino-2-methylpropanoic acid

<400> SEQUENCE: 66

Xaa Lys Cys Asn Thr Ala Thr Cys Ala Thr Gln Arg Leu Ala Asn Phe
1               5                   10                  15

Leu Arg His Ser Ser Xaa Asn Phe Gly Pro Ile Leu Pro Pro Thr Asn
            20                  25                  30

Val Gly Ser Asn Thr Tyr
            35

<210> SEQ ID NO 67
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-gamma-Glu-C18diacid
```

```
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid

<400> SEQUENCE: 67

Xaa Cys Asn Thr Ala Thr Cys Ala Thr Gln Arg Leu Ala Asn Phe Leu
1               5                   10                  15

Val His Ser Ser Xaa Asn Phe Gly Pro Ile Leu Pro Pro Thr Arg Val
            20                  25                  30

Gly Ser Asn Thr Tyr
        35

<210> SEQ ID NO 68
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: C18diacid-gamma-Glu
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid

<400> SEQUENCE: 68

Xaa Cys Asn Thr Ala Thr Cys Ala Thr Gln Arg Leu Ala Asn Phe Leu
1               5                   10                  15

Val His Ser Ser Xaa Asn Phe Gly Pro Ile Leu Pro Pro Thr Arg Val
            20                  25                  30

Gly Ser Asn Thr Tyr
        35

<210> SEQ ID NO 69
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (22)..(22)
<223> OTHER INFORMATION: 2-amino-2-methylpropanoic acid

<400> SEQUENCE: 69

Xaa Lys Cys Asn Thr Ala Thr Cys Ala Thr Gln Arg Leu Ala Asn Phe
1               5                   10                  15
```

Leu Val His Ser Ser Xaa Asn Phe Gly Pro Ile Leu Pro Pro Thr Arg
            20                  25                  30

Val Gly Ser Asn Thr Tyr
        35

<210> SEQ ID NO 70
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (22)..(22)
<223> OTHER INFORMATION: 2-amino-2-methylpropanoic acid

<400> SEQUENCE: 70

Xaa Lys Cys Asn Thr Ala Thr Cys Ala Thr Gln Arg Leu Ala Asn Phe
1               5                   10                  15

Leu Val His Ser Ser Xaa Asn Phe Gly Pro Ile Leu Pro Pro Thr Arg
            20                  25                  30

Val Gly Ser Asn Thr Tyr
        35

<210> SEQ ID NO 71
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: C18diacid-gamma-Glu
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (22)..(22)
<223> OTHER INFORMATION: 2-amino-2-methylpropanoic acid

<400> SEQUENCE: 71

Xaa Lys Cys Asn Thr Ala Thr Cys Ala Thr Gln Arg Leu Ala Asn Phe
1               5                   10                  15

Leu Val His Ser Ser Xaa Asn Phe Gly Pro Ile Leu Pro Pro Thr Arg
            20                  25                  30

Val Gly Ser Asn Thr Tyr
        35

<210> SEQ ID NO 72
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

```
<220> FEATURE:
<221> NAME/KEY: MOD_RES
<222> LOCATION: (1)..(1)
<223> OTHER INFORMATION: Lys, wherein the side chain of Lys is
      connected to gamma-Glu-gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid

<400> SEQUENCE: 72

Xaa Cys Asn Thr Ala Thr Cys Ala Thr Gln Arg Leu Ala Asn Phe Leu
1               5                   10                  15

Val His Ser Ser Xaa Asn Phe Gly Pro Ile Leu Pro Pro Thr Asn Val
            20                  25                  30

Gly Ser Arg Thr Tyr
            35

<210> SEQ ID NO 73
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (22)..(22)
<223> OTHER INFORMATION: 2-amino-2-methylpropanoic acid

<400> SEQUENCE: 73

Xaa Lys Cys Asn Thr Ala Thr Cys Ala Thr Gln Arg Leu Ala Asn Phe
1               5                   10                  15

Leu Val His Ser Ser Xaa Asn Phe Gly Pro Ile Leu Pro Pro Thr Asn
            20                  25                  30

Val Gly Ser Arg Thr Tyr
            35

<210> SEQ ID NO 74
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (22)..(22)
<223> OTHER INFORMATION: 2-amino-2-methylpropanoic acid
```

<400> SEQUENCE: 74

Xaa Lys Cys Asn Thr Ala Thr Cys Ala Thr Gln Arg Leu Ala Asn Phe
1               5                   10                  15

Leu Val His Ser Ser Xaa Asn Phe Gly Pro Ile Leu Pro Pro Thr Asn
            20                  25                  30

Val Gly Ser Arg Thr Tyr
                35

<210> SEQ ID NO 75
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid

<400> SEQUENCE: 75

Xaa Cys Asn Thr Ala Thr Cys Ala Thr Gln Arg Leu Ala Asn Phe Leu
1               5                   10                  15

Arg His Ser Ser Xaa Asn Phe Gly Pro Ile Leu Pro Pro Thr Asn Val
            20                  25                  30

Gly Ser Asn Thr Tyr
                35

<210> SEQ ID NO 76
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid

<400> SEQUENCE: 76

Xaa Cys Asn Thr Ala Thr Cys Ala Thr Gln Arg Leu Ala Asn Phe Leu
1               5                   10                  15

Arg His Ser Ser Xaa Asn Phe Gly Pro Ile Leu Pro Pro Thr Arg Val
            20                  25                  30

Gly Ser Asn Thr Tyr
                35

```
<210> SEQ ID NO 77
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid

<400> SEQUENCE: 77

Xaa Cys Asn Thr Ala Thr Cys Ala Thr Gln Arg Leu Ala Asn Phe Leu
1               5                   10                  15

Arg His Ser Ser Xaa Asn Phe Gly Pro Ile Leu Pro Pro Thr Arg Val
            20                  25                  30

Gly Ser Asn Thr Tyr
        35

<210> SEQ ID NO 78
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (22)..(22)
<223> OTHER INFORMATION: 2-amino-2-methylpropanoic acid
<220> FEATURE:
<221> NAME/KEY: MOD_RES
<222> LOCATION: (27)..(27)
<223> OTHER INFORMATION: 2-amino-2-methylpropanoic acid

<400> SEQUENCE: 78

Xaa Lys Cys Asn Thr Ala Thr Cys Ala Thr Gln Arg Leu Ala Asn Phe
1               5                   10                  15

Leu Val His Ser Ser Xaa Asn Phe Gly Pro Xaa Leu Pro Pro Thr Asn
            20                  25                  30

Val Gly Ser Asn Thr Tyr
        35

<210> SEQ ID NO 79
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
```

```
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (22)..(22)
<223> OTHER INFORMATION: 2-amino-2-methylpropanoic acid
<220> FEATURE:
<221> NAME/KEY: MOD_RES
<222> LOCATION: (28)..(28)
<223> OTHER INFORMATION: 2-amino-2-methylpropanoic acid

<400> SEQUENCE: 79

Xaa Lys Cys Asn Thr Ala Thr Cys Ala Thr Gln Arg Leu Ala Asn Phe
1               5                   10                  15

Leu Val His Ser Ser Xaa Asn Phe Gly Pro Ile Xaa Pro Pro Thr Asn
            20                  25                  30

Val Gly Ser Asn Thr Tyr
        35

<210> SEQ ID NO 80
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (22)..(22)
<223> OTHER INFORMATION: 2-amino-2-methylpropanoic acid
<220> FEATURE:
<221> NAME/KEY: MOD_RES
<222> LOCATION: (32)..(32)
<223> OTHER INFORMATION: 2-amino-2-methylpropanoic acid

<400> SEQUENCE: 80

Xaa Lys Cys Asn Thr Ala Thr Cys Ala Thr Gln Arg Leu Ala Asn Phe
1               5                   10                  15

Leu Val His Ser Ser Xaa Asn Phe Gly Pro Ile Leu Pro Pro Thr Xaa
            20                  25                  30

Val Gly Ser Asn Thr Tyr
        35

<210> SEQ ID NO 81
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
```

<222> LOCATION: (3)..(8)
<223> OTHER INFORMATION: Disulphide bridge between Cys residues
<220> FEATURE:
<221> NAME/KEY: MOD_RES
<222> LOCATION: (22)..(22)
<223> OTHER INFORMATION: 2-amino-2-methylpropanoic acid
<220> FEATURE:
<221> NAME/KEY: MOD_RES
<222> LOCATION: (34)..(34)
<223> OTHER INFORMATION: 2-amino-2-methylpropanoic acid

<400> SEQUENCE: 81

Xaa Lys Cys Asn Thr Ala Thr Cys Ala Thr Gln Arg Leu Ala Asn Phe
1               5                   10                  15

Leu Val His Ser Ser Xaa Asn Phe Gly Pro Ile Leu Pro Pro Thr Asn
            20                  25                  30

Val Xaa Ser Asn Thr Tyr
        35

<210> SEQ ID NO 82
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (22)..(22)
<223> OTHER INFORMATION: 2-amino-2-methylpropanoic acid
<220> FEATURE:
<221> NAME/KEY: MOD_RES
<222> LOCATION: (36)..(36)
<223> OTHER INFORMATION: 2-amino-2-methylpropanoic acid

<400> SEQUENCE: 82

Xaa Lys Cys Asn Thr Ala Thr Cys Ala Thr Gln Arg Leu Ala Asn Phe
1               5                   10                  15

Leu Val His Ser Ser Xaa Asn Phe Gly Pro Ile Leu Pro Pro Thr Asn
            20                  25                  30

Val Gly Ser Xaa Thr Tyr
        35

<210> SEQ ID NO 83
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (22)..(22)

```
<223> OTHER INFORMATION: 2-amino-2-methylpropanoic acid
<220> FEATURE:
<221> NAME/KEY: MOD_RES
<222> LOCATION: (37)..(37)
<223> OTHER INFORMATION: 2-amino-2-methylpropanoic acid

<400> SEQUENCE: 83

Xaa Lys Cys Asn Thr Ala Thr Cys Ala Thr Gln Arg Leu Ala Asn Phe
1               5                   10                  15

Leu Val His Ser Ser Xaa Asn Phe Gly Pro Ile Leu Pro Pro Thr Asn
            20                  25                  30

Val Gly Ser Asn Xaa Tyr
            35

<210> SEQ ID NO 84
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (22)..(22)
<223> OTHER INFORMATION: 2-amino-2-methylpropanoic acid
<220> FEATURE:
<221> NAME/KEY: MOD_RES
<222> LOCATION: (35)..(35)
<223> OTHER INFORMATION: 2-amino-2-methylpropanoic acid

<400> SEQUENCE: 84

Xaa Lys Cys Asn Thr Ala Thr Cys Ala Thr Gln Arg Leu Ala Asn Phe
1               5                   10                  15

Leu Val His Ser Ser Xaa Asn Phe Gly Pro Ile Leu Pro Pro Thr Asn
            20                  25                  30

Val Gly Xaa Asn Thr Tyr
            35

<210> SEQ ID NO 85
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (22)..(22)
<223> OTHER INFORMATION: 2-amino-2-methylpropanoic acid
<220> FEATURE:
<221> NAME/KEY: MOD_RES
<222> LOCATION: (38)..(38)
<223> OTHER INFORMATION: 2-amino-2-methylpropanoic acid
```

<400> SEQUENCE: 85

Xaa Lys Cys Asn Thr Ala Thr Cys Ala Thr Gln Arg Leu Ala Asn Phe
1               5                   10                  15

Leu Val His Ser Ser Xaa Asn Phe Gly Pro Ile Leu Pro Pro Thr Asn
            20                  25                  30

Val Gly Ser Asn Thr Xaa
            35

<210> SEQ ID NO 86
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (18)..(18)
<223> OTHER INFORMATION: 2-amino-2-methylpropanoic acid
<220> FEATURE:
<221> NAME/KEY: MOD_RES
<222> LOCATION: (22)..(22)
<223> OTHER INFORMATION: 2-amino-2-methylpropanoic acid

<400> SEQUENCE: 86

Xaa Lys Cys Asn Thr Ala Thr Cys Ala Thr Gln Arg Leu Ala His Phe
1               5                   10                  15

Leu Xaa His Ser Ser Xaa Asn Phe Gly Pro Ile Leu Pro Pro Thr Glu
            20                  25                  30

Val Gly Ser Asn Thr Tyr
            35

<210> SEQ ID NO 87
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (18)..(18)
<223> OTHER INFORMATION: 2-amino-2-methylpropanoic acid
<220> FEATURE:
<221> NAME/KEY: MOD_RES
<222> LOCATION: (22)..(22)
<223> OTHER INFORMATION: 2-amino-2-methylpropanoic acid

<400> SEQUENCE: 87

Xaa Lys Cys Asn Thr Ala Thr Cys Ala Thr Gln Arg Leu Ala Asn Phe
1               5                   10                  15

-continued

```
Leu Xaa His Ser Ser Xaa Asn Phe Gly Pro Ile Leu Pro Pro Thr Asn
         20                  25                  30

Val Gly Ser Asn Thr Pro
         35

<210> SEQ ID NO 88
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (22)..(22)
<223> OTHER INFORMATION: 2-amino-2-methylpropanoic acid
<220> FEATURE:
<221> NAME/KEY: MOD_RES
<222> LOCATION: (29)..(29)
<223> OTHER INFORMATION: 2-amino-2-methylpropanoic acid

<400> SEQUENCE: 88

Xaa Lys Cys Asn Thr Ala Thr Cys Ala Thr Gln Arg Leu Ala Asn Phe
1               5                   10                  15

Leu Val His Ser Ser Xaa Asn Phe Gly Pro Ile Leu Xaa Pro Thr Asn
         20                  25                  30

Val Gly Ser Asn Thr Tyr
         35

<210> SEQ ID NO 89
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid
<220> FEATURE:
<221> NAME/KEY: MOD_RES
<222> LOCATION: (31)..(31)
<223> OTHER INFORMATION: 2-amino-2-methylpropanoic acid

<400> SEQUENCE: 89

Xaa Cys Asn Thr Ala Thr Cys Ala Thr Gln Arg Leu Ala Asn Phe Leu
1               5                   10                  15

Val His Ser Ser Xaa Asn Phe Gly Pro Ile Leu Pro Pro Thr Xaa Val
         20                  25                  30

Gly Ser Asn Thr Tyr
```

```
<210> SEQ ID NO 90
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid
<220> FEATURE:
<221> NAME/KEY: MOD_RES
<222> LOCATION: (31)..(31)
<223> OTHER INFORMATION: 2-amino-2-methylpropanoic acid

<400> SEQUENCE: 90

Xaa Cys Asn Thr Ala Thr Cys Ala Thr Gln Arg Leu Ala Asn Phe Leu
1               5                   10                  15

Arg His Ser Ser Xaa Asn Phe Gly Pro Ile Leu Pro Pro Thr Xaa Val
            20                  25                  30

Gly Ser Asn Thr Tyr
            35

<210> SEQ ID NO 91
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid
<220> FEATURE:
<221> NAME/KEY: MOD_RES
<222> LOCATION: (35)..(35)
<223> OTHER INFORMATION: 2-amino-2-methylpropanoic acid

<400> SEQUENCE: 91

Xaa Cys Asn Thr Ala Thr Cys Ala Thr Gln Arg Leu Ala Asn Phe Leu
1               5                   10                  15

Val His Ser Ser Xaa Asn Phe Gly Pro Ile Leu Pro Pro Thr Asn Val
            20                  25                  30

Gly Ser Xaa Thr Tyr
            35

<210> SEQ ID NO 92
<211> LENGTH: 37
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid
<220> FEATURE:
<221> NAME/KEY: MOD_RES
<222> LOCATION: (35)..(35)
<223> OTHER INFORMATION: 2-amino-2-methylpropanoic acid

<400> SEQUENCE: 92

Xaa Cys Asn Thr Ala Thr Cys Ala Thr Gln Arg Leu Ala Asn Phe Leu
1               5                   10                  15

Arg His Ser Ser Xaa Asn Phe Gly Pro Ile Leu Pro Pro Thr Asn Val
            20                  25                  30

Gly Ser Xaa Thr Tyr
            35

<210> SEQ ID NO 93
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (18)..(18)
<223> OTHER INFORMATION: 2-amino-2-methylpropanoic acid
<220> FEATURE:
<221> NAME/KEY: MOD_RES
<222> LOCATION: (22)..(22)
<223> OTHER INFORMATION: 2,4-diaminobutanoic acid
<220> FEATURE:
<221> NAME/KEY: MOD_RES
<222> LOCATION: (26)..(26)
<223> OTHER INFORMATION: 2-amino-2-methylpropanoic acid

<400> SEQUENCE: 93

Xaa Lys Cys Asn Thr Ala Thr Cys Ala Thr Gln Arg Leu Ala Asn Phe
1               5                   10                  15

Leu Xaa His Ser Ser Xaa Asn Phe Gly Xaa Ile Leu Pro Pro Thr Asn
            20                  25                  30

Val Gly Ser Asn Thr Tyr
            35

<210> SEQ ID NO 94
<211> LENGTH: 38
<212> TYPE: PRT
```

```
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (18)..(18)
<223> OTHER INFORMATION: 2-amino-2-methylpropanoic acid
<220> FEATURE:
<221> NAME/KEY: MOD_RES
<222> LOCATION: (27)..(27)
<223> OTHER INFORMATION: 2-amino-2-methylpropanoic acid

<400> SEQUENCE: 94

Xaa Lys Cys Asn Thr Ala Thr Cys Ala Thr Gln Arg Leu Ala Asn Phe
1               5                   10                  15

Leu Xaa His Ser Ser Asn Asn Phe Gly Pro Xaa Leu Pro Pro Thr Asn
            20                  25                  30

Val Gly Ser Asn Thr Tyr
            35

<210> SEQ ID NO 95
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (18)..(18)
<223> OTHER INFORMATION: 2-amino-2-methylpropanoic acid
<220> FEATURE:
<221> NAME/KEY: MOD_RES
<222> LOCATION: (28)..(28)
<223> OTHER INFORMATION: 2-amino-2-methylpropanoic acid

<400> SEQUENCE: 95

Xaa Lys Cys Asn Thr Ala Thr Cys Ala Thr Gln Arg Leu Ala Asn Phe
1               5                   10                  15

Leu Xaa His Ser Ser Asn Asn Phe Gly Pro Ile Xaa Pro Pro Thr Asn
            20                  25                  30

Val Gly Ser Asn Thr Tyr
            35

<210> SEQ ID NO 96
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (18)..(18)
<223> OTHER INFORMATION: 2-amino-2-methylpropanoic acid
<220> FEATURE:
<221> NAME/KEY: MOD_RES
<222> LOCATION: (29)..(29)
<223> OTHER INFORMATION: 2-amino-2-methylpropanoic acid

<400> SEQUENCE: 96

Xaa Lys Cys Asn Thr Ala Thr Cys Ala Thr Gln Arg Leu Ala Asn Phe
1               5                   10                  15

Leu Xaa His Ser Ser Asn Asn Phe Gly Pro Ile Leu Xaa Pro Thr Asn
            20                  25                  30

Val Gly Ser Asn Thr Tyr
            35

<210> SEQ ID NO 97
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (18)..(18)
<223> OTHER INFORMATION: 2-amino-2-methylpropanoic acid
<220> FEATURE:
<221> NAME/KEY: MOD_RES
<222> LOCATION: (30)..(30)
<223> OTHER INFORMATION: 2-amino-2-methylpropanoic acid

<400> SEQUENCE: 97

Xaa Lys Cys Asn Thr Ala Thr Cys Ala Thr Gln Arg Leu Ala Asn Phe
1               5                   10                  15

Leu Xaa His Ser Ser Asn Asn Phe Gly Pro Ile Leu Pro Xaa Thr Asn
            20                  25                  30

Val Gly Ser Asn Thr Tyr
            35

<210> SEQ ID NO 98
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
```

```
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (18)..(18)
<223> OTHER INFORMATION: 2-amino-2-methylpropanoic acid
<220> FEATURE:
<221> NAME/KEY: MOD_RES
<222> LOCATION: (32)..(32)
<223> OTHER INFORMATION: 2-amino-2-methylpropanoic acid

<400> SEQUENCE: 98

Xaa Lys Cys Asn Thr Ala Thr Cys Ala Thr Gln Arg Leu Ala Asn Phe
 1               5                  10                  15

Leu Xaa His Ser Ser Asn Asn Phe Gly Pro Ile Leu Pro Pro Thr Xaa
            20                  25                  30

Val Gly Ser Asn Thr Tyr
        35

<210> SEQ ID NO 99
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (18)..(18)
<223> OTHER INFORMATION: 2-amino-2-methylpropanoic acid
<220> FEATURE:
<221> NAME/KEY: MOD_RES
<222> LOCATION: (33)..(33)
<223> OTHER INFORMATION: 2-amino-2-methylpropanoic acid

<400> SEQUENCE: 99

Xaa Lys Cys Asn Thr Ala Thr Cys Ala Thr Gln Arg Leu Ala Asn Phe
 1               5                  10                  15

Leu Xaa His Ser Ser Asn Asn Phe Gly Pro Ile Leu Pro Pro Thr Asn
            20                  25                  30

Xaa Gly Ser Asn Thr Tyr
        35

<210> SEQ ID NO 100
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
```

```
<222> LOCATION: (18)..(18)
<223> OTHER INFORMATION: 2-amino-2-methylpropanoic acid
<220> FEATURE:
<221> NAME/KEY: MOD_RES
<222> LOCATION: (34)..(34)
<223> OTHER INFORMATION: 2-amino-2-methylpropanoic acid

<400> SEQUENCE: 100

Xaa Lys Cys Asn Thr Ala Thr Cys Ala Thr Gln Arg Leu Ala Asn Phe
 1               5                  10                  15

Leu Xaa His Ser Ser Asn Asn Phe Gly Pro Ile Leu Pro Pro Thr Asn
            20                  25                  30

Val Xaa Ser Asn Thr Tyr
         35

<210> SEQ ID NO 101
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (18)..(18)
<223> OTHER INFORMATION: 2-amino-2-methylpropanoic acid
<220> FEATURE:
<221> NAME/KEY: MOD_RES
<222> LOCATION: (35)..(35)
<223> OTHER INFORMATION: 2-amino-2-methylpropanoic acid

<400> SEQUENCE: 101

Xaa Lys Cys Asn Thr Ala Thr Cys Ala Thr Gln Arg Leu Ala Asn Phe
 1               5                  10                  15

Leu Xaa His Ser Ser Asn Asn Phe Gly Pro Ile Leu Pro Pro Thr Asn
            20                  25                  30

Val Gly Xaa Asn Thr Tyr
         35

<210> SEQ ID NO 102
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (18)..(18)
<223> OTHER INFORMATION: 2-amino-2-methylpropanoic acid
<220> FEATURE:
<221> NAME/KEY: MOD_RES
<222> LOCATION: (36)..(36)
```

<223> OTHER INFORMATION: 2-amino-2-methylpropanoic acid

<400> SEQUENCE: 102

Xaa Lys Cys Asn Thr Ala Thr Cys Ala Thr Gln Arg Leu Ala Asn Phe
1               5                   10                  15

Leu Xaa His Ser Ser Asn Asn Phe Gly Pro Ile Leu Pro Pro Thr Asn
            20                  25                  30

Val Gly Ser Xaa Thr Tyr
        35

<210> SEQ ID NO 103
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (27)..(27)
<223> OTHER INFORMATION: D-Leu

<400> SEQUENCE: 103

Xaa Cys Asn Thr Ala Thr Cys Ala Thr Gln Arg Leu Ala Asn Phe Leu
1               5                   10                  15

Val His Ser Ser Asn Asn Phe Gly Pro Ile Xaa Pro Pro Thr Asn Val
            20                  25                  30

Gly Ser Asn Thr Tyr
        35

<210> SEQ ID NO 104
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (28)..(28)
<223> OTHER INFORMATION: D-Pro

<400> SEQUENCE: 104

Xaa Cys Asn Thr Ala Thr Cys Ala Thr Gln Arg Leu Ala Asn Phe Leu
1               5                   10                  15

Val His Ser Ser Asn Asn Phe Gly Pro Ile Leu Xaa Pro Thr Asn Val
            20                  25                  30

Gly Ser Asn Thr Tyr
        35

```
<210> SEQ ID NO 105
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (22)..(22)
<223> OTHER INFORMATION: 2,4-diaminobutanoic acid
<220> FEATURE:
<221> NAME/KEY: MOD_RES
<222> LOCATION: (26)..(26)
<223> OTHER INFORMATION: 2-amino-2-methylpropanoic acid

<400> SEQUENCE: 105

Xaa Lys Cys Asn Thr Ala Thr Cys Ala Thr Gln Arg Leu Ala Asn Phe
1               5                   10                  15

Leu Ser His Ser Ser Xaa Asn Phe Gly Xaa Ile Leu Pro Pro Thr Asn
            20                  25                  30

Val Gly Ser Asn Thr Tyr
            35

<210> SEQ ID NO 106
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (27)..(27)
<223> OTHER INFORMATION: 2-amino-2-methylpropanoic acid

<400> SEQUENCE: 106

Xaa Lys Cys Asn Thr Ala Thr Cys Ala Thr Gln Arg Leu Ala Asn Phe
1               5                   10                  15

Leu Val His Ser Ser Asn Asn Phe Gly Pro Xaa Leu Pro Pro Thr Asn
            20                  25                  30

Val Gly Ser Asn Thr Tyr
            35

<210> SEQ ID NO 107
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (27)..(27)
<223> OTHER INFORMATION: 2-amino-2-methylpropanoic acid

<400> SEQUENCE: 107

Xaa Lys Cys Asn Thr Ala Thr Cys Ala Thr Gln Arg Leu Ala Asn Phe
1               5                   10                  15

Leu Arg His Ser Ser Asn Asn Phe Gly Pro Xaa Leu Pro Pro Thr Asn
            20                  25                  30

Val Gly Ser Asn Thr Tyr
            35

<210> SEQ ID NO 108
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (28)..(28)
<223> OTHER INFORMATION: 2-amino-2-methylpropanoic acid

<400> SEQUENCE: 108

Xaa Lys Cys Asn Thr Ala Thr Cys Ala Thr Gln Arg Leu Ala Asn Phe
1               5                   10                  15

Leu Val His Ser Ser Asn Asn Phe Gly Pro Ile Xaa Pro Pro Thr Asn
            20                  25                  30

Val Gly Ser Asn Thr Tyr
            35

<210> SEQ ID NO 109
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (23)..(23)
<223> OTHER INFORMATION: 2-amino-2-methylpropanoic acid
```

<400> SEQUENCE: 109

Xaa Lys Cys Asn Thr Ala Thr Cys Ala Thr Gln Arg Leu Ala Asn Phe
1               5                   10                  15

Leu Val His Ser Ser Asn Xaa Phe Gly Pro Ile Leu Pro Pro Thr Asn
            20                  25                  30

Val Gly Ser Asn Thr Tyr
            35

<210> SEQ ID NO 110
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (25)..(25)
<223> OTHER INFORMATION: 2-amino-2-methylpropanoic acid

<400> SEQUENCE: 110

Xaa Lys Cys Asn Thr Ala Thr Cys Ala Thr Gln Arg Leu Ala Asn Phe
1               5                   10                  15

Leu Val His Ser Ser Asn Asn Phe Xaa Pro Ile Leu Pro Pro Thr Asn
            20                  25                  30

Val Gly Ser Asn Thr Tyr
            35

<210> SEQ ID NO 111
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues

<400> SEQUENCE: 111

Xaa Lys Cys Asn Thr Ala Thr Cys Ala Thr Gln Arg Leu Ala Asn Phe
1               5                   10                  15

Leu Val His Ser Ser Asn His Phe Gly Pro Ile Leu Pro Pro Thr Asn
            20                  25                  30

Val Gly Ser Glu Thr Tyr
            35

<210> SEQ ID NO 112
<211> LENGTH: 38
<212> TYPE: PRT
<213> ORGANISM: Artificial Sequence
<220> FEATURE:

```
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: C20diacid-gamma-Glu
<220> FEATURE:
<221> NAME/KEY: SITE
<222> LOCATION: (3)..(8)
<223> OTHER INFORMATION: Disulphide bridge between Cys residues

<400> SEQUENCE: 112

Xaa Lys Cys Asn Thr Ala Thr Cys Ala Thr Gln Arg Leu Ala Asn Phe
1               5                   10                  15

Leu Val His Ser Ser Asn Asn Phe Gly Pro Ile Leu Pro Pro Thr Asn
            20                  25                  30

Val Gly Ser Asn Thr Tyr
            35

<210> SEQ ID NO 113
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: C20diacid-gamma-Glu
<220> FEATURE:
<221> NAME/KEY: MOD_RES
<222> LOCATION: (2)..(2)
<223> OTHER INFORMATION: O2Oc-O2Oc-Lys
<220> FEATURE:
<221> NAME/KEY: SITE
<222> LOCATION: (3)..(8)
<223> OTHER INFORMATION: Disulphide bridge between Cys residues

<400> SEQUENCE: 113

Xaa Xaa Cys Asn Thr Ala Thr Cys Ala Thr Gln Arg Leu Ala Asn Phe
1               5                   10                  15

Leu Val His Ser Ser Asn Asn Phe Gly Pro Ile Leu Pro Pro Thr Asn
            20                  25                  30

Val Gly Ser Asn Thr Tyr
            35

<210> SEQ ID NO 114
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-gamma-Glu-C20diacid
<220> FEATURE:
<221> NAME/KEY: SITE
<222> LOCATION: (2)..(7)
<223> OTHER INFORMATION: Disulphide bridge between Cys residues

<400> SEQUENCE: 114

Xaa Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Pro Thr Asn Val
            20                  25                  30
```

Gly Ser Arg Thr Tyr
        35

<210> SEQ ID NO 115
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-gamma-Glu-C20diacid
<220> FEATURE:
<221> NAME/KEY: SITE
<222> LOCATION: (2)..(7)
<223> OTHER INFORMATION: Disulphide bridge between Cys residues

<400> SEQUENCE: 115

Xaa Cys Asn Thr Ala Thr Cys Ala Thr Gln Arg Leu Ala Asn Phe Leu
1               5                   10                  15

Val His Ser Ser Pro Asn Phe Pro Ala Ile Leu Ser Pro Thr Asn Val
            20                  25                  30

Gly Ser Asn Thr Tyr
        35

<210> SEQ ID NO 116
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-gamma-Glu-C20diacid
<220> FEATURE:
<221> NAME/KEY: SITE
<222> LOCATION: (2)..(7)
<223> OTHER INFORMATION: Disulphide bridge between Cys residues

<400> SEQUENCE: 116

Xaa Cys Asn Thr Ala Thr Cys Ala Thr Gln Arg Leu Ala Glu Phe Leu
1               5                   10                  15

Arg His Ser Ser Asn Asn Phe Gly Pro Ile Leu Pro Pro Thr Asn Val
            20                  25                  30

Gly Ser Asn Thr Tyr
        35

<210> SEQ ID NO 117
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-gamma-Glu-C20diacid
<220> FEATURE:
<221> NAME/KEY: SITE
<222> LOCATION: (2)..(7)
<223> OTHER INFORMATION: Disulphide bridge between Cys residues

```
<220> FEATURE:
<221> NAME/KEY: MOD_RES
<222> LOCATION: (21)..(21)
<223> OTHER INFORMATION: 2-amino-2-methylpropanoic acid

<400> SEQUENCE: 117

Xaa Cys Asn Thr Ala Thr Cys Ala Thr Gln Arg Leu Ala Asn Phe Leu
1               5                   10                  15

Val His Ser Ser Xaa Asn Phe Pro Ala Ile Leu Ser Pro Thr Asn Val
            20                  25                  30

Gly Ser Asn Thr Tyr
        35

<210> SEQ ID NO 118
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-gamma-Glu-C20diacid
<220> FEATURE:
<221> NAME/KEY: SITE
<222> LOCATION: (2)..(7)
<223> OTHER INFORMATION: Disulphide bridge between Cys residues

<400> SEQUENCE: 118

Xaa Cys Asn Ile Ala Thr Cys Ala Thr Gln Arg Leu Ala Asn Phe Leu
1               5                   10                  15

Val His Ser Ile Ala Asn Phe Gly Pro Ile Leu Pro Pro Thr Asn Val
            20                  25                  30

Gly Ser Arg Thr Tyr
        35

<210> SEQ ID NO 119
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-gamma-Glu-C20diacid
<220> FEATURE:
<221> NAME/KEY: SITE
<222> LOCATION: (2)..(7)
<223> OTHER INFORMATION: Disulphide bridge between Cys residues

<400> SEQUENCE: 119

Xaa Cys Asn Thr Ala Thr Cys Ala Thr Gln Arg Leu Ala Asn Phe Leu
1               5                   10                  15

Val His Ser Pro Pro Asn Phe Pro Ala Ile Leu Ser Pro Thr Asn Val
            20                  25                  30

Gly Ser Asn Thr Tyr
        35

<210> SEQ ID NO 120
<211> LENGTH: 37
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-gamma-Glu-C20diacid
<220> FEATURE:
<221> NAME/KEY: SITE
<222> LOCATION: (2)..(7)
<223> OTHER INFORMATION: Disulphide bridge between Cys residues

<400> SEQUENCE: 120

Xaa Cys Asn Ala Ala Thr Cys Ala Thr Gln Arg Leu Ala Asn Trp Leu
1               5                   10                  15

Val His Ser Ser Pro Asn Phe Pro Ala Ile Leu Ser Pro Thr Asn Val
            20                  25                  30

Gly Ser Asn Thr Tyr
        35

<210> SEQ ID NO 121
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-gamma-Glu-C20diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid
<220> FEATURE:
<221> NAME/KEY: MOD_RES
<222> LOCATION: (24)..(24)
<223> OTHER INFORMATION: (2S,4R)-4-hydroxypyrrolidine-2-carboxylic acid

<400> SEQUENCE: 121

Xaa Cys Asn Thr Ala Thr Cys Ala Thr Gln Arg Leu Ala Asn Phe Leu
1               5                   10                  15

Val His Ser Ser Xaa Asn Phe Xaa Ala Ile Leu Ser Pro Thr Asn Val
            20                  25                  30

Gly Ser Asn Thr Tyr
        35

<210> SEQ ID NO 122
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
```

```
<221> NAME/KEY: MOD_RES
<222> LOCATION: (21)..(21)
<223> OTHER INFORMATION: 2-amino-2-methylpropanoic acid
<220> FEATURE:
<221> NAME/KEY: MOD_RES
<222> LOCATION: (31)..(31)
<223> OTHER INFORMATION: 2,4-diaminobutanoic acid

<400> SEQUENCE: 122

Xaa Cys Asn Thr Ala Thr Cys Ala Thr Gln Arg Leu Ala Asn Phe Leu
1               5                   10                  15

Val His Ser Ser Xaa Asn Phe Pro Ala Ile Leu Ser Pro Thr Xaa Val
            20                  25                  30

Gly Ser Asn Thr Tyr
        35

<210> SEQ ID NO 123
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-gamma-Glu-C20diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid
<220> FEATURE:
<221> NAME/KEY: MOD_RES
<222> LOCATION: (31)..(31)
<223> OTHER INFORMATION: 2,4-diaminobutanoic acid

<400> SEQUENCE: 123

Xaa Cys Asn Thr Ala Thr Cys Ala Thr Gln Arg Leu Ala Asn Phe Leu
1               5                   10                  15

Val His Ser Ser Xaa Asn Phe Pro Ala Ile Leu Ser Pro Thr Xaa Val
            20                  25                  30

Gly Ser Asn Thr Tyr
        35

<210> SEQ ID NO 124
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid
<220> FEATURE:
<221> NAME/KEY: MOD_RES
```

```
<222> LOCATION: (35)..(35)
<223> OTHER INFORMATION: 2,4-diaminobutanoic acid

<400> SEQUENCE: 124

Xaa Cys Asn Thr Ala Thr Cys Ala Thr Gln Arg Leu Ala Asn Phe Leu
1               5                   10                  15

Val His Ser Ser Xaa Asn Phe Pro Ala Ile Leu Ser Pro Thr Asn Val
            20                  25                  30

Gly Ser Xaa Thr Tyr
        35

<210> SEQ ID NO 125
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-gamma-Glu-C20diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid
<220> FEATURE:
<221> NAME/KEY: MOD_RES
<222> LOCATION: (35)..(35)
<223> OTHER INFORMATION: 2,4-diaminobutanoic acid

<400> SEQUENCE: 125

Xaa Cys Asn Thr Ala Thr Cys Ala Thr Gln Arg Leu Ala Asn Phe Leu
1               5                   10                  15

Val His Ser Ser Xaa Asn Phe Pro Ala Ile Leu Ser Pro Thr Asn Val
            20                  25                  30

Gly Ser Xaa Thr Tyr
        35

<210> SEQ ID NO 126
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (18)..(18)
<223> OTHER INFORMATION: 2-amino-2-methylpropanoic acid
<220> FEATURE:
<221> NAME/KEY: MOD_RES
<222> LOCATION: (22)..(22)
<223> OTHER INFORMATION: 2,4-diaminobutanoic acid

<400> SEQUENCE: 126
```

```
Xaa Lys Cys Asn Thr Ala Thr Cys Ala Thr Gln Arg Leu Ala Asn Phe
1               5                   10                  15

Leu Xaa His Ser Ser Xaa Asn Phe Gly Pro Ile Leu Pro Pro Thr Asn
            20                  25                  30

Val Gly Ser Asn Thr Tyr
                35
```

<210> SEQ ID NO 127
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid

<400> SEQUENCE: 127

```
Xaa Cys Asn Thr Ala Thr Cys Ala Thr Gln Arg Leu Ala Asn Phe Leu
1               5                   10                  15

Xaa His Ser Ser Asn Asn Phe Gly Pro Ile Leu Pro Pro Thr Asn Val
            20                  25                  30

Gly Ser Asn Thr Tyr
                35
```

<210> SEQ ID NO 128
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (18)..(18)
<223> OTHER INFORMATION: 2-amino-2-methylpropanoic acid

<400> SEQUENCE: 128

```
Xaa Lys Cys Asn Thr Ala Thr Cys Ala Thr Gln Arg Leu Ala Glu Phe
1               5                   10                  15

Leu Xaa His Ser Ser Asn Asn Phe Gly Pro Ile Leu Pro Pro Thr Asn
            20                  25                  30

Val Gly Ser Asn Thr Tyr
                35
```

<210> SEQ ID NO 129
<211> LENGTH: 38
<212> TYPE: PRT

<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (18)..(18)
<223> OTHER INFORMATION: 2-amino-2-methylpropanoic acid

<400> SEQUENCE: 129

Xaa Lys Cys Asn Thr Ala Thr Cys Ala Thr Gln Arg Leu Ala Asn Phe
1               5                   10                  15

Leu Xaa His Ser Ser Asn Asn Phe Gly Pro Ile Leu Pro Pro Thr Asn
            20                  25                  30

Val Gly Ser Asn Thr Tyr
            35

<210> SEQ ID NO 130
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (18)..(18)
<223> OTHER INFORMATION: 2-amino-2-methylpropanoic acid

<400> SEQUENCE: 130

Xaa Lys Cys Asn Thr Ala Thr Cys Ala Thr Gln Arg Leu Ala Glu Phe
1               5                   10                  15

Leu Xaa His Ser Ser His Asn Phe Gly Pro Ile Leu Pro Pro Thr Asn
            20                  25                  30

Val Gly Ser Asn Thr Tyr
            35

<210> SEQ ID NO 131
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues

```
<220> FEATURE:
<221> NAME/KEY: MOD_RES
<222> LOCATION: (18)..(18)
<223> OTHER INFORMATION: 2-amino-2-methylpropanoic acid

<400> SEQUENCE: 131

Xaa Lys Cys Asn Thr Ala Thr Cys Ala Thr Gln Arg Leu Ala Asn Phe
1               5                   10                  15

Leu Xaa His Ser Ser His Asn Phe Gly Pro Ile Leu Pro Pro Thr Asn
            20                  25                  30

Val Gly Ser Asn Thr Tyr
            35

<210> SEQ ID NO 132
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (18)..(18)
<223> OTHER INFORMATION: 2-amino-2-methylpropanoic acid

<400> SEQUENCE: 132

Xaa Lys Cys Asn Thr Ala Thr Cys Ala Thr Gln Arg Leu Ala Asn Phe
1               5                   10                  15

Leu Xaa His Ser Ser Pro Asn Phe Gly Pro Ile Leu Pro Pro Thr Asn
            20                  25                  30

Val Gly Ser Asn Thr Tyr
            35

<210> SEQ ID NO 133
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (18)..(18)
<223> OTHER INFORMATION: 2-amino-2-methylpropanoic acid

<400> SEQUENCE: 133

Xaa Lys Cys Asn Thr Ala Thr Cys Ala Thr Gln Arg Leu Ala Asn Phe
1               5                   10                  15

Leu Xaa His Ser Ser Ser Asn Phe Gly Pro Ile Leu Pro Pro Thr Asn
            20                  25                  30
```

Val Gly Ser Asn Thr Tyr
        35

<210> SEQ ID NO 134
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (18)..(18)
<223> OTHER INFORMATION: 2-amino-2-methylpropanoic acid

<400> SEQUENCE: 134

Xaa Lys Cys Asn Thr Ala Thr Cys Ala Thr Gln Arg Leu Ala Asn Phe
1               5                   10                  15

Leu Xaa His Ser Ser Asn Asn Phe Gly Pro Ile Leu Pro Pro Thr Pro
            20                  25                  30

Val Gly Ser Asn Thr Tyr
        35

<210> SEQ ID NO 135
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (18)..(18)
<223> OTHER INFORMATION: 2-amino-2-methylpropanoic acid

<400> SEQUENCE: 135

Xaa Lys Cys Asn Thr Ala Thr Cys Ala Thr Gln Arg Leu Ala Asn Phe
1               5                   10                  15

Leu Xaa His Ser Ser Asn His Phe Gly Pro Ile Leu Pro Pro Thr Asn
            20                  25                  30

Val Gly Ser Asn Thr Tyr
        35

<210> SEQ ID NO 136
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (18)..(18)
<223> OTHER INFORMATION: 2-amino-2-methylpropanoic acid

<400> SEQUENCE: 136

Xaa Lys Cys Asn Thr Ala Thr Cys Ala Thr Gln Arg Leu Ala Asn Phe
1               5                   10                  15

Leu Xaa His Ser Ser Asn Asn Phe Gly Pro Ile Leu Pro Pro Thr Asn
            20                  25                  30

Val Gly Ser Asn Thr Pro
        35

<210> SEQ ID NO 137
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (18)..(18)
<223> OTHER INFORMATION: 2-amino-2-methylpropanoic acid

<400> SEQUENCE: 137

Xaa Lys Cys Asn Thr Ala Thr Cys Ala Thr Gln Arg Leu Ala Asn Phe
1               5                   10                  15

Leu Xaa His Ser Ser Arg Asn Phe Gly Pro Ile Leu Pro Pro Thr Asn
            20                  25                  30

Val Gly Ser Asn Thr Tyr
        35

<210> SEQ ID NO 138
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (18)..(18)
<223> OTHER INFORMATION: 2-amino-2-methylpropanoic acid

<400> SEQUENCE: 138

```
Xaa Lys Cys Asn Thr Ala Thr Cys Ala Thr Gln Arg Leu Ala Asn Phe
1               5                   10                  15

Leu Xaa His Ser Ser Pro Asn Phe Gly Pro Ile Leu Pro Pro Thr Glu
            20                  25                  30

Val Gly Ser Asn Thr Tyr
            35

<210> SEQ ID NO 139
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (18)..(18)
<223> OTHER INFORMATION: 2-amino-2-methylpropanoic acid

<400> SEQUENCE: 139

Xaa Lys Cys Asn Thr Ala Thr Cys Ala Thr Gln Arg Leu Ala Asn Phe
1               5                   10                  15

Leu Xaa His Ser Ser Pro Asn Phe Gly Pro Ile Leu Pro Pro Thr Asn
            20                  25                  30

Val Gly Ser Glu Thr Tyr
            35

<210> SEQ ID NO 140
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (18)..(18)
<223> OTHER INFORMATION: 2-amino-2-methylpropanoic acid

<400> SEQUENCE: 140

Xaa Lys Cys Asn Thr Ala Thr Cys Ala Thr Gln Arg Leu Ala Asn Phe
1               5                   10                  15

Leu Xaa His Ser Ser Asn Asn Phe Gly Pro Ile Leu Pro Pro Thr Glu
            20                  25                  30

Val Gly Ser Asn Thr Tyr
            35

<210> SEQ ID NO 141
<211> LENGTH: 38
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (18)..(18)
<223> OTHER INFORMATION: 2-amino-2-methylpropanoic acid

<400> SEQUENCE: 141

Xaa Lys Cys Asn Thr Ala Thr Cys Ala Thr Gln Arg Leu Ala Asn Phe
1               5                   10                  15

Leu Xaa His Ser Ser Asn Asn Phe Gly Pro Ile Leu Pro Pro Thr Asn
            20                  25                  30

Val Gly Ser Arg Thr Tyr
        35

<210> SEQ ID NO 142
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (18)..(18)
<223> OTHER INFORMATION: 2-amino-2-methylpropanoic acid

<400> SEQUENCE: 142

Xaa Lys Cys Asn Thr Ala Thr Cys Ala Thr Gln Arg Leu Ala Asn Phe
1               5                   10                  15

Leu Xaa His Ser Ser Asn Asn Phe Gly Pro Ile Leu Pro Pro Thr Asn
            20                  25                  30

Val Gly Ser Glu Thr Tyr
        35

<210> SEQ ID NO 143
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (5)..(10)
```

```
<223> OTHER INFORMATION: Disulphide bridge between Cys residues
<220> FEATURE:
<221> NAME/KEY: MOD_RES
<222> LOCATION: (20)..(20)
<223> OTHER INFORMATION: 2-amino-2-methylpropanoic acid

<400> SEQUENCE: 143

Xaa Gly Gly Lys Cys Asn Thr Ala Thr Cys Ala Thr Gln Arg Leu Ala
1               5                   10                  15

Asn Phe Leu Xaa His Ser Ser Asn Asn Phe Gly Pro Ile Leu Pro Pro
            20                  25                  30

Thr Asn Val Gly Ser Asn Thr Tyr
        35                  40

<210> SEQ ID NO 144
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid

<400> SEQUENCE: 144

Xaa Cys Asn Thr Ala Thr Cys Ala Thr Gln Arg Leu Ala His Phe Leu
1               5                   10                  15

Xaa His Ser Ser Asn Asn Phe Gly Pro Ile Leu Pro Pro Thr Asn Val
            20                  25                  30

Gly Ser Asn Thr Tyr
        35

<210> SEQ ID NO 145
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (18)..(18)
<223> OTHER INFORMATION: 2-amino-2-methylpropanoic acid

<400> SEQUENCE: 145

Xaa Lys Cys Asn Thr Ala Thr Cys Ala Thr Gln Arg Leu Ala Asn Phe
1               5                   10                  15

Leu Xaa His Ser Ser Asn Asn Phe Gly Pro Ile Leu Pro Pro Thr Asn
            20                  25                  30
```

Val Gly His Asn Thr Tyr
        35

<210> SEQ ID NO 146
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (18)..(18)
<223> OTHER INFORMATION: 2-amino-2-methylpropanoic acid

<400> SEQUENCE: 146

Xaa Lys Cys Asn Thr Ala Thr Cys Ala Thr Gln Arg Leu Ala Asn Phe
1               5                   10                  15

Leu Xaa His Ser Ser Asn Asn Phe Gly Pro Ile Leu Pro Pro Thr His
            20                  25                  30

Val Gly Ser Glu Thr Tyr
        35

<210> SEQ ID NO 147
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (18)..(18)
<223> OTHER INFORMATION: 2-amino-2-methylpropanoic acid

<400> SEQUENCE: 147

Xaa Lys Cys Asn Thr Ala Thr Cys Ala Thr Gln Arg Leu Ala Asn Phe
1               5                   10                  15

Leu Xaa His Ser Ser Asn His Phe Gly Pro Ile Leu Pro Pro Thr Asn
            20                  25                  30

Val Gly Ser Glu Thr Tyr
        35

<210> SEQ ID NO 148
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:

```
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (18)..(18)
<223> OTHER INFORMATION: 2-amino-2-methylpropanoic acid

<400> SEQUENCE: 148

Xaa Lys Cys Asn Thr Ala Thr Cys Ala Thr Gln Arg Leu Ala Asn Phe
1               5                   10                  15

Leu Xaa His Ser Ser Asn Asn Phe Gly Pro Ile Leu Pro Pro Thr Asn
            20                  25                  30

Val Gly Pro Asn Thr Tyr
        35

<210> SEQ ID NO 149
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid

<400> SEQUENCE: 149

Xaa Cys Asn Thr Ala Thr Cys Ala Thr Gln Arg Leu Ala Asn Phe Leu
1               5                   10                  15

Xaa His Ser Ser Asn Asn Phe Gly Pro Ile Leu Pro Pro Thr Asn Val
            20                  25                  30

Gly Ser Asn Thr Tyr
        35

<210> SEQ ID NO 150
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid
<220> FEATURE:
```

```
<221> NAME/KEY: MOD_RES
<222> LOCATION: (21)..(21)
<223> OTHER INFORMATION: 2,4-diaminobutanoic acid

<400> SEQUENCE: 150

Xaa Cys Asn Thr Ala Thr Cys Ala Thr Gln Arg Leu Ala Asn Phe Leu
1               5                   10                  15

Xaa His Ser Ser Xaa Asn Phe Gly Pro Ile Leu Pro Pro Thr Asn Val
            20                  25                  30

Gly Ser Asn Thr Tyr
            35

<210> SEQ ID NO 151
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid
<220> FEATURE:
<221> NAME/KEY: MOD_RES
<222> LOCATION: (27)..(27)
<223> OTHER INFORMATION: D-Leu

<400> SEQUENCE: 151

Xaa Cys Asn Thr Ala Thr Cys Ala Thr Gln Arg Leu Ala Asn Phe Leu
1               5                   10                  15

Xaa His Ser Ser Asn Asn Phe Gly Pro Ile Xaa Pro Pro Thr Asn Val
            20                  25                  30

Gly Ser Asn Thr Tyr
            35

<210> SEQ ID NO 152
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (18)..(18)
<223> OTHER INFORMATION: 2-amino-2-methylpropanoic acid

<400> SEQUENCE: 152

Xaa Lys Cys Asn Thr Ala Thr Cys Ala Thr Gln Arg Leu Ala Asn Phe
1               5                   10                  15
```

```
Leu Xaa His Ser Ser Asn Asn Phe Gly Pro Arg Leu Pro Pro Thr Asn
            20                  25                  30

Val Gly Ser Asn Thr Tyr
        35

<210> SEQ ID NO 153
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (18)..(18)
<223> OTHER INFORMATION: 2-amino-2-methylpropanoic acid

<400> SEQUENCE: 153

Xaa Lys Cys Asn Thr Ala Thr Cys Ala Thr Gln Arg Leu Ala Asn Phe
1               5                   10                  15

Leu Xaa His Ser Ser Lys Asn Phe Gly Pro Ile Leu Pro Pro Thr Asn
            20                  25                  30

Val Gly Ser Asn Thr Tyr
        35

<210> SEQ ID NO 154
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (18)..(18)
<223> OTHER INFORMATION: 2-amino-2-methylpropanoic acid

<400> SEQUENCE: 154

Xaa Lys Cys Asn Thr Ala Thr Cys Ala Thr Gln Arg Leu Ala Asn Phe
1               5                   10                  15

Leu Xaa His Ser Ser Gly Asn Phe Gly Pro Ile Leu Pro Pro Thr Asn
            20                  25                  30

Val Gly Ser Asn Thr Tyr
        35

<210> SEQ ID NO 155
<211> LENGTH: 37
<212> TYPE: PRT
<213> ORGANISM: Artificial Sequence
<220> FEATURE:
<223> OTHER INFORMATION: Description of Artificial Sequence: Synthetic
```

```
                           polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid

<400> SEQUENCE: 155

Xaa Cys Asn Thr Ala Thr Cys Ala Thr Gln Arg Leu Ala Asn Phe Leu
1               5                   10                  15

Xaa His Ser Ser Asn Asn Phe Gly Pro Ile Leu Pro Pro Thr Arg Val
            20                  25                  30

Gly Ser Asn Thr Tyr
        35

<210> SEQ ID NO 156
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to gamma-Glu-C18diacid
<220> FEATURE:
<221> NAME/KEY: SITE
<222> LOCATION: (3)..(8)
<223> OTHER INFORMATION: Disulphide bridge between Cys residues
<220> FEATURE:
<221> NAME/KEY: MOD_RES
<222> LOCATION: (15)..(15)
<223> OTHER INFORMATION: 2,4-diaminobutanoic acid
<220> FEATURE:
<221> NAME/KEY: MOD_RES
<222> LOCATION: (18)..(18)
<223> OTHER INFORMATION: 2-amino-2-methylpropanoic acid

<400> SEQUENCE: 156

Xaa Lys Cys Asn Thr Ala Thr Cys Ala Thr Gln Arg Leu Ala Xaa Phe
1               5                   10                  15

Leu Xaa His Ser Ser Asn Asn Phe Gly Pro Ile Leu Pro Pro Thr Glu
            20                  25                  30

Val Gly Ser Asn Thr Tyr
        35

<210> SEQ ID NO 157
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to C18diacid
<220> FEATURE:
<221> NAME/KEY: SITE
<222> LOCATION: (2)..(7)
```

```
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid
<220> FEATURE:
<221> NAME/KEY: MOD_RES
<222> LOCATION: (31)..(31)
<223> OTHER INFORMATION: 2-amino-2-methylpropanoic acid

<400> SEQUENCE: 157

Xaa Cys Asn Thr Ala Thr Cys Ala Thr Gln Arg Leu Ala Asn Phe Leu
1               5                   10                  15

Val His Ser Ser Xaa Asn Phe Gly Pro Ile Leu Pro Pro Thr Xaa Val
            20                  25                  30

Gly Ser Asn Thr Tyr
        35

<210> SEQ ID NO 158
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys, wherein the side chain of Lys is
      connected to C18diacid
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid
<220> FEATURE:
<221> NAME/KEY: MOD_RES
<222> LOCATION: (31)..(31)
<223> OTHER INFORMATION: 2-amino-2-methylpropanoic acid

<400> SEQUENCE: 158

Xaa Cys Asn Thr Ala Thr Cys Ala Thr Gln Arg Leu Ala Asn Phe Leu
1               5                   10                  15

Val His Ser Ser Xaa Asn Phe Gly Pro Ile Leu Pro Pro Thr Xaa Val
            20                  25                  30

Gly Ser Asn Thr Tyr
        35

<210> SEQ ID NO 159
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys (linker-lipid), or absent
<220> FEATURE:
<221> NAME/KEY: MOD_RES
<222> LOCATION: (2)..(2)
<223> OTHER INFORMATION: Gly or absent
<220> FEATURE:
<221> NAME/KEY: MOD_RES
<222> LOCATION: (3)..(3)
<223> OTHER INFORMATION: Gly or absent
<220> FEATURE:
```

```
<221> NAME/KEY: MOD_RES
<222> LOCATION: (4)..(4)
<223> OTHER INFORMATION: Gly, Lys (linker-lipid), or absent
<220> FEATURE:
<221> NAME/KEY: MOD_RES
<222> LOCATION: (5)..(5)
<223> OTHER INFORMATION: Lys, Lys (linker-lipid), or absent
<220> FEATURE:
<221> NAME/KEY: MOD_RES
<222> LOCATION: (8)..(8)
<223> OTHER INFORMATION: Thr, Ile, Ala
<220> FEATURE:
<221> NAME/KEY: MOD_RES
<222> LOCATION: (18)..(18)
<223> OTHER INFORMATION: Asn, His, Glu, 2,4-diaminobutanoic acid (Dab),
      alpha methyl amino acid
<220> FEATURE:
<221> NAME/KEY: MOD_RES
<222> LOCATION: (19)..(19)
<223> OTHER INFORMATION: Phe or Trp
<220> FEATURE:
<221> NAME/KEY: MOD_RES
<222> LOCATION: (20)..(20)
<223> OTHER INFORMATION: Leu or D-Leu
<220> FEATURE:
<221> NAME/KEY: MOD_RES
<222> LOCATION: (21)..(21)
<223> OTHER INFORMATION: Val, Ser, Glu, Arg, (2S,4R)-4-
      hydroxypyrrolidine-2-carboxylic acid (Hyp), Dab, alpha methyl
      amino acid
<220> FEATURE:
<221> NAME/KEY: MOD_RES
<222> LOCATION: (24)..(24)
<223> OTHER INFORMATION: Ser, Ile, Pro, alpha methyl amino acid
<220> FEATURE:
<221> NAME/KEY: MOD_RES
<222> LOCATION: (25)..(25)
<223> OTHER INFORMATION: Asn, Dab, His, Pro, Ser, Arg, Lys,
      Gly, Glu, Ala, Hyp , alpha methyl amino acid
<220> FEATURE:
<221> NAME/KEY: MOD_RES
<222> LOCATION: (26)..(26)
<223> OTHER INFORMATION: Asn, His, Hyp, Dab, alpha methyl amino acid
<220> FEATURE:
<221> NAME/KEY: MOD_RES
<222> LOCATION: (27)..(27)
<223> OTHER INFORMATION: Phe, Hyp, alpha methyl amino acid
<220> FEATURE:
<221> NAME/KEY: MOD_RES
<222> LOCATION: (28)..(28)
<223> OTHER INFORMATION: Gly, Pro, Hyp, alpha methyl amino acid
<220> FEATURE:
<221> NAME/KEY: MOD_RES
<222> LOCATION: (29)..(29)
<223> OTHER INFORMATION: Pro, Ala, Hyp, alpha methyl amino acid
<220> FEATURE:
<221> NAME/KEY: MOD_RES
<222> LOCATION: (30)..(30)
<223> OTHER INFORMATION: Ile, D-Ile, Arg, Hyp, alpha methyl amino acid
<220> FEATURE:
<221> NAME/KEY: MOD_RES
<222> LOCATION: (31)..(31)
<223> OTHER INFORMATION: Leu, D-Leu, Hyp, alpha methyl amino acid
<220> FEATURE:
<221> NAME/KEY: MOD_RES
<222> LOCATION: (32)..(32)
<223> OTHER INFORMATION: Pro, D-Pro, Ser, Hyp, alpha methyl amino acid
<220> FEATURE:
<221> NAME/KEY: MOD_RES
<222> LOCATION: (33)..(33)
<223> OTHER INFORMATION: Pro, Hyp, alpha methyl amino acid
<220> FEATURE:
<221> NAME/KEY: MOD_RES
<222> LOCATION: (35)..(35)
<223> OTHER INFORMATION: Asn, Glu, His, Arg, Pro, Dab,
      alpha methyl amino acid
<220> FEATURE:
<221> NAME/KEY: MOD_RES
<222> LOCATION: (36)..(36)
```

```
<223> OTHER INFORMATION: Val, Hyp, Dab, alpha methyl amino acid
<220> FEATURE:
<221> NAME/KEY: MOD_RES
<222> LOCATION: (37)..(37)
<223> OTHER INFORMATION: Gly, Pro, Hyp, alpha methyl amino acid
<220> FEATURE:
<221> NAME/KEY: MOD_RES
<222> LOCATION: (38)..(38)
<223> OTHER INFORMATION: Ser, Pro, His, Hyp, alpha methyl amino acid
<220> FEATURE:
<221> NAME/KEY: MOD_RES
<222> LOCATION: (39)..(39)
<223> OTHER INFORMATION: Asn, Pro, Arg, Glu, Dab, Hyp,
      alpha methyl amino acid
<220> FEATURE:
<221> NAME/KEY: MOD_RES
<222> LOCATION: (40)..(40)
<223> OTHER INFORMATION: Thr, Hyp, alpha methyl amino acid
<220> FEATURE:
<221> NAME/KEY: MOD_RES
<222> LOCATION: (41)..(41)
<223> OTHER INFORMATION: Tyr, Pro, Hyp, alpha methyl amino acid
<220> FEATURE:
<221> NAME/KEY: SITE
<222> LOCATION: (1)..(41)
<223> OTHER INFORMATION: Variant residues given in the sequence have no
      preference with respect to those in the annotations
      for variant positions

<400> SEQUENCE: 159

Xaa Xaa Xaa Xaa Xaa Cys Asn Xaa Ala Thr Cys Ala Thr Gln Arg Leu
1               5                   10                  15

Ala Xaa Xaa Xaa Xaa His Ser Xaa Xaa Xaa Xaa Xaa Xaa Xaa Xaa
            20                  25                  30

Xaa Thr Xaa Xaa Xaa Xaa Xaa Xaa Xaa
        35                  40

<210> SEQ ID NO 160
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys or absent
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (4)..(4)
<223> OTHER INFORMATION: Thr, Ile, or Ala
<220> FEATURE:
<221> NAME/KEY: MOD_RES
<222> LOCATION: (14)..(14)
<223> OTHER INFORMATION: Asn, Glu, or His
<220> FEATURE:
<221> NAME/KEY: MOD_RES
<222> LOCATION: (15)..(15)
<223> OTHER INFORMATION: Phe or Trp
<220> FEATURE:
<221> NAME/KEY: MOD_RES
<222> LOCATION: (17)..(17)
<223> OTHER INFORMATION: Val, Arg, Ser, Glu
<220> FEATURE:
<221> NAME/KEY: MOD_RES
<222> LOCATION: (20)..(20)
<223> OTHER INFORMATION: Ser, Pro, or Ile
<220> FEATURE:
<221> NAME/KEY: MOD_RES
<222> LOCATION: (21)..(21)
```

```
<223> OTHER INFORMATION: Asn, His, Ala, Glu, Gly, Lys, Pro, Arg, or Ser
<220> FEATURE:
<221> NAME/KEY: MOD_RES
<222> LOCATION: (22)..(22)
<223> OTHER INFORMATION: Asn or His
<220> FEATURE:
<221> NAME/KEY: MOD_RES
<222> LOCATION: (24)..(24)
<223> OTHER INFORMATION: Gly or Pro
<220> FEATURE:
<221> NAME/KEY: MOD_RES
<222> LOCATION: (25)..(25)
<223> OTHER INFORMATION: Pro or Ala
<220> FEATURE:
<221> NAME/KEY: MOD_RES
<222> LOCATION: (26)..(26)
<223> OTHER INFORMATION: Ile or Arg
<220> FEATURE:
<221> NAME/KEY: MOD_RES
<222> LOCATION: (28)..(28)
<223> OTHER INFORMATION: Pro or Ser
<220> FEATURE:
<221> NAME/KEY: MOD_RES
<222> LOCATION: (31)..(31)
<223> OTHER INFORMATION: Asn, His, Pro, Arg, or Glu
<220> FEATURE:
<221> NAME/KEY: MOD_RES
<222> LOCATION: (33)..(33)
<223> OTHER INFORMATION: Gly or Pro
<220> FEATURE:
<221> NAME/KEY: MOD_RES
<222> LOCATION: (34)..(34)
<223> OTHER INFORMATION: Ser, His, or Pro
<220> FEATURE:
<221> NAME/KEY: MOD_RES
<222> LOCATION: (35)..(35)
<223> OTHER INFORMATION: Asn, Glu, Arg, Pro
<220> FEATURE:
<221> NAME/KEY: MOD_RES
<222> LOCATION: (37)..(37)
<223> OTHER INFORMATION: Tyr or Pro

<400> SEQUENCE: 160

Xaa Cys Asn Xaa Ala Thr Cys Ala Thr Gln Arg Leu Ala Xaa Xaa Leu
1               5                   10                  15

Xaa His Ser Xaa Xaa Xaa Phe Xaa Xaa Xaa Leu Xaa Pro Thr Xaa Val
            20                  25                  30

Xaa Xaa Xaa Thr Xaa
        35

<210> SEQ ID NO 161
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(albumin binding moiety) or absent
<220> FEATURE:
<221> NAME/KEY: MOD_RES
<222> LOCATION: (2)..(2)
<223> OTHER INFORMATION: Gly or absent
<220> FEATURE:
<221> NAME/KEY: MOD_RES
<222> LOCATION: (3)..(3)
<223> OTHER INFORMATION: Gly or absent
<220> FEATURE:
<221> NAME/KEY: MOD_RES
<222> LOCATION: (4)..(4)
<223> OTHER INFORMATION: Gly, Lys(albumin binding moiety) or absent
<220> FEATURE:
<221> NAME/KEY: MOD_RES
```

```
<222> LOCATION: (5)..(5)
<223> OTHER INFORMATION: Lys, Lys(albumin binding moiety) or absent
<220> FEATURE:
<221> NAME/KEY: MOD_RES
<222> LOCATION: (8)..(8)
<223> OTHER INFORMATION: Thr, Ile or Ala
<220> FEATURE:
<221> NAME/KEY: MOD_RES
<222> LOCATION: (18)..(18)
<223> OTHER INFORMATION: Asn, His, Glu, 2,4-diaminobutanoic acid (Dab),
      or an alpha methyl amino acid
<220> FEATURE:
<221> NAME/KEY: MOD_RES
<222> LOCATION: (19)..(19)
<223> OTHER INFORMATION: Phe or Trp
<220> FEATURE:
<221> NAME/KEY: MOD_RES
<222> LOCATION: (20)..(20)
<223> OTHER INFORMATION: Leu or D-Leu (dL)
<220> FEATURE:
<221> NAME/KEY: MOD_RES
<222> LOCATION: (21)..(21)
<223> OTHER INFORMATION: Val, Ser, Glu, Arg, (2S,4R)-4-
      hydroxypyrrolidine-2-carboxylic acid (Hyp), 2,4-diaminobutanoic
      acid (Dab) or an alpha methyl amino acid
<220> FEATURE:
<221> NAME/KEY: MOD_RES
<222> LOCATION: (24)..(24)
<223> OTHER INFORMATION: alpha methylSer
<220> FEATURE:
<221> NAME/KEY: MOD_RES
<222> LOCATION: (25)..(25)
<223> OTHER INFORMATION: Asn, 2,4-diaminobutanoic acid (Dab), His, Pro,
      Ser, Arg, Lys, Gly or Glu, Ala, Hyp  or an alpha methyl amino acid
<220> FEATURE:
<221> NAME/KEY: MOD_RES
<222> LOCATION: (26)..(26)
<223> OTHER INFORMATION: Asn, His, Hyp, 2,4-diaminobutanoic acid (Dab)
      or an alpha methyl amino acid
<220> FEATURE:
<221> NAME/KEY: MOD_RES
<222> LOCATION: (27)..(27)
<223> OTHER INFORMATION: Phe, Hyp or an alpha methyl amino acid
<220> FEATURE:
<221> NAME/KEY: MOD_RES
<222> LOCATION: (28)..(28)
<223> OTHER INFORMATION: Gly, Pro, Hyp or an alpha methyl amino acid
<220> FEATURE:
<221> NAME/KEY: MOD_RES
<222> LOCATION: (29)..(29)
<223> OTHER INFORMATION: Pro, Ala, Hyp or an alpha methyl amino acid
<220> FEATURE:
<221> NAME/KEY: MOD_RES
<222> LOCATION: (30)..(30)
<223> OTHER INFORMATION: Ile, D-Ile (dI), Arg, Hyp or an alpha methyl
      amino acid
<220> FEATURE:
<221> NAME/KEY: MOD_RES
<222> LOCATION: (31)..(31)
<223> OTHER INFORMATION: Leu, dL, Hyp or an alpha methyl amino acid
<220> FEATURE:
<221> NAME/KEY: MOD_RES
<222> LOCATION: (32)..(32)
<223> OTHER INFORMATION: Pro, D-Pro (dP), Ser, Hyp or an alpha methyl
      amino acid
<220> FEATURE:
<221> NAME/KEY: MOD_RES
<222> LOCATION: (33)..(33)
<223> OTHER INFORMATION: Pro, Hyp or an alpha methyl amino acid
<220> FEATURE:
<221> NAME/KEY: MOD_RES
<222> LOCATION: (35)..(35)
<223> OTHER INFORMATION: Asn, Glu, His, Arg, Pro, 2,4-diaminobutanoic
      acid (Dab) or an alpha methyl amino acid
<220> FEATURE:
<221> NAME/KEY: MOD_RES
<222> LOCATION: (36)..(36)
<223> OTHER INFORMATION: Val, Hyp, 2,4-diaminobutanoic acid (Dab) or an
      alpha methyl amino acid
```

-continued

```
<220> FEATURE:
<221> NAME/KEY: MOD_RES
<222> LOCATION: (37)..(37)
<223> OTHER INFORMATION: Gly, Pro, Hyp or an alpha methyl amino acid
<220> FEATURE:
<221> NAME/KEY: MOD_RES
<222> LOCATION: (38)..(38)
<223> OTHER INFORMATION: Ser, Pro, His, Hyp or an alpha methyl amino
      acid
<220> FEATURE:
<221> NAME/KEY: MOD_RES
<222> LOCATION: (39)..(39)
<223> OTHER INFORMATION: Asn, Pro, Arg, Glu, 2,4-diaminobutanoic acid
      (Dab), Hyp or an alpha methyl amino acid
<220> FEATURE:
<221> NAME/KEY: MOD_RES
<222> LOCATION: (40)..(40)
<223> OTHER INFORMATION: Thr, Hyp or an alpha methyl amino acid
<220> FEATURE:
<221> NAME/KEY: MOD_RES
<222> LOCATION: (41)..(41)
<223> OTHER INFORMATION: Tyr, Pro, Hyp or an alpha methyl amino acid

<400> SEQUENCE: 161

Xaa Xaa Xaa Xaa Xaa Cys Asn Xaa Ala Thr Cys Ala Thr Gln Arg Leu
1               5                   10                  15

Ala Xaa Xaa Xaa Xaa His Ser Xaa Xaa Xaa Xaa Xaa Xaa Xaa Xaa Xaa
            20                  25                  30

Xaa Thr Xaa Xaa Xaa Xaa Xaa Xaa Xaa
        35                  40

<210> SEQ ID NO 162
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(albumin binding moiety) or absent
<220> FEATURE:
<221> NAME/KEY: MOD_RES
<222> LOCATION: (2)..(2)
<223> OTHER INFORMATION: Gly or absent
<220> FEATURE:
<221> NAME/KEY: MOD_RES
<222> LOCATION: (3)..(3)
<223> OTHER INFORMATION: Gly or absent
<220> FEATURE:
<221> NAME/KEY: MOD_RES
<222> LOCATION: (4)..(4)
<223> OTHER INFORMATION: Gly, Lys(albumin binding moiety) or absent
<220> FEATURE:
<221> NAME/KEY: MOD_RES
<222> LOCATION: (17)..(17)
<223> OTHER INFORMATION: Asn, His, Glu, 2,4-diaminobutanoic acid (Dab),
      or an alpha methyl amino acid
<220> FEATURE:
<221> NAME/KEY: MOD_RES
<222> LOCATION: (18)..(18)
<223> OTHER INFORMATION: Phe or Trp
<220> FEATURE:
<221> NAME/KEY: MOD_RES
<222> LOCATION: (19)..(19)
<223> OTHER INFORMATION: Leu or D-Leu (dL)
<220> FEATURE:
<221> NAME/KEY: MOD_RES
<222> LOCATION: (20)..(20)
<223> OTHER INFORMATION: Val, Ser, Glu, Arg, (2S,4R)-4-
      hydroxypyrrolidine-2-carboxylic acid (Hyp), Dab or an alpha methyl
      amino acid
<220> FEATURE:
<221> NAME/KEY: MOD_RES
```

```
<222> LOCATION: (23)..(23)
<223> OTHER INFORMATION: Ser, Ile, Pro or an alpha methyl amino acid
<220> FEATURE:
<221> NAME/KEY: MOD_RES
<222> LOCATION: (24)..(24)
<223> OTHER INFORMATION: Dab
<220> FEATURE:
<221> NAME/KEY: MOD_RES
<222> LOCATION: (25)..(25)
<223> OTHER INFORMATION: Asn, His, Hyp, Dab or an alpha methyl amino
      acid
<220> FEATURE:
<221> NAME/KEY: MOD_RES
<222> LOCATION: (26)..(26)
<223> OTHER INFORMATION: Phe, Hyp or an alpha methyl amino acid
<220> FEATURE:
<221> NAME/KEY: MOD_RES
<222> LOCATION: (27)..(27)
<223> OTHER INFORMATION: Gly, Pro, Hyp or an alpha methyl amino acid
<220> FEATURE:
<221> NAME/KEY: MOD_RES
<222> LOCATION: (28)..(28)
<223> OTHER INFORMATION: Pro, Ala, Hyp or an alpha methyl amino acid
<220> FEATURE:
<221> NAME/KEY: MOD_RES
<222> LOCATION: (29)..(29)
<223> OTHER INFORMATION: Ile, D-Ile (dI), Arg, Hyp or an alpha methyl
      amino acid
<220> FEATURE:
<221> NAME/KEY: MOD_RES
<222> LOCATION: (30)..(30)
<223> OTHER INFORMATION: Leu, dL, Hyp or an alpha methyl amino acid
<220> FEATURE:
<221> NAME/KEY: MOD_RES
<222> LOCATION: (31)..(31)
<223> OTHER INFORMATION: Pro, D-Pro (dP), Ser, Hyp or an alpha methyl
      amino acid
<220> FEATURE:
<221> NAME/KEY: MOD_RES
<222> LOCATION: (32)..(32)
<223> OTHER INFORMATION: Pro, Hyp or an alpha methyl amino acid
<220> FEATURE:
<221> NAME/KEY: MOD_RES
<222> LOCATION: (34)..(34)
<223> OTHER INFORMATION: Asn, Glu, His, Arg, Pro, Dab or an alpha methyl
      amino acid
<220> FEATURE:
<221> NAME/KEY: MOD_RES
<222> LOCATION: (35)..(35)
<223> OTHER INFORMATION: Val, Hyp, Dab or an alpha methyl amino acid
<220> FEATURE:
<221> NAME/KEY: MOD_RES
<222> LOCATION: (36)..(36)
<223> OTHER INFORMATION: Gly, Pro, Hyp or an alpha methyl amino acid
<220> FEATURE:
<221> NAME/KEY: MOD_RES
<222> LOCATION: (37)..(37)
<223> OTHER INFORMATION: Ser, Pro, His, Hyp or an alpha methyl amino
      acid
<220> FEATURE:
<221> NAME/KEY: MOD_RES
<222> LOCATION: (39)..(39)
<223> OTHER INFORMATION: Thr, Hyp or an alpha methyl amino acid
<220> FEATURE:
<221> NAME/KEY: MOD_RES
<222> LOCATION: (40)..(40)
<223> OTHER INFORMATION: Tyr, Pro, Hyp or an alpha methyl amino acid

<400> SEQUENCE: 162

Xaa Xaa Xaa Xaa Cys Asn Ile Ala Thr Cys Ala Thr Gln Arg Leu Ala
1               5                   10                  15

Xaa Xaa Xaa Xaa His Ser Xaa Xaa Xaa Xaa Xaa Xaa Xaa Xaa Xaa
            20                  25                  30

Thr Xaa Xaa Xaa Xaa Arg Xaa Xaa
        35                  40
```

```
<210> SEQ ID NO 163
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(albumin binding moiety) or absent
<220> FEATURE:
<221> NAME/KEY: MOD_RES
<222> LOCATION: (2)..(2)
<223> OTHER INFORMATION: Gly or absent
<220> FEATURE:
<221> NAME/KEY: MOD_RES
<222> LOCATION: (3)..(3)
<223> OTHER INFORMATION: Gly or absent
<220> FEATURE:
<221> NAME/KEY: MOD_RES
<222> LOCATION: (4)..(4)
<223> OTHER INFORMATION: Gly, Lys(albumin binding moiety) or absent
<220> FEATURE:
<221> NAME/KEY: MOD_RES
<222> LOCATION: (7)..(7)
<223> OTHER INFORMATION: Thr, Ile or Ala
<220> FEATURE:
<221> NAME/KEY: MOD_RES
<222> LOCATION: (17)..(17)
<223> OTHER INFORMATION: Asn, His, Glu, 2,4-diaminobutanoic acid (Dab),
      or an alpha methyl amino acid
<220> FEATURE:
<221> NAME/KEY: MOD_RES
<222> LOCATION: (18)..(18)
<223> OTHER INFORMATION: Phe or Trp
<220> FEATURE:
<221> NAME/KEY: MOD_RES
<222> LOCATION: (19)..(19)
<223> OTHER INFORMATION: Leu or D-Leu (dL)
<220> FEATURE:
<221> NAME/KEY: MOD_RES
<222> LOCATION: (20)..(20)
<223> OTHER INFORMATION: Val, Ser, Glu, Arg, (2S,4R)-4-
      hydroxypyrrolidine-2-carboxylic acid (Hyp), Dab or an alpha methyl
      amino acid
<220> FEATURE:
<221> NAME/KEY: MOD_RES
<222> LOCATION: (23)..(23)
<223> OTHER INFORMATION: Ser, Ile, Pro or an alpha methyl amino acid
<220> FEATURE:
<221> NAME/KEY: MOD_RES
<222> LOCATION: (24)..(24)
<223> OTHER INFORMATION: Aib
<220> FEATURE:
<221> NAME/KEY: MOD_RES
<222> LOCATION: (25)..(25)
<223> OTHER INFORMATION: Asn, His, Hyp, Dab or an alpha methyl amino
      acid
<220> FEATURE:
<221> NAME/KEY: MOD_RES
<222> LOCATION: (26)..(26)
<223> OTHER INFORMATION: Phe, Hyp or an alpha methyl amino acid
<220> FEATURE:
<221> NAME/KEY: MOD_RES
<222> LOCATION: (27)..(27)
<223> OTHER INFORMATION: Gly, Pro, Hyp or an alpha methyl amino acid
<220> FEATURE:
<221> NAME/KEY: MOD_RES
<222> LOCATION: (28)..(28)
<223> OTHER INFORMATION: Pro, Ala, Hyp or an alpha methyl amino acid
<220> FEATURE:
<221> NAME/KEY: MOD_RES
<222> LOCATION: (29)..(29)
<223> OTHER INFORMATION: Ile, D-Ile (dI), Arg, Hyp or an alpha methyl
      amino acid
<220> FEATURE:
<221> NAME/KEY: MOD_RES
```

```
<222> LOCATION: (30)..(30)
<223> OTHER INFORMATION: Leu, dL, Hyp or an alpha methyl amino acid
<220> FEATURE:
<221> NAME/KEY: MOD_RES
<222> LOCATION: (31)..(31)
<223> OTHER INFORMATION: Pro, D-Pro (dP), Ser, Hyp or an alpha methyl
      amino acid
<220> FEATURE:
<221> NAME/KEY: MOD_RES
<222> LOCATION: (32)..(32)
<223> OTHER INFORMATION: Pro, Hyp or an alpha methyl amino acid
<220> FEATURE:
<221> NAME/KEY: MOD_RES
<222> LOCATION: (35)..(35)
<223> OTHER INFORMATION: Val, Hyp, Dab or an alpha methyl amino acid
<220> FEATURE:
<221> NAME/KEY: MOD_RES
<222> LOCATION: (36)..(36)
<223> OTHER INFORMATION: Gly, Pro, Hyp or an alpha methyl amino acid
<220> FEATURE:
<221> NAME/KEY: MOD_RES
<222> LOCATION: (37)..(37)
<223> OTHER INFORMATION: Ser, Pro, His, Hyp or an alpha methyl amino
      acid
<220> FEATURE:
<221> NAME/KEY: MOD_RES
<222> LOCATION: (38)..(38)
<223> OTHER INFORMATION: Asn, Pro, Arg, Glu, Dab, Hyp or an alpha methyl
      amino acid
<220> FEATURE:
<221> NAME/KEY: MOD_RES
<222> LOCATION: (39)..(39)
<223> OTHER INFORMATION: Thr, Hyp or an alpha methyl amino acid
<220> FEATURE:
<221> NAME/KEY: MOD_RES
<222> LOCATION: (40)..(40)
<223> OTHER INFORMATION: Tyr, Pro, Hyp or an alpha methyl amino acid

<400> SEQUENCE: 163

Xaa Xaa Xaa Xaa Cys Asn Xaa Ala Thr Cys Ala Thr Gln Arg Leu Ala
1               5                   10                  15

Xaa Xaa Xaa Xaa His Ser Xaa Xaa Xaa Xaa Xaa Xaa Xaa Xaa Xaa
            20                  25                  30

Thr Arg Xaa Xaa Xaa Xaa Xaa Xaa
        35                  40

<210> SEQ ID NO 164
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(albumin binding moiety) or absent
<220> FEATURE:
<221> NAME/KEY: MOD_RES
<222> LOCATION: (2)..(2)
<223> OTHER INFORMATION: Gly or absent
<220> FEATURE:
<221> NAME/KEY: MOD_RES
<222> LOCATION: (3)..(3)
<223> OTHER INFORMATION: Gly or absent
<220> FEATURE:
<221> NAME/KEY: MOD_RES
<222> LOCATION: (4)..(4)
<223> OTHER INFORMATION: Gly, Lys(albumin binding moiety) or absent
<220> FEATURE:
<221> NAME/KEY: MOD_RES
<222> LOCATION: (5)..(5)
<223> OTHER INFORMATION: Lys, Lys(albumin binding moiety) or absent
<220> FEATURE:
<221> NAME/KEY: MOD_RES
```

```
<222> LOCATION: (8)..(8)
<223> OTHER INFORMATION: Thr, Ile or Ala
<220> FEATURE:
<221> NAME/KEY: MOD_RES
<222> LOCATION: (18)..(18)
<223> OTHER INFORMATION: 2,4-diaminobutanoic acid (Dab)
<220> FEATURE:
<221> NAME/KEY: MOD_RES
<222> LOCATION: (19)..(19)
<223> OTHER INFORMATION: Phe or Trp
<220> FEATURE:
<221> NAME/KEY: MOD_RES
<222> LOCATION: (20)..(20)
<223> OTHER INFORMATION: Leu or D-Leu (dL)
<220> FEATURE:
<221> NAME/KEY: MOD_RES
<222> LOCATION: (21)..(21)
<223> OTHER INFORMATION: Val, Ser, Glu, Arg, (2S,4R)-4-
     hydroxypyrrolidine-2-carboxylic acid (Hyp), 2,4-diaminobutanoic
     acid (Dab) or an alpha methyl amino acid
<220> FEATURE:
<221> NAME/KEY: MOD_RES
<222> LOCATION: (24)..(24)
<223> OTHER INFORMATION: Ser, Ile, Pro or an alpha methyl amino acid
<220> FEATURE:
<221> NAME/KEY: MOD_RES
<222> LOCATION: (25)..(25)
<223> OTHER INFORMATION: Asn, 2,4-diaminobutanoic acid (Dab), His, Pro,
     Ser, Arg, Lys, Gly or Glu, Ala, Hyp  or an alpha methyl amino acid
<220> FEATURE:
<221> NAME/KEY: MOD_RES
<222> LOCATION: (26)..(26)
<223> OTHER INFORMATION: Asn, His, Hyp, 2,4-diaminobutanoic acid (Dab)
     or an alpha methyl amino acid
<220> FEATURE:
<221> NAME/KEY: MOD_RES
<222> LOCATION: (27)..(27)
<223> OTHER INFORMATION: Phe, Hyp or an alpha methyl amino acid
<220> FEATURE:
<221> NAME/KEY: MOD_RES
<222> LOCATION: (28)..(28)
<223> OTHER INFORMATION: Gly, Pro, Hyp or an alpha methyl amino acid
<220> FEATURE:
<221> NAME/KEY: MOD_RES
<222> LOCATION: (29)..(29)
<223> OTHER INFORMATION: Pro, Ala, Hyp or an alpha methyl amino acid
<220> FEATURE:
<221> NAME/KEY: MOD_RES
<222> LOCATION: (30)..(30)
<223> OTHER INFORMATION: Ile, D-Ile (dI), Arg, Hyp or an alpha methyl
     amino acid
<220> FEATURE:
<221> NAME/KEY: MOD_RES
<222> LOCATION: (31)..(31)
<223> OTHER INFORMATION: Leu, dL, Hyp or an alpha methyl amino acid
<220> FEATURE:
<221> NAME/KEY: MOD_RES
<222> LOCATION: (32)..(32)
<223> OTHER INFORMATION: Pro, D-Pro (dP), Ser, Hyp or an alpha methyl
     amino acid
<220> FEATURE:
<221> NAME/KEY: MOD_RES
<222> LOCATION: (33)..(33)
<223> OTHER INFORMATION: Pro, Hyp or an alpha methyl amino acid
<220> FEATURE:
<221> NAME/KEY: MOD_RES
<222> LOCATION: (35)..(35)
<223> OTHER INFORMATION: Asn, Glu, His, Arg, Pro, 2,4-diaminobutanoic
     acid (Dab) or an alpha methyl amino acid
<220> FEATURE:
<221> NAME/KEY: MOD_RES
<222> LOCATION: (36)..(36)
<223> OTHER INFORMATION: Val, Hyp, 2,4-diaminobutanoic acid (Dab) or an
     alpha methyl amino acid
<220> FEATURE:
<221> NAME/KEY: MOD_RES
<222> LOCATION: (37)..(37)
<223> OTHER INFORMATION: Gly, Pro, Hyp or an alpha methyl amino acid
<220> FEATURE:
```

```
<221> NAME/KEY: MOD_RES
<222> LOCATION: (38)..(38)
<223> OTHER INFORMATION: Ser, Pro, His, Hyp or an alpha methyl amino
      acid
<220> FEATURE:
<221> NAME/KEY: MOD_RES
<222> LOCATION: (39)..(39)
<223> OTHER INFORMATION: Asn, Pro, Arg, Glu, 2,4-diaminobutanoic acid
      (Dab), Hyp or an alpha methyl amino acid
<220> FEATURE:
<221> NAME/KEY: MOD_RES
<222> LOCATION: (40)..(40)
<223> OTHER INFORMATION: Thr, Hyp or an alpha methyl amino acid
<220> FEATURE:
<221> NAME/KEY: MOD_RES
<222> LOCATION: (41)..(41)
<223> OTHER INFORMATION: Tyr, Pro, Hyp or an alpha methyl amino acid

<400> SEQUENCE: 164

Xaa Xaa Xaa Xaa Xaa Cys Asn Xaa Ala Thr Cys Ala Thr Gln Arg Leu
1               5                   10                  15

Ala Xaa Xaa Xaa Xaa His Ser Xaa Xaa Xaa Xaa Xaa Xaa Xaa Xaa
            20                  25                  30

Xaa Thr Xaa Xaa Xaa Xaa Xaa Xaa Xaa
        35                  40

<210> SEQ ID NO 165
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(albumin binding moiety) or absent
<220> FEATURE:
<221> NAME/KEY: MOD_RES
<222> LOCATION: (2)..(2)
<223> OTHER INFORMATION: Gly or absent
<220> FEATURE:
<221> NAME/KEY: MOD_RES
<222> LOCATION: (3)..(3)
<223> OTHER INFORMATION: Gly or absent
<220> FEATURE:
<221> NAME/KEY: MOD_RES
<222> LOCATION: (4)..(4)
<223> OTHER INFORMATION: Gly, Lys(albumin binding moiety) or absent
<220> FEATURE:
<221> NAME/KEY: MOD_RES
<222> LOCATION: (5)..(5)
<223> OTHER INFORMATION: Lys, Lys(albumin binding moiety) or absent
<220> FEATURE:
<221> NAME/KEY: MOD_RES
<222> LOCATION: (8)..(8)
<223> OTHER INFORMATION: Thr, Ile or Ala
<220> FEATURE:
<221> NAME/KEY: MOD_RES
<222> LOCATION: (18)..(18)
<223> OTHER INFORMATION: Asn, His, Glu, 2,4-diaminobutanoic acid (Dab),
      or an alpha methyl amino acid
<220> FEATURE:
<221> NAME/KEY: MOD_RES
<222> LOCATION: (19)..(19)
<223> OTHER INFORMATION: Phe or Trp
<220> FEATURE:
<221> NAME/KEY: MOD_RES
<222> LOCATION: (20)..(20)
<223> OTHER INFORMATION: dL
<220> FEATURE:
<221> NAME/KEY: MOD_RES
<222> LOCATION: (21)..(21)
<223> OTHER INFORMATION: Val, Ser, Glu, Arg, (2S,4R)-4-
      hydroxypyrrolidine-2-carboxylic acid (Hyp), 2,4-diaminobutanoic
```

```
      acid (Dab) or an alpha methyl amino acid
<220> FEATURE:
<221> NAME/KEY: MOD_RES
<222> LOCATION: (24)..(24)
<223> OTHER INFORMATION: Ser, Ile, Pro or an alpha methyl amino acid
<220> FEATURE:
<221> NAME/KEY: MOD_RES
<222> LOCATION: (25)..(25)
<223> OTHER INFORMATION: Asn, 2,4-diaminobutanoic acid (Dab), His, Pro,
      Ser, Arg, Lys, Gly or Glu, Ala, Hyp or an alpha methyl amino acid
<220> FEATURE:
<221> NAME/KEY: MOD_RES
<222> LOCATION: (26)..(26)
<223> OTHER INFORMATION: Asn, His, Hyp, 2,4-diaminobutanoic acid (Dab)
      or an alpha methyl amino acid
<220> FEATURE:
<221> NAME/KEY: MOD_RES
<222> LOCATION: (27)..(27)
<223> OTHER INFORMATION: Phe, Hyp or an alpha methyl amino acid
<220> FEATURE:
<221> NAME/KEY: MOD_RES
<222> LOCATION: (28)..(28)
<223> OTHER INFORMATION: Gly, Pro, Hyp or an alpha methyl amino acid
<220> FEATURE:
<221> NAME/KEY: MOD_RES
<222> LOCATION: (29)..(29)
<223> OTHER INFORMATION: Pro, Ala, Hyp or an alpha methyl amino acid
<220> FEATURE:
<221> NAME/KEY: MOD_RES
<222> LOCATION: (30)..(30)
<223> OTHER INFORMATION: Ile, D-Ile (dI), Arg, Hyp or an alpha methyl
      amino acid
<220> FEATURE:
<221> NAME/KEY: MOD_RES
<222> LOCATION: (31)..(31)
<223> OTHER INFORMATION: Leu, dL, Hyp or an alpha methyl amino acid
<220> FEATURE:
<221> NAME/KEY: MOD_RES
<222> LOCATION: (32)..(32)
<223> OTHER INFORMATION: Pro, D-Pro (dP), Ser, Hyp or an alpha methyl
      amino acid
<220> FEATURE:
<221> NAME/KEY: MOD_RES
<222> LOCATION: (33)..(33)
<223> OTHER INFORMATION: Pro, Hyp or an alpha methyl amino acid
<220> FEATURE:
<221> NAME/KEY: MOD_RES
<222> LOCATION: (35)..(35)
<223> OTHER INFORMATION: Asn, Glu, His, Arg, Pro, 2,4-diaminobutanoic
      acid (Dab) or an alpha methyl amino acid
<220> FEATURE:
<221> NAME/KEY: MOD_RES
<222> LOCATION: (36)..(36)
<223> OTHER INFORMATION: Val, Hyp, 2,4-diaminobutanoic acid (Dab) or an
      alpha methyl amino acid
<220> FEATURE:
<221> NAME/KEY: MOD_RES
<222> LOCATION: (37)..(37)
<223> OTHER INFORMATION: Gly, Pro, Hyp or an alpha methyl amino acid
<220> FEATURE:
<221> NAME/KEY: MOD_RES
<222> LOCATION: (38)..(38)
<223> OTHER INFORMATION: Ser, Pro, His, Hyp or an alpha methyl amino
      acid
<220> FEATURE:
<221> NAME/KEY: MOD_RES
<222> LOCATION: (39)..(39)
<223> OTHER INFORMATION: Asn, Pro, Arg, Glu, 2,4-diaminobutanoic acid
      (Dab), Hyp or an alpha methyl amino acid
<220> FEATURE:
<221> NAME/KEY: MOD_RES
<222> LOCATION: (40)..(40)
<223> OTHER INFORMATION: Thr, Hyp or an alpha methyl amino acid
<220> FEATURE:
<221> NAME/KEY: MOD_RES
<222> LOCATION: (41)..(41)
<223> OTHER INFORMATION: Tyr, Pro, Hyp or an alpha methyl amino acid

<400> SEQUENCE: 165
```

```
Xaa Xaa Xaa Xaa Xaa Cys Asn Xaa Ala Thr Cys Ala Thr Gln Arg Leu
1               5                  10                  15

Ala Xaa Xaa Leu Xaa His Ser Xaa Xaa Xaa Xaa Xaa Xaa Xaa
            20              25              30

Xaa Thr Xaa Xaa Xaa Xaa Xaa Xaa Xaa
    35                  40
```

```
<210> SEQ ID NO 166
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(albumin binding moiety) or absent
<220> FEATURE:
<221> NAME/KEY: MOD_RES
<222> LOCATION: (2)..(2)
<223> OTHER INFORMATION: Gly or absent
<220> FEATURE:
<221> NAME/KEY: MOD_RES
<222> LOCATION: (3)..(3)
<223> OTHER INFORMATION: Gly or absent
<220> FEATURE:
<221> NAME/KEY: MOD_RES
<222> LOCATION: (4)..(4)
<223> OTHER INFORMATION: Gly, Lys(albumin binding moiety) or absent
<220> FEATURE:
<221> NAME/KEY: MOD_RES
<222> LOCATION: (5)..(5)
<223> OTHER INFORMATION: Lys, Lys(albumin binding moiety) or absent
<220> FEATURE:
<221> NAME/KEY: MOD_RES
<222> LOCATION: (8)..(8)
<223> OTHER INFORMATION: Thr, Ile or Ala
<220> FEATURE:
<221> NAME/KEY: MOD_RES
<222> LOCATION: (18)..(18)
<223> OTHER INFORMATION: Asn, His, Glu, 2,4-diaminobutanoic acid (Dab),
      or an alpha methyl amino acid
<220> FEATURE:
<221> NAME/KEY: MOD_RES
<222> LOCATION: (19)..(19)
<223> OTHER INFORMATION: Phe or Trp
<220> FEATURE:
<221> NAME/KEY: MOD_RES
<222> LOCATION: (20)..(20)
<223> OTHER INFORMATION: Leu or D-Leu (dL)
<220> FEATURE:
<221> NAME/KEY: MOD_RES
<222> LOCATION: (21)..(21)
<223> OTHER INFORMATION: an alpha methyl amino acid
<220> FEATURE:
<221> NAME/KEY: MOD_RES
<222> LOCATION: (24)..(24)
<223> OTHER INFORMATION: Ser, Ile, Pro or an alpha methyl amino acid
<220> FEATURE:
<221> NAME/KEY: MOD_RES
<222> LOCATION: (25)..(25)
<223> OTHER INFORMATION: Asn, 2,4-diaminobutanoic acid (Dab), His, Pro,
      Ser, Arg, Lys, Gly or Glu, Ala, Hyp or an alpha methyl amino acid
<220> FEATURE:
<221> NAME/KEY: MOD_RES
<222> LOCATION: (26)..(26)
<223> OTHER INFORMATION: Asn, His, Hyp, 2,4-diaminobutanoic acid (Dab)
      or an alpha methyl amino acid
<220> FEATURE:
<221> NAME/KEY: MOD_RES
<222> LOCATION: (27)..(27)
<223> OTHER INFORMATION: Phe, Hyp or an alpha methyl amino acid
<220> FEATURE:
<221> NAME/KEY: MOD_RES
```

```
<222> LOCATION: (28)..(28)
<223> OTHER INFORMATION: Gly, Pro, Hyp or an alpha methyl amino acid
<220> FEATURE:
<221> NAME/KEY: MOD_RES
<222> LOCATION: (29)..(29)
<223> OTHER INFORMATION: Pro, Ala, Hyp or an alpha methyl amino acid
<220> FEATURE:
<221> NAME/KEY: MOD_RES
<222> LOCATION: (30)..(30)
<223> OTHER INFORMATION: Ile, D-Ile (dI), Arg, Hyp or an alpha methyl
      amino acid
<220> FEATURE:
<221> NAME/KEY: MOD_RES
<222> LOCATION: (31)..(31)
<223> OTHER INFORMATION: Leu, dL, Hyp or an alpha methyl amino acid
<220> FEATURE:
<221> NAME/KEY: MOD_RES
<222> LOCATION: (32)..(32)
<223> OTHER INFORMATION: Pro, D-Pro (dP), Ser, Hyp or an alpha methyl
      amino acid
<220> FEATURE:
<221> NAME/KEY: MOD_RES
<222> LOCATION: (33)..(33)
<223> OTHER INFORMATION: Pro, Hyp or an alpha methyl amino acid
<220> FEATURE:
<221> NAME/KEY: MOD_RES
<222> LOCATION: (35)..(35)
<223> OTHER INFORMATION: Asn, Glu, His, Arg, Pro, 2,4-diaminobutanoic
      acid (Dab) or an alpha methyl amino acid
<220> FEATURE:
<221> NAME/KEY: MOD_RES
<222> LOCATION: (36)..(36)
<223> OTHER INFORMATION: Val, Hyp, 2,4-diaminobutanoic acid (Dab) or an
      alpha methyl amino acid
<220> FEATURE:
<221> NAME/KEY: MOD_RES
<222> LOCATION: (37)..(37)
<223> OTHER INFORMATION: Gly, Pro, Hyp or an alpha methyl amino acid
<220> FEATURE:
<221> NAME/KEY: MOD_RES
<222> LOCATION: (38)..(38)
<223> OTHER INFORMATION: Ser, Pro, His, Hyp or an alpha methyl amino
      acid
<220> FEATURE:
<221> NAME/KEY: MOD_RES
<222> LOCATION: (39)..(39)
<223> OTHER INFORMATION: Asn, Pro, Arg, Glu, 2,4-diaminobutanoic acid
      (Dab), Hyp or an alpha methyl amino acid
<220> FEATURE:
<221> NAME/KEY: MOD_RES
<222> LOCATION: (40)..(40)
<223> OTHER INFORMATION: Thr, Hyp or an alpha methyl amino acid
<220> FEATURE:
<221> NAME/KEY: MOD_RES
<222> LOCATION: (41)..(41)
<223> OTHER INFORMATION: Tyr, Pro, Hyp or an alpha methyl amino acid

<400> SEQUENCE: 166

Xaa Xaa Xaa Xaa Xaa Cys Asn Xaa Ala Thr Cys Ala Thr Gln Arg Leu
1               5                   10                  15

Ala Xaa Xaa Xaa Xaa His Ser Xaa Xaa Xaa Xaa Xaa Xaa Xaa Xaa
            20                  25                  30

Xaa Thr Xaa Xaa Xaa Xaa Xaa Xaa Xaa
        35                  40

<210> SEQ ID NO 167
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
```

```
<223> OTHER INFORMATION: Lys(albumin binding moiety) or absent
<220> FEATURE:
<221> NAME/KEY: MOD_RES
<222> LOCATION: (2)..(2)
<223> OTHER INFORMATION: Gly or absent
<220> FEATURE:
<221> NAME/KEY: MOD_RES
<222> LOCATION: (3)..(3)
<223> OTHER INFORMATION: Gly or absent
<220> FEATURE:
<221> NAME/KEY: MOD_RES
<222> LOCATION: (4)..(4)
<223> OTHER INFORMATION: Gly, Lys(albumin binding moiety) or absent
<220> FEATURE:
<221> NAME/KEY: MOD_RES
<222> LOCATION: (5)..(5)
<223> OTHER INFORMATION: Lys, Lys(albumin binding moiety) or absent
<220> FEATURE:
<221> NAME/KEY: MOD_RES
<222> LOCATION: (8)..(8)
<223> OTHER INFORMATION: Thr, Ile or Ala
<220> FEATURE:
<221> NAME/KEY: MOD_RES
<222> LOCATION: (18)..(18)
<223> OTHER INFORMATION: Asn, His, Glu, 2,4-diaminobutanoic acid (Dab),
      or an alpha methyl amino acid
<220> FEATURE:
<221> NAME/KEY: MOD_RES
<222> LOCATION: (19)..(19)
<223> OTHER INFORMATION: Phe or Trp
<220> FEATURE:
<221> NAME/KEY: MOD_RES
<222> LOCATION: (20)..(20)
<223> OTHER INFORMATION: Leu or D-Leu (dL)
<220> FEATURE:
<221> NAME/KEY: MOD_RES
<222> LOCATION: (21)..(21)
<223> OTHER INFORMATION: Val, Ser, Glu, Arg, (2S,4R)-4-
      hydroxypyrrolidine-2-carboxylic acid (Hyp), 2,4-diaminobutanoic
      acid (Dab) or an alpha methyl amino acid
<220> FEATURE:
<221> NAME/KEY: MOD_RES
<222> LOCATION: (24)..(24)
<223> OTHER INFORMATION: an alpha methyl amino acid
<220> FEATURE:
<221> NAME/KEY: MOD_RES
<222> LOCATION: (25)..(25)
<223> OTHER INFORMATION: Asn, 2,4-diaminobutanoic acid (Dab), His, Pro,
      Ser, Arg, Lys, Gly or Glu, Ala, Hyp  or an alpha methyl amino acid
<220> FEATURE:
<221> NAME/KEY: MOD_RES
<222> LOCATION: (26)..(26)
<223> OTHER INFORMATION: Asn, His, Hyp, 2,4-diaminobutanoic acid (Dab)
      or an alpha methyl amino acid
<220> FEATURE:
<221> NAME/KEY: MOD_RES
<222> LOCATION: (27)..(27)
<223> OTHER INFORMATION: Phe, Hyp or an alpha methyl amino acid
<220> FEATURE:
<221> NAME/KEY: MOD_RES
<222> LOCATION: (28)..(28)
<223> OTHER INFORMATION: Gly, Pro, Hyp or an alpha methyl amino acid
<220> FEATURE:
<221> NAME/KEY: MOD_RES
<222> LOCATION: (29)..(29)
<223> OTHER INFORMATION: Pro, Ala, Hyp or an alpha methyl amino acid
<220> FEATURE:
<221> NAME/KEY: MOD_RES
<222> LOCATION: (30)..(30)
<223> OTHER INFORMATION: Ile, D-Ile (dI), Arg, Hyp or an alpha methyl
      amino acid
<220> FEATURE:
<221> NAME/KEY: MOD_RES
<222> LOCATION: (31)..(31)
<223> OTHER INFORMATION: Leu, dL, Hyp or an alpha methyl amino acid
<220> FEATURE:
<221> NAME/KEY: MOD_RES
<222> LOCATION: (32)..(32)
<223> OTHER INFORMATION: Pro, D-Pro (dP), Ser, Hyp or an alpha methyl
```

```
        amino acid
<220> FEATURE:
<221> NAME/KEY: MOD_RES
<222> LOCATION: (33)..(33)
<223> OTHER INFORMATION: Pro, Hyp or an alpha methyl amino acid
<220> FEATURE:
<221> NAME/KEY: MOD_RES
<222> LOCATION: (35)..(35)
<223> OTHER INFORMATION: Asn, Glu, His, Arg, Pro, 2,4-diaminobutanoic
      acid (Dab) or an alpha methyl amino acid
<220> FEATURE:
<221> NAME/KEY: MOD_RES
<222> LOCATION: (36)..(36)
<223> OTHER INFORMATION: Val, Hyp, 2,4-diaminobutanoic acid (Dab) or an
      alpha methyl amino acid
<220> FEATURE:
<221> NAME/KEY: MOD_RES
<222> LOCATION: (37)..(37)
<223> OTHER INFORMATION: Gly, Pro, Hyp or an alpha methyl amino acid
<220> FEATURE:
<221> NAME/KEY: MOD_RES
<222> LOCATION: (38)..(38)
<223> OTHER INFORMATION: Ser, Pro, His, Hyp or an alpha methyl amino
      acid
<220> FEATURE:
<221> NAME/KEY: MOD_RES
<222> LOCATION: (39)..(39)
<223> OTHER INFORMATION: Asn, Pro, Arg, Glu, 2,4-diaminobutanoic acid
      (Dab), Hyp or an alpha methyl amino acid
<220> FEATURE:
<221> NAME/KEY: MOD_RES
<222> LOCATION: (40)..(40)
<223> OTHER INFORMATION: Thr, Hyp or an alpha methyl amino acid
<220> FEATURE:
<221> NAME/KEY: MOD_RES
<222> LOCATION: (41)..(41)
<223> OTHER INFORMATION: Tyr, Pro, Hyp or an alpha methyl amino acid

<400> SEQUENCE: 167

Xaa Xaa Xaa Xaa Xaa Cys Asn Xaa Ala Thr Cys Ala Thr Gln Arg Leu
1               5                   10                  15

Ala Xaa Xaa Xaa Xaa His Ser Xaa Xaa Xaa Xaa Xaa Xaa Xaa Xaa
            20                  25                  30

Xaa Thr Xaa Xaa Xaa Xaa Xaa Xaa Xaa
        35                  40

<210> SEQ ID NO 168
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(albumin binding moiety) or absent
<220> FEATURE:
<221> NAME/KEY: MOD_RES
<222> LOCATION: (2)..(2)
<223> OTHER INFORMATION: Gly or absent
<220> FEATURE:
<221> NAME/KEY: MOD_RES
<222> LOCATION: (3)..(3)
<223> OTHER INFORMATION: Gly or absent
<220> FEATURE:
<221> NAME/KEY: MOD_RES
<222> LOCATION: (4)..(4)
<223> OTHER INFORMATION: Gly, Lys(albumin binding moiety) or absent
<220> FEATURE:
<221> NAME/KEY: MOD_RES
<222> LOCATION: (5)..(5)
<223> OTHER INFORMATION: Lys, Lys(albumin binding moiety) or absent
<220> FEATURE:
<221> NAME/KEY: MOD_RES
```

```
<222> LOCATION: (8)..(8)
<223> OTHER INFORMATION: Thr, Ile or Ala
<220> FEATURE:
<221> NAME/KEY: MOD_RES
<222> LOCATION: (18)..(18)
<223> OTHER INFORMATION: Asn, His, Glu, 2,4-diaminobutanoic acid (Dab),
      or an alpha methyl amino acid
<220> FEATURE:
<221> NAME/KEY: MOD_RES
<222> LOCATION: (19)..(19)
<223> OTHER INFORMATION: Phe or Trp
<220> FEATURE:
<221> NAME/KEY: MOD_RES
<222> LOCATION: (20)..(20)
<223> OTHER INFORMATION: Leu or D-Leu (dL)
<220> FEATURE:
<221> NAME/KEY: MOD_RES
<222> LOCATION: (21)..(21)
<223> OTHER INFORMATION: Val, Ser, Glu, Arg, (2S,4R)-4-
      hydroxypyrrolidine-2-carboxylic acid (Hyp), 2,4-diaminobutanoic
      acid (Dab) or an alpha methyl amino acid
<220> FEATURE:
<221> NAME/KEY: MOD_RES
<222> LOCATION: (24)..(24)
<223> OTHER INFORMATION: Ser, Ile, Pro or an alpha methyl amino acid
<220> FEATURE:
<221> NAME/KEY: MOD_RES
<222> LOCATION: (25)..(25)
<223> OTHER INFORMATION: an alpha methyl amino acid
<220> FEATURE:
<221> NAME/KEY: MOD_RES
<222> LOCATION: (26)..(26)
<223> OTHER INFORMATION: Asn, His, Hyp, 2,4-diaminobutanoic acid (Dab)
      or an alpha methyl amino acid
<220> FEATURE:
<221> NAME/KEY: MOD_RES
<222> LOCATION: (27)..(27)
<223> OTHER INFORMATION: Phe, Hyp or an alpha methyl amino acid
<220> FEATURE:
<221> NAME/KEY: MOD_RES
<222> LOCATION: (28)..(28)
<223> OTHER INFORMATION: Gly, Pro, Hyp or an alpha methyl amino acid
<220> FEATURE:
<221> NAME/KEY: MOD_RES
<222> LOCATION: (29)..(29)
<223> OTHER INFORMATION: Pro, Ala, Hyp or an alpha methyl amino acid
<220> FEATURE:
<221> NAME/KEY: MOD_RES
<222> LOCATION: (30)..(30)
<223> OTHER INFORMATION: Ile, D-Ile (dI), Arg, Hyp or an alpha methyl
      amino acid
<220> FEATURE:
<221> NAME/KEY: MOD_RES
<222> LOCATION: (31)..(31)
<223> OTHER INFORMATION: Leu, dL, Hyp or an alpha methyl amino acid
<220> FEATURE:
<221> NAME/KEY: MOD_RES
<222> LOCATION: (32)..(32)
<223> OTHER INFORMATION: Pro, D-Pro (dP), Ser, Hyp or an alpha methyl
      amino acid
<220> FEATURE:
<221> NAME/KEY: MOD_RES
<222> LOCATION: (33)..(33)
<223> OTHER INFORMATION: Pro, Hyp or an alpha methyl amino acid
<220> FEATURE:
<221> NAME/KEY: MOD_RES
<222> LOCATION: (35)..(35)
<223> OTHER INFORMATION: Asn, Glu, His, Arg, Pro, 2,4-diaminobutanoic
      acid (Dab) or an alpha methyl amino acid
<220> FEATURE:
<221> NAME/KEY: MOD_RES
<222> LOCATION: (36)..(36)
<223> OTHER INFORMATION: Val, Hyp, 2,4-diaminobutanoic acid (Dab) or an
      alpha methyl amino acid
<220> FEATURE:
<221> NAME/KEY: MOD_RES
<222> LOCATION: (37)..(37)
<223> OTHER INFORMATION: Gly, Pro, Hyp or an alpha methyl amino acid
<220> FEATURE:
```

<221> NAME/KEY: MOD_RES
<222> LOCATION: (38)..(38)
<223> OTHER INFORMATION: Ser, Pro, His, Hyp or an alpha methyl amino
      acid
<220> FEATURE:
<221> NAME/KEY: MOD_RES
<222> LOCATION: (39)..(39)
<223> OTHER INFORMATION: Asn, Pro, Arg, Glu, 2,4-diaminobutanoic acid
      (Dab), Hyp or an alpha methyl amino acid
<220> FEATURE:
<221> NAME/KEY: MOD_RES
<222> LOCATION: (40)..(40)
<223> OTHER INFORMATION: Thr, Hyp or an alpha methyl amino acid
<220> FEATURE:
<221> NAME/KEY: MOD_RES
<222> LOCATION: (41)..(41)
<223> OTHER INFORMATION: Tyr, Pro, Hyp or an alpha methyl amino acid

<400> SEQUENCE: 168

Xaa Xaa Xaa Xaa Xaa Cys Asn Xaa Ala Thr Cys Ala Thr Gln Arg Leu
1               5                   10                  15

Ala Xaa Xaa Xaa Xaa His Ser Xaa Xaa Xaa Xaa Xaa Xaa Xaa Xaa Xaa
            20                  25                  30

Xaa Thr Xaa Xaa Xaa Xaa Xaa Xaa Xaa
        35                  40

<210> SEQ ID NO 169
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(albumin binding moiety) or absent
<220> FEATURE:
<221> NAME/KEY: MOD_RES
<222> LOCATION: (2)..(2)
<223> OTHER INFORMATION: Gly or absent
<220> FEATURE:
<221> NAME/KEY: MOD_RES
<222> LOCATION: (3)..(3)
<223> OTHER INFORMATION: Gly or absent
<220> FEATURE:
<221> NAME/KEY: MOD_RES
<222> LOCATION: (4)..(4)
<223> OTHER INFORMATION: Gly, Lys(albumin binding moiety) or absent
<220> FEATURE:
<221> NAME/KEY: MOD_RES
<222> LOCATION: (5)..(5)
<223> OTHER INFORMATION: Lys, Lys(albumin binding moiety) or absent
<220> FEATURE:
<221> NAME/KEY: MOD_RES
<222> LOCATION: (8)..(8)
<223> OTHER INFORMATION: Thr, Ile or Ala
<220> FEATURE:
<221> NAME/KEY: MOD_RES
<222> LOCATION: (18)..(18)
<223> OTHER INFORMATION: Asn, His, Glu, 2,4-diaminobutanoic acid (Dab),
      or an alpha methyl amino acid
<220> FEATURE:
<221> NAME/KEY: MOD_RES
<222> LOCATION: (19)..(19)
<223> OTHER INFORMATION: Phe or Trp
<220> FEATURE:
<221> NAME/KEY: MOD_RES
<222> LOCATION: (20)..(20)
<223> OTHER INFORMATION: Leu or D-Leu (dL)
<220> FEATURE:
<221> NAME/KEY: MOD_RES
<222> LOCATION: (21)..(21)
<223> OTHER INFORMATION: Val, Ser, Glu, Arg, (2S,4R)-4-
      hydroxypyrrolidine-2-carboxylic acid (Hyp), 2,4-diaminobutanoic -continued

```
      acid (Dab) or an alpha methyl amino acid
<220> FEATURE:
<221> NAME/KEY: MOD_RES
<222> LOCATION: (24)..(24)
<223> OTHER INFORMATION: Ser, Ile, Pro or an alpha methyl amino acid
<220> FEATURE:
<221> NAME/KEY: MOD_RES
<222> LOCATION: (25)..(25)
<223> OTHER INFORMATION: 2,4-diaminobutanoic acid (Dab)
<220> FEATURE:
<221> NAME/KEY: MOD_RES
<222> LOCATION: (26)..(26)
<223> OTHER INFORMATION: Asn, His, Hyp, 2,4-diaminobutanoic acid (Dab)
      or an alpha methyl amino acid
<220> FEATURE:
<221> NAME/KEY: MOD_RES
<222> LOCATION: (27)..(27)
<223> OTHER INFORMATION: Phe, Hyp or an alpha methyl amino acid
<220> FEATURE:
<221> NAME/KEY: MOD_RES
<222> LOCATION: (28)..(28)
<223> OTHER INFORMATION: Gly, Pro, Hyp or an alpha methyl amino acid
<220> FEATURE:
<221> NAME/KEY: MOD_RES
<222> LOCATION: (29)..(29)
<223> OTHER INFORMATION: Pro, Ala, Hyp or an alpha methyl amino acid
<220> FEATURE:
<221> NAME/KEY: MOD_RES
<222> LOCATION: (30)..(30)
<223> OTHER INFORMATION: Ile, D-Ile (dI), Arg, Hyp or an alpha methyl
      amino acid
<220> FEATURE:
<221> NAME/KEY: MOD_RES
<222> LOCATION: (31)..(31)
<223> OTHER INFORMATION: Leu, dL, Hyp or an alpha methyl amino acid
<220> FEATURE:
<221> NAME/KEY: MOD_RES
<222> LOCATION: (32)..(32)
<223> OTHER INFORMATION: Pro, D-Pro (dP), Ser, Hyp or an alpha methyl
      amino acid
<220> FEATURE:
<221> NAME/KEY: MOD_RES
<222> LOCATION: (33)..(33)
<223> OTHER INFORMATION: Pro, Hyp or an alpha methyl amino acid
<220> FEATURE:
<221> NAME/KEY: MOD_RES
<222> LOCATION: (35)..(35)
<223> OTHER INFORMATION: Asn, Glu, His, Arg, Pro, 2,4-diaminobutanoic
      acid (Dab) or an alpha methyl amino acid
<220> FEATURE:
<221> NAME/KEY: MOD_RES
<222> LOCATION: (36)..(36)
<223> OTHER INFORMATION: Val, Hyp, 2,4-diaminobutanoic acid (Dab) or an
      alpha methyl amino acid
<220> FEATURE:
<221> NAME/KEY: MOD_RES
<222> LOCATION: (37)..(37)
<223> OTHER INFORMATION: Gly, Pro, Hyp or an alpha methyl amino acid
<220> FEATURE:
<221> NAME/KEY: MOD_RES
<222> LOCATION: (38)..(38)
<223> OTHER INFORMATION: Ser, Pro, His, Hyp or an alpha methyl amino
      acid
<220> FEATURE:
<221> NAME/KEY: MOD_RES
<222> LOCATION: (39)..(39)
<223> OTHER INFORMATION: Asn, Pro, Arg, Glu, 2,4-diaminobutanoic acid
      (Dab), Hyp or an alpha methyl amino acid
<220> FEATURE:
<221> NAME/KEY: MOD_RES
<222> LOCATION: (40)..(40)
<223> OTHER INFORMATION: Thr, Hyp or an alpha methyl amino acid
<220> FEATURE:
<221> NAME/KEY: MOD_RES
<222> LOCATION: (41)..(41)
<223> OTHER INFORMATION: Tyr, Pro, Hyp or an alpha methyl amino acid

<400> SEQUENCE: 169
```

-continued

```
Xaa Xaa Xaa Xaa Xaa Cys Asn Xaa Ala Thr Cys Ala Thr Gln Arg Leu
1               5                   10                  15

Ala Xaa Xaa Xaa Xaa His Ser Xaa Xaa Xaa Xaa Xaa Xaa Xaa Xaa
            20                  25                  30

Xaa Thr Xaa Xaa Xaa Xaa Xaa Xaa Xaa
        35                  40
```

```
<210> SEQ ID NO 170
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(albumin binding moiety) or absent
<220> FEATURE:
<221> NAME/KEY: MOD_RES
<222> LOCATION: (2)..(2)
<223> OTHER INFORMATION: Gly or absent
<220> FEATURE:
<221> NAME/KEY: MOD_RES
<222> LOCATION: (3)..(3)
<223> OTHER INFORMATION: Gly or absent
<220> FEATURE:
<221> NAME/KEY: MOD_RES
<222> LOCATION: (4)..(4)
<223> OTHER INFORMATION: Gly, Lys(albumin binding moiety) or absent
<220> FEATURE:
<221> NAME/KEY: MOD_RES
<222> LOCATION: (5)..(5)
<223> OTHER INFORMATION: Lys, Lys(albumin binding moiety) or absent
<220> FEATURE:
<221> NAME/KEY: MOD_RES
<222> LOCATION: (8)..(8)
<223> OTHER INFORMATION: Thr, Ile or Ala
<220> FEATURE:
<221> NAME/KEY: MOD_RES
<222> LOCATION: (18)..(18)
<223> OTHER INFORMATION: Asn, His, Glu, 2,4-diaminobutanoic acid (Dab),
      or an alpha methyl amino acid
<220> FEATURE:
<221> NAME/KEY: MOD_RES
<222> LOCATION: (19)..(19)
<223> OTHER INFORMATION: Phe or Trp
<220> FEATURE:
<221> NAME/KEY: MOD_RES
<222> LOCATION: (20)..(20)
<223> OTHER INFORMATION: Leu or D-Leu (dL)
<220> FEATURE:
<221> NAME/KEY: MOD_RES
<222> LOCATION: (21)..(21)
<223> OTHER INFORMATION: Val, Ser, Glu, Arg, (2S,4R)-4-
      hydroxypyrrolidine-2-carboxylic acid (Hyp), 2,4-diaminobutanoic
      acid (Dab) or an alpha methyl amino acid
<220> FEATURE:
<221> NAME/KEY: MOD_RES
<222> LOCATION: (24)..(24)
<223> OTHER INFORMATION: Ser, Ile, Pro or an alpha methyl amino acid
<220> FEATURE:
<221> NAME/KEY: MOD_RES
<222> LOCATION: (25)..(25)
<223> OTHER INFORMATION: Asn, 2,4-diaminobutanoic acid (Dab), His, Pro,
      Ser, Arg, Lys, Gly or Glu, Ala, Hyp or an alpha methyl amino acid
<220> FEATURE:
<221> NAME/KEY: MOD_RES
<222> LOCATION: (26)..(26)
<223> OTHER INFORMATION: an alpha methyl amino acid
<220> FEATURE:
<221> NAME/KEY: MOD_RES
<222> LOCATION: (27)..(27)
<223> OTHER INFORMATION: Phe, Hyp or an alpha methyl amino acid
<220> FEATURE:
<221> NAME/KEY: MOD_RES
```

```
<222> LOCATION: (28)..(28)
<223> OTHER INFORMATION: Gly, Pro, Hyp or an alpha methyl amino acid
<220> FEATURE:
<221> NAME/KEY: MOD_RES
<222> LOCATION: (29)..(29)
<223> OTHER INFORMATION: Pro, Ala, Hyp or an alpha methyl amino acid
<220> FEATURE:
<221> NAME/KEY: MOD_RES
<222> LOCATION: (30)..(30)
<223> OTHER INFORMATION: Ile, D-Ile (dI), Arg, Hyp or an alpha methyl
      amino acid
<220> FEATURE:
<221> NAME/KEY: MOD_RES
<222> LOCATION: (31)..(31)
<223> OTHER INFORMATION: Leu, dL, Hyp or an alpha methyl amino acid
<220> FEATURE:
<221> NAME/KEY: MOD_RES
<222> LOCATION: (32)..(32)
<223> OTHER INFORMATION: Pro, D-Pro (dP), Ser, Hyp or an alpha methyl
      amino acid
<220> FEATURE:
<221> NAME/KEY: MOD_RES
<222> LOCATION: (33)..(33)
<223> OTHER INFORMATION: Pro, Hyp or an alpha methyl amino acid
<220> FEATURE:
<221> NAME/KEY: MOD_RES
<222> LOCATION: (35)..(35)
<223> OTHER INFORMATION: Asn, Glu, His, Arg, Pro, 2,4-diaminobutanoic
      acid (Dab) or an alpha methyl amino acid
<220> FEATURE:
<221> NAME/KEY: MOD_RES
<222> LOCATION: (36)..(36)
<223> OTHER INFORMATION: Val, Hyp, 2,4-diaminobutanoic acid (Dab) or an
      alpha methyl amino acid
<220> FEATURE:
<221> NAME/KEY: MOD_RES
<222> LOCATION: (37)..(37)
<223> OTHER INFORMATION: Gly, Pro, Hyp or an alpha methyl amino acid
<220> FEATURE:
<221> NAME/KEY: MOD_RES
<222> LOCATION: (38)..(38)
<223> OTHER INFORMATION: Ser, Pro, His, Hyp or an alpha methyl amino
      acid
<220> FEATURE:
<221> NAME/KEY: MOD_RES
<222> LOCATION: (39)..(39)
<223> OTHER INFORMATION: Asn, Pro, Arg, Glu, 2,4-diaminobutanoic acid
      (Dab), Hyp or an alpha methyl amino acid
<220> FEATURE:
<221> NAME/KEY: MOD_RES
<222> LOCATION: (40)..(40)
<223> OTHER INFORMATION: Thr, Hyp or an alpha methyl amino acid
<220> FEATURE:
<221> NAME/KEY: MOD_RES
<222> LOCATION: (41)..(41)
<223> OTHER INFORMATION: Tyr, Pro, Hyp or an alpha methyl amino acid

<400> SEQUENCE: 170

Xaa Xaa Xaa Xaa Xaa Cys Asn Xaa Ala Thr Cys Ala Thr Gln Arg Leu
1               5                   10                  15

Ala Xaa Xaa Xaa Xaa His Ser Xaa Xaa Xaa Xaa Xaa Xaa Xaa Xaa
            20                  25                  30

Xaa Thr Xaa Xaa Xaa Xaa Xaa Xaa Xaa
        35                  40

<210> SEQ ID NO 171
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
```

```
<223> OTHER INFORMATION: Lys(albumin binding moiety) or absent
<220> FEATURE:
<221> NAME/KEY: MOD_RES
<222> LOCATION: (2)..(2)
<223> OTHER INFORMATION: Gly or absent
<220> FEATURE:
<221> NAME/KEY: MOD_RES
<222> LOCATION: (3)..(3)
<223> OTHER INFORMATION: Gly or absent
<220> FEATURE:
<221> NAME/KEY: MOD_RES
<222> LOCATION: (4)..(4)
<223> OTHER INFORMATION: Gly, Lys(albumin binding moiety) or absent
<220> FEATURE:
<221> NAME/KEY: MOD_RES
<222> LOCATION: (5)..(5)
<223> OTHER INFORMATION: Lys, Lys(albumin binding moiety) or absent
<220> FEATURE:
<221> NAME/KEY: MOD_RES
<222> LOCATION: (8)..(8)
<223> OTHER INFORMATION: Thr, Ile or Ala
<220> FEATURE:
<221> NAME/KEY: MOD_RES
<222> LOCATION: (18)..(18)
<223> OTHER INFORMATION: Asn, His, Glu, 2,4-diaminobutanoic acid (Dab),
      or an alpha methyl amino acid
<220> FEATURE:
<221> NAME/KEY: MOD_RES
<222> LOCATION: (19)..(19)
<223> OTHER INFORMATION: Phe or Trp
<220> FEATURE:
<221> NAME/KEY: MOD_RES
<222> LOCATION: (20)..(20)
<223> OTHER INFORMATION: Leu or D-Leu (dL)
<220> FEATURE:
<221> NAME/KEY: MOD_RES
<222> LOCATION: (21)..(21)
<223> OTHER INFORMATION: Val, Ser, Glu, Arg, (2S,4R)-4-
      hydroxypyrrolidine-2-carboxylic acid (Hyp), 2,4-diaminobutanoic
      acid (Dab) or an alpha methyl amino acid
<220> FEATURE:
<221> NAME/KEY: MOD_RES
<222> LOCATION: (24)..(24)
<223> OTHER INFORMATION: Ser, Ile, Pro or an alpha methyl amino acid
<220> FEATURE:
<221> NAME/KEY: MOD_RES
<222> LOCATION: (25)..(25)
<223> OTHER INFORMATION: Asn, 2,4-diaminobutanoic acid (Dab), His, Pro,
      Ser, Arg, Lys, Gly or Glu, Ala, Hyp  or an alpha methyl amino acid
<220> FEATURE:
<221> NAME/KEY: MOD_RES
<222> LOCATION: (26)..(26)
<223> OTHER INFORMATION: Asn, His, Hyp, 2,4-diaminobutanoic acid (Dab)
      or an alpha methyl amino acid
<220> FEATURE:
<221> NAME/KEY: MOD_RES
<222> LOCATION: (27)..(27)
<223> OTHER INFORMATION: an alpha methyl amino acid
<220> FEATURE:
<221> NAME/KEY: MOD_RES
<222> LOCATION: (28)..(28)
<223> OTHER INFORMATION: Gly, Pro, Hyp or an alpha methyl amino acid
<220> FEATURE:
<221> NAME/KEY: MOD_RES
<222> LOCATION: (29)..(29)
<223> OTHER INFORMATION: Pro, Ala, Hyp or an alpha methyl amino acid
<220> FEATURE:
<221> NAME/KEY: MOD_RES
<222> LOCATION: (30)..(30)
<223> OTHER INFORMATION: Ile, D-Ile (dI), Arg, Hyp or an alpha methyl
      amino acid
<220> FEATURE:
<221> NAME/KEY: MOD_RES
<222> LOCATION: (31)..(31)
<223> OTHER INFORMATION: Leu, dL, Hyp or an alpha methyl amino acid
<220> FEATURE:
<221> NAME/KEY: MOD_RES
<222> LOCATION: (32)..(32)
<223> OTHER INFORMATION: Pro, D-Pro (dP), Ser, Hyp or an alpha methyl
```

```
      amino acid
<220> FEATURE:
<221> NAME/KEY: MOD_RES
<222> LOCATION: (33)..(33)
<223> OTHER INFORMATION: Pro, Hyp or an alpha methyl amino acid
<220> FEATURE:
<221> NAME/KEY: MOD_RES
<222> LOCATION: (35)..(35)
<223> OTHER INFORMATION: Asn, Glu, His, Arg, Pro, 2,4-diaminobutanoic
      acid (Dab) or an alpha methyl amino acid
<220> FEATURE:
<221> NAME/KEY: MOD_RES
<222> LOCATION: (36)..(36)
<223> OTHER INFORMATION: Val, Hyp, 2,4-diaminobutanoic acid (Dab) or an
      alpha methyl amino acid
<220> FEATURE:
<221> NAME/KEY: MOD_RES
<222> LOCATION: (37)..(37)
<223> OTHER INFORMATION: Gly, Pro, Hyp or an alpha methyl amino acid
<220> FEATURE:
<221> NAME/KEY: MOD_RES
<222> LOCATION: (38)..(38)
<223> OTHER INFORMATION: Ser, Pro, His, Hyp or an alpha methyl amino
      acid
<220> FEATURE:
<221> NAME/KEY: MOD_RES
<222> LOCATION: (39)..(39)
<223> OTHER INFORMATION: Asn, Pro, Arg, Glu, 2,4-diaminobutanoic acid
      (Dab), Hyp or an alpha methyl amino acid
<220> FEATURE:
<221> NAME/KEY: MOD_RES
<222> LOCATION: (40)..(40)
<223> OTHER INFORMATION: Thr, Hyp or an alpha methyl amino acid
<220> FEATURE:
<221> NAME/KEY: MOD_RES
<222> LOCATION: (41)..(41)
<223> OTHER INFORMATION: Tyr, Pro, Hyp or an alpha methyl amino acid

<400> SEQUENCE: 171

Xaa Xaa Xaa Xaa Xaa Cys Asn Xaa Ala Thr Cys Ala Thr Gln Arg Leu
1               5                   10                  15

Ala Xaa Xaa Xaa Xaa His Ser Xaa Xaa Xaa Xaa Xaa Xaa Xaa Xaa
            20                  25                  30

Xaa Thr Xaa Xaa Xaa Xaa Xaa Xaa Xaa
        35                  40

<210> SEQ ID NO 172
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(albumin binding moiety) or absent
<220> FEATURE:
<221> NAME/KEY: MOD_RES
<222> LOCATION: (2)..(2)
<223> OTHER INFORMATION: Gly or absent
<220> FEATURE:
<221> NAME/KEY: MOD_RES
<222> LOCATION: (3)..(3)
<223> OTHER INFORMATION: Gly or absent
<220> FEATURE:
<221> NAME/KEY: MOD_RES
<222> LOCATION: (4)..(4)
<223> OTHER INFORMATION: Gly, Lys(albumin binding moiety) or absent
<220> FEATURE:
<221> NAME/KEY: MOD_RES
<222> LOCATION: (5)..(5)
<223> OTHER INFORMATION: Lys, Lys(albumin binding moiety) or absent
<220> FEATURE:
<221> NAME/KEY: MOD_RES
```

```
<222> LOCATION: (8)..(8)
<223> OTHER INFORMATION: Thr, Ile or Ala
<220> FEATURE:
<221> NAME/KEY: MOD_RES
<222> LOCATION: (18)..(18)
<223> OTHER INFORMATION: Asn, His, Glu, 2,4-diaminobutanoic acid (Dab),
      or an alpha methyl amino acid
<220> FEATURE:
<221> NAME/KEY: MOD_RES
<222> LOCATION: (19)..(19)
<223> OTHER INFORMATION: Phe or Trp
<220> FEATURE:
<221> NAME/KEY: MOD_RES
<222> LOCATION: (20)..(20)
<223> OTHER INFORMATION: Leu or D-Leu (dL)
<220> FEATURE:
<221> NAME/KEY: MOD_RES
<222> LOCATION: (21)..(21)
<223> OTHER INFORMATION: Val, Ser, Glu, Arg, (2S,4R)-4-
      hydroxypyrrolidine-2-carboxylic acid (Hyp), 2,4-diaminobutanoic
      acid (Dab) or an alpha methyl amino acid
<220> FEATURE:
<221> NAME/KEY: MOD_RES
<222> LOCATION: (24)..(24)
<223> OTHER INFORMATION: Ser, Ile, Pro or an alpha methyl amino acid
<220> FEATURE:
<221> NAME/KEY: MOD_RES
<222> LOCATION: (25)..(25)
<223> OTHER INFORMATION: Asn, 2,4-diaminobutanoic acid (Dab), His, Pro,
      Ser, Arg, Lys, Gly or Glu, Ala, Hyp  or an alpha methyl amino acid
<220> FEATURE:
<221> NAME/KEY: MOD_RES
<222> LOCATION: (26)..(26)
<223> OTHER INFORMATION: Asn, His, Hyp, 2,4-diaminobutanoic acid (Dab)
      or an alpha methyl amino acid
<220> FEATURE:
<221> NAME/KEY: MOD_RES
<222> LOCATION: (27)..(27)
<223> OTHER INFORMATION: Phe, Hyp or an alpha methyl amino acid
<220> FEATURE:
<221> NAME/KEY: MOD_RES
<222> LOCATION: (28)..(28)
<223> OTHER INFORMATION: an alpha methyl amino acid
<220> FEATURE:
<221> NAME/KEY: MOD_RES
<222> LOCATION: (29)..(29)
<223> OTHER INFORMATION: Pro, Ala, Hyp or an alpha methyl amino acid
<220> FEATURE:
<221> NAME/KEY: MOD_RES
<222> LOCATION: (30)..(30)
<223> OTHER INFORMATION: Ile, D-Ile (dI), Arg, Hyp or an alpha methyl
      amino acid
<220> FEATURE:
<221> NAME/KEY: MOD_RES
<222> LOCATION: (31)..(31)
<223> OTHER INFORMATION: Leu, dL, Hyp or an alpha methyl amino acid
<220> FEATURE:
<221> NAME/KEY: MOD_RES
<222> LOCATION: (32)..(32)
<223> OTHER INFORMATION: Pro, D-Pro (dP), Ser, Hyp or an alpha methyl
      amino acid
<220> FEATURE:
<221> NAME/KEY: MOD_RES
<222> LOCATION: (33)..(33)
<223> OTHER INFORMATION: Pro, Hyp or an alpha methyl amino acid
<220> FEATURE:
<221> NAME/KEY: MOD_RES
<222> LOCATION: (35)..(35)
<223> OTHER INFORMATION: Asn, Glu, His, Arg, Pro, 2,4-diaminobutanoic
      acid (Dab) or an alpha methyl amino acid
<220> FEATURE:
<221> NAME/KEY: MOD_RES
<222> LOCATION: (36)..(36)
<223> OTHER INFORMATION: Val, Hyp, 2,4-diaminobutanoic acid (Dab) or an
      alpha methyl amino acid
<220> FEATURE:
<221> NAME/KEY: MOD_RES
<222> LOCATION: (37)..(37)
<223> OTHER INFORMATION: Gly, Pro, Hyp or an alpha methyl amino acid
```

```
<220> FEATURE:
<221> NAME/KEY: MOD_RES
<222> LOCATION: (38)..(38)
<223> OTHER INFORMATION: Ser, Pro, His, Hyp or an alpha methyl amino
      acid
<220> FEATURE:
<221> NAME/KEY: MOD_RES
<222> LOCATION: (39)..(39)
<223> OTHER INFORMATION: Asn, Pro, Arg, Glu, 2,4-diaminobutanoic acid
      (Dab), Hyp or an alpha methyl amino acid
<220> FEATURE:
<221> NAME/KEY: MOD_RES
<222> LOCATION: (40)..(40)
<223> OTHER INFORMATION: Thr, Hyp or an alpha methyl amino acid
<220> FEATURE:
<221> NAME/KEY: MOD_RES
<222> LOCATION: (41)..(41)
<223> OTHER INFORMATION: Tyr, Pro, Hyp or an alpha methyl amino acid

<400> SEQUENCE: 172

Xaa Xaa Xaa Xaa Xaa Cys Asn Xaa Ala Thr Cys Ala Thr Gln Arg Leu
1               5                   10                  15

Ala Xaa Xaa Xaa Xaa His Ser Xaa Xaa Xaa Xaa Xaa Xaa Xaa Xaa Xaa
            20                  25                  30

Xaa Thr Xaa Xaa Xaa Xaa Xaa Xaa Xaa
        35                  40

<210> SEQ ID NO 173
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(albumin binding moiety) or absent
<220> FEATURE:
<221> NAME/KEY: MOD_RES
<222> LOCATION: (2)..(2)
<223> OTHER INFORMATION: Gly or absent
<220> FEATURE:
<221> NAME/KEY: MOD_RES
<222> LOCATION: (3)..(3)
<223> OTHER INFORMATION: Gly or absent
<220> FEATURE:
<221> NAME/KEY: MOD_RES
<222> LOCATION: (4)..(4)
<223> OTHER INFORMATION: Gly, Lys(albumin binding moiety) or absent
<220> FEATURE:
<221> NAME/KEY: MOD_RES
<222> LOCATION: (5)..(5)
<223> OTHER INFORMATION: Lys, Lys(albumin binding moiety) or absent
<220> FEATURE:
<221> NAME/KEY: MOD_RES
<222> LOCATION: (8)..(8)
<223> OTHER INFORMATION: Thr, Ile or Ala
<220> FEATURE:
<221> NAME/KEY: MOD_RES
<222> LOCATION: (18)..(18)
<223> OTHER INFORMATION: Asn, His, Glu, 2,4-diaminobutanoic acid (Dab),
      or an alpha methyl amino acid
<220> FEATURE:
<221> NAME/KEY: MOD_RES
<222> LOCATION: (19)..(19)
<223> OTHER INFORMATION: Phe or Trp
<220> FEATURE:
<221> NAME/KEY: MOD_RES
<222> LOCATION: (20)..(20)
<223> OTHER INFORMATION: Leu or D-Leu (dL)
<220> FEATURE:
<221> NAME/KEY: MOD_RES
<222> LOCATION: (21)..(21)
<223> OTHER INFORMATION: Val, Ser, Glu, Arg, (2S,4R)-4-
```

```
    hydroxypyrrolidine-2-carboxylic acid (Hyp), 2,4-diaminobutanoic
    acid (Dab) or an alpha methyl amino acid
<220> FEATURE:
<221> NAME/KEY: MOD_RES
<222> LOCATION: (24)..(24)
<223> OTHER INFORMATION: Ser, Ile, Pro or an alpha methyl amino acid
<220> FEATURE:
<221> NAME/KEY: MOD_RES
<222> LOCATION: (25)..(25)
<223> OTHER INFORMATION: Asn, 2,4-diaminobutanoic acid (Dab), His, Pro,
    Ser, Arg, Lys, Gly or Glu, Ala, Hyp  or an alpha methyl amino acid
<220> FEATURE:
<221> NAME/KEY: MOD_RES
<222> LOCATION: (26)..(26)
<223> OTHER INFORMATION: Asn, His, Hyp, 2,4-diaminobutanoic acid (Dab)
    or an alpha methyl amino acid
<220> FEATURE:
<221> NAME/KEY: MOD_RES
<222> LOCATION: (27)..(27)
<223> OTHER INFORMATION: Phe, Hyp or an alpha methyl amino acid
<220> FEATURE:
<221> NAME/KEY: MOD_RES
<222> LOCATION: (28)..(28)
<223> OTHER INFORMATION: Hyp
<220> FEATURE:
<221> NAME/KEY: MOD_RES
<222> LOCATION: (29)..(29)
<223> OTHER INFORMATION: Pro, Ala, Hyp or an alpha methyl amino acid
<220> FEATURE:
<221> NAME/KEY: MOD_RES
<222> LOCATION: (30)..(30)
<223> OTHER INFORMATION: Ile, D-Ile (dI), Arg, Hyp or an alpha methyl
    amino acid
<220> FEATURE:
<221> NAME/KEY: MOD_RES
<222> LOCATION: (31)..(31)
<223> OTHER INFORMATION: Leu, dL, Hyp or an alpha methyl amino acid
<220> FEATURE:
<221> NAME/KEY: MOD_RES
<222> LOCATION: (32)..(32)
<223> OTHER INFORMATION: Pro, D-Pro (dP), Ser, Hyp or an alpha methyl
    amino acid
<220> FEATURE:
<221> NAME/KEY: MOD_RES
<222> LOCATION: (33)..(33)
<223> OTHER INFORMATION: Pro, Hyp or an alpha methyl amino acid
<220> FEATURE:
<221> NAME/KEY: MOD_RES
<222> LOCATION: (35)..(35)
<223> OTHER INFORMATION: Asn, Glu, His, Arg, Pro, 2,4-diaminobutanoic
    acid (Dab) or an alpha methyl amino acid
<220> FEATURE:
<221> NAME/KEY: MOD_RES
<222> LOCATION: (36)..(36)
<223> OTHER INFORMATION: Val, Hyp, 2,4-diaminobutanoic acid (Dab) or an
    alpha methyl amino acid
<220> FEATURE:
<221> NAME/KEY: MOD_RES
<222> LOCATION: (37)..(37)
<223> OTHER INFORMATION: Gly, Pro, Hyp or an alpha methyl amino acid
<220> FEATURE:
<221> NAME/KEY: MOD_RES
<222> LOCATION: (38)..(38)
<223> OTHER INFORMATION: Ser, Pro, His, Hyp or an alpha methyl amino
    acid
<220> FEATURE:
<221> NAME/KEY: MOD_RES
<222> LOCATION: (39)..(39)
<223> OTHER INFORMATION: Asn, Pro, Arg, Glu, 2,4-diaminobutanoic acid
    (Dab), Hyp or an alpha methyl amino acid
<220> FEATURE:
<221> NAME/KEY: MOD_RES
<222> LOCATION: (40)..(40)
<223> OTHER INFORMATION: Thr, Hyp or an alpha methyl amino acid
<220> FEATURE:
<221> NAME/KEY: MOD_RES
<222> LOCATION: (41)..(41)
<223> OTHER INFORMATION: Tyr, Pro, Hyp or an alpha methyl amino acid
```

-continued

<400> SEQUENCE: 173

Xaa Xaa Xaa Xaa Xaa Cys Asn Xaa Ala Thr Cys Ala Thr Gln Arg Leu
1               5                   10                  15

Ala Xaa Xaa Xaa Xaa His Ser Xaa Xaa Xaa Xaa Xaa Xaa Xaa Xaa
            20                  25                  30

Xaa Thr Xaa Xaa Xaa Xaa Xaa Xaa Xaa
        35                  40

<210> SEQ ID NO 174
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(albumin binding moiety) or absent
<220> FEATURE:
<221> NAME/KEY: MOD_RES
<222> LOCATION: (2)..(2)
<223> OTHER INFORMATION: Gly or absent
<220> FEATURE:
<221> NAME/KEY: MOD_RES
<222> LOCATION: (3)..(3)
<223> OTHER INFORMATION: Gly or absent
<220> FEATURE:
<221> NAME/KEY: MOD_RES
<222> LOCATION: (4)..(4)
<223> OTHER INFORMATION: Gly, Lys(albumin binding moiety) or absent
<220> FEATURE:
<221> NAME/KEY: MOD_RES
<222> LOCATION: (5)..(5)
<223> OTHER INFORMATION: Lys, Lys(albumin binding moiety) or absent
<220> FEATURE:
<221> NAME/KEY: MOD_RES
<222> LOCATION: (8)..(8)
<223> OTHER INFORMATION: Thr, Ile or Ala
<220> FEATURE:
<221> NAME/KEY: MOD_RES
<222> LOCATION: (18)..(18)
<223> OTHER INFORMATION: Asn, His, Glu, 2,4-diaminobutanoic acid (Dab),
      or an alpha methyl amino acid
<220> FEATURE:
<221> NAME/KEY: MOD_RES
<222> LOCATION: (19)..(19)
<223> OTHER INFORMATION: Phe or Trp
<220> FEATURE:
<221> NAME/KEY: MOD_RES
<222> LOCATION: (20)..(20)
<223> OTHER INFORMATION: Leu or D-Leu (dL)
<220> FEATURE:
<221> NAME/KEY: MOD_RES
<222> LOCATION: (21)..(21)
<223> OTHER INFORMATION: Val, Ser, Glu, Arg, (2S,4R)-4-
      hydroxypyrrolidine-2-carboxylic acid (Hyp), 2,4-diaminobutanoic
      acid (Dab) or an alpha methyl amino acid
<220> FEATURE:
<221> NAME/KEY: MOD_RES
<222> LOCATION: (24)..(24)
<223> OTHER INFORMATION: Ser, Ile, Pro or an alpha methyl amino acid
<220> FEATURE:
<221> NAME/KEY: MOD_RES
<222> LOCATION: (25)..(25)
<223> OTHER INFORMATION: Asn, 2,4-diaminobutanoic acid (Dab), His, Pro,
      Ser, Arg, Lys, Gly or Glu, Ala, Hyp  or an alpha methyl amino acid
<220> FEATURE:
<221> NAME/KEY: MOD_RES
<222> LOCATION: (26)..(26)
<223> OTHER INFORMATION: Asn, His, Hyp, 2,4-diaminobutanoic acid (Dab)
      or an alpha methyl amino acid
<220> FEATURE:
<221> NAME/KEY: MOD_RES
<222> LOCATION: (27)..(27)

<223> OTHER INFORMATION: Phe, Hyp or an alpha methyl amino acid
<220> FEATURE:
<221> NAME/KEY: MOD_RES
<222> LOCATION: (28)..(28)
<223> OTHER INFORMATION: Gly, Pro, Hyp or an alpha methyl amino acid
<220> FEATURE:
<221> NAME/KEY: MOD_RES
<222> LOCATION: (29)..(29)
<223> OTHER INFORMATION: an alpha methyl amino acid
<220> FEATURE:
<221> NAME/KEY: MOD_RES
<222> LOCATION: (30)..(30)
<223> OTHER INFORMATION: Ile, D-Ile (dI), Arg, Hyp or an alpha methyl
      amino acid
<220> FEATURE:
<221> NAME/KEY: MOD_RES
<222> LOCATION: (31)..(31)
<223> OTHER INFORMATION: Leu, dL, Hyp or an alpha methyl amino acid
<220> FEATURE:
<221> NAME/KEY: MOD_RES
<222> LOCATION: (32)..(32)
<223> OTHER INFORMATION: Pro, D-Pro (dP), Ser, Hyp or an alpha methyl
      amino acid
<220> FEATURE:
<221> NAME/KEY: MOD_RES
<222> LOCATION: (33)..(33)
<223> OTHER INFORMATION: Pro, Hyp or an alpha methyl amino acid
<220> FEATURE:
<221> NAME/KEY: MOD_RES
<222> LOCATION: (35)..(35)
<223> OTHER INFORMATION: Asn, Glu, His, Arg, Pro, 2,4-diaminobutanoic
      acid (Dab) or an alpha methyl amino acid
<220> FEATURE:
<221> NAME/KEY: MOD_RES
<222> LOCATION: (36)..(36)
<223> OTHER INFORMATION: Val, Hyp, 2,4-diaminobutanoic acid (Dab) or an
      alpha methyl amino acid
<220> FEATURE:
<221> NAME/KEY: MOD_RES
<222> LOCATION: (37)..(37)
<223> OTHER INFORMATION: Gly, Pro, Hyp or an alpha methyl amino acid
<220> FEATURE:
<221> NAME/KEY: MOD_RES
<222> LOCATION: (38)..(38)
<223> OTHER INFORMATION: Ser, Pro, His, Hyp or an alpha methyl amino
      acid
<220> FEATURE:
<221> NAME/KEY: MOD_RES
<222> LOCATION: (39)..(39)
<223> OTHER INFORMATION: Asn, Pro, Arg, Glu, 2,4-diaminobutanoic acid
      (Dab), Hyp or an alpha methyl amino acid
<220> FEATURE:
<221> NAME/KEY: MOD_RES
<222> LOCATION: (40)..(40)
<223> OTHER INFORMATION: Thr, Hyp or an alpha methyl amino acid
<220> FEATURE:
<221> NAME/KEY: MOD_RES
<222> LOCATION: (41)..(41)
<223> OTHER INFORMATION: Tyr, Pro, Hyp or an alpha methyl amino acid

<400> SEQUENCE: 174

Xaa Xaa Xaa Xaa Xaa Cys Asn Xaa Ala Thr Cys Ala Thr Gln Arg Leu
1               5                   10                  15

Ala Xaa Xaa Xaa Xaa His Ser Xaa Xaa Xaa Xaa Xaa Xaa Xaa Xaa Xaa
            20                  25                  30

Xaa Thr Xaa Xaa Xaa Xaa Xaa Xaa Xaa
            35                  40

<210> SEQ ID NO 175
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

```
<220> FEATURE:
<221> NAME/KEY: MOD_RES
<222> LOCATION: (1)..(1)
<223> OTHER INFORMATION: Lys(albumin binding moiety) or absent
<220> FEATURE:
<221> NAME/KEY: MOD_RES
<222> LOCATION: (2)..(2)
<223> OTHER INFORMATION: Gly or absent
<220> FEATURE:
<221> NAME/KEY: MOD_RES
<222> LOCATION: (3)..(3)
<223> OTHER INFORMATION: Gly or absent
<220> FEATURE:
<221> NAME/KEY: MOD_RES
<222> LOCATION: (4)..(4)
<223> OTHER INFORMATION: Gly, Lys(albumin binding moiety) or absent
<220> FEATURE:
<221> NAME/KEY: MOD_RES
<222> LOCATION: (5)..(5)
<223> OTHER INFORMATION: Lys, Lys(albumin binding moiety) or absent
<220> FEATURE:
<221> NAME/KEY: MOD_RES
<222> LOCATION: (8)..(8)
<223> OTHER INFORMATION: Thr, Ile or Ala
<220> FEATURE:
<221> NAME/KEY: MOD_RES
<222> LOCATION: (18)..(18)
<223> OTHER INFORMATION: Asn, His, Glu, 2,4-diaminobutanoic acid (Dab),
      or an alpha methyl amino acid
<220> FEATURE:
<221> NAME/KEY: MOD_RES
<222> LOCATION: (19)..(19)
<223> OTHER INFORMATION: Phe or Trp
<220> FEATURE:
<221> NAME/KEY: MOD_RES
<222> LOCATION: (20)..(20)
<223> OTHER INFORMATION: Leu or D-Leu (dL)
<220> FEATURE:
<221> NAME/KEY: MOD_RES
<222> LOCATION: (21)..(21)
<223> OTHER INFORMATION: Val, Ser, Glu, Arg, (2S,4R)-4-
      hydroxypyrrolidine-2-carboxylic acid (Hyp), 2,4-diaminobutanoic
      acid (Dab) or an alpha methyl amino acid
<220> FEATURE:
<221> NAME/KEY: MOD_RES
<222> LOCATION: (24)..(24)
<223> OTHER INFORMATION: Ser, Ile, Pro or an alpha methyl amino acid
<220> FEATURE:
<221> NAME/KEY: MOD_RES
<222> LOCATION: (25)..(25)
<223> OTHER INFORMATION: Asn, 2,4-diaminobutanoic acid (Dab), His, Pro,
      Ser, Arg, Lys, Gly or Glu, Ala, Hyp  or an alpha methyl amino acid
<220> FEATURE:
<221> NAME/KEY: MOD_RES
<222> LOCATION: (26)..(26)
<223> OTHER INFORMATION: Asn, His, Hyp, 2,4-diaminobutanoic acid (Dab)
      or an alpha methyl amino acid
<220> FEATURE:
<221> NAME/KEY: MOD_RES
<222> LOCATION: (27)..(27)
<223> OTHER INFORMATION: Phe, Hyp or an alpha methyl amino acid
<220> FEATURE:
<221> NAME/KEY: MOD_RES
<222> LOCATION: (28)..(28)
<223> OTHER INFORMATION: Gly, Pro, Hyp or an alpha methyl amino acid
<220> FEATURE:
<221> NAME/KEY: MOD_RES
<222> LOCATION: (29)..(29)
<223> OTHER INFORMATION: Pro, Ala, Hyp or an alpha methyl amino acid
<220> FEATURE:
<221> NAME/KEY: MOD_RES
<222> LOCATION: (30)..(30)
<223> OTHER INFORMATION: an alpha methyl amino acid
<220> FEATURE:
<221> NAME/KEY: MOD_RES
<222> LOCATION: (31)..(31)
<223> OTHER INFORMATION: Leu, dL, Hyp or an alpha methyl amino acid
<220> FEATURE:
<221> NAME/KEY: MOD_RES
```

```
<222> LOCATION: (32)..(32)
<223> OTHER INFORMATION: Pro, D-Pro (dP), Ser, Hyp or an alpha methyl
      amino acid
<220> FEATURE:
<221> NAME/KEY: MOD_RES
<222> LOCATION: (33)..(33)
<223> OTHER INFORMATION: Pro, Hyp or an alpha methyl amino acid
<220> FEATURE:
<221> NAME/KEY: MOD_RES
<222> LOCATION: (35)..(35)
<223> OTHER INFORMATION: Asn, Glu, His, Arg, Pro, 2,4-diaminobutanoic
      acid (Dab) or an alpha methyl amino acid
<220> FEATURE:
<221> NAME/KEY: MOD_RES
<222> LOCATION: (36)..(36)
<223> OTHER INFORMATION: Val, Hyp, 2,4-diaminobutanoic acid (Dab) or an
      alpha methyl amino acid
<220> FEATURE:
<221> NAME/KEY: MOD_RES
<222> LOCATION: (37)..(37)
<223> OTHER INFORMATION: Gly, Pro, Hyp or an alpha methyl amino acid
<220> FEATURE:
<221> NAME/KEY: MOD_RES
<222> LOCATION: (38)..(38)
<223> OTHER INFORMATION: Ser, Pro, His, Hyp or an alpha methyl amino
      acid
<220> FEATURE:
<221> NAME/KEY: MOD_RES
<222> LOCATION: (39)..(39)
<223> OTHER INFORMATION: Asn, Pro, Arg, Glu, 2,4-diaminobutanoic acid
      (Dab), Hyp or an alpha methyl amino acid
<220> FEATURE:
<221> NAME/KEY: MOD_RES
<222> LOCATION: (40)..(40)
<223> OTHER INFORMATION: Thr, Hyp or an alpha methyl amino acid
<220> FEATURE:
<221> NAME/KEY: MOD_RES
<222> LOCATION: (41)..(41)
<223> OTHER INFORMATION: Tyr, Pro, Hyp or an alpha methyl amino acid

<400> SEQUENCE: 175

Xaa Xaa Xaa Xaa Xaa Cys Asn Xaa Ala Thr Cys Ala Thr Gln Arg Leu
1               5                   10                  15

Ala Xaa Xaa Xaa Xaa His Ser Xaa Xaa Xaa Xaa Xaa Xaa Xaa Xaa
            20                  25                  30

Xaa Thr Xaa Xaa Xaa Xaa Xaa Xaa Xaa
        35                  40

<210> SEQ ID NO 176
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(albumin binding moiety) or absent
<220> FEATURE:
<221> NAME/KEY: MOD_RES
<222> LOCATION: (2)..(2)
<223> OTHER INFORMATION: Gly or absent
<220> FEATURE:
<221> NAME/KEY: MOD_RES
<222> LOCATION: (3)..(3)
<223> OTHER INFORMATION: Gly or absent
<220> FEATURE:
<221> NAME/KEY: MOD_RES
<222> LOCATION: (4)..(4)
<223> OTHER INFORMATION: Gly, Lys(albumin binding moiety) or absent
<220> FEATURE:
<221> NAME/KEY: MOD_RES
<222> LOCATION: (5)..(5)
<223> OTHER INFORMATION: Lys, Lys(albumin binding moiety) or absent
```

```
<220> FEATURE:
<221> NAME/KEY: MOD_RES
<222> LOCATION: (8)..(8)
<223> OTHER INFORMATION: Thr, Ile or Ala
<220> FEATURE:
<221> NAME/KEY: MOD_RES
<222> LOCATION: (18)..(18)
<223> OTHER INFORMATION: Asn, His, Glu, 2,4-diaminobutanoic acid (Dab),
      or an alpha methyl amino acid
<220> FEATURE:
<221> NAME/KEY: MOD_RES
<222> LOCATION: (19)..(19)
<223> OTHER INFORMATION: Phe or Trp
<220> FEATURE:
<221> NAME/KEY: MOD_RES
<222> LOCATION: (20)..(20)
<223> OTHER INFORMATION: Leu or D-Leu (dL)
<220> FEATURE:
<221> NAME/KEY: MOD_RES
<222> LOCATION: (21)..(21)
<223> OTHER INFORMATION: Val, Ser, Glu, Arg, (2S,4R)-4-
      hydroxypyrrolidine-2-carboxylic acid (Hyp), 2,4-diaminobutanoic
      acid (Dab) or an alpha methyl amino acid
<220> FEATURE:
<221> NAME/KEY: MOD_RES
<222> LOCATION: (24)..(24)
<223> OTHER INFORMATION: Ser, Ile, Pro or an alpha methyl amino acid
<220> FEATURE:
<221> NAME/KEY: MOD_RES
<222> LOCATION: (25)..(25)
<223> OTHER INFORMATION: Asn, 2,4-diaminobutanoic acid (Dab), His, Pro,
      Ser, Arg, Lys, Gly or Glu, Ala, Hyp or an alpha methyl amino acid
<220> FEATURE:
<221> NAME/KEY: MOD_RES
<222> LOCATION: (26)..(26)
<223> OTHER INFORMATION: Asn, His, Hyp, 2,4-diaminobutanoic acid (Dab)
      or an alpha methyl amino acid
<220> FEATURE:
<221> NAME/KEY: MOD_RES
<222> LOCATION: (27)..(27)
<223> OTHER INFORMATION: Phe, Hyp or an alpha methyl amino acid
<220> FEATURE:
<221> NAME/KEY: MOD_RES
<222> LOCATION: (28)..(28)
<223> OTHER INFORMATION: Gly, Pro, Hyp or an alpha methyl amino acid
<220> FEATURE:
<221> NAME/KEY: MOD_RES
<222> LOCATION: (29)..(29)
<223> OTHER INFORMATION: Pro, Ala, Hyp or an alpha methyl amino acid
<220> FEATURE:
<221> NAME/KEY: MOD_RES
<222> LOCATION: (30)..(30)
<223> OTHER INFORMATION: dI
<220> FEATURE:
<221> NAME/KEY: MOD_RES
<222> LOCATION: (31)..(31)
<223> OTHER INFORMATION: Leu, dL, Hyp or an alpha methyl amino acid
<220> FEATURE:
<221> NAME/KEY: MOD_RES
<222> LOCATION: (32)..(32)
<223> OTHER INFORMATION: Pro, D-Pro (dP), Ser, Hyp or an alpha methyl
      amino acid
<220> FEATURE:
<221> NAME/KEY: MOD_RES
<222> LOCATION: (33)..(33)
<223> OTHER INFORMATION: Pro, Hyp or an alpha methyl amino acid
<220> FEATURE:
<221> NAME/KEY: MOD_RES
<222> LOCATION: (35)..(35)
<223> OTHER INFORMATION: Asn, Glu, His, Arg, Pro, 2,4-diaminobutanoic
      acid (Dab) or an alpha methyl amino acid
<220> FEATURE:
<221> NAME/KEY: MOD_RES
<222> LOCATION: (36)..(36)
<223> OTHER INFORMATION: Val, Hyp, 2,4-diaminobutanoic acid (Dab) or an
      alpha methyl amino acid
<220> FEATURE:
<221> NAME/KEY: MOD_RES
<222> LOCATION: (37)..(37)
```

-continued

```
<223> OTHER INFORMATION: Gly, Pro, Hyp or an alpha methyl amino acid
<220> FEATURE:
<221> NAME/KEY: MOD_RES
<222> LOCATION: (38)..(38)
<223> OTHER INFORMATION: Ser, Pro, His, Hyp or an alpha methyl amino
      acid
<220> FEATURE:
<221> NAME/KEY: MOD_RES
<222> LOCATION: (39)..(39)
<223> OTHER INFORMATION: Asn, Pro, Arg, Glu, 2,4-diaminobutanoic acid
      (Dab), Hyp or an alpha methyl amino acid
<220> FEATURE:
<221> NAME/KEY: MOD_RES
<222> LOCATION: (40)..(40)
<223> OTHER INFORMATION: Thr, Hyp or an alpha methyl amino acid
<220> FEATURE:
<221> NAME/KEY: MOD_RES
<222> LOCATION: (41)..(41)
<223> OTHER INFORMATION: Tyr, Pro, Hyp or an alpha methyl amino acid

<400> SEQUENCE: 176

Xaa Xaa Xaa Xaa Xaa Cys Asn Xaa Ala Thr Cys Ala Thr Gln Arg Leu
1               5                   10                  15

Ala Xaa Xaa Xaa Xaa His Ser Xaa Xaa Xaa Xaa Xaa Ile Xaa Xaa
            20                  25                  30

Xaa Thr Xaa Xaa Xaa Xaa Xaa Xaa Xaa
        35                  40

<210> SEQ ID NO 177
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(albumin binding moiety) or absent
<220> FEATURE:
<221> NAME/KEY: MOD_RES
<222> LOCATION: (2)..(2)
<223> OTHER INFORMATION: Gly or absent
<220> FEATURE:
<221> NAME/KEY: MOD_RES
<222> LOCATION: (3)..(3)
<223> OTHER INFORMATION: Gly or absent
<220> FEATURE:
<221> NAME/KEY: MOD_RES
<222> LOCATION: (4)..(4)
<223> OTHER INFORMATION: Gly, Lys(albumin binding moiety) or absent
<220> FEATURE:
<221> NAME/KEY: MOD_RES
<222> LOCATION: (5)..(5)
<223> OTHER INFORMATION: Lys, Lys(albumin binding moiety) or absent
<220> FEATURE:
<221> NAME/KEY: MOD_RES
<222> LOCATION: (8)..(8)
<223> OTHER INFORMATION: Thr, Ile or Ala
<220> FEATURE:
<221> NAME/KEY: MOD_RES
<222> LOCATION: (18)..(18)
<223> OTHER INFORMATION: Asn, His, Glu, 2,4-diaminobutanoic acid (Dab),
      or an alpha methyl amino acid
<220> FEATURE:
<221> NAME/KEY: MOD_RES
<222> LOCATION: (19)..(19)
<223> OTHER INFORMATION: Phe or Trp
<220> FEATURE:
<221> NAME/KEY: MOD_RES
<222> LOCATION: (20)..(20)
<223> OTHER INFORMATION: Leu or D-Leu (dL)
<220> FEATURE:
<221> NAME/KEY: MOD_RES
<222> LOCATION: (21)..(21)
```

```
<223> OTHER INFORMATION: Val, Ser, Glu, Arg, (2S,4R)-4-
      hydroxypyrrolidine-2-carboxylic acid (Hyp), 2,4-diaminobutanoic
      acid (Dab) or an alpha methyl amino acid
<220> FEATURE:
<221> NAME/KEY: MOD_RES
<222> LOCATION: (24)..(24)
<223> OTHER INFORMATION: Ser, Ile, Pro or an alpha methyl amino acid
<220> FEATURE:
<221> NAME/KEY: MOD_RES
<222> LOCATION: (25)..(25)
<223> OTHER INFORMATION: Asn, 2,4-diaminobutanoic acid (Dab), His, Pro,
      Ser, Arg, Lys, Gly or Glu, Ala, Hyp  or an alpha methyl amino acid
<220> FEATURE:
<221> NAME/KEY: MOD_RES
<222> LOCATION: (26)..(26)
<223> OTHER INFORMATION: Asn, His, Hyp, 2,4-diaminobutanoic acid (Dab)
      or an alpha methyl amino acid
<220> FEATURE:
<221> NAME/KEY: MOD_RES
<222> LOCATION: (27)..(27)
<223> OTHER INFORMATION: Phe, Hyp or an alpha methyl amino acid
<220> FEATURE:
<221> NAME/KEY: MOD_RES
<222> LOCATION: (28)..(28)
<223> OTHER INFORMATION: Gly, Pro, Hyp or an alpha methyl amino acid
<220> FEATURE:
<221> NAME/KEY: MOD_RES
<222> LOCATION: (29)..(29)
<223> OTHER INFORMATION: Pro, Ala, Hyp or an alpha methyl amino acid
<220> FEATURE:
<221> NAME/KEY: MOD_RES
<222> LOCATION: (30)..(30)
<223> OTHER INFORMATION: Ile, D-Ile (dI), Arg, Hyp or an alpha methyl
      amino acid
<220> FEATURE:
<221> NAME/KEY: MOD_RES
<222> LOCATION: (31)..(31)
<223> OTHER INFORMATION: an alpha methyl amino acid
<220> FEATURE:
<221> NAME/KEY: MOD_RES
<222> LOCATION: (32)..(32)
<223> OTHER INFORMATION: Pro, D-Pro (dP), Ser, Hyp or an alpha methyl
      amino acid
<220> FEATURE:
<221> NAME/KEY: MOD_RES
<222> LOCATION: (33)..(33)
<223> OTHER INFORMATION: Pro, Hyp or an alpha methyl amino acid
<220> FEATURE:
<221> NAME/KEY: MOD_RES
<222> LOCATION: (35)..(35)
<223> OTHER INFORMATION: Asn, Glu, His, Arg, Pro, 2,4-diaminobutanoic
      acid (Dab) or an alpha methyl amino acid
<220> FEATURE:
<221> NAME/KEY: MOD_RES
<222> LOCATION: (36)..(36)
<223> OTHER INFORMATION: Val, Hyp, 2,4-diaminobutanoic acid (Dab) or an
      alpha methyl amino acid
<220> FEATURE:
<221> NAME/KEY: MOD_RES
<222> LOCATION: (37)..(37)
<223> OTHER INFORMATION: Gly, Pro, Hyp or an alpha methyl amino acid
<220> FEATURE:
<221> NAME/KEY: MOD_RES
<222> LOCATION: (38)..(38)
<223> OTHER INFORMATION: Ser, Pro, His, Hyp or an alpha methyl amino
      acid
<220> FEATURE:
<221> NAME/KEY: MOD_RES
<222> LOCATION: (39)..(39)
<223> OTHER INFORMATION: Asn, Pro, Arg, Glu, 2,4-diaminobutanoic acid
      (Dab), Hyp or an alpha methyl amino acid
<220> FEATURE:
<221> NAME/KEY: MOD_RES
<222> LOCATION: (40)..(40)
<223> OTHER INFORMATION: Thr, Hyp or an alpha methyl amino acid
<220> FEATURE:
<221> NAME/KEY: MOD_RES
<222> LOCATION: (41)..(41)
<223> OTHER INFORMATION: Tyr, Pro, Hyp or an alpha methyl amino acid
```

<400> SEQUENCE: 177

Xaa Xaa Xaa Xaa Xaa Cys Asn Xaa Ala Thr Cys Ala Thr Gln Arg Leu
1               5                   10                  15

Ala Xaa Xaa Xaa Xaa His Ser Xaa Xaa Xaa Xaa Xaa Xaa Xaa Xaa
            20                  25                  30

Xaa Thr Xaa Xaa Xaa Xaa Xaa Xaa Xaa
        35                  40

```
<210> SEQ ID NO 178
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(albumin binding moiety) or absent
<220> FEATURE:
<221> NAME/KEY: MOD_RES
<222> LOCATION: (2)..(2)
<223> OTHER INFORMATION: Gly or absent
<220> FEATURE:
<221> NAME/KEY: MOD_RES
<222> LOCATION: (3)..(3)
<223> OTHER INFORMATION: Gly or absent
<220> FEATURE:
<221> NAME/KEY: MOD_RES
<222> LOCATION: (4)..(4)
<223> OTHER INFORMATION: Gly, Lys(albumin binding moiety) or absent
<220> FEATURE:
<221> NAME/KEY: MOD_RES
<222> LOCATION: (5)..(5)
<223> OTHER INFORMATION: Lys, Lys(albumin binding moiety) or absent
<220> FEATURE:
<221> NAME/KEY: MOD_RES
<222> LOCATION: (8)..(8)
<223> OTHER INFORMATION: Thr, Ile or Ala
<220> FEATURE:
<221> NAME/KEY: MOD_RES
<222> LOCATION: (18)..(18)
<223> OTHER INFORMATION: Asn, His, Glu, 2,4-diaminobutanoic acid (Dab),
      or an alpha methyl amino acid
<220> FEATURE:
<221> NAME/KEY: MOD_RES
<222> LOCATION: (19)..(19)
<223> OTHER INFORMATION: Phe or Trp
<220> FEATURE:
<221> NAME/KEY: MOD_RES
<222> LOCATION: (20)..(20)
<223> OTHER INFORMATION: Leu or D-Leu (dL)
<220> FEATURE:
<221> NAME/KEY: MOD_RES
<222> LOCATION: (21)..(21)
<223> OTHER INFORMATION: Val, Ser, Glu, Arg, (2S,4R)-4-
      hydroxypyrrolidine-2-carboxylic acid (Hyp), 2,4-diaminobutanoic
      acid (Dab) or an alpha methyl amino acid
<220> FEATURE:
<221> NAME/KEY: MOD_RES
<222> LOCATION: (24)..(24)
<223> OTHER INFORMATION: Ser, Ile, Pro or an alpha methyl amino acid
<220> FEATURE:
<221> NAME/KEY: MOD_RES
<222> LOCATION: (25)..(25)
<223> OTHER INFORMATION: Asn, 2,4-diaminobutanoic acid (Dab), His, Pro,
      Ser, Arg, Lys, Gly or Glu, Ala, Hyp  or an alpha methyl amino acid
<220> FEATURE:
<221> NAME/KEY: MOD_RES
<222> LOCATION: (26)..(26)
<223> OTHER INFORMATION: Asn, His, Hyp, 2,4-diaminobutanoic acid (Dab)
      or an alpha methyl amino acid
<220> FEATURE:
<221> NAME/KEY: MOD_RES
```

```
<222> LOCATION: (27)..(27)
<223> OTHER INFORMATION: Phe, Hyp or an alpha methyl amino acid
<220> FEATURE:
<221> NAME/KEY: MOD_RES
<222> LOCATION: (28)..(28)
<223> OTHER INFORMATION: Gly, Pro, Hyp or an alpha methyl amino acid
<220> FEATURE:
<221> NAME/KEY: MOD_RES
<222> LOCATION: (29)..(29)
<223> OTHER INFORMATION: Pro, Ala, Hyp or an alpha methyl amino acid
<220> FEATURE:
<221> NAME/KEY: MOD_RES
<222> LOCATION: (30)..(30)
<223> OTHER INFORMATION: Ile, D-Ile (dI), Arg, Hyp or an alpha methyl
      amino acid
<220> FEATURE:
<221> NAME/KEY: MOD_RES
<222> LOCATION: (31)..(31)
<223> OTHER INFORMATION: dL
<220> FEATURE:
<221> NAME/KEY: MOD_RES
<222> LOCATION: (32)..(32)
<223> OTHER INFORMATION: Pro, D-Pro (dP), Ser, Hyp or an alpha methyl
      amino acid
<220> FEATURE:
<221> NAME/KEY: MOD_RES
<222> LOCATION: (33)..(33)
<223> OTHER INFORMATION: Pro, Hyp or an alpha methyl amino acid
<220> FEATURE:
<221> NAME/KEY: MOD_RES
<222> LOCATION: (35)..(35)
<223> OTHER INFORMATION: Asn, Glu, His, Arg, Pro, 2,4-diaminobutanoic
      acid (Dab) or an alpha methyl amino acid
<220> FEATURE:
<221> NAME/KEY: MOD_RES
<222> LOCATION: (36)..(36)
<223> OTHER INFORMATION: Val, Hyp, 2,4-diaminobutanoic acid (Dab) or an
      alpha methyl amino acid
<220> FEATURE:
<221> NAME/KEY: MOD_RES
<222> LOCATION: (37)..(37)
<223> OTHER INFORMATION: Gly, Pro, Hyp or an alpha methyl amino acid
<220> FEATURE:
<221> NAME/KEY: MOD_RES
<222> LOCATION: (38)..(38)
<223> OTHER INFORMATION: Ser, Pro, His, Hyp or an alpha methyl amino
      acid
<220> FEATURE:
<221> NAME/KEY: MOD_RES
<222> LOCATION: (39)..(39)
<223> OTHER INFORMATION: Asn, Pro, Arg, Glu, 2,4-diaminobutanoic acid
      (Dab), Hyp or an alpha methyl amino acid
<220> FEATURE:
<221> NAME/KEY: MOD_RES
<222> LOCATION: (40)..(40)
<223> OTHER INFORMATION: Thr, Hyp or an alpha methyl amino acid
<220> FEATURE:
<221> NAME/KEY: MOD_RES
<222> LOCATION: (41)..(41)
<223> OTHER INFORMATION: Tyr, Pro, Hyp or an alpha methyl amino acid

<400> SEQUENCE: 178

Xaa Xaa Xaa Xaa Xaa Cys Asn Xaa Ala Thr Cys Ala Thr Gln Arg Leu
1               5                   10                  15

Ala Xaa Xaa Xaa Xaa His Ser Xaa Xaa Xaa Xaa Xaa Xaa Xaa Leu Xaa
            20                  25                  30

Xaa Thr Xaa Xaa Xaa Xaa Xaa Xaa Xaa
        35                  40

<210> SEQ ID NO 179
<211> LENGTH: 41
<212> TYPE: PRT
<213> ORGANISM: Artificial Sequence
<220> FEATURE:
<223> OTHER INFORMATION: Description of Artificial Sequence: Synthetic
```

```
           polypeptide
<220> FEATURE:
<221> NAME/KEY: MOD_RES
<222> LOCATION: (1)..(1)
<223> OTHER INFORMATION: Lys(albumin binding moiety) or absent
<220> FEATURE:
<221> NAME/KEY: MOD_RES
<222> LOCATION: (2)..(2)
<223> OTHER INFORMATION: Gly or absent
<220> FEATURE:
<221> NAME/KEY: MOD_RES
<222> LOCATION: (3)..(3)
<223> OTHER INFORMATION: Gly or absent
<220> FEATURE:
<221> NAME/KEY: MOD_RES
<222> LOCATION: (4)..(4)
<223> OTHER INFORMATION: Gly, Lys(albumin binding moiety) or absent
<220> FEATURE:
<221> NAME/KEY: MOD_RES
<222> LOCATION: (5)..(5)
<223> OTHER INFORMATION: Lys, Lys(albumin binding moiety) or absent
<220> FEATURE:
<221> NAME/KEY: MOD_RES
<222> LOCATION: (8)..(8)
<223> OTHER INFORMATION: Thr, Ile or Ala
<220> FEATURE:
<221> NAME/KEY: MOD_RES
<222> LOCATION: (18)..(18)
<223> OTHER INFORMATION: Asn, His, Glu, 2,4-diaminobutanoic acid (Dab),
      or an alpha methyl amino acid
<220> FEATURE:
<221> NAME/KEY: MOD_RES
<222> LOCATION: (19)..(19)
<223> OTHER INFORMATION: Phe or Trp
<220> FEATURE:
<221> NAME/KEY: MOD_RES
<222> LOCATION: (20)..(20)
<223> OTHER INFORMATION: Leu or D-Leu (dL)
<220> FEATURE:
<221> NAME/KEY: MOD_RES
<222> LOCATION: (21)..(21)
<223> OTHER INFORMATION: Val, Ser, Glu, Arg, (2S,4R)-4-
      hydroxypyrrolidine-2-carboxylic acid (Hyp), 2,4-diaminobutanoic
      acid (Dab) or an alpha methyl amino acid
<220> FEATURE:
<221> NAME/KEY: MOD_RES
<222> LOCATION: (24)..(24)
<223> OTHER INFORMATION: Ser, Ile, Pro or an alpha methyl amino acid
<220> FEATURE:
<221> NAME/KEY: MOD_RES
<222> LOCATION: (25)..(25)
<223> OTHER INFORMATION: Asn, 2,4-diaminobutanoic acid (Dab), His, Pro,
      Ser, Arg, Lys, Gly or Glu, Ala, Hyp or an alpha methyl amino acid
<220> FEATURE:
<221> NAME/KEY: MOD_RES
<222> LOCATION: (26)..(26)
<223> OTHER INFORMATION: Asn, His, Hyp, 2,4-diaminobutanoic acid (Dab)
      or an alpha methyl amino acid
<220> FEATURE:
<221> NAME/KEY: MOD_RES
<222> LOCATION: (27)..(27)
<223> OTHER INFORMATION: Phe, Hyp or an alpha methyl amino acid
<220> FEATURE:
<221> NAME/KEY: MOD_RES
<222> LOCATION: (28)..(28)
<223> OTHER INFORMATION: Gly, Pro, Hyp or an alpha methyl amino acid
<220> FEATURE:
<221> NAME/KEY: MOD_RES
<222> LOCATION: (29)..(29)
<223> OTHER INFORMATION: Pro, Ala, Hyp or an alpha methyl amino acid
<220> FEATURE:
<221> NAME/KEY: MOD_RES
<222> LOCATION: (30)..(30)
<223> OTHER INFORMATION: Ile, D-Ile (dI), Arg, Hyp or an alpha methyl
      amino acid
<220> FEATURE:
<221> NAME/KEY: MOD_RES
<222> LOCATION: (31)..(31)
<223> OTHER INFORMATION: Leu, dL, Hyp or an alpha methyl amino acid
```

```
<220> FEATURE:
<221> NAME/KEY: MOD_RES
<222> LOCATION: (32)..(32)
<223> OTHER INFORMATION: an alpha methyl amino acid
<220> FEATURE:
<221> NAME/KEY: MOD_RES
<222> LOCATION: (33)..(33)
<223> OTHER INFORMATION: Pro, Hyp or an alpha methyl amino acid
<220> FEATURE:
<221> NAME/KEY: MOD_RES
<222> LOCATION: (35)..(35)
<223> OTHER INFORMATION: Asn, Glu, His, Arg, Pro, 2,4-diaminobutanoic
      acid (Dab) or an alpha methyl amino acid
<220> FEATURE:
<221> NAME/KEY: MOD_RES
<222> LOCATION: (36)..(36)
<223> OTHER INFORMATION: Val, Hyp, 2,4-diaminobutanoic acid (Dab) or an
      alpha methyl amino acid
<220> FEATURE:
<221> NAME/KEY: MOD_RES
<222> LOCATION: (37)..(37)
<223> OTHER INFORMATION: Gly, Pro, Hyp or an alpha methyl amino acid
<220> FEATURE:
<221> NAME/KEY: MOD_RES
<222> LOCATION: (38)..(38)
<223> OTHER INFORMATION: Ser, Pro, His, Hyp or an alpha methyl amino
      acid
<220> FEATURE:
<221> NAME/KEY: MOD_RES
<222> LOCATION: (39)..(39)
<223> OTHER INFORMATION: Asn, Pro, Arg, Glu, 2,4-diaminobutanoic acid
      (Dab), Hyp or an alpha methyl amino acid
<220> FEATURE:
<221> NAME/KEY: MOD_RES
<222> LOCATION: (40)..(40)
<223> OTHER INFORMATION: Thr, Hyp or an alpha methyl amino acid
<220> FEATURE:
<221> NAME/KEY: MOD_RES
<222> LOCATION: (41)..(41)
<223> OTHER INFORMATION: Tyr, Pro, Hyp or an alpha methyl amino acid

<400> SEQUENCE: 179

Xaa Xaa Xaa Xaa Xaa Cys Asn Xaa Ala Thr Cys Ala Thr Gln Arg Leu
1               5                   10                  15

Ala Xaa Xaa Xaa Xaa His Ser Xaa Xaa Xaa Xaa Xaa Xaa Xaa Xaa Xaa
            20                  25                  30

Xaa Thr Xaa Xaa Xaa Xaa Xaa Xaa Xaa
        35                  40

<210> SEQ ID NO 180
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(albumin binding moiety) or absent
<220> FEATURE:
<221> NAME/KEY: MOD_RES
<222> LOCATION: (2)..(2)
<223> OTHER INFORMATION: Gly or absent
<220> FEATURE:
<221> NAME/KEY: MOD_RES
<222> LOCATION: (3)..(3)
<223> OTHER INFORMATION: Gly or absent
<220> FEATURE:
<221> NAME/KEY: MOD_RES
<222> LOCATION: (4)..(4)
<223> OTHER INFORMATION: Gly, Lys(albumin binding moiety) or absent
<220> FEATURE:
<221> NAME/KEY: MOD_RES
<222> LOCATION: (5)..(5)
```

```
<223> OTHER INFORMATION: Lys, Lys(albumin binding moiety) or absent
<220> FEATURE:
<221> NAME/KEY: MOD_RES
<222> LOCATION: (8)..(8)
<223> OTHER INFORMATION: Thr, Ile or Ala
<220> FEATURE:
<221> NAME/KEY: MOD_RES
<222> LOCATION: (18)..(18)
<223> OTHER INFORMATION: Asn, His, Glu, 2,4-diaminobutanoic acid (Dab),
      or an alpha methyl amino acid
<220> FEATURE:
<221> NAME/KEY: MOD_RES
<222> LOCATION: (19)..(19)
<223> OTHER INFORMATION: Phe or Trp
<220> FEATURE:
<221> NAME/KEY: MOD_RES
<222> LOCATION: (20)..(20)
<223> OTHER INFORMATION: Leu or D-Leu (dL)
<220> FEATURE:
<221> NAME/KEY: MOD_RES
<222> LOCATION: (21)..(21)
<223> OTHER INFORMATION: Val, Ser, Glu, Arg, (2S,4R)-4-
      hydroxypyrrolidine-2-carboxylic acid (Hyp), 2,4-diaminobutanoic
      acid (Dab) or an alpha methyl amino acid
<220> FEATURE:
<221> NAME/KEY: MOD_RES
<222> LOCATION: (24)..(24)
<223> OTHER INFORMATION: Ser, Ile, Pro or an alpha methyl amino acid
<220> FEATURE:
<221> NAME/KEY: MOD_RES
<222> LOCATION: (25)..(25)
<223> OTHER INFORMATION: Asn, 2,4-diaminobutanoic acid (Dab), His, Pro,
      Ser, Arg, Lys, Gly or Glu, Ala, Hyp  or an alpha methyl amino acid
<220> FEATURE:
<221> NAME/KEY: MOD_RES
<222> LOCATION: (26)..(26)
<223> OTHER INFORMATION: Asn, His, Hyp, 2,4-diaminobutanoic acid (Dab)
      or an alpha methyl amino acid
<220> FEATURE:
<221> NAME/KEY: MOD_RES
<222> LOCATION: (27)..(27)
<223> OTHER INFORMATION: Phe, Hyp or an alpha methyl amino acid
<220> FEATURE:
<221> NAME/KEY: MOD_RES
<222> LOCATION: (28)..(28)
<223> OTHER INFORMATION: Gly, Pro, Hyp or an alpha methyl amino acid
<220> FEATURE:
<221> NAME/KEY: MOD_RES
<222> LOCATION: (29)..(29)
<223> OTHER INFORMATION: Pro, Ala, Hyp or an alpha methyl amino acid
<220> FEATURE:
<221> NAME/KEY: MOD_RES
<222> LOCATION: (30)..(30)
<223> OTHER INFORMATION: Ile, D-Ile (dI), Arg, Hyp or an alpha methyl
      amino acid
<220> FEATURE:
<221> NAME/KEY: MOD_RES
<222> LOCATION: (31)..(31)
<223> OTHER INFORMATION: Leu, dL, Hyp or an alpha methyl amino acid
<220> FEATURE:
<221> NAME/KEY: MOD_RES
<222> LOCATION: (32)..(32)
<223> OTHER INFORMATION: dP
<220> FEATURE:
<221> NAME/KEY: MOD_RES
<222> LOCATION: (33)..(33)
<223> OTHER INFORMATION: Pro, Hyp or an alpha methyl amino acid
<220> FEATURE:
<221> NAME/KEY: MOD_RES
<222> LOCATION: (35)..(35)
<223> OTHER INFORMATION: Asn, Glu, His, Arg, Pro, 2,4-diaminobutanoic
      acid (Dab) or an alpha methyl amino acid
<220> FEATURE:
<221> NAME/KEY: MOD_RES
<222> LOCATION: (36)..(36)
<223> OTHER INFORMATION: Val, Hyp, 2,4-diaminobutanoic acid (Dab) or an
      alpha methyl amino acid
<220> FEATURE:
<221> NAME/KEY: MOD_RES
```

```
-continued

<222> LOCATION: (37)..(37)
<223> OTHER INFORMATION: Gly, Pro, Hyp or an alpha methyl amino acid
<220> FEATURE:
<221> NAME/KEY: MOD_RES
<222> LOCATION: (38)..(38)
<223> OTHER INFORMATION: Ser, Pro, His, Hyp or an alpha methyl amino
      acid
<220> FEATURE:
<221> NAME/KEY: MOD_RES
<222> LOCATION: (39)..(39)
<223> OTHER INFORMATION: Asn, Pro, Arg, Glu, 2,4-diaminobutanoic acid
      (Dab), Hyp or an alpha methyl amino acid
<220> FEATURE:
<221> NAME/KEY: MOD_RES
<222> LOCATION: (40)..(40)
<223> OTHER INFORMATION: Thr, Hyp or an alpha methyl amino acid
<220> FEATURE:
<221> NAME/KEY: MOD_RES
<222> LOCATION: (41)..(41)
<223> OTHER INFORMATION: Tyr, Pro, Hyp or an alpha methyl amino acid

<400> SEQUENCE: 180

Xaa Xaa Xaa Xaa Xaa Cys Asn Xaa Ala Thr Cys Ala Thr Gln Arg Leu
1               5                   10                  15

Ala Xaa Xaa Xaa Xaa His Ser Xaa Xaa Xaa Xaa Xaa Xaa Xaa Pro
            20                  25                  30

Xaa Thr Xaa Xaa Xaa Xaa Xaa Xaa Xaa
        35                  40

<210> SEQ ID NO 181
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(albumin binding moiety) or absent
<220> FEATURE:
<221> NAME/KEY: MOD_RES
<222> LOCATION: (2)..(2)
<223> OTHER INFORMATION: Gly or absent
<220> FEATURE:
<221> NAME/KEY: MOD_RES
<222> LOCATION: (3)..(3)
<223> OTHER INFORMATION: Gly or absent
<220> FEATURE:
<221> NAME/KEY: MOD_RES
<222> LOCATION: (4)..(4)
<223> OTHER INFORMATION: Gly, Lys(albumin binding moiety) or absent
<220> FEATURE:
<221> NAME/KEY: MOD_RES
<222> LOCATION: (5)..(5)
<223> OTHER INFORMATION: Lys, Lys(albumin binding moiety) or absent
<220> FEATURE:
<221> NAME/KEY: MOD_RES
<222> LOCATION: (8)..(8)
<223> OTHER INFORMATION: Thr, Ile or Ala
<220> FEATURE:
<221> NAME/KEY: MOD_RES
<222> LOCATION: (18)..(18)
<223> OTHER INFORMATION: Asn, His, Glu, 2,4-diaminobutanoic acid (Dab),
      or an alpha methyl amino acid
<220> FEATURE:
<221> NAME/KEY: MOD_RES
<222> LOCATION: (19)..(19)
<223> OTHER INFORMATION: Phe or Trp
<220> FEATURE:
<221> NAME/KEY: MOD_RES
<222> LOCATION: (20)..(20)
<223> OTHER INFORMATION: Leu or D-Leu (dL)
<220> FEATURE:
<221> NAME/KEY: MOD_RES
```

```
<222> LOCATION: (21)..(21)
<223> OTHER INFORMATION: Val, Ser, Glu, Arg, (2S,4R)-4-
      hydroxypyrrolidine-2-carboxylic acid (Hyp), 2,4-diaminobutanoic
      acid (Dab) or an alpha methyl amino acid
<220> FEATURE:
<221> NAME/KEY: MOD_RES
<222> LOCATION: (24)..(24)
<223> OTHER INFORMATION: Ser, Ile, Pro or an alpha methyl amino acid
<220> FEATURE:
<221> NAME/KEY: MOD_RES
<222> LOCATION: (25)..(25)
<223> OTHER INFORMATION: Asn, 2,4-diaminobutanoic acid (Dab), His, Pro,
      Ser, Arg, Lys, Gly or Glu, Ala, Hyp  or an alpha methyl amino acid
<220> FEATURE:
<221> NAME/KEY: MOD_RES
<222> LOCATION: (26)..(26)
<223> OTHER INFORMATION: Asn, His, Hyp, 2,4-diaminobutanoic acid (Dab)
      or an alpha methyl amino acid
<220> FEATURE:
<221> NAME/KEY: MOD_RES
<222> LOCATION: (27)..(27)
<223> OTHER INFORMATION: Phe, Hyp or an alpha methyl amino acid
<220> FEATURE:
<221> NAME/KEY: MOD_RES
<222> LOCATION: (28)..(28)
<223> OTHER INFORMATION: Gly, Pro, Hyp or an alpha methyl amino acid
<220> FEATURE:
<221> NAME/KEY: MOD_RES
<222> LOCATION: (29)..(29)
<223> OTHER INFORMATION: Pro, Ala, Hyp or an alpha methyl amino acid
<220> FEATURE:
<221> NAME/KEY: MOD_RES
<222> LOCATION: (30)..(30)
<223> OTHER INFORMATION: Ile, D-Ile (dI), Arg, Hyp or an alpha methyl
      amino acid
<220> FEATURE:
<221> NAME/KEY: MOD_RES
<222> LOCATION: (31)..(31)
<223> OTHER INFORMATION: Leu, dL, Hyp or an alpha methyl amino acid
<220> FEATURE:
<221> NAME/KEY: MOD_RES
<222> LOCATION: (32)..(32)
<223> OTHER INFORMATION: Pro, D-Pro (dP), Ser, Hyp or an alpha methyl
      amino acid
<220> FEATURE:
<221> NAME/KEY: MOD_RES
<222> LOCATION: (33)..(33)
<223> OTHER INFORMATION: an alpha methyl amino acid
<220> FEATURE:
<221> NAME/KEY: MOD_RES
<222> LOCATION: (35)..(35)
<223> OTHER INFORMATION: Asn, Glu, His, Arg, Pro, 2,4-diaminobutanoic
      acid (Dab) or an alpha methyl amino acid
<220> FEATURE:
<221> NAME/KEY: MOD_RES
<222> LOCATION: (36)..(36)
<223> OTHER INFORMATION: Val, Hyp, 2,4-diaminobutanoic acid (Dab) or an
      alpha methyl amino acid
<220> FEATURE:
<221> NAME/KEY: MOD_RES
<222> LOCATION: (37)..(37)
<223> OTHER INFORMATION: Gly, Pro, Hyp or an alpha methyl amino acid
<220> FEATURE:
<221> NAME/KEY: MOD_RES
<222> LOCATION: (38)..(38)
<223> OTHER INFORMATION: Ser, Pro, His, Hyp or an alpha methyl amino
      acid
<220> FEATURE:
<221> NAME/KEY: MOD_RES
<222> LOCATION: (39)..(39)
<223> OTHER INFORMATION: Asn, Pro, Arg, Glu, 2,4-diaminobutanoic acid
      (Dab), Hyp or an alpha methyl amino acid
<220> FEATURE:
<221> NAME/KEY: MOD_RES
<222> LOCATION: (40)..(40)
<223> OTHER INFORMATION: Thr, Hyp or an alpha methyl amino acid
<220> FEATURE:
<221> NAME/KEY: MOD_RES
<222> LOCATION: (41)..(41)
```

<223> OTHER INFORMATION: Tyr, Pro, Hyp or an alpha methyl amino acid

<400> SEQUENCE: 181

```
Xaa Xaa Xaa Xaa Xaa Cys Asn Xaa Ala Thr Cys Ala Thr Gln Arg Leu
1               5                   10                  15
Ala Xaa Xaa Xaa Xaa His Ser Xaa Xaa Xaa Xaa Xaa Xaa Xaa Xaa
            20                  25                  30
Xaa Thr Xaa Xaa Xaa Xaa Xaa Xaa Xaa
        35                  40
```

<210> SEQ ID NO 182
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(albumin binding moiety) or absent
<220> FEATURE:
<221> NAME/KEY: MOD_RES
<222> LOCATION: (2)..(2)
<223> OTHER INFORMATION: Gly or absent
<220> FEATURE:
<221> NAME/KEY: MOD_RES
<222> LOCATION: (3)..(3)
<223> OTHER INFORMATION: Gly or absent
<220> FEATURE:
<221> NAME/KEY: MOD_RES
<222> LOCATION: (4)..(4)
<223> OTHER INFORMATION: Gly, Lys(albumin binding moiety) or absent
<220> FEATURE:
<221> NAME/KEY: MOD_RES
<222> LOCATION: (5)..(5)
<223> OTHER INFORMATION: Lys, Lys(albumin binding moiety) or absent
<220> FEATURE:
<221> NAME/KEY: MOD_RES
<222> LOCATION: (8)..(8)
<223> OTHER INFORMATION: Thr, Ile or Ala
<220> FEATURE:
<221> NAME/KEY: MOD_RES
<222> LOCATION: (18)..(18)
<223> OTHER INFORMATION: Asn, His, Glu, 2,4-diaminobutanoic acid (Dab),
      or an alpha methyl amino acid
<220> FEATURE:
<221> NAME/KEY: MOD_RES
<222> LOCATION: (19)..(19)
<223> OTHER INFORMATION: Phe or Trp
<220> FEATURE:
<221> NAME/KEY: MOD_RES
<222> LOCATION: (20)..(20)
<223> OTHER INFORMATION: Leu or D-Leu (dL)
<220> FEATURE:
<221> NAME/KEY: MOD_RES
<222> LOCATION: (21)..(21)
<223> OTHER INFORMATION: Val, Ser, Glu, Arg, (2S,4R)-4-
      hydroxypyrrolidine-2-carboxylic acid (Hyp), 2,4-diaminobutanoic
      acid (Dab) or an alpha methyl amino acid
<220> FEATURE:
<221> NAME/KEY: MOD_RES
<222> LOCATION: (24)..(24)
<223> OTHER INFORMATION: Ser, Ile, Pro or an alpha methyl amino acid
<220> FEATURE:
<221> NAME/KEY: MOD_RES
<222> LOCATION: (25)..(25)
<223> OTHER INFORMATION: Asn, 2,4-diaminobutanoic acid (Dab), His, Pro,
      Ser, Arg, Lys, Gly or Glu, Ala, Hyp  or an alpha methyl amino acid
<220> FEATURE:
<221> NAME/KEY: MOD_RES
<222> LOCATION: (26)..(26)
<223> OTHER INFORMATION: Asn, His, Hyp, 2,4-diaminobutanoic acid (Dab)
      or an alpha methyl amino acid
<220> FEATURE:

<220> FEATURE:
<221> NAME/KEY: MOD_RES
<222> LOCATION: (27)..(27)
<223> OTHER INFORMATION: Phe, Hyp or an alpha methyl amino acid
<220> FEATURE:
<221> NAME/KEY: MOD_RES
<222> LOCATION: (28)..(28)
<223> OTHER INFORMATION: Gly, Pro, Hyp or an alpha methyl amino acid
<220> FEATURE:
<221> NAME/KEY: MOD_RES
<222> LOCATION: (29)..(29)
<223> OTHER INFORMATION: Pro, Ala, Hyp or an alpha methyl amino acid
<220> FEATURE:
<221> NAME/KEY: MOD_RES
<222> LOCATION: (30)..(30)
<223> OTHER INFORMATION: Ile, D-Ile (dI), Arg, Hyp or an alpha methyl
      amino acid
<220> FEATURE:
<221> NAME/KEY: MOD_RES
<222> LOCATION: (31)..(31)
<223> OTHER INFORMATION: Leu, dL, Hyp or an alpha methyl amino acid
<220> FEATURE:
<221> NAME/KEY: MOD_RES
<222> LOCATION: (32)..(32)
<223> OTHER INFORMATION: Pro, D-Pro (dP), Ser, Hyp or an alpha methyl
      amino acid
<220> FEATURE:
<221> NAME/KEY: MOD_RES
<222> LOCATION: (33)..(33)
<223> OTHER INFORMATION: Pro, Hyp or an alpha methyl amino acid
<220> FEATURE:
<221> NAME/KEY: MOD_RES
<222> LOCATION: (35)..(35)
<223> OTHER INFORMATION: an alpha methyl amino acid
<220> FEATURE:
<221> NAME/KEY: MOD_RES
<222> LOCATION: (36)..(36)
<223> OTHER INFORMATION: Val, Hyp, 2,4-diaminobutanoic acid (Dab) or an
      alpha methyl amino acid
<220> FEATURE:
<221> NAME/KEY: MOD_RES
<222> LOCATION: (37)..(37)
<223> OTHER INFORMATION: Gly, Pro, Hyp or an alpha methyl amino acid
<220> FEATURE:
<221> NAME/KEY: MOD_RES
<222> LOCATION: (38)..(38)
<223> OTHER INFORMATION: Ser, Pro, His, Hyp or an alpha methyl amino
      acid
<220> FEATURE:
<221> NAME/KEY: MOD_RES
<222> LOCATION: (39)..(39)
<223> OTHER INFORMATION: Asn, Pro, Arg, Glu, 2,4-diaminobutanoic acid
      (Dab), Hyp or an alpha methyl amino acid
<220> FEATURE:
<221> NAME/KEY: MOD_RES
<222> LOCATION: (40)..(40)
<223> OTHER INFORMATION: Thr, Hyp or an alpha methyl amino acid
<220> FEATURE:
<221> NAME/KEY: MOD_RES
<222> LOCATION: (41)..(41)
<223> OTHER INFORMATION: Tyr, Pro, Hyp or an alpha methyl amino acid

<400> SEQUENCE: 182

Xaa Xaa Xaa Xaa Xaa Cys Asn Xaa Ala Thr Cys Ala Thr Gln Arg Leu
1               5                   10                  15

Ala Xaa Xaa Xaa Xaa His Ser Xaa Xaa Xaa Xaa Xaa Xaa Xaa Xaa
            20                  25                  30

Xaa Thr Xaa Xaa Xaa Xaa Xaa Xaa Xaa
        35                  40

<210> SEQ ID NO 183
<211> LENGTH: 41
<212> TYPE: PRT
<213> ORGANISM: Artificial Sequence
<220> FEATURE:
<223> OTHER INFORMATION: Description of Artificial Sequence: Synthetic

```
            polypeptide
<220> FEATURE:
<221> NAME/KEY: MOD_RES
<222> LOCATION: (1)..(1)
<223> OTHER INFORMATION: Lys(albumin binding moiety) or absent
<220> FEATURE:
<221> NAME/KEY: MOD_RES
<222> LOCATION: (2)..(2)
<223> OTHER INFORMATION: Gly or absent
<220> FEATURE:
<221> NAME/KEY: MOD_RES
<222> LOCATION: (3)..(3)
<223> OTHER INFORMATION: Gly or absent
<220> FEATURE:
<221> NAME/KEY: MOD_RES
<222> LOCATION: (4)..(4)
<223> OTHER INFORMATION: Gly, Lys(albumin binding moiety) or absent
<220> FEATURE:
<221> NAME/KEY: MOD_RES
<222> LOCATION: (5)..(5)
<223> OTHER INFORMATION: Lys, Lys(albumin binding moiety) or absent
<220> FEATURE:
<221> NAME/KEY: MOD_RES
<222> LOCATION: (8)..(8)
<223> OTHER INFORMATION: Thr, Ile or Ala
<220> FEATURE:
<221> NAME/KEY: MOD_RES
<222> LOCATION: (18)..(18)
<223> OTHER INFORMATION: Asn, His, Glu, 2,4-diaminobutanoic acid (Dab),
      or an alpha methyl amino acid
<220> FEATURE:
<221> NAME/KEY: MOD_RES
<222> LOCATION: (19)..(19)
<223> OTHER INFORMATION: Phe or Trp
<220> FEATURE:
<221> NAME/KEY: MOD_RES
<222> LOCATION: (20)..(20)
<223> OTHER INFORMATION: Leu or D-Leu (dL)
<220> FEATURE:
<221> NAME/KEY: MOD_RES
<222> LOCATION: (21)..(21)
<223> OTHER INFORMATION: Val, Ser, Glu, Arg, (2S,4R)-4-
      hydroxypyrrolidine-2-carboxylic acid (Hyp), 2,4-diaminobutanoic
      acid (Dab) or an alpha methyl amino acid
<220> FEATURE:
<221> NAME/KEY: MOD_RES
<222> LOCATION: (24)..(24)
<223> OTHER INFORMATION: Ser, Ile, Pro or an alpha methyl amino acid
<220> FEATURE:
<221> NAME/KEY: MOD_RES
<222> LOCATION: (25)..(25)
<223> OTHER INFORMATION: Asn, 2,4-diaminobutanoic acid (Dab), His, Pro,
      Ser, Arg, Lys, Gly or Glu, Ala, Hyp  or an alpha methyl amino acid
<220> FEATURE:
<221> NAME/KEY: MOD_RES
<222> LOCATION: (26)..(26)
<223> OTHER INFORMATION: Asn, His, Hyp, 2,4-diaminobutanoic acid (Dab)
      or an alpha methyl amino acid
<220> FEATURE:
<221> NAME/KEY: MOD_RES
<222> LOCATION: (27)..(27)
<223> OTHER INFORMATION: Phe, Hyp or an alpha methyl amino acid
<220> FEATURE:
<221> NAME/KEY: MOD_RES
<222> LOCATION: (28)..(28)
<223> OTHER INFORMATION: Gly, Pro, Hyp or an alpha methyl amino acid
<220> FEATURE:
<221> NAME/KEY: MOD_RES
<222> LOCATION: (29)..(29)
<223> OTHER INFORMATION: Pro, Ala, Hyp or an alpha methyl amino acid
<220> FEATURE:
<221> NAME/KEY: MOD_RES
<222> LOCATION: (30)..(30)
<223> OTHER INFORMATION: Ile, D-Ile (dI), Arg, Hyp or an alpha methyl
      amino acid
<220> FEATURE:
<221> NAME/KEY: MOD_RES
<222> LOCATION: (31)..(31)
<223> OTHER INFORMATION: Leu, dL, Hyp or an alpha methyl amino acid
```

```
<220> FEATURE:
<221> NAME/KEY: MOD_RES
<222> LOCATION: (32)..(32)
<223> OTHER INFORMATION: Pro, D-Pro (dP), Ser, Hyp or an alpha methyl
      amino acid
<220> FEATURE:
<221> NAME/KEY: MOD_RES
<222> LOCATION: (33)..(33)
<223> OTHER INFORMATION: Pro, Hyp or an alpha methyl amino acid
<220> FEATURE:
<221> NAME/KEY: MOD_RES
<222> LOCATION: (35)..(35)
<223> OTHER INFORMATION: 2,4-diaminobutanoic acid (Dab)
<220> FEATURE:
<221> NAME/KEY: MOD_RES
<222> LOCATION: (36)..(36)
<223> OTHER INFORMATION: Val, Hyp, 2,4-diaminobutanoic acid (Dab) or an
      alpha methyl amino acid
<220> FEATURE:
<221> NAME/KEY: MOD_RES
<222> LOCATION: (37)..(37)
<223> OTHER INFORMATION: Gly, Pro, Hyp or an alpha methyl amino acid
<220> FEATURE:
<221> NAME/KEY: MOD_RES
<222> LOCATION: (38)..(38)
<223> OTHER INFORMATION: Ser, Pro, His, Hyp or an alpha methyl amino
      acid
<220> FEATURE:
<221> NAME/KEY: MOD_RES
<222> LOCATION: (39)..(39)
<223> OTHER INFORMATION: Asn, Pro, Arg, Glu, 2,4-diaminobutanoic acid
      (Dab), Hyp or an alpha methyl amino acid
<220> FEATURE:
<221> NAME/KEY: MOD_RES
<222> LOCATION: (40)..(40)
<223> OTHER INFORMATION: Thr, Hyp or an alpha methyl amino acid
<220> FEATURE:
<221> NAME/KEY: MOD_RES
<222> LOCATION: (41)..(41)
<223> OTHER INFORMATION: Tyr, Pro, Hyp or an alpha methyl amino acid

<400> SEQUENCE: 183

Xaa Xaa Xaa Xaa Xaa Cys Asn Xaa Ala Thr Cys Ala Thr Gln Arg Leu
1               5                   10                  15

Ala Xaa Xaa Xaa Xaa His Ser Xaa Xaa Xaa Xaa Xaa Xaa Xaa Xaa Xaa
            20                  25                  30

Xaa Thr Xaa Xaa Xaa Xaa Xaa Xaa Xaa
        35                  40

<210> SEQ ID NO 184
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(albumin binding moiety) or absent
<220> FEATURE:
<221> NAME/KEY: MOD_RES
<222> LOCATION: (2)..(2)
<223> OTHER INFORMATION: Gly or absent
<220> FEATURE:
<221> NAME/KEY: MOD_RES
<222> LOCATION: (3)..(3)
<223> OTHER INFORMATION: Gly or absent
<220> FEATURE:
<221> NAME/KEY: MOD_RES
<222> LOCATION: (4)..(4)
<223> OTHER INFORMATION: Gly, Lys(albumin binding moiety) or absent
<220> FEATURE:
<221> NAME/KEY: MOD_RES
<222> LOCATION: (5)..(5)
```

```
<223> OTHER INFORMATION: Lys, Lys(albumin binding moiety) or absent
<220> FEATURE:
<221> NAME/KEY: MOD_RES
<222> LOCATION: (8)..(8)
<223> OTHER INFORMATION: Thr, Ile or Ala
<220> FEATURE:
<221> NAME/KEY: MOD_RES
<222> LOCATION: (18)..(18)
<223> OTHER INFORMATION: Asn, His, Glu, 2,4-diaminobutanoic acid (Dab),
      or an alpha methyl amino acid
<220> FEATURE:
<221> NAME/KEY: MOD_RES
<222> LOCATION: (19)..(19)
<223> OTHER INFORMATION: Phe or Trp
<220> FEATURE:
<221> NAME/KEY: MOD_RES
<222> LOCATION: (20)..(20)
<223> OTHER INFORMATION: Leu or D-Leu (dL)
<220> FEATURE:
<221> NAME/KEY: MOD_RES
<222> LOCATION: (21)..(21)
<223> OTHER INFORMATION: Val, Ser, Glu, Arg, (2S,4R)-4-
      hydroxypyrrolidine-2-carboxylic acid (Hyp), 2,4-diaminobutanoic
      acid (Dab) or an alpha methyl amino acid
<220> FEATURE:
<221> NAME/KEY: MOD_RES
<222> LOCATION: (24)..(24)
<223> OTHER INFORMATION: Ser, Ile, Pro or an alpha methyl amino acid
<220> FEATURE:
<221> NAME/KEY: MOD_RES
<222> LOCATION: (25)..(25)
<223> OTHER INFORMATION: Asn, 2,4-diaminobutanoic acid (Dab), His, Pro,
      Ser, Arg, Lys, Gly or Glu, Ala, Hyp  or an alpha methyl amino acid
<220> FEATURE:
<221> NAME/KEY: MOD_RES
<222> LOCATION: (26)..(26)
<223> OTHER INFORMATION: Asn, His, Hyp, 2,4-diaminobutanoic acid (Dab)
      or an alpha methyl amino acid
<220> FEATURE:
<221> NAME/KEY: MOD_RES
<222> LOCATION: (27)..(27)
<223> OTHER INFORMATION: Phe, Hyp or an alpha methyl amino acid
<220> FEATURE:
<221> NAME/KEY: MOD_RES
<222> LOCATION: (28)..(28)
<223> OTHER INFORMATION: Gly, Pro, Hyp or an alpha methyl amino acid
<220> FEATURE:
<221> NAME/KEY: MOD_RES
<222> LOCATION: (29)..(29)
<223> OTHER INFORMATION: Pro, Ala, Hyp or an alpha methyl amino acid
<220> FEATURE:
<221> NAME/KEY: MOD_RES
<222> LOCATION: (30)..(30)
<223> OTHER INFORMATION: Ile, D-Ile (dI), Arg, Hyp or an alpha methyl
      amino acid
<220> FEATURE:
<221> NAME/KEY: MOD_RES
<222> LOCATION: (31)..(31)
<223> OTHER INFORMATION: Leu, dL, Hyp or an alpha methyl amino acid
<220> FEATURE:
<221> NAME/KEY: MOD_RES
<222> LOCATION: (32)..(32)
<223> OTHER INFORMATION: Pro, D-Pro (dP), Ser, Hyp or an alpha methyl
      amino acid
<220> FEATURE:
<221> NAME/KEY: MOD_RES
<222> LOCATION: (33)..(33)
<223> OTHER INFORMATION: Pro, Hyp or an alpha methyl amino acid
<220> FEATURE:
<221> NAME/KEY: MOD_RES
<222> LOCATION: (35)..(35)
<223> OTHER INFORMATION: Asn, Glu, His, Arg, Pro, 2,4-diaminobutanoic
      acid (Dab) or an alpha methyl amino acid
<220> FEATURE:
<221> NAME/KEY: MOD_RES
<222> LOCATION: (36)..(36)
<223> OTHER INFORMATION: an alpha methyl amino acid
<220> FEATURE:
<221> NAME/KEY: MOD_RES
```

```
<222> LOCATION: (37)..(37)
<223> OTHER INFORMATION: Gly, Pro, Hyp or an alpha methyl amino acid
<220> FEATURE:
<221> NAME/KEY: MOD_RES
<222> LOCATION: (38)..(38)
<223> OTHER INFORMATION: Ser, Pro, His, Hyp or an alpha methyl amino
      acid
<220> FEATURE:
<221> NAME/KEY: MOD_RES
<222> LOCATION: (39)..(39)
<223> OTHER INFORMATION: Asn, Pro, Arg, Glu, 2,4-diaminobutanoic acid
      (Dab), Hyp or an alpha methyl amino acid
<220> FEATURE:
<221> NAME/KEY: MOD_RES
<222> LOCATION: (40)..(40)
<223> OTHER INFORMATION: Thr, Hyp or an alpha methyl amino acid
<220> FEATURE:
<221> NAME/KEY: MOD_RES
<222> LOCATION: (41)..(41)
<223> OTHER INFORMATION: Tyr, Pro, Hyp or an alpha methyl amino acid

<400> SEQUENCE: 184

Xaa Xaa Xaa Xaa Xaa Cys Asn Xaa Ala Thr Cys Ala Thr Gln Arg Leu
1               5                   10                  15

Ala Xaa Xaa Xaa Xaa His Ser Xaa Xaa Xaa Xaa Xaa Xaa Xaa Xaa
            20                  25                  30

Xaa Thr Xaa Xaa Xaa Xaa Xaa Xaa Xaa
        35                  40

<210> SEQ ID NO 185
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(albumin binding moiety) or absent
<220> FEATURE:
<221> NAME/KEY: MOD_RES
<222> LOCATION: (2)..(2)
<223> OTHER INFORMATION: Gly or absent
<220> FEATURE:
<221> NAME/KEY: MOD_RES
<222> LOCATION: (3)..(3)
<223> OTHER INFORMATION: Gly or absent
<220> FEATURE:
<221> NAME/KEY: MOD_RES
<222> LOCATION: (4)..(4)
<223> OTHER INFORMATION: Gly, Lys(albumin binding moiety) or absent
<220> FEATURE:
<221> NAME/KEY: MOD_RES
<222> LOCATION: (5)..(5)
<223> OTHER INFORMATION: Lys, Lys(albumin binding moiety) or absent
<220> FEATURE:
<221> NAME/KEY: MOD_RES
<222> LOCATION: (8)..(8)
<223> OTHER INFORMATION: Thr, Ile or Ala
<220> FEATURE:
<221> NAME/KEY: MOD_RES
<222> LOCATION: (18)..(18)
<223> OTHER INFORMATION: Asn, His, Glu, 2,4-diaminobutanoic acid (Dab),
      or an alpha methyl amino acid
<220> FEATURE:
<221> NAME/KEY: MOD_RES
<222> LOCATION: (19)..(19)
<223> OTHER INFORMATION: Phe or Trp
<220> FEATURE:
<221> NAME/KEY: MOD_RES
<222> LOCATION: (20)..(20)
<223> OTHER INFORMATION: Leu or D-Leu (dL)
<220> FEATURE:
<221> NAME/KEY: MOD_RES
```

```
<222> LOCATION: (21)..(21)
<223> OTHER INFORMATION: Val, Ser, Glu, Arg, (2S,4R)-4-
      hydroxypyrrolidine-2-carboxylic acid (Hyp), 2,4-diaminobutanoic
      acid (Dab) or an alpha methyl amino acid
<220> FEATURE:
<221> NAME/KEY: MOD_RES
<222> LOCATION: (24)..(24)
<223> OTHER INFORMATION: Ser, Ile, Pro or an alpha methyl amino acid
<220> FEATURE:
<221> NAME/KEY: MOD_RES
<222> LOCATION: (25)..(25)
<223> OTHER INFORMATION: Asn, 2,4-diaminobutanoic acid (Dab), His, Pro,
      Ser, Arg, Lys, Gly or Glu, Ala, Hyp or an alpha methyl amino acid
<220> FEATURE:
<221> NAME/KEY: MOD_RES
<222> LOCATION: (26)..(26)
<223> OTHER INFORMATION: Asn, His, Hyp, 2,4-diaminobutanoic acid (Dab)
      or an alpha methyl amino acid
<220> FEATURE:
<221> NAME/KEY: MOD_RES
<222> LOCATION: (27)..(27)
<223> OTHER INFORMATION: Phe, Hyp or an alpha methyl amino acid
<220> FEATURE:
<221> NAME/KEY: MOD_RES
<222> LOCATION: (28)..(28)
<223> OTHER INFORMATION: Gly, Pro, Hyp or an alpha methyl amino acid
<220> FEATURE:
<221> NAME/KEY: MOD_RES
<222> LOCATION: (29)..(29)
<223> OTHER INFORMATION: Pro, Ala, Hyp or an alpha methyl amino acid
<220> FEATURE:
<221> NAME/KEY: MOD_RES
<222> LOCATION: (30)..(30)
<223> OTHER INFORMATION: Ile, D-Ile (dI), Arg, Hyp or an alpha methyl
      amino acid
<220> FEATURE:
<221> NAME/KEY: MOD_RES
<222> LOCATION: (31)..(31)
<223> OTHER INFORMATION: Leu, dL, Hyp or an alpha methyl amino acid
<220> FEATURE:
<221> NAME/KEY: MOD_RES
<222> LOCATION: (32)..(32)
<223> OTHER INFORMATION: Pro, D-Pro (dP), Ser, Hyp or an alpha methyl
      amino acid
<220> FEATURE:
<221> NAME/KEY: MOD_RES
<222> LOCATION: (33)..(33)
<223> OTHER INFORMATION: Pro, Hyp or an alpha methyl amino acid
<220> FEATURE:
<221> NAME/KEY: MOD_RES
<222> LOCATION: (35)..(35)
<223> OTHER INFORMATION: Asn, Glu, His, Arg, Pro, 2,4-diaminobutanoic
      acid (Dab) or an alpha methyl amino acid
<220> FEATURE:
<221> NAME/KEY: MOD_RES
<222> LOCATION: (36)..(36)
<223> OTHER INFORMATION: Val, Hyp, 2,4-diaminobutanoic acid (Dab) or an
      alpha methyl amino acid
<220> FEATURE:
<221> NAME/KEY: MOD_RES
<222> LOCATION: (37)..(37)
<223> OTHER INFORMATION: an alpha methyl amino acid
<220> FEATURE:
<221> NAME/KEY: MOD_RES
<222> LOCATION: (38)..(38)
<223> OTHER INFORMATION: Ser, Pro, His, Hyp or an alpha methyl amino
      acid
<220> FEATURE:
<221> NAME/KEY: MOD_RES
<222> LOCATION: (39)..(39)
<223> OTHER INFORMATION: Asn, Pro, Arg, Glu, 2,4-diaminobutanoic acid
      (Dab), Hyp or an alpha methyl amino acid
<220> FEATURE:
<221> NAME/KEY: MOD_RES
<222> LOCATION: (40)..(40)
<223> OTHER INFORMATION: Thr, Hyp or an alpha methyl amino acid
<220> FEATURE:
<221> NAME/KEY: MOD_RES
<222> LOCATION: (41)..(41)
```

<223> OTHER INFORMATION: Tyr, Pro, Hyp or an alpha methyl amino acid

<400> SEQUENCE: 185

Xaa Xaa Xaa Xaa Xaa Cys Asn Xaa Ala Thr Cys Ala Thr Gln Arg Leu
1               5                   10                  15

Ala Xaa Xaa Xaa Xaa His Ser Xaa Xaa Xaa Xaa Xaa Xaa Xaa Xaa
            20                  25                  30

Xaa Thr Xaa Xaa Xaa Xaa Xaa Xaa Xaa
        35                  40

<210> SEQ ID NO 186
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(albumin binding moiety) or absent
<220> FEATURE:
<221> NAME/KEY: MOD_RES
<222> LOCATION: (2)..(2)
<223> OTHER INFORMATION: Gly or absent
<220> FEATURE:
<221> NAME/KEY: MOD_RES
<222> LOCATION: (3)..(3)
<223> OTHER INFORMATION: Gly or absent
<220> FEATURE:
<221> NAME/KEY: MOD_RES
<222> LOCATION: (4)..(4)
<223> OTHER INFORMATION: Gly, Lys(albumin binding moiety) or absent
<220> FEATURE:
<221> NAME/KEY: MOD_RES
<222> LOCATION: (5)..(5)
<223> OTHER INFORMATION: Lys, Lys(albumin binding moiety) or absent
<220> FEATURE:
<221> NAME/KEY: MOD_RES
<222> LOCATION: (8)..(8)
<223> OTHER INFORMATION: Thr, Ile or Ala
<220> FEATURE:
<221> NAME/KEY: MOD_RES
<222> LOCATION: (18)..(18)
<223> OTHER INFORMATION: Asn, His, Glu, 2,4-diaminobutanoic acid (Dab),
      or an alpha methyl amino acid
<220> FEATURE:
<221> NAME/KEY: MOD_RES
<222> LOCATION: (19)..(19)
<223> OTHER INFORMATION: Phe or Trp
<220> FEATURE:
<221> NAME/KEY: MOD_RES
<222> LOCATION: (20)..(20)
<223> OTHER INFORMATION: Leu or D-Leu (dL)
<220> FEATURE:
<221> NAME/KEY: MOD_RES
<222> LOCATION: (21)..(21)
<223> OTHER INFORMATION: Val, Ser, Glu, Arg, (2S,4R)-4-
      hydroxypyrrolidine-2-carboxylic acid (Hyp), 2,4-diaminobutanoic
      acid (Dab) or an alpha methyl amino acid
<220> FEATURE:
<221> NAME/KEY: MOD_RES
<222> LOCATION: (24)..(24)
<223> OTHER INFORMATION: Ser, Ile, Pro or an alpha methyl amino acid
<220> FEATURE:
<221> NAME/KEY: MOD_RES
<222> LOCATION: (25)..(25)
<223> OTHER INFORMATION: Asn, 2,4-diaminobutanoic acid (Dab), His, Pro,
      Ser, Arg, Lys, Gly or Glu, Ala, Hyp  or an alpha methyl amino acid
<220> FEATURE:
<221> NAME/KEY: MOD_RES
<222> LOCATION: (26)..(26)
<223> OTHER INFORMATION: Asn, His, Hyp, 2,4-diaminobutanoic acid (Dab)
      or an alpha methyl amino acid
<220> FEATURE:

```
<221> NAME/KEY: MOD_RES
<222> LOCATION: (27)..(27)
<223> OTHER INFORMATION: Phe, Hyp or an alpha methyl amino acid
<220> FEATURE:
<221> NAME/KEY: MOD_RES
<222> LOCATION: (28)..(28)
<223> OTHER INFORMATION: Gly, Pro, Hyp or an alpha methyl amino acid
<220> FEATURE:
<221> NAME/KEY: MOD_RES
<222> LOCATION: (29)..(29)
<223> OTHER INFORMATION: Pro, Ala, Hyp or an alpha methyl amino acid
<220> FEATURE:
<221> NAME/KEY: MOD_RES
<222> LOCATION: (30)..(30)
<223> OTHER INFORMATION: Ile, D-Ile (dI), Arg, Hyp or an alpha methyl
      amino acid
<220> FEATURE:
<221> NAME/KEY: MOD_RES
<222> LOCATION: (31)..(31)
<223> OTHER INFORMATION: Leu, dL, Hyp or an alpha methyl amino acid
<220> FEATURE:
<221> NAME/KEY: MOD_RES
<222> LOCATION: (32)..(32)
<223> OTHER INFORMATION: Pro, D-Pro (dP), Ser, Hyp or an alpha methyl
      amino acid
<220> FEATURE:
<221> NAME/KEY: MOD_RES
<222> LOCATION: (33)..(33)
<223> OTHER INFORMATION: Pro, Hyp or an alpha methyl amino acid
<220> FEATURE:
<221> NAME/KEY: MOD_RES
<222> LOCATION: (35)..(35)
<223> OTHER INFORMATION: Asn, Glu, His, Arg, Pro, 2,4-diaminobutanoic
      acid (Dab) or an alpha methyl amino acid
<220> FEATURE:
<221> NAME/KEY: MOD_RES
<222> LOCATION: (36)..(36)
<223> OTHER INFORMATION: Val, Hyp, 2,4-diaminobutanoic acid (Dab) or an
      alpha methyl amino acid
<220> FEATURE:
<221> NAME/KEY: MOD_RES
<222> LOCATION: (37)..(37)
<223> OTHER INFORMATION: Gly, Pro, Hyp or an alpha methyl amino acid
<220> FEATURE:
<221> NAME/KEY: MOD_RES
<222> LOCATION: (38)..(38)
<223> OTHER INFORMATION: an alpha methyl amino acid
<220> FEATURE:
<221> NAME/KEY: MOD_RES
<222> LOCATION: (39)..(39)
<223> OTHER INFORMATION: Asn, Pro, Arg, Glu, 2,4-diaminobutanoic acid
      (Dab), Hyp or an alpha methyl amino acid
<220> FEATURE:
<221> NAME/KEY: MOD_RES
<222> LOCATION: (40)..(40)
<223> OTHER INFORMATION: Thr, Hyp or an alpha methyl amino acid
<220> FEATURE:
<221> NAME/KEY: MOD_RES
<222> LOCATION: (41)..(41)
<223> OTHER INFORMATION: Tyr, Pro, Hyp or an alpha methyl amino acid

<400> SEQUENCE: 186

Xaa Xaa Xaa Xaa Xaa Cys Asn Xaa Ala Thr Cys Ala Thr Gln Arg Leu
1               5                   10                  15

Ala Xaa Xaa Xaa Xaa His Ser Xaa Xaa Xaa Xaa Xaa Xaa Xaa Xaa Xaa
            20                  25                  30

Xaa Thr Xaa Xaa Xaa Xaa Xaa Xaa Xaa
        35                  40

<210> SEQ ID NO 187
<211> LENGTH: 41
<212> TYPE: PRT
<213> ORGANISM: Artificial Sequence
<220> FEATURE:
<223> OTHER INFORMATION: Description of Artificial Sequence: Synthetic
```

```
           polypeptide
<220> FEATURE:
<221> NAME/KEY: MOD_RES
<222> LOCATION: (1)..(1)
<223> OTHER INFORMATION: Lys(albumin binding moiety) or absent
<220> FEATURE:
<221> NAME/KEY: MOD_RES
<222> LOCATION: (2)..(2)
<223> OTHER INFORMATION: Gly or absent
<220> FEATURE:
<221> NAME/KEY: MOD_RES
<222> LOCATION: (3)..(3)
<223> OTHER INFORMATION: Gly or absent
<220> FEATURE:
<221> NAME/KEY: MOD_RES
<222> LOCATION: (4)..(4)
<223> OTHER INFORMATION: Gly, Lys(albumin binding moiety) or absent
<220> FEATURE:
<221> NAME/KEY: MOD_RES
<222> LOCATION: (5)..(5)
<223> OTHER INFORMATION: Lys, Lys(albumin binding moiety) or absent
<220> FEATURE:
<221> NAME/KEY: MOD_RES
<222> LOCATION: (8)..(8)
<223> OTHER INFORMATION: Thr, Ile or Ala
<220> FEATURE:
<221> NAME/KEY: MOD_RES
<222> LOCATION: (18)..(18)
<223> OTHER INFORMATION: Asn, His, Glu, 2,4-diaminobutanoic acid (Dab),
      or an alpha methyl amino acid
<220> FEATURE:
<221> NAME/KEY: MOD_RES
<222> LOCATION: (19)..(19)
<223> OTHER INFORMATION: Phe or Trp
<220> FEATURE:
<221> NAME/KEY: MOD_RES
<222> LOCATION: (20)..(20)
<223> OTHER INFORMATION: Leu or D-Leu (dL)
<220> FEATURE:
<221> NAME/KEY: MOD_RES
<222> LOCATION: (21)..(21)
<223> OTHER INFORMATION: Val, Ser, Glu, Arg, (2S,4R)-4-
      hydroxypyrrolidine-2-carboxylic acid (Hyp), 2,4-diaminobutanoic
      acid (Dab) or an alpha methyl amino acid
<220> FEATURE:
<221> NAME/KEY: MOD_RES
<222> LOCATION: (24)..(24)
<223> OTHER INFORMATION: Ser, Ile, Pro or an alpha methyl amino acid
<220> FEATURE:
<221> NAME/KEY: MOD_RES
<222> LOCATION: (25)..(25)
<223> OTHER INFORMATION: Asn, 2,4-diaminobutanoic acid (Dab), His, Pro,
      Ser, Arg, Lys, Gly or Glu, Ala, Hyp  or an alpha methyl amino acid
<220> FEATURE:
<221> NAME/KEY: MOD_RES
<222> LOCATION: (26)..(26)
<223> OTHER INFORMATION: Asn, His, Hyp, 2,4-diaminobutanoic acid (Dab)
      or an alpha methyl amino acid
<220> FEATURE:
<221> NAME/KEY: MOD_RES
<222> LOCATION: (27)..(27)
<223> OTHER INFORMATION: Phe, Hyp or an alpha methyl amino acid
<220> FEATURE:
<221> NAME/KEY: MOD_RES
<222> LOCATION: (28)..(28)
<223> OTHER INFORMATION: Gly, Pro, Hyp or an alpha methyl amino acid
<220> FEATURE:
<221> NAME/KEY: MOD_RES
<222> LOCATION: (29)..(29)
<223> OTHER INFORMATION: Pro, Ala, Hyp or an alpha methyl amino acid
<220> FEATURE:
<221> NAME/KEY: MOD_RES
<222> LOCATION: (30)..(30)
<223> OTHER INFORMATION: Ile, D-Ile (dI), Arg, Hyp or an alpha methyl
      amino acid
<220> FEATURE:
<221> NAME/KEY: MOD_RES
<222> LOCATION: (31)..(31)
<223> OTHER INFORMATION: Leu, dL, Hyp or an alpha methyl amino acid
```

```
<220> FEATURE:
<221> NAME/KEY: MOD_RES
<222> LOCATION: (32)..(32)
<223> OTHER INFORMATION: Pro, D-Pro (dP), Ser, Hyp or an alpha methyl
      amino acid
<220> FEATURE:
<221> NAME/KEY: MOD_RES
<222> LOCATION: (33)..(33)
<223> OTHER INFORMATION: Pro, Hyp or an alpha methyl amino acid
<220> FEATURE:
<221> NAME/KEY: MOD_RES
<222> LOCATION: (35)..(35)
<223> OTHER INFORMATION: Asn, Glu, His, Arg, Pro, 2,4-diaminobutanoic
      acid (Dab) or an alpha methyl amino acid
<220> FEATURE:
<221> NAME/KEY: MOD_RES
<222> LOCATION: (36)..(36)
<223> OTHER INFORMATION: Val, Hyp, 2,4-diaminobutanoic acid (Dab) or an
      alpha methyl amino acid
<220> FEATURE:
<221> NAME/KEY: MOD_RES
<222> LOCATION: (37)..(37)
<223> OTHER INFORMATION: Gly, Pro, Hyp or an alpha methyl amino acid
<220> FEATURE:
<221> NAME/KEY: MOD_RES
<222> LOCATION: (38)..(38)
<223> OTHER INFORMATION: Ser, Pro, His, Hyp or an alpha methyl amino
      acid
<220> FEATURE:
<221> NAME/KEY: MOD_RES
<222> LOCATION: (39)..(39)
<223> OTHER INFORMATION: an alpha methyl amino acid
<220> FEATURE:
<221> NAME/KEY: MOD_RES
<222> LOCATION: (40)..(40)
<223> OTHER INFORMATION: Thr, Hyp or an alpha methyl amino acid
<220> FEATURE:
<221> NAME/KEY: MOD_RES
<222> LOCATION: (41)..(41)
<223> OTHER INFORMATION: Tyr, Pro, Hyp or an alpha methyl amino acid

<400> SEQUENCE: 187

Xaa Xaa Xaa Xaa Xaa Cys Asn Xaa Ala Thr Cys Ala Thr Gln Arg Leu
1               5                   10                  15

Ala Xaa Xaa Xaa Xaa His Ser Xaa Xaa Xaa Xaa Xaa Xaa Xaa Xaa Xaa
            20                  25                  30

Xaa Thr Xaa Xaa Xaa Xaa Xaa Xaa Xaa
        35                  40

<210> SEQ ID NO 188
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(albumin binding moiety) or absent
<220> FEATURE:
<221> NAME/KEY: MOD_RES
<222> LOCATION: (2)..(2)
<223> OTHER INFORMATION: Gly or absent
<220> FEATURE:
<221> NAME/KEY: MOD_RES
<222> LOCATION: (3)..(3)
<223> OTHER INFORMATION: Gly or absent
<220> FEATURE:
<221> NAME/KEY: MOD_RES
<222> LOCATION: (4)..(4)
<223> OTHER INFORMATION: Gly, Lys(albumin binding moiety) or absent
<220> FEATURE:
<221> NAME/KEY: MOD_RES
<222> LOCATION: (5)..(5)
```

-continued

```
<223> OTHER INFORMATION: Lys, Lys(albumin binding moiety) or absent
<220> FEATURE:
<221> NAME/KEY: MOD_RES
<222> LOCATION: (8)..(8)
<223> OTHER INFORMATION: Thr, Ile or Ala
<220> FEATURE:
<221> NAME/KEY: MOD_RES
<222> LOCATION: (18)..(18)
<223> OTHER INFORMATION: Asn, His, Glu, 2,4-diaminobutanoic acid (Dab),
      or an alpha methyl amino acid
<220> FEATURE:
<221> NAME/KEY: MOD_RES
<222> LOCATION: (19)..(19)
<223> OTHER INFORMATION: Phe or Trp
<220> FEATURE:
<221> NAME/KEY: MOD_RES
<222> LOCATION: (20)..(20)
<223> OTHER INFORMATION: Leu or D-Leu (dL)
<220> FEATURE:
<221> NAME/KEY: MOD_RES
<222> LOCATION: (21)..(21)
<223> OTHER INFORMATION: Val, Ser, Glu, Arg, (2S,4R)-4-
      hydroxypyrrolidine-2-carboxylic acid (Hyp), 2,4-diaminobutanoic
      acid (Dab) or an alpha methyl amino acid
<220> FEATURE:
<221> NAME/KEY: MOD_RES
<222> LOCATION: (24)..(24)
<223> OTHER INFORMATION: Ser, Ile, Pro or an alpha methyl amino acid
<220> FEATURE:
<221> NAME/KEY: MOD_RES
<222> LOCATION: (25)..(25)
<223> OTHER INFORMATION: Asn, 2,4-diaminobutanoic acid (Dab), His, Pro,
      Ser, Arg, Lys, Gly or Glu, Ala, Hyp  or an alpha methyl amino acid
<220> FEATURE:
<221> NAME/KEY: MOD_RES
<222> LOCATION: (26)..(26)
<223> OTHER INFORMATION: Asn, His, Hyp, 2,4-diaminobutanoic acid (Dab)
      or an alpha methyl amino acid
<220> FEATURE:
<221> NAME/KEY: MOD_RES
<222> LOCATION: (27)..(27)
<223> OTHER INFORMATION: Phe, Hyp or an alpha methyl amino acid
<220> FEATURE:
<221> NAME/KEY: MOD_RES
<222> LOCATION: (28)..(28)
<223> OTHER INFORMATION: Gly, Pro, Hyp or an alpha methyl amino acid
<220> FEATURE:
<221> NAME/KEY: MOD_RES
<222> LOCATION: (29)..(29)
<223> OTHER INFORMATION: Pro, Ala, Hyp or an alpha methyl amino acid
<220> FEATURE:
<221> NAME/KEY: MOD_RES
<222> LOCATION: (30)..(30)
<223> OTHER INFORMATION: Ile, D-Ile (dI), Arg, Hyp or an alpha methyl
      amino acid
<220> FEATURE:
<221> NAME/KEY: MOD_RES
<222> LOCATION: (31)..(31)
<223> OTHER INFORMATION: Leu, dL, Hyp or an alpha methyl amino acid
<220> FEATURE:
<221> NAME/KEY: MOD_RES
<222> LOCATION: (32)..(32)
<223> OTHER INFORMATION: Pro, D-Pro (dP), Ser, Hyp or an alpha methyl
      amino acid
<220> FEATURE:
<221> NAME/KEY: MOD_RES
<222> LOCATION: (33)..(33)
<223> OTHER INFORMATION: Pro, Hyp or an alpha methyl amino acid
<220> FEATURE:
<221> NAME/KEY: MOD_RES
<222> LOCATION: (35)..(35)
<223> OTHER INFORMATION: Asn, Glu, His, Arg, Pro, 2,4-diaminobutanoic
      acid (Dab) or an alpha methyl amino acid
<220> FEATURE:
<221> NAME/KEY: MOD_RES
<222> LOCATION: (36)..(36)
<223> OTHER INFORMATION: Val, Hyp, 2,4-diaminobutanoic acid (Dab) or an
      alpha methyl amino acid
<220> FEATURE:
```

```
<221> NAME/KEY: MOD_RES
<222> LOCATION: (37)..(37)
<223> OTHER INFORMATION: Gly, Pro, Hyp or an alpha methyl amino acid
<220> FEATURE:
<221> NAME/KEY: MOD_RES
<222> LOCATION: (38)..(38)
<223> OTHER INFORMATION: Ser, Pro, His, Hyp or an alpha methyl amino
      acid
<220> FEATURE:
<221> NAME/KEY: MOD_RES
<222> LOCATION: (39)..(39)
<223> OTHER INFORMATION: 2,4-diaminobutanoic acid (Dab)
<220> FEATURE:
<221> NAME/KEY: MOD_RES
<222> LOCATION: (40)..(40)
<223> OTHER INFORMATION: Thr, Hyp or an alpha methyl amino acid
<220> FEATURE:
<221> NAME/KEY: MOD_RES
<222> LOCATION: (41)..(41)
<223> OTHER INFORMATION: Tyr, Pro, Hyp or an alpha methyl amino acid

<400> SEQUENCE: 188

Xaa Xaa Xaa Xaa Xaa Cys Asn Xaa Ala Thr Cys Ala Thr Gln Arg Leu
1               5                   10                  15

Ala Xaa Xaa Xaa Xaa His Ser Xaa Xaa Xaa Xaa Xaa Xaa Xaa Xaa
            20                  25                  30

Xaa Thr Xaa Xaa Xaa Xaa Xaa Xaa Xaa
        35                  40

<210> SEQ ID NO 189
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(albumin binding moiety) or absent
<220> FEATURE:
<221> NAME/KEY: MOD_RES
<222> LOCATION: (2)..(2)
<223> OTHER INFORMATION: Gly or absent
<220> FEATURE:
<221> NAME/KEY: MOD_RES
<222> LOCATION: (3)..(3)
<223> OTHER INFORMATION: Gly or absent
<220> FEATURE:
<221> NAME/KEY: MOD_RES
<222> LOCATION: (4)..(4)
<223> OTHER INFORMATION: Gly, Lys(albumin binding moiety) or absent
<220> FEATURE:
<221> NAME/KEY: MOD_RES
<222> LOCATION: (5)..(5)
<223> OTHER INFORMATION: Lys, Lys(albumin binding moiety) or absent
<220> FEATURE:
<221> NAME/KEY: MOD_RES
<222> LOCATION: (8)..(8)
<223> OTHER INFORMATION: Thr, Ile or Ala
<220> FEATURE:
<221> NAME/KEY: MOD_RES
<222> LOCATION: (18)..(18)
<223> OTHER INFORMATION: Asn, His, Glu, 2,4-diaminobutanoic acid (Dab),
      or an alpha methyl amino acid
<220> FEATURE:
<221> NAME/KEY: MOD_RES
<222> LOCATION: (19)..(19)
<223> OTHER INFORMATION: Phe or Trp
<220> FEATURE:
<221> NAME/KEY: MOD_RES
<222> LOCATION: (20)..(20)
<223> OTHER INFORMATION: Leu or D-Leu (dL)
<220> FEATURE:
<221> NAME/KEY: MOD_RES
```

```
<222> LOCATION: (21)..(21)
<223> OTHER INFORMATION: Val, Ser, Glu, Arg, (2S,4R)-4-
      hydroxypyrrolidine-2-carboxylic acid (Hyp), 2,4-diaminobutanoic
      acid (Dab) or an alpha methyl amino acid
<220> FEATURE:
<221> NAME/KEY: MOD_RES
<222> LOCATION: (24)..(24)
<223> OTHER INFORMATION: Ser, Ile, Pro or an alpha methyl amino acid
<220> FEATURE:
<221> NAME/KEY: MOD_RES
<222> LOCATION: (25)..(25)
<223> OTHER INFORMATION: Asn, 2,4-diaminobutanoic acid (Dab), His, Pro,
      Ser, Arg, Lys, Gly or Glu, Ala, Hyp  or an alpha methyl amino acid
<220> FEATURE:
<221> NAME/KEY: MOD_RES
<222> LOCATION: (26)..(26)
<223> OTHER INFORMATION: Asn, His, Hyp, 2,4-diaminobutanoic acid (Dab)
      or an alpha methyl amino acid
<220> FEATURE:
<221> NAME/KEY: MOD_RES
<222> LOCATION: (27)..(27)
<223> OTHER INFORMATION: Phe, Hyp or an alpha methyl amino acid
<220> FEATURE:
<221> NAME/KEY: MOD_RES
<222> LOCATION: (28)..(28)
<223> OTHER INFORMATION: Gly, Pro, Hyp or an alpha methyl amino acid
<220> FEATURE:
<221> NAME/KEY: MOD_RES
<222> LOCATION: (29)..(29)
<223> OTHER INFORMATION: Pro, Ala, Hyp or an alpha methyl amino acid
<220> FEATURE:
<221> NAME/KEY: MOD_RES
<222> LOCATION: (30)..(30)
<223> OTHER INFORMATION: Ile, D-Ile (dI), Arg, Hyp or an alpha methyl
      amino acid
<220> FEATURE:
<221> NAME/KEY: MOD_RES
<222> LOCATION: (31)..(31)
<223> OTHER INFORMATION: Leu, dL, Hyp or an alpha methyl amino acid
<220> FEATURE:
<221> NAME/KEY: MOD_RES
<222> LOCATION: (32)..(32)
<223> OTHER INFORMATION: Pro, D-Pro (dP), Ser, Hyp or an alpha methyl
      amino acid
<220> FEATURE:
<221> NAME/KEY: MOD_RES
<222> LOCATION: (33)..(33)
<223> OTHER INFORMATION: Pro, Hyp or an alpha methyl amino acid
<220> FEATURE:
<221> NAME/KEY: MOD_RES
<222> LOCATION: (35)..(35)
<223> OTHER INFORMATION: Asn, Glu, His, Arg, Pro, 2,4-diaminobutanoic
      acid (Dab) or an alpha methyl amino acid
<220> FEATURE:
<221> NAME/KEY: MOD_RES
<222> LOCATION: (36)..(36)
<223> OTHER INFORMATION: Val, Hyp, 2,4-diaminobutanoic acid (Dab) or an
      alpha methyl amino acid
<220> FEATURE:
<221> NAME/KEY: MOD_RES
<222> LOCATION: (37)..(37)
<223> OTHER INFORMATION: Gly, Pro, Hyp or an alpha methyl amino acid
<220> FEATURE:
<221> NAME/KEY: MOD_RES
<222> LOCATION: (38)..(38)
<223> OTHER INFORMATION: Ser, Pro, His, Hyp or an alpha methyl amino
      acid
<220> FEATURE:
<221> NAME/KEY: MOD_RES
<222> LOCATION: (39)..(39)
<223> OTHER INFORMATION: Asn, Pro, Arg, Glu, 2,4-diaminobutanoic acid
      (Dab), Hyp or an alpha methyl amino acid
<220> FEATURE:
<221> NAME/KEY: MOD_RES
<222> LOCATION: (40)..(40)
<223> OTHER INFORMATION: an alpha methyl amino acid
<220> FEATURE:
<221> NAME/KEY: MOD_RES
<222> LOCATION: (41)..(41)
```

<223> OTHER INFORMATION: Tyr, Pro, Hyp or an alpha methyl amino acid

<400> SEQUENCE: 189

```
Xaa Xaa Xaa Xaa Xaa Cys Asn Xaa Ala Thr Cys Ala Thr Gln Arg Leu
1               5                   10                  15

Ala Xaa Xaa Xaa Xaa His Ser Xaa Xaa Xaa Xaa Xaa Xaa Xaa Xaa
            20                  25                  30

Xaa Thr Xaa Xaa Xaa Xaa Xaa Xaa Xaa
        35                  40
```

<210> SEQ ID NO 190
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(albumin binding moiety) or absent
<220> FEATURE:
<221> NAME/KEY: MOD_RES
<222> LOCATION: (2)..(2)
<223> OTHER INFORMATION: Gly or absent
<220> FEATURE:
<221> NAME/KEY: MOD_RES
<222> LOCATION: (3)..(3)
<223> OTHER INFORMATION: Gly or absent
<220> FEATURE:
<221> NAME/KEY: MOD_RES
<222> LOCATION: (4)..(4)
<223> OTHER INFORMATION: Gly, Lys(albumin binding moiety) or absent
<220> FEATURE:
<221> NAME/KEY: MOD_RES
<222> LOCATION: (5)..(5)
<223> OTHER INFORMATION: Lys, Lys(albumin binding moiety) or absent
<220> FEATURE:
<221> NAME/KEY: MOD_RES
<222> LOCATION: (8)..(8)
<223> OTHER INFORMATION: Thr, Ile or Ala
<220> FEATURE:
<221> NAME/KEY: MOD_RES
<222> LOCATION: (18)..(18)
<223> OTHER INFORMATION: Asn, His, Glu, 2,4-diaminobutanoic acid (Dab),
      or an alpha methyl amino acid
<220> FEATURE:
<221> NAME/KEY: MOD_RES
<222> LOCATION: (19)..(19)
<223> OTHER INFORMATION: Phe or Trp
<220> FEATURE:
<221> NAME/KEY: MOD_RES
<222> LOCATION: (20)..(20)
<223> OTHER INFORMATION: Leu or D-Leu (dL)
<220> FEATURE:
<221> NAME/KEY: MOD_RES
<222> LOCATION: (21)..(21)
<223> OTHER INFORMATION: Val, Ser, Glu, Arg, (2S,4R)-4-
      hydroxypyrrolidine-2-carboxylic acid (Hyp), 2,4-diaminobutanoic
      acid (Dab) or an alpha methyl amino acid
<220> FEATURE:
<221> NAME/KEY: MOD_RES
<222> LOCATION: (24)..(24)
<223> OTHER INFORMATION: Ser, Ile, Pro or an alpha methyl amino acid
<220> FEATURE:
<221> NAME/KEY: MOD_RES
<222> LOCATION: (25)..(25)
<223> OTHER INFORMATION: Asn, 2,4-diaminobutanoic acid (Dab), His, Pro,
      Ser, Arg, Lys, Gly or Glu, Ala, Hyp  or an alpha methyl amino acid
<220> FEATURE:
<221> NAME/KEY: MOD_RES
<222> LOCATION: (26)..(26)
<223> OTHER INFORMATION: Asn, His, Hyp, 2,4-diaminobutanoic acid (Dab)
      or an alpha methyl amino acid
<220> FEATURE:

<220> FEATURE:
<221> NAME/KEY: MOD_RES
<222> LOCATION: (27)..(27)
<223> OTHER INFORMATION: Phe, Hyp or an alpha methyl amino acid
<220> FEATURE:
<221> NAME/KEY: MOD_RES
<222> LOCATION: (28)..(28)
<223> OTHER INFORMATION: Gly, Pro, Hyp or an alpha methyl amino acid
<220> FEATURE:
<221> NAME/KEY: MOD_RES
<222> LOCATION: (29)..(29)
<223> OTHER INFORMATION: Pro, Ala, Hyp or an alpha methyl amino acid
<220> FEATURE:
<221> NAME/KEY: MOD_RES
<222> LOCATION: (30)..(30)
<223> OTHER INFORMATION: Ile, D-Ile (dI), Arg, Hyp or an alpha methyl
      amino acid
<220> FEATURE:
<221> NAME/KEY: MOD_RES
<222> LOCATION: (31)..(31)
<223> OTHER INFORMATION: Leu, dL, Hyp or an alpha methyl amino acid
<220> FEATURE:
<221> NAME/KEY: MOD_RES
<222> LOCATION: (32)..(32)
<223> OTHER INFORMATION: Pro, D-Pro (dP), Ser, Hyp or an alpha methyl
      amino acid
<220> FEATURE:
<221> NAME/KEY: MOD_RES
<222> LOCATION: (33)..(33)
<223> OTHER INFORMATION: Pro, Hyp or an alpha methyl amino acid
<220> FEATURE:
<221> NAME/KEY: MOD_RES
<222> LOCATION: (35)..(35)
<223> OTHER INFORMATION: Asn, Glu, His, Arg, Pro, 2,4-diaminobutanoic
      acid (Dab) or an alpha methyl amino acid
<220> FEATURE:
<221> NAME/KEY: MOD_RES
<222> LOCATION: (36)..(36)
<223> OTHER INFORMATION: Val, Hyp, 2,4-diaminobutanoic acid (Dab) or an
      alpha methyl amino acid
<220> FEATURE:
<221> NAME/KEY: MOD_RES
<222> LOCATION: (37)..(37)
<223> OTHER INFORMATION: Gly, Pro, Hyp or an alpha methyl amino acid
<220> FEATURE:
<221> NAME/KEY: MOD_RES
<222> LOCATION: (38)..(38)
<223> OTHER INFORMATION: Ser, Pro, His, Hyp or an alpha methyl amino
      acid
<220> FEATURE:
<221> NAME/KEY: MOD_RES
<222> LOCATION: (39)..(39)
<223> OTHER INFORMATION: Asn, Pro, Arg, Glu, 2,4-diaminobutanoic acid
      (Dab), Hyp or an alpha methyl amino acid
<220> FEATURE:
<221> NAME/KEY: MOD_RES
<222> LOCATION: (40)..(40)
<223> OTHER INFORMATION: Thr, Hyp or an alpha methyl amino acid
<220> FEATURE:
<221> NAME/KEY: MOD_RES
<222> LOCATION: (41)..(41)
<223> OTHER INFORMATION: an alpha methyl amino acid

<400> SEQUENCE: 190

Xaa Xaa Xaa Xaa Xaa Cys Asn Xaa Ala Thr Cys Ala Thr Gln Arg Leu
1               5                   10                  15

Ala Xaa Xaa Xaa Xaa His Ser Xaa Xaa Xaa Xaa Xaa Xaa Xaa Xaa
            20                  25                  30

Xaa Thr Xaa Xaa Xaa Xaa Xaa Xaa Xaa
        35                  40

<210> SEQ ID NO 191
<211> LENGTH: 41
<212> TYPE: PRT
<213> ORGANISM: Artificial Sequence
<220> FEATURE:

```
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(albumin binding moiety) or absent
<220> FEATURE:
<221> NAME/KEY: MOD_RES
<222> LOCATION: (2)..(2)
<223> OTHER INFORMATION: Gly or absent
<220> FEATURE:
<221> NAME/KEY: MOD_RES
<222> LOCATION: (3)..(3)
<223> OTHER INFORMATION: Gly or absent
<220> FEATURE:
<221> NAME/KEY: MOD_RES
<222> LOCATION: (4)..(4)
<223> OTHER INFORMATION: Lys(albumin binding moiety) or absent
<220> FEATURE:
<221> NAME/KEY: MOD_RES
<222> LOCATION: (5)..(5)
<223> OTHER INFORMATION: Lys, Lys(albumin binding moiety) or absent
<220> FEATURE:
<221> NAME/KEY: MOD_RES
<222> LOCATION: (18)..(18)
<223> OTHER INFORMATION: Asn, Glu or 2,4-diaminobutanoic acid (Dab)
<220> FEATURE:
<221> NAME/KEY: MOD_RES
<222> LOCATION: (21)..(21)
<223> OTHER INFORMATION: Val, Arg or Aib
<220> FEATURE:
<221> NAME/KEY: MOD_RES
<222> LOCATION: (27)..(27)
<223> OTHER INFORMATION: Phe or alpha-MePhe
<220> FEATURE:
<221> NAME/KEY: MOD_RES
<222> LOCATION: (35)..(35)
<223> OTHER INFORMATION: Asn, Glu or Arg
<220> FEATURE:
<221> NAME/KEY: MOD_RES
<222> LOCATION: (39)..(39)
<223> OTHER INFORMATION: Asn or Arg

<400> SEQUENCE: 191

Xaa Xaa Xaa Xaa Xaa Cys Asn Thr Ala Thr Cys Ala Thr Gln Arg Leu
1               5                   10                  15

Ala Xaa Phe Leu Xaa His Ser Ser Asn Asn Xaa Gly Pro Ile Leu Pro
            20                  25                  30

Pro Thr Xaa Val Gly Ser Xaa Thr Tyr
        35                  40

<210> SEQ ID NO 192
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(albumin binding moiety) or absent
<220> FEATURE:
<221> NAME/KEY: MOD_RES
<222> LOCATION: (2)..(2)
<223> OTHER INFORMATION: Gly or absent
<220> FEATURE:
<221> NAME/KEY: MOD_RES
<222> LOCATION: (3)..(3)
<223> OTHER INFORMATION: Gly or absent
<220> FEATURE:
<221> NAME/KEY: MOD_RES
<222> LOCATION: (4)..(4)
<223> OTHER INFORMATION: Gly, Lys(albumin binding moiety) or absent
<220> FEATURE:
```

```
<221> NAME/KEY: MOD_RES
<222> LOCATION: (5)..(5)
<223> OTHER INFORMATION: Lys, Lys(albumin binding moiety) or absent
<220> FEATURE:
<221> NAME/KEY: MOD_RES
<222> LOCATION: (18)..(18)
<223> OTHER INFORMATION: Asn or His
<220> FEATURE:
<221> NAME/KEY: MOD_RES
<222> LOCATION: (21)..(21)
<223> OTHER INFORMATION: Val, Arg or Aib
<220> FEATURE:
<221> NAME/KEY: MOD_RES
<222> LOCATION: (25)..(25)
<223> OTHER INFORMATION: Asn, 2,4-diaminobutanoic acid (Dab) or Aib
<220> FEATURE:
<221> NAME/KEY: MOD_RES
<222> LOCATION: (27)..(27)
<223> OTHER INFORMATION: Phe or alpha-MePhe
<220> FEATURE:
<221> NAME/KEY: MOD_RES
<222> LOCATION: (30)..(30)
<223> OTHER INFORMATION: Ile or Aib
<220> FEATURE:
<221> NAME/KEY: MOD_RES
<222> LOCATION: (31)..(31)
<223> OTHER INFORMATION: Leu or Aib
<220> FEATURE:
<221> NAME/KEY: MOD_RES
<222> LOCATION: (32)..(32)
<223> OTHER INFORMATION: Pro or Aib
<220> FEATURE:
<221> NAME/KEY: MOD_RES
<222> LOCATION: (33)..(33)
<223> OTHER INFORMATION: Pro or Aib
<220> FEATURE:
<221> NAME/KEY: MOD_RES
<222> LOCATION: (35)..(35)
<223> OTHER INFORMATION: Asn, Glu or Aib
<220> FEATURE:
<221> NAME/KEY: MOD_RES
<222> LOCATION: (36)..(36)
<223> OTHER INFORMATION: Val or Aib
<220> FEATURE:
<221> NAME/KEY: MOD_RES
<222> LOCATION: (37)..(37)
<223> OTHER INFORMATION: Gly or Aib
<220> FEATURE:
<221> NAME/KEY: MOD_RES
<222> LOCATION: (38)..(38)
<223> OTHER INFORMATION: Ser or Aib
<220> FEATURE:
<221> NAME/KEY: MOD_RES
<222> LOCATION: (39)..(39)
<223> OTHER INFORMATION: Asn or Aib
<220> FEATURE:
<221> NAME/KEY: MOD_RES
<222> LOCATION: (40)..(40)
<223> OTHER INFORMATION: Thr or Aib
<220> FEATURE:
<221> NAME/KEY: MOD_RES
<222> LOCATION: (41)..(41)
<223> OTHER INFORMATION: Tyr, Pro or Aib

<400> SEQUENCE: 192

Xaa Xaa Xaa Xaa Xaa Cys Asn Thr Ala Thr Cys Ala Thr Gln Arg Leu
1               5                   10                  15

Ala Xaa Phe Leu Xaa His Ser Ser Xaa Asn Xaa Gly Pro Xaa Xaa Xaa
            20                  25                  30

Xaa Thr Xaa Xaa Xaa Xaa Xaa Xaa Xaa
        35                  40

<210> SEQ ID NO 193
<211> LENGTH: 41
<212> TYPE: PRT
```

```
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(albumin binding moiety) or absent
<220> FEATURE:
<221> NAME/KEY: MOD_RES
<222> LOCATION: (2)..(2)
<223> OTHER INFORMATION: Gly or absent
<220> FEATURE:
<221> NAME/KEY: MOD_RES
<222> LOCATION: (3)..(3)
<223> OTHER INFORMATION: Gly or absent
<220> FEATURE:
<221> NAME/KEY: MOD_RES
<222> LOCATION: (4)..(4)
<223> OTHER INFORMATION: Gly, Lys(albumin binding moiety), or absent
<220> FEATURE:
<221> NAME/KEY: MOD_RES
<222> LOCATION: (5)..(5)
<223> OTHER INFORMATION: Lys, Lys(albumin binding moiety) or absent
<220> FEATURE:
<221> NAME/KEY: MOD_RES
<222> LOCATION: (8)..(8)
<223> OTHER INFORMATION: Thr, Ile or Ala
<220> FEATURE:
<221> NAME/KEY: MOD_RES
<222> LOCATION: (18)..(18)
<223> OTHER INFORMATION: Asn, Glu or His
<220> FEATURE:
<221> NAME/KEY: MOD_RES
<222> LOCATION: (20)..(20)
<223> OTHER INFORMATION: Leu or D-Leu (dL)
<220> FEATURE:
<221> NAME/KEY: MOD_RES
<222> LOCATION: (21)..(21)
<223> OTHER INFORMATION: Val, Ser, Glu, Arg or Aib
<220> FEATURE:
<221> NAME/KEY: MOD_RES
<222> LOCATION: (25)..(25)
<223> OTHER INFORMATION: Asn or Aib
<220> FEATURE:
<221> NAME/KEY: MOD_RES
<222> LOCATION: (28)..(28)
<223> OTHER INFORMATION: Gly, Hyp or Pro
<220> FEATURE:
<221> NAME/KEY: MOD_RES
<222> LOCATION: (29)..(29)
<223> OTHER INFORMATION: Pro or Ala
<220> FEATURE:
<221> NAME/KEY: MOD_RES
<222> LOCATION: (30)..(30)
<223> OTHER INFORMATION: Ile, dI, or Aib
<220> FEATURE:
<221> NAME/KEY: MOD_RES
<222> LOCATION: (31)..(31)
<223> OTHER INFORMATION: Leu, dL, or Aib
<220> FEATURE:
<221> NAME/KEY: MOD_RES
<222> LOCATION: (32)..(32)
<223> OTHER INFORMATION: Pro, dP, Ser, or Aib
<220> FEATURE:
<221> NAME/KEY: MOD_RES
<222> LOCATION: (35)..(35)
<223> OTHER INFORMATION: Asn, Glu, His, Arg, Pro, 2,4-diaminobutanoic
      acid (Dab) or an alpha methyl amino acid
<220> FEATURE:
<221> NAME/KEY: MOD_RES
<222> LOCATION: (37)..(37)
<223> OTHER INFORMATION: Gly, Pro or Aib
<220> FEATURE:
<221> NAME/KEY: MOD_RES
<222> LOCATION: (38)..(38)
<223> OTHER INFORMATION: Ser or Aib
<220> FEATURE:
<221> NAME/KEY: MOD_RES
```

```
<222> LOCATION: (39)..(39)
<223> OTHER INFORMATION: Asn, Pro, Arg, Glu, 2,4-diaminobutanoic acid
      (Dab), or Aib
<220> FEATURE:
<221> NAME/KEY: MOD_RES
<222> LOCATION: (40)..(40)
<223> OTHER INFORMATION: Thr, or Aib
<220> FEATURE:
<221> NAME/KEY: MOD_RES
<222> LOCATION: (41)..(41)
<223> OTHER INFORMATION: Tyr, Pro or Aib

<400> SEQUENCE: 193

Xaa Xaa Xaa Xaa Xaa Cys Asn Xaa Ala Thr Cys Ala Thr Gln Arg Leu
1               5                   10                  15

Ala Xaa Phe Xaa Xaa His Ser Ser Xaa Asn Phe Xaa Xaa Xaa Xaa Xaa
            20                  25                  30

Pro Thr Xaa Val Xaa Xaa Xaa Xaa Xaa
        35                  40

<210> SEQ ID NO 194
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(albumin binding moiety) or absent
<220> FEATURE:
<221> NAME/KEY: MOD_RES
<222> LOCATION: (2)..(2)
<223> OTHER INFORMATION: Gly or absent
<220> FEATURE:
<221> NAME/KEY: MOD_RES
<222> LOCATION: (3)..(3)
<223> OTHER INFORMATION: Gly or absent
<220> FEATURE:
<221> NAME/KEY: MOD_RES
<222> LOCATION: (4)..(4)
<223> OTHER INFORMATION: Lys(albumin binding moiety) or absent
<220> FEATURE:
<221> NAME/KEY: MOD_RES
<222> LOCATION: (5)..(5)
<223> OTHER INFORMATION: Lys, Lys(albumin binding moiety) or absent
<220> FEATURE:
<221> NAME/KEY: MOD_RES
<222> LOCATION: (18)..(18)
<223> OTHER INFORMATION: Asn, His, Glu, 2,4-diaminobutanoic acid (Dab),
      or an alpha methyl amino acid
<220> FEATURE:
<221> NAME/KEY: MOD_RES
<222> LOCATION: (21)..(21)
<223> OTHER INFORMATION: Val or Aib
<220> FEATURE:
<221> NAME/KEY: MOD_RES
<222> LOCATION: (25)..(25)
<223> OTHER INFORMATION: Asn, His, Pro, Ser, Arg, 2,4-diaminobutanoic
      acid (Dab), Lys or Gly
<220> FEATURE:
<221> NAME/KEY: MOD_RES
<222> LOCATION: (26)..(26)
<223> OTHER INFORMATION: Asn or His
<220> FEATURE:
<221> NAME/KEY: MOD_RES
<222> LOCATION: (30)..(30)
<223> OTHER INFORMATION: Ile or Arg
<220> FEATURE:
<221> NAME/KEY: MOD_RES
<222> LOCATION: (31)..(31)
<223> OTHER INFORMATION: Leu or dL
<220> FEATURE:
<221> NAME/KEY: MOD_RES
```

<222> LOCATION: (35)..(35)
<223> OTHER INFORMATION: Asn, Glu, His, Arg or Pro
<220> FEATURE:
<221> NAME/KEY: MOD_RES
<222> LOCATION: (38)..(38)
<223> OTHER INFORMATION: Ser, Pro or His
<220> FEATURE:
<221> NAME/KEY: MOD_RES
<222> LOCATION: (39)..(39)
<223> OTHER INFORMATION: Asn, Glu or Arg

<400> SEQUENCE: 194

Xaa Xaa Xaa Xaa Xaa Cys Asn Thr Ala Thr Cys Ala Thr Gln Arg Leu
1               5                   10                  15

Ala Xaa Phe Leu Xaa His Ser Ser Xaa Xaa Phe Gly Pro Xaa Xaa Pro
            20                  25                  30

Pro Thr Xaa Val Gly Xaa Xaa Thr Tyr
        35                  40

<210> SEQ ID NO 195
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys (albumin binding moiety), or absent
<220> FEATURE:
<221> NAME/KEY: MOD_RES
<222> LOCATION: (2)..(2)
<223> OTHER INFORMATION: Gly or absent
<220> FEATURE:
<221> NAME/KEY: MOD_RES
<222> LOCATION: (3)..(3)
<223> OTHER INFORMATION: Gly or absent
<220> FEATURE:
<221> NAME/KEY: MOD_RES
<222> LOCATION: (4)..(4)
<223> OTHER INFORMATION: Gly, Lys (albumin binding moiety), or absent
<220> FEATURE:
<221> NAME/KEY: MOD_RES
<222> LOCATION: (5)..(5)
<223> OTHER INFORMATION: Lys, Lys (albumin binding moiety), or absent
<220> FEATURE:
<221> NAME/KEY: MOD_RES
<222> LOCATION: (8)..(8)
<223> OTHER INFORMATION: Thr, Ile, Ala
<220> FEATURE:
<221> NAME/KEY: MOD_RES
<222> LOCATION: (18)..(18)
<223> OTHER INFORMATION: Asn, His, Glu, 2,4-diaminobutanoic acid (Dab),
      alpha methyl amino acid
<220> FEATURE:
<221> NAME/KEY: MOD_RES
<222> LOCATION: (19)..(19)
<223> OTHER INFORMATION: Phe or Trp
<220> FEATURE:
<221> NAME/KEY: MOD_RES
<222> LOCATION: (20)..(20)
<223> OTHER INFORMATION: Leu or D-Leu
<220> FEATURE:
<221> NAME/KEY: MOD_RES
<222> LOCATION: (21)..(21)
<223> OTHER INFORMATION: Val, Ser, Glu, Arg, (2S,4R)-4-
      hydroxypyrrolidine-2-carboxylic acid (Hyp), Dab, alpha methyl
      amino acid
<220> FEATURE:
<221> NAME/KEY: MOD_RES
<222> LOCATION: (24)..(24)
<223> OTHER INFORMATION: Ser, Ile, Pro, alpha methyl amino acid
<220> FEATURE:
<221> NAME/KEY: MOD_RES

```
<222> LOCATION: (25)..(25)
<223> OTHER INFORMATION: Asn, Dab, His, Pro, Ser, Arg, Lys,
      Gly, Glu, Ala, Hyp , alpha methyl amino acid
<220> FEATURE:
<221> NAME/KEY: MOD_RES
<222> LOCATION: (26)..(26)
<223> OTHER INFORMATION: Asn, His, Hyp, Dab, alpha methyl amino acid
<220> FEATURE:
<221> NAME/KEY: MOD_RES
<222> LOCATION: (27)..(27)
<223> OTHER INFORMATION: Phe, Hyp, alpha methyl amino acid
<220> FEATURE:
<221> NAME/KEY: MOD_RES
<222> LOCATION: (28)..(28)
<223> OTHER INFORMATION: Gly, Pro, Hyp, alpha methyl amino acid
<220> FEATURE:
<221> NAME/KEY: MOD_RES
<222> LOCATION: (29)..(29)
<223> OTHER INFORMATION: Pro, Ala, Hyp, alpha methyl amino acid
<220> FEATURE:
<221> NAME/KEY: MOD_RES
<222> LOCATION: (30)..(30)
<223> OTHER INFORMATION: Ile, D-Ile, Arg, Hyp, alpha methyl amino acid
<220> FEATURE:
<221> NAME/KEY: MOD_RES
<222> LOCATION: (31)..(31)
<223> OTHER INFORMATION: Leu, D-Leu, Hyp, alpha methyl amino acid
<220> FEATURE:
<221> NAME/KEY: MOD_RES
<222> LOCATION: (32)..(32)
<223> OTHER INFORMATION: Pro, D-Pro, Ser, Hyp, alpha methyl amino acid
<220> FEATURE:
<221> NAME/KEY: MOD_RES
<222> LOCATION: (33)..(33)
<223> OTHER INFORMATION: Pro, Hyp, alpha methyl amino acid
<220> FEATURE:
<221> NAME/KEY: MOD_RES
<222> LOCATION: (35)..(35)
<223> OTHER INFORMATION: Asn, Glu, His, Arg, Pro, Dab,
      alpha methyl amino acid
<220> FEATURE:
<221> NAME/KEY: MOD_RES
<222> LOCATION: (36)..(36)
<223> OTHER INFORMATION: Val, Hyp, Dab, alpha methyl amino acid
<220> FEATURE:
<221> NAME/KEY: MOD_RES
<222> LOCATION: (37)..(37)
<223> OTHER INFORMATION: Gly, Pro, Hyp, alpha methyl amino acid
<220> FEATURE:
<221> NAME/KEY: MOD_RES
<222> LOCATION: (38)..(38)
<223> OTHER INFORMATION: Ser, Pro, His, Hyp, alpha methyl amino acid
<220> FEATURE:
<221> NAME/KEY: MOD_RES
<222> LOCATION: (39)..(39)
<223> OTHER INFORMATION: Asn, Pro, Arg, Glu, Dab, Hyp,
      alpha methyl amino acid
<220> FEATURE:
<221> NAME/KEY: MOD_RES
<222> LOCATION: (40)..(40)
<223> OTHER INFORMATION: Thr, Hyp, alpha methyl amino acid
<220> FEATURE:
<221> NAME/KEY: MOD_RES
<222> LOCATION: (41)..(41)
<223> OTHER INFORMATION: Tyr, Pro, Hyp, alpha methyl amino acid
<220> FEATURE:
<221> NAME/KEY: SITE
<222> LOCATION: (1)..(41)
<223> OTHER INFORMATION: At least one of positions 14, 17 or 20-37
      comprises Dab, Hyp or an alpha methyl amino acid

<400> SEQUENCE: 195

Xaa Xaa Xaa Xaa Xaa Cys Asn Xaa Ala Thr Cys Ala Thr Gln Arg Leu
1               5                   10                  15

Ala Xaa Xaa Xaa Xaa His Ser Xaa Xaa Xaa Xaa Xaa Xaa Xaa Xaa Xaa
            20                  25                  30
```

Xaa Thr Xaa Xaa Xaa Xaa Xaa Xaa Xaa
         35                  40

<210> SEQ ID NO 196
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys (albumin binding moiety)
<220> FEATURE:
<221> NAME/KEY: MOD_RES
<222> LOCATION: (2)..(2)
<223> OTHER INFORMATION: Gly or absent
<220> FEATURE:
<221> NAME/KEY: MOD_RES
<222> LOCATION: (3)..(3)
<223> OTHER INFORMATION: Gly or absent
<220> FEATURE:
<221> NAME/KEY: MOD_RES
<222> LOCATION: (4)..(4)
<223> OTHER INFORMATION: Gly, Lys (albumin binding moiety), or absent
<220> FEATURE:
<221> NAME/KEY: MOD_RES
<222> LOCATION: (5)..(5)
<223> OTHER INFORMATION: Lys, Lys (albumin binding moiety), or absent
<220> FEATURE:
<221> NAME/KEY: MOD_RES
<222> LOCATION: (8)..(8)
<223> OTHER INFORMATION: Thr, Ile, Ala
<220> FEATURE:
<221> NAME/KEY: MOD_RES
<222> LOCATION: (18)..(18)
<223> OTHER INFORMATION: Asn, His, Glu, 2,4-diaminobutanoic acid (Dab),
      alpha methyl amino acid
<220> FEATURE:
<221> NAME/KEY: MOD_RES
<222> LOCATION: (19)..(19)
<223> OTHER INFORMATION: Phe or Trp
<220> FEATURE:
<221> NAME/KEY: MOD_RES
<222> LOCATION: (20)..(20)
<223> OTHER INFORMATION: Leu or D-Leu
<220> FEATURE:
<221> NAME/KEY: MOD_RES
<222> LOCATION: (21)..(21)
<223> OTHER INFORMATION: Val, Ser, Glu, Arg, (2S,4R)-4-
      hydroxypyrrolidine-2-carboxylic acid (Hyp), Dab, alpha methyl
      amino acid
<220> FEATURE:
<221> NAME/KEY: MOD_RES
<222> LOCATION: (24)..(24)
<223> OTHER INFORMATION: Ser, Ile, Pro, alpha methyl amino acid
<220> FEATURE:
<221> NAME/KEY: MOD_RES
<222> LOCATION: (25)..(25)
<223> OTHER INFORMATION: Asn, Dab, His, Pro, Ser, Arg, Lys,
      Gly, Glu, Ala, Hyp , alpha methyl amino acid
<220> FEATURE:
<221> NAME/KEY: MOD_RES
<222> LOCATION: (26)..(26)
<223> OTHER INFORMATION: Asn, His, Hyp, Dab, alpha methyl amino acid
<220> FEATURE:
<221> NAME/KEY: MOD_RES
<222> LOCATION: (27)..(27)
<223> OTHER INFORMATION: Phe, Hyp, alpha methyl amino acid
<220> FEATURE:
<221> NAME/KEY: MOD_RES
<222> LOCATION: (28)..(28)
<223> OTHER INFORMATION: Gly, Pro, Hyp, alpha methyl amino acid
<220> FEATURE:
<221> NAME/KEY: MOD_RES
<222> LOCATION: (29)..(29)
<223> OTHER INFORMATION: Pro, Ala, Hyp, alpha methyl amino acid

```
<220> FEATURE:
<221> NAME/KEY: MOD_RES
<222> LOCATION: (30)..(30)
<223> OTHER INFORMATION: Ile, D-Ile, Arg, Hyp, alpha methyl amino acid
<220> FEATURE:
<221> NAME/KEY: MOD_RES
<222> LOCATION: (31)..(31)
<223> OTHER INFORMATION: Leu, D-Leu, Hyp, alpha methyl amino acid
<220> FEATURE:
<221> NAME/KEY: MOD_RES
<222> LOCATION: (32)..(32)
<223> OTHER INFORMATION: Pro, D-Pro, Ser, Hyp, alpha methyl amino acid
<220> FEATURE:
<221> NAME/KEY: MOD_RES
<222> LOCATION: (33)..(33)
<223> OTHER INFORMATION: Pro, Hyp, alpha methyl amino acid
<220> FEATURE:
<221> NAME/KEY: MOD_RES
<222> LOCATION: (35)..(35)
<223> OTHER INFORMATION: Asn, Glu, His, Arg, Pro, Dab,
      alpha methyl amino acid
<220> FEATURE:
<221> NAME/KEY: MOD_RES
<222> LOCATION: (36)..(36)
<223> OTHER INFORMATION: Val, Hyp, Dab, alpha methyl amino acid
<220> FEATURE:
<221> NAME/KEY: MOD_RES
<222> LOCATION: (37)..(37)
<223> OTHER INFORMATION: Gly, Pro, Hyp, alpha methyl amino acid
<220> FEATURE:
<221> NAME/KEY: MOD_RES
<222> LOCATION: (38)..(38)
<223> OTHER INFORMATION: Ser, Pro, His, Hyp, alpha methyl amino acid
<220> FEATURE:
<221> NAME/KEY: MOD_RES
<222> LOCATION: (39)..(39)
<223> OTHER INFORMATION: Asn, Pro, Arg, Glu, Dab, Hyp,
      alpha methyl amino acid
<220> FEATURE:
<221> NAME/KEY: MOD_RES
<222> LOCATION: (40)..(40)
<223> OTHER INFORMATION: Thr, Hyp, alpha methyl amino acid
<220> FEATURE:
<221> NAME/KEY: MOD_RES
<222> LOCATION: (41)..(41)
<223> OTHER INFORMATION: Tyr, Pro, Hyp, alpha methyl amino acid

<400> SEQUENCE: 196

Xaa Xaa Xaa Xaa Xaa Cys Asn Xaa Ala Thr Cys Ala Thr Gln Arg Leu
1               5                   10                  15

Ala Xaa Xaa Xaa Xaa His Ser Xaa Xaa Xaa Xaa Xaa Xaa Xaa Xaa
            20                  25                  30

Xaa Thr Xaa Xaa Xaa Xaa Xaa Xaa Xaa
        35                  40

<210> SEQ ID NO 197
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys (albumin binding moiety), or absent
<220> FEATURE:
<221> NAME/KEY: MOD_RES
<222> LOCATION: (2)..(2)
<223> OTHER INFORMATION: Gly or absent
<220> FEATURE:
<221> NAME/KEY: MOD_RES
<222> LOCATION: (3)..(3)
<223> OTHER INFORMATION: Gly or absent
<220> FEATURE:
```

```
<221> NAME/KEY: MOD_RES
<222> LOCATION: (4)..(4)
<223> OTHER INFORMATION: Lys (albumin binding moiety), or absent
<220> FEATURE:
<221> NAME/KEY: MOD_RES
<222> LOCATION: (5)..(5)
<223> OTHER INFORMATION: Lys, Lys (albumin binding moiety), or absent
<220> FEATURE:
<221> NAME/KEY: MOD_RES
<222> LOCATION: (8)..(8)
<223> OTHER INFORMATION: Thr, Ile, Ala
<220> FEATURE:
<221> NAME/KEY: MOD_RES
<222> LOCATION: (18)..(18)
<223> OTHER INFORMATION: Asn, His, Glu, 2,4-diaminobutanoic acid (Dab),
      alpha methyl amino acid
<220> FEATURE:
<221> NAME/KEY: MOD_RES
<222> LOCATION: (19)..(19)
<223> OTHER INFORMATION: Phe or Trp
<220> FEATURE:
<221> NAME/KEY: MOD_RES
<222> LOCATION: (20)..(20)
<223> OTHER INFORMATION: Leu or D-Leu
<220> FEATURE:
<221> NAME/KEY: MOD_RES
<222> LOCATION: (21)..(21)
<223> OTHER INFORMATION: Val, Ser, Glu, Arg, (2S,4R)-4-
      hydroxypyrrolidine-2-carboxylic acid (Hyp), Dab, alpha methyl
      amino acid
<220> FEATURE:
<221> NAME/KEY: MOD_RES
<222> LOCATION: (24)..(24)
<223> OTHER INFORMATION: Ser, Ile, Pro, alpha methyl amino acid
<220> FEATURE:
<221> NAME/KEY: MOD_RES
<222> LOCATION: (25)..(25)
<223> OTHER INFORMATION: Asn, Dab, His, Pro, Ser, Arg, Lys,
      Gly, Glu, Ala, Hyp , alpha methyl amino acid
<220> FEATURE:
<221> NAME/KEY: MOD_RES
<222> LOCATION: (26)..(26)
<223> OTHER INFORMATION: Asn, His, Hyp, Dab, alpha methyl amino acid
<220> FEATURE:
<221> NAME/KEY: MOD_RES
<222> LOCATION: (27)..(27)
<223> OTHER INFORMATION: Phe, Hyp, alpha methyl amino acid
<220> FEATURE:
<221> NAME/KEY: MOD_RES
<222> LOCATION: (28)..(28)
<223> OTHER INFORMATION: Gly, Pro, Hyp, alpha methyl amino acid
<220> FEATURE:
<221> NAME/KEY: MOD_RES
<222> LOCATION: (29)..(29)
<223> OTHER INFORMATION: Pro, Ala, Hyp, alpha methyl amino acid
<220> FEATURE:
<221> NAME/KEY: MOD_RES
<222> LOCATION: (30)..(30)
<223> OTHER INFORMATION: Ile, D-Ile, Arg, Hyp, alpha methyl amino acid
<220> FEATURE:
<221> NAME/KEY: MOD_RES
<222> LOCATION: (31)..(31)
<223> OTHER INFORMATION: Leu, D-Leu, Hyp, alpha methyl amino acid
<220> FEATURE:
<221> NAME/KEY: MOD_RES
<222> LOCATION: (32)..(32)
<223> OTHER INFORMATION: Pro, D-Pro, Ser, Hyp, alpha methyl amino acid
<220> FEATURE:
<221> NAME/KEY: MOD_RES
<222> LOCATION: (33)..(33)
<223> OTHER INFORMATION: Pro, Hyp, alpha methyl amino acid
<220> FEATURE:
<221> NAME/KEY: MOD_RES
<222> LOCATION: (35)..(35)
<223> OTHER INFORMATION: Asn, Glu, His, Arg, Pro, Dab,
      alpha methyl amino acid
<220> FEATURE:
<221> NAME/KEY: MOD_RES
<222> LOCATION: (36)..(36)
```

```
<223> OTHER INFORMATION: Val, Hyp, Dab, alpha methyl amino acid
<220> FEATURE:
<221> NAME/KEY: MOD_RES
<222> LOCATION: (37)..(37)
<223> OTHER INFORMATION: Gly, Pro, Hyp, alpha methyl amino acid
<220> FEATURE:
<221> NAME/KEY: MOD_RES
<222> LOCATION: (38)..(38)
<223> OTHER INFORMATION: Ser, Pro, His, Hyp, alpha methyl amino acid
<220> FEATURE:
<221> NAME/KEY: MOD_RES
<222> LOCATION: (39)..(39)
<223> OTHER INFORMATION: Asn, Pro, Arg, Glu, Dab, Hyp,
      alpha methyl amino acid
<220> FEATURE:
<221> NAME/KEY: MOD_RES
<222> LOCATION: (40)..(40)
<223> OTHER INFORMATION: Thr, Hyp, alpha methyl amino acid
<220> FEATURE:
<221> NAME/KEY: MOD_RES
<222> LOCATION: (41)..(41)
<223> OTHER INFORMATION: Tyr, Pro, Hyp, alpha methyl amino acid

<400> SEQUENCE: 197

Xaa Xaa Xaa Xaa Xaa Cys Asn Xaa Ala Thr Cys Ala Thr Gln Arg Leu
1               5                   10                  15

Ala Xaa Xaa Xaa Xaa His Ser Xaa Xaa Xaa Xaa Xaa Xaa Xaa Xaa Xaa
            20                  25                  30

Xaa Thr Xaa Xaa Xaa Xaa Xaa Xaa Xaa
        35                  40

<210> SEQ ID NO 198
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys (albumin binding moiety), or absent
<220> FEATURE:
<221> NAME/KEY: MOD_RES
<222> LOCATION: (2)..(2)
<223> OTHER INFORMATION: Gly or absent
<220> FEATURE:
<221> NAME/KEY: MOD_RES
<222> LOCATION: (3)..(3)
<223> OTHER INFORMATION: Gly or absent
<220> FEATURE:
<221> NAME/KEY: MOD_RES
<222> LOCATION: (4)..(4)
<223> OTHER INFORMATION: Gly, Lys (albumin binding moiety), or absent
<220> FEATURE:
<221> NAME/KEY: MOD_RES
<222> LOCATION: (5)..(5)
<223> OTHER INFORMATION: Lys (albumin binding moiety)
<220> FEATURE:
<221> NAME/KEY: MOD_RES
<222> LOCATION: (8)..(8)
<223> OTHER INFORMATION: Thr, Ile, Ala
<220> FEATURE:
<221> NAME/KEY: MOD_RES
<222> LOCATION: (18)..(18)
<223> OTHER INFORMATION: Asn, His, Glu, 2,4-diaminobutanoic acid (Dab),
      alpha methyl amino acid
<220> FEATURE:
<221> NAME/KEY: MOD_RES
<222> LOCATION: (19)..(19)
<223> OTHER INFORMATION: Phe or Trp
<220> FEATURE:
<221> NAME/KEY: MOD_RES
<222> LOCATION: (20)..(20)
<223> OTHER INFORMATION: Leu or D-Leu
```

```
<220> FEATURE:
<221> NAME/KEY: MOD_RES
<222> LOCATION: (21)..(21)
<223> OTHER INFORMATION: Val, Ser, Glu, Arg, (2S,4R)-4-
      hydroxypyrrolidine-2-carboxylic acid (Hyp), Dab, alpha methyl
      amino acid
<220> FEATURE:
<221> NAME/KEY: MOD_RES
<222> LOCATION: (24)..(24)
<223> OTHER INFORMATION: Ser, Ile, Pro, alpha methyl amino acid
<220> FEATURE:
<221> NAME/KEY: MOD_RES
<222> LOCATION: (25)..(25)
<223> OTHER INFORMATION: Asn, Dab, His, Pro, Ser, Arg, Lys,
      Gly, Glu, Ala, Hyp , alpha methyl amino acid
<220> FEATURE:
<221> NAME/KEY: MOD_RES
<222> LOCATION: (26)..(26)
<223> OTHER INFORMATION: Asn, His, Hyp, Dab, alpha methyl amino acid
<220> FEATURE:
<221> NAME/KEY: MOD_RES
<222> LOCATION: (27)..(27)
<223> OTHER INFORMATION: Phe, Hyp, alpha methyl amino acid
<220> FEATURE:
<221> NAME/KEY: MOD_RES
<222> LOCATION: (28)..(28)
<223> OTHER INFORMATION: Gly, Pro, Hyp, alpha methyl amino acid
<220> FEATURE:
<221> NAME/KEY: MOD_RES
<222> LOCATION: (29)..(29)
<223> OTHER INFORMATION: Pro, Ala, Hyp, alpha methyl amino acid
<220> FEATURE:
<221> NAME/KEY: MOD_RES
<222> LOCATION: (30)..(30)
<223> OTHER INFORMATION: Ile, D-Ile, Arg, Hyp, alpha methyl amino acid
<220> FEATURE:
<221> NAME/KEY: MOD_RES
<222> LOCATION: (31)..(31)
<223> OTHER INFORMATION: Leu, D-Leu, Hyp, alpha methyl amino acid
<220> FEATURE:
<221> NAME/KEY: MOD_RES
<222> LOCATION: (32)..(32)
<223> OTHER INFORMATION: Pro, D-Pro, Ser, Hyp, alpha methyl amino acid
<220> FEATURE:
<221> NAME/KEY: MOD_RES
<222> LOCATION: (33)..(33)
<223> OTHER INFORMATION: Pro, Hyp, alpha methyl amino acid
<220> FEATURE:
<221> NAME/KEY: MOD_RES
<222> LOCATION: (35)..(35)
<223> OTHER INFORMATION: Asn, Glu, His, Arg, Pro, Dab,
      alpha methyl amino acid
<220> FEATURE:
<221> NAME/KEY: MOD_RES
<222> LOCATION: (36)..(36)
<223> OTHER INFORMATION: Val, Hyp, Dab, alpha methyl amino acid
<220> FEATURE:
<221> NAME/KEY: MOD_RES
<222> LOCATION: (37)..(37)
<223> OTHER INFORMATION: Gly, Pro, Hyp, alpha methyl amino acid
<220> FEATURE:
<221> NAME/KEY: MOD_RES
<222> LOCATION: (38)..(38)
<223> OTHER INFORMATION: Ser, Pro, His, Hyp, alpha methyl amino acid
<220> FEATURE:
<221> NAME/KEY: MOD_RES
<222> LOCATION: (39)..(39)
<223> OTHER INFORMATION: Asn, Pro, Arg, Glu, Dab, Hyp,
      alpha methyl amino acid
<220> FEATURE:
<221> NAME/KEY: MOD_RES
<222> LOCATION: (40)..(40)
<223> OTHER INFORMATION: Thr, Hyp, alpha methyl amino acid
<220> FEATURE:
<221> NAME/KEY: MOD_RES
<222> LOCATION: (41)..(41)
<223> OTHER INFORMATION: Tyr, Pro, Hyp, alpha methyl amino acid

<400> SEQUENCE: 198
```

```
Xaa Xaa Xaa Xaa Xaa Cys Asn Xaa Ala Thr Cys Ala Thr Gln Arg Leu
1               5                  10                  15

Ala Xaa Xaa Xaa Xaa His Ser Xaa Xaa Xaa Xaa Xaa Xaa Xaa
            20                  25                  30

Xaa Thr Xaa Xaa Xaa Xaa Xaa Xaa Xaa
        35                  40
```

```
<210> SEQ ID NO 199
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (4)..(9)
<223> OTHER INFORMATION: Disulphide bridge between Cys residues
<220> FEATURE:
<221> NAME/KEY: MOD_RES
<222> LOCATION: (19)..(19)
<223> OTHER INFORMATION: 2-amino-2-methylpropanoic acid

<400> SEQUENCE: 199

Gly Gly Lys Cys Asn Thr Ala Thr Cys Ala Thr Gln Arg Leu Ala Asn
1               5                  10                  15

Phe Leu Xaa His Ser Ser Asn Asn Phe Gly Pro Ile Leu Pro Pro Thr
            20                  25                  30

Asn Val Gly Ser Asn Thr Tyr
        35
```

```
<210> SEQ ID NO 200
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues

<400> SEQUENCE: 200

Lys Cys Asn Ala Ala Thr Cys Ala Thr Gln Arg Leu Ala Asn Trp Leu
1               5                  10                  15

Val His Ser Ser Pro Asn Phe Pro Ala Ile Leu Ser Pro Thr Asn Val
            20                  25                  30

Gly Ser Asn Thr Tyr
        35
```

```
<210> SEQ ID NO 201
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues

<400> SEQUENCE: 201

Lys Cys Asn Ile Ala Thr Cys Ala Thr Gln Arg Leu Ala Asn Phe Leu
1               5                  10                  15
```

Val His Ser Ile Ala Asn Phe Gly Pro Ile Leu Pro Pro Thr Asn Val
            20                  25                  30

Gly Ser Arg Thr Tyr
        35

<210> SEQ ID NO 202
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2,4-diaminobutanoic acid (Dab)

<400> SEQUENCE: 202

Lys Cys Asn Ile Ala Thr Cys Ala Thr Gln Arg Leu Ala Asn Phe Leu
1               5                   10                  15

Val His Ser Ser Xaa Asn Phe Gly Pro Ile Leu Pro Pro Thr Asn Val
            20                  25                  30

Gly Ser Arg Thr Tyr
        35

<210> SEQ ID NO 203
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (14)..(14)
<223> OTHER INFORMATION: 2,4-diaminobutanoic acid (Dab)

<400> SEQUENCE: 203

Lys Cys Asn Thr Ala Thr Cys Ala Thr Gln Arg Leu Ala Xaa Phe Leu
1               5                   10                  15

Val His Ser Ser Asn Asn Phe Gly Pro Ile Leu Pro Pro Thr Asn Val
            20                  25                  30

Gly Ser Asn Thr Tyr
        35

<210> SEQ ID NO 204
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (14)..(14)
<223> OTHER INFORMATION: 2,4-diaminobutanoic acid (Dab)

```
<220> FEATURE:
<221> NAME/KEY: MOD_RES
<222> LOCATION: (17)..(17)
<223> OTHER INFORMATION: 2-amino-2-methylpropanoic acid

<400> SEQUENCE: 204

Lys Cys Asn Thr Ala Thr Cys Ala Thr Gln Arg Leu Ala Xaa Phe Leu
1               5                   10                  15

Xaa His Ser Ser Asn Asn Phe Gly Pro Ile Leu Pro Pro Thr Glu Val
            20                  25                  30

Gly Ser Asn Thr Tyr
        35

<210> SEQ ID NO 205
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (14)..(14)
<223> OTHER INFORMATION: 2,4-diaminobutanoic acid (Dab)
<220> FEATURE:
<221> NAME/KEY: MOD_RES
<222> LOCATION: (23)..(23)
<223> OTHER INFORMATION: (S)-2-amino-2-methyl-3-phenylpropanoic acid

<400> SEQUENCE: 205

Lys Cys Asn Thr Ala Thr Cys Ala Thr Gln Arg Leu Ala Xaa Phe Leu
1               5                   10                  15

Val His Ser Ser Asn Asn Xaa Gly Pro Ile Leu Pro Pro Thr Glu Val
            20                  25                  30

Gly Ser Asn Thr Tyr
        35

<210> SEQ ID NO 206
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (14)..(14)
<223> OTHER INFORMATION: 2,4-diaminobutanoic acid (Dab)

<400> SEQUENCE: 206

Lys Cys Asn Thr Ala Thr Cys Ala Thr Gln Arg Leu Ala Xaa Phe Leu
1               5                   10                  15

Val His Ser Ser Asn Asn Phe Gly Pro Ile Leu Pro Pro Thr Glu Val
            20                  25                  30

Gly Ser Asn Thr Tyr
        35

<210> SEQ ID NO 207
<211> LENGTH: 37
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid

<400> SEQUENCE: 207

Lys Cys Asn Thr Ala Thr Cys Ala Thr Gln Arg Leu Ala Glu Phe Leu
1               5                   10                  15

Xaa His Ser Ser Asn Asn Phe Gly Pro Ile Leu Pro Pro Thr Asn Val
            20                  25                  30

Gly Ser Asn Thr Tyr
        35

<210> SEQ ID NO 208
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid

<400> SEQUENCE: 208

Lys Cys Asn Thr Ala Thr Cys Ala Thr Gln Arg Leu Ala Glu Phe Leu
1               5                   10                  15

Xaa His Ser Ser His Asn Phe Gly Pro Ile Leu Pro Pro Thr Asn Val
            20                  25                  30

Gly Ser Asn Thr Tyr
        35

<210> SEQ ID NO 209
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues

<400> SEQUENCE: 209

Lys Cys Asn Thr Ala Thr Cys Ala Thr Gln Arg Leu Ala Glu Phe Leu
1               5                   10                  15

Arg His Ser Ser Asn Asn Phe Gly Pro Ile Leu Pro Pro Thr Asn Val
            20                  25                  30

Gly Ser Asn Thr Tyr
        35

<210> SEQ ID NO 210
```

```
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (23)..(23)
<223> OTHER INFORMATION: (S)-2-amino-2-methyl-3-phenylpropanoic acid

<400> SEQUENCE: 210

Lys Cys Asn Thr Ala Thr Cys Ala Thr Gln Arg Leu Ala Glu Phe Leu
1               5                   10                  15

Arg His Ser Ser Asn Asn Xaa Gly Pro Ile Leu Pro Pro Thr Asn Val
            20                  25                  30

Gly Ser Asn Thr Tyr
        35

<210> SEQ ID NO 211
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid

<400> SEQUENCE: 211

Lys Cys Asn Thr Ala Thr Cys Ala Thr Gln Arg Leu Ala Glu Phe Leu
1               5                   10                  15

Val His Ser Ser Xaa Asn Phe Gly Pro Ile Leu Pro Pro Thr Asn Val
            20                  25                  30

Gly Ser Asn Thr Tyr
        35

<210> SEQ ID NO 212
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid

<400> SEQUENCE: 212

Lys Cys Asn Thr Ala Thr Cys Ala Thr Gln Arg Leu Ala His Phe Leu
1               5                   10                  15

Xaa His Ser Ser Asn Asn Phe Gly Pro Ile Leu Pro Pro Thr Asn Val
            20                  25                  30
```

Gly Ser Asn Thr Tyr
        35

<210> SEQ ID NO 213
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid
<220> FEATURE:
<221> NAME/KEY: MOD_RES
<222> LOCATION: (21)..(21)
<223> OTHER INFORMATION: 2-amino-2-methylpropanoic acid

<400> SEQUENCE: 213

Lys Cys Asn Thr Ala Thr Cys Ala Thr Gln Arg Leu Ala His Phe Leu
1               5                   10                  15

Xaa His Ser Ser Xaa Asn Phe Gly Pro Ile Leu Pro Pro Thr Glu Val
            20                  25                  30

Gly Ser Asn Thr Tyr
        35

<210> SEQ ID NO 214
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid

<400> SEQUENCE: 214

Lys Cys Asn Thr Ala Thr Cys Ala Thr Gln Arg Leu Ala His Phe Leu
1               5                   10                  15

Val His Ser Ser Xaa Asn Phe Gly Pro Ile Leu Pro Pro Thr Asn Val
            20                  25                  30

Gly Ser Asn Thr Tyr
        35

<210> SEQ ID NO 215
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid

```
<400> SEQUENCE: 215

Lys Cys Asn Thr Ala Thr Cys Ala Thr Gln Arg Leu Ala His Phe Leu
1               5                   10                  15

Val His Ser Ser Xaa Asn Phe Gly Pro Ile Leu Pro Pro Thr Asn Val
                20                  25                  30

Gly Ser Glu Thr Tyr
            35

<210> SEQ ID NO 216
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (16)..(16)
<223> OTHER INFORMATION: D-Leu
<220> FEATURE:
<221> NAME/KEY: MOD_RES
<222> LOCATION: (21)..(21)
<223> OTHER INFORMATION: 2-amino-2-methylpropanoic acid

<400> SEQUENCE: 216

Lys Cys Asn Thr Ala Thr Cys Ala Thr Gln Arg Leu Ala Asn Phe Xaa
1               5                   10                  15

Val His Ser Ser Xaa Asn Phe Gly Pro Ile Leu Pro Pro Thr Asn Val
                20                  25                  30

Gly Ser Asn Thr Tyr
            35

<210> SEQ ID NO 217
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid

<400> SEQUENCE: 217

Lys Cys Asn Thr Ala Thr Cys Ala Thr Gln Arg Leu Ala Asn Phe Leu
1               5                   10                  15

Xaa His Ser Ser Asn Asn Phe Gly Pro Ile Leu Pro Pro Thr Asn Val
                20                  25                  30

Gly Ser Asn Thr Tyr
            35

<210> SEQ ID NO 218
<211> LENGTH: 37
<212> TYPE: PRT
<213> ORGANISM: Artificial Sequence
<220> FEATURE:
<223> OTHER INFORMATION: Description of Artificial Sequence: Synthetic
```

```
                    polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid

<400> SEQUENCE: 218

Lys Cys Asn Thr Ala Thr Cys Ala Thr Gln Arg Leu Ala Asn Phe Leu
1               5                   10                  15

Xaa His Ser Ser Asn Asn Phe Gly Pro Ile Leu Pro Pro Thr Asn Val
            20                  25                  30

Gly Ser Asn Thr Pro
        35

<210> SEQ ID NO 219
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid
<220> FEATURE:
<221> NAME/KEY: MOD_RES
<222> LOCATION: (21)..(21)
<223> OTHER INFORMATION: 2-amino-2-methylpropanoic acid

<400> SEQUENCE: 219

Lys Cys Asn Thr Ala Thr Cys Ala Thr Gln Arg Leu Ala Asn Phe Leu
1               5                   10                  15

Xaa His Ser Ser Xaa Asn Phe Gly Pro Ile Leu Pro Pro Thr Asn Val
            20                  25                  30

Gly Ser Asn Thr Tyr
        35

<210> SEQ ID NO 220
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid
<220> FEATURE:
<221> NAME/KEY: MOD_RES
<222> LOCATION: (21)..(21)
<223> OTHER INFORMATION: 2-amino-2-methylpropanoic acid

<400> SEQUENCE: 220

Lys Cys Asn Thr Ala Thr Cys Ala Thr Gln Arg Leu Ala Asn Phe Leu
1               5                   10                  15
```

```
Xaa His Ser Ser Xaa Asn Phe Gly Pro Ile Leu Pro Pro Thr Asn Val
            20                  25                  30

Gly Ser Asn Thr Pro
        35

<210> SEQ ID NO 221
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid

<400> SEQUENCE: 221

Lys Cys Asn Thr Ala Thr Cys Ala Thr Gln Arg Leu Ala Asn Phe Leu
1               5                   10                  15

Xaa His Ser Ser Gly Asn Phe Gly Pro Ile Leu Pro Pro Thr Asn Val
            20                  25                  30

Gly Ser Asn Thr Tyr
        35

<210> SEQ ID NO 222
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid

<400> SEQUENCE: 222

Lys Cys Asn Thr Ala Thr Cys Ala Thr Gln Arg Leu Ala Asn Phe Leu
1               5                   10                  15

Xaa His Ser Ser His Asn Phe Gly Pro Ile Leu Pro Pro Thr Asn Val
            20                  25                  30

Gly Ser Asn Thr Tyr
        35

<210> SEQ ID NO 223
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid
```

<400> SEQUENCE: 223

Lys Cys Asn Thr Ala Thr Cys Ala Thr Gln Arg Leu Ala Asn Phe Leu
1               5                   10                  15

Xaa His Ser Ser Lys Asn Phe Gly Pro Ile Leu Pro Pro Thr Asn Val
            20                  25                  30

Gly Ser Asn Thr Tyr
        35

<210> SEQ ID NO 224
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid

<400> SEQUENCE: 224

Lys Cys Asn Thr Ala Thr Cys Ala Thr Gln Arg Leu Ala Asn Phe Leu
1               5                   10                  15

Xaa His Ser Ser Pro Asn Phe Gly Pro Ile Leu Pro Pro Thr Asn Val
            20                  25                  30

Gly Ser Asn Thr Tyr
        35

<210> SEQ ID NO 225
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid

<400> SEQUENCE: 225

Lys Cys Asn Thr Ala Thr Cys Ala Thr Gln Arg Leu Ala Asn Phe Leu
1               5                   10                  15

Xaa His Ser Ser Pro Asn Phe Gly Pro Ile Leu Pro Pro Thr Glu Val
            20                  25                  30

Gly Ser Asn Thr Tyr
        35

<210> SEQ ID NO 226
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues

```
<220> FEATURE:
<221> NAME/KEY: MOD_RES
<222> LOCATION: (17)..(17)
<223> OTHER INFORMATION: 2-amino-2-methylpropanoic acid

<400> SEQUENCE: 226

Lys Cys Asn Thr Ala Thr Cys Ala Thr Gln Arg Leu Ala Asn Phe Leu
1               5                   10                  15

Xaa His Ser Ser Pro Asn Phe Gly Pro Ile Leu Pro Pro Thr Asn Val
            20                  25                  30

Gly Ser Glu Thr Tyr
        35

<210> SEQ ID NO 227
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid

<400> SEQUENCE: 227

Lys Cys Asn Thr Ala Thr Cys Ala Thr Gln Arg Leu Ala Asn Phe Leu
1               5                   10                  15

Xaa His Ser Ser Arg Asn Phe Gly Pro Ile Leu Pro Pro Thr Asn Val
            20                  25                  30

Gly Ser Asn Thr Tyr
        35

<210> SEQ ID NO 228
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid

<400> SEQUENCE: 228

Lys Cys Asn Thr Ala Thr Cys Ala Thr Gln Arg Leu Ala Asn Phe Leu
1               5                   10                  15

Xaa His Ser Ser Ser Asn Phe Gly Pro Ile Leu Pro Pro Thr Asn Val
            20                  25                  30

Gly Ser Asn Thr Tyr
        35

<210> SEQ ID NO 229
<211> LENGTH: 37
<212> TYPE: PRT
<213> ORGANISM: Artificial Sequence
<220> FEATURE:
<223> OTHER INFORMATION: Description of Artificial Sequence: Synthetic
```

```
        polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid
<220> FEATURE:
<221> NAME/KEY: MOD_RES
<222> LOCATION: (21)..(21)
<223> OTHER INFORMATION: 2,4-diaminobutanoic acid (Dab)

<400> SEQUENCE: 229

Lys Cys Asn Thr Ala Thr Cys Ala Thr Gln Arg Leu Ala Asn Phe Leu
1               5                   10                  15

Xaa His Ser Ser Xaa Asn Phe Gly Pro Ile Leu Pro Pro Thr Asn Val
                20                  25                  30

Gly Ser Asn Thr Tyr
            35

<210> SEQ ID NO 230
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid
<220> FEATURE:
<221> NAME/KEY: MOD_RES
<222> LOCATION: (21)..(21)
<223> OTHER INFORMATION: 2,4-diaminobutanoic acid (Dab)

<400> SEQUENCE: 230

Lys Cys Asn Thr Ala Thr Cys Ala Thr Gln Arg Leu Ala Asn Phe Leu
1               5                   10                  15

Xaa His Ser Ser Xaa Asn Phe Gly Pro Ile Leu Pro Pro Thr Glu Val
                20                  25                  30

Gly Ser Asn Thr Tyr
            35

<210> SEQ ID NO 231
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid

<400> SEQUENCE: 231

Lys Cys Asn Thr Ala Thr Cys Ala Thr Gln Arg Leu Ala Asn Phe Leu
1               5                   10                  15
```

```
Xaa His Ser Ser Asn His Phe Gly Pro Ile Leu Pro Pro Thr Asn Val
            20                  25                  30

Gly Ser Asn Thr Tyr
        35

<210> SEQ ID NO 232
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid

<400> SEQUENCE: 232

Lys Cys Asn Thr Ala Thr Cys Ala Thr Gln Arg Leu Ala Asn Phe Leu
1               5                   10                  15

Xaa His Ser Ser Asn His Phe Gly Pro Ile Leu Pro Pro Thr Asn Val
            20                  25                  30

Gly Ser Glu Thr Tyr
        35

<210> SEQ ID NO 233
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid
<220> FEATURE:
<221> NAME/KEY: MOD_RES
<222> LOCATION: (23)..(23)
<223> OTHER INFORMATION: (S)-2-amino-2-methyl-3-phenylpropanoic acid

<400> SEQUENCE: 233

Lys Cys Asn Thr Ala Thr Cys Ala Thr Gln Arg Leu Ala Asn Phe Leu
1               5                   10                  15

Xaa His Ser Ser Asn Asn Xaa Gly Pro Ile Leu Pro Pro Thr Asn Val
            20                  25                  30

Gly Ser Asn Thr Tyr
        35

<210> SEQ ID NO 234
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
```

```
<221> NAME/KEY: MOD_RES
<222> LOCATION: (17)..(17)
<223> OTHER INFORMATION: 2-amino-2-methylpropanoic acid
<220> FEATURE:
<221> NAME/KEY: MOD_RES
<222> LOCATION: (26)..(26)
<223> OTHER INFORMATION: 2-amino-2-methylpropanoic acid

<400> SEQUENCE: 234

Lys Cys Asn Thr Ala Thr Cys Ala Thr Gln Arg Leu Ala Asn Phe Leu
1               5                   10                  15

Xaa His Ser Ser Asn Asn Phe Gly Pro Xaa Leu Pro Pro Thr Asn Val
            20                  25                  30

Gly Ser Asn Thr Tyr
        35

<210> SEQ ID NO 235
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid

<400> SEQUENCE: 235

Lys Cys Asn Thr Ala Thr Cys Ala Thr Gln Arg Leu Ala Asn Phe Leu
1               5                   10                  15

Xaa His Ser Ser Asn Asn Phe Gly Pro Arg Leu Pro Pro Thr Asn Val
            20                  25                  30

Gly Ser Asn Thr Tyr
        35

<210> SEQ ID NO 236
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid
<220> FEATURE:
<221> NAME/KEY: MOD_RES
<222> LOCATION: (27)..(27)
<223> OTHER INFORMATION: 2-amino-2-methylpropanoic acid

<400> SEQUENCE: 236

Lys Cys Asn Thr Ala Thr Cys Ala Thr Gln Arg Leu Ala Asn Phe Leu
1               5                   10                  15

Xaa His Ser Ser Asn Asn Phe Gly Pro Ile Xaa Pro Pro Thr Asn Val
            20                  25                  30

Gly Ser Asn Thr Tyr
        35
```

```
<210> SEQ ID NO 237
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid
<220> FEATURE:
<221> NAME/KEY: MOD_RES
<222> LOCATION: (27)..(27)
<223> OTHER INFORMATION: D-Leu

<400> SEQUENCE: 237

Lys Cys Asn Thr Ala Thr Cys Ala Thr Gln Arg Leu Ala Asn Phe Leu
1               5                   10                  15

Xaa His Ser Ser Asn Asn Phe Gly Pro Ile Xaa Pro Pro Thr Asn Val
            20                  25                  30

Gly Ser Asn Thr Tyr
        35

<210> SEQ ID NO 238
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid
<220> FEATURE:
<221> NAME/KEY: MOD_RES
<222> LOCATION: (28)..(28)
<223> OTHER INFORMATION: 2-amino-2-methylpropanoic acid

<400> SEQUENCE: 238

Lys Cys Asn Thr Ala Thr Cys Ala Thr Gln Arg Leu Ala Asn Phe Leu
1               5                   10                  15

Xaa His Ser Ser Asn Asn Phe Gly Pro Ile Leu Xaa Pro Thr Asn Val
            20                  25                  30

Gly Ser Asn Thr Tyr
        35

<210> SEQ ID NO 239
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
```

<223> OTHER INFORMATION: 2-amino-2-methylpropanoic acid
<220> FEATURE:
<221> NAME/KEY: MOD_RES
<222> LOCATION: (29)..(29)
<223> OTHER INFORMATION: 2-amino-2-methylpropanoic acid

<400> SEQUENCE: 239

Lys Cys Asn Thr Ala Thr Cys Ala Thr Gln Arg Leu Ala Asn Phe Leu
1               5                   10                  15

Xaa His Ser Ser Asn Asn Phe Gly Pro Ile Leu Pro Xaa Thr Asn Val
            20                  25                  30

Gly Ser Asn Thr Tyr
        35

<210> SEQ ID NO 240
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid
<220> FEATURE:
<221> NAME/KEY: MOD_RES
<222> LOCATION: (31)..(31)
<223> OTHER INFORMATION: 2-amino-2-methylpropanoic acid

<400> SEQUENCE: 240

Lys Cys Asn Thr Ala Thr Cys Ala Thr Gln Arg Leu Ala Asn Phe Leu
1               5                   10                  15

Xaa His Ser Ser Asn Asn Phe Gly Pro Ile Leu Pro Pro Thr Xaa Val
            20                  25                  30

Gly Ser Asn Thr Tyr
        35

<210> SEQ ID NO 241
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid

<400> SEQUENCE: 241

Lys Cys Asn Thr Ala Thr Cys Ala Thr Gln Arg Leu Ala Asn Phe Leu
1               5                   10                  15

Xaa His Ser Ser Asn Asn Phe Gly Pro Ile Leu Pro Pro Thr Glu Val
            20                  25                  30

Gly Ser Asn Thr Tyr
        35

<210> SEQ ID NO 242

```
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid

<400> SEQUENCE: 242

Lys Cys Asn Thr Ala Thr Cys Ala Thr Gln Arg Leu Ala Asn Phe Leu
1               5                   10                  15

Xaa His Ser Ser Asn Asn Phe Gly Pro Ile Leu Pro Pro Thr His Val
            20                  25                  30

Gly Ser Glu Thr Tyr
        35

<210> SEQ ID NO 243
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid

<400> SEQUENCE: 243

Lys Cys Asn Thr Ala Thr Cys Ala Thr Gln Arg Leu Ala Asn Phe Leu
1               5                   10                  15

Xaa His Ser Ser Asn Asn Phe Gly Pro Ile Leu Pro Pro Thr Pro Val
            20                  25                  30

Gly Ser Asn Thr Tyr
        35

<210> SEQ ID NO 244
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid

<400> SEQUENCE: 244

Lys Cys Asn Thr Ala Thr Cys Ala Thr Gln Arg Leu Ala Asn Phe Leu
1               5                   10                  15

Xaa His Ser Ser Asn Asn Phe Gly Pro Ile Leu Pro Pro Thr Arg Val
            20                  25                  30
```

Gly Ser Asn Thr Tyr
        35

<210> SEQ ID NO 245
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid
<220> FEATURE:
<221> NAME/KEY: MOD_RES
<222> LOCATION: (32)..(32)
<223> OTHER INFORMATION: 2-amino-2-methylpropanoic acid

<400> SEQUENCE: 245

Lys Cys Asn Thr Ala Thr Cys Ala Thr Gln Arg Leu Ala Asn Phe Leu
1               5                   10                  15

Xaa His Ser Ser Asn Asn Phe Gly Pro Ile Leu Pro Pro Thr Asn Xaa
            20                  25                  30

Gly Ser Asn Thr Tyr
        35

<210> SEQ ID NO 246
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid
<220> FEATURE:
<221> NAME/KEY: MOD_RES
<222> LOCATION: (33)..(33)
<223> OTHER INFORMATION: 2-amino-2-methylpropanoic acid

<400> SEQUENCE: 246

Lys Cys Asn Thr Ala Thr Cys Ala Thr Gln Arg Leu Ala Asn Phe Leu
1               5                   10                  15

Xaa His Ser Ser Asn Asn Phe Gly Pro Ile Leu Pro Pro Thr Asn Val
            20                  25                  30

Xaa Ser Asn Thr Tyr
        35

<210> SEQ ID NO 247
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues

```
<220> FEATURE:
<221> NAME/KEY: MOD_RES
<222> LOCATION: (17)..(17)
<223> OTHER INFORMATION: 2-amino-2-methylpropanoic acid
<220> FEATURE:
<221> NAME/KEY: MOD_RES
<222> LOCATION: (34)..(34)
<223> OTHER INFORMATION: 2-amino-2-methylpropanoic acid

<400> SEQUENCE: 247

Lys Cys Asn Thr Ala Thr Cys Ala Thr Gln Arg Leu Ala Asn Phe Leu
1               5                   10                  15

Xaa His Ser Ser Asn Asn Phe Gly Pro Ile Leu Pro Pro Thr Asn Val
            20                  25                  30

Gly Xaa Asn Thr Tyr
        35

<210> SEQ ID NO 248
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid

<400> SEQUENCE: 248

Lys Cys Asn Thr Ala Thr Cys Ala Thr Gln Arg Leu Ala Asn Phe Leu
1               5                   10                  15

Xaa His Ser Ser Asn Asn Phe Gly Pro Ile Leu Pro Pro Thr Asn Val
            20                  25                  30

Gly His Asn Thr Tyr
        35

<210> SEQ ID NO 249
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid

<400> SEQUENCE: 249

Lys Cys Asn Thr Ala Thr Cys Ala Thr Gln Arg Leu Ala Asn Phe Leu
1               5                   10                  15

Xaa His Ser Ser Asn Asn Phe Gly Pro Ile Leu Pro Pro Thr Asn Val
            20                  25                  30

Gly Pro Asn Thr Tyr
        35

<210> SEQ ID NO 250
<211> LENGTH: 37
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid
<220> FEATURE:
<221> NAME/KEY: MOD_RES
<222> LOCATION: (35)..(35)
<223> OTHER INFORMATION: 2-amino-2-methylpropanoic acid

<400> SEQUENCE: 250

Lys Cys Asn Thr Ala Thr Cys Ala Thr Gln Arg Leu Ala Asn Phe Leu
1               5                   10                  15

Xaa His Ser Ser Asn Asn Phe Gly Pro Ile Leu Pro Pro Thr Asn Val
            20                  25                  30

Gly Ser Xaa Thr Tyr
        35

<210> SEQ ID NO 251
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid

<400> SEQUENCE: 251

Lys Cys Asn Thr Ala Thr Cys Ala Thr Gln Arg Leu Ala Asn Phe Leu
1               5                   10                  15

Xaa His Ser Ser Asn Asn Phe Gly Pro Ile Leu Pro Pro Thr Asn Val
            20                  25                  30

Gly Ser Glu Thr Tyr
        35

<210> SEQ ID NO 252
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (17)..(17)
<223> OTHER INFORMATION: 2-amino-2-methylpropanoic acid

<400> SEQUENCE: 252

Lys Cys Asn Thr Ala Thr Cys Ala Thr Gln Arg Leu Ala Asn Phe Leu
1               5                   10                  15
```

```
Xaa His Ser Ser Asn Asn Phe Gly Pro Ile Leu Pro Pro Thr Asn Val
        20                  25                  30

Gly Ser Arg Thr Tyr
        35

<210> SEQ ID NO 253
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid

<400> SEQUENCE: 253

Lys Cys Asn Thr Ala Thr Cys Ala Thr Gln Arg Leu Ala Asn Phe Leu
1               5                   10                  15

Glu His Ser Ser Xaa Asn Phe Gly Pro Ile Leu Pro Pro Thr Asn Val
        20                  25                  30

Gly Ser Asn Thr Tyr
        35

<210> SEQ ID NO 254
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid

<400> SEQUENCE: 254

Lys Cys Asn Thr Ala Thr Cys Ala Thr Gln Arg Leu Ala Asn Phe Leu
1               5                   10                  15

Arg His Ser Ser Xaa Asn Phe Gly Pro Ile Leu Pro Pro Thr Asn Val
        20                  25                  30

Gly Ser Asn Thr Tyr
        35

<210> SEQ ID NO 255
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid
<220> FEATURE:
```

```
<221> NAME/KEY: MOD_RES
<222> LOCATION: (31)..(31)
<223> OTHER INFORMATION: 2-amino-2-methylpropanoic acid

<400> SEQUENCE: 255

Lys Cys Asn Thr Ala Thr Cys Ala Thr Gln Arg Leu Ala Asn Phe Leu
1               5                   10                  15

Arg His Ser Ser Xaa Asn Phe Gly Pro Ile Leu Pro Pro Thr Xaa Val
            20                  25                  30

Gly Ser Asn Thr Tyr
        35

<210> SEQ ID NO 256
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid

<400> SEQUENCE: 256

Lys Cys Asn Thr Ala Thr Cys Ala Thr Gln Arg Leu Ala Asn Phe Leu
1               5                   10                  15

Arg His Ser Ser Xaa Asn Phe Gly Pro Ile Leu Pro Pro Thr Glu Val
            20                  25                  30

Gly Ser Asn Thr Tyr
        35

<210> SEQ ID NO 257
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid

<400> SEQUENCE: 257

Lys Cys Asn Thr Ala Thr Cys Ala Thr Gln Arg Leu Ala Asn Phe Leu
1               5                   10                  15

Arg His Ser Ser Xaa Asn Phe Gly Pro Ile Leu Pro Pro Thr Arg Val
            20                  25                  30

Gly Ser Asn Thr Tyr
        35

<210> SEQ ID NO 258
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid
<220> FEATURE:
<221> NAME/KEY: MOD_RES
<222> LOCATION: (35)..(35)
<223> OTHER INFORMATION: 2-amino-2-methylpropanoic acid

<400> SEQUENCE: 258

Lys Cys Asn Thr Ala Thr Cys Ala Thr Gln Arg Leu Ala Asn Phe Leu
1               5                   10                  15

Arg His Ser Ser Xaa Asn Phe Gly Pro Ile Leu Pro Pro Thr Asn Val
            20                  25                  30

Gly Ser Xaa Thr Tyr
        35

<210> SEQ ID NO 259
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (23)..(23)
<223> OTHER INFORMATION: (S)-2-amino-2-methyl-3-phenylpropanoic acid

<400> SEQUENCE: 259

Lys Cys Asn Thr Ala Thr Cys Ala Thr Gln Arg Leu Ala Asn Phe Leu
1               5                   10                  15

Arg His Ser Ser Asn Asn Xaa Gly Pro Ile Leu Pro Pro Thr Asn Val
            20                  25                  30

Gly Ser Asn Thr Tyr
        35

<210> SEQ ID NO 260
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (23)..(23)
<223> OTHER INFORMATION: (S)-2-amino-2-methyl-3-phenylpropanoic acid

<400> SEQUENCE: 260

Lys Cys Asn Thr Ala Thr Cys Ala Thr Gln Arg Leu Ala Asn Phe Leu
1               5                   10                  15

Arg His Ser Ser Asn Asn Xaa Gly Pro Ile Leu Pro Pro Thr Glu Val
            20                  25                  30

Gly Ser Asn Thr Tyr
        35
```

```
<210> SEQ ID NO 261
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (26)..(26)
<223> OTHER INFORMATION: 2-amino-2-methylpropanoic acid

<400> SEQUENCE: 261

Lys Cys Asn Thr Ala Thr Cys Ala Thr Gln Arg Leu Ala Asn Phe Leu
1               5                   10                  15

Arg His Ser Ser Asn Asn Phe Gly Pro Xaa Leu Pro Pro Thr Asn Val
            20                  25                  30

Gly Ser Asn Thr Tyr
        35

<210> SEQ ID NO 262
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid

<400> SEQUENCE: 262

Lys Cys Asn Thr Ala Thr Cys Ala Thr Gln Arg Leu Ala Asn Phe Leu
1               5                   10                  15

Ser His Ser Ser Xaa Asn Phe Gly Pro Ile Leu Pro Pro Thr Asn Val
            20                  25                  30

Gly Ser Asn Thr Tyr
        35

<210> SEQ ID NO 263
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid

<400> SEQUENCE: 263

Lys Cys Asn Thr Ala Thr Cys Ala Thr Gln Arg Leu Ala Asn Phe Leu
1               5                   10                  15
```

Ser His Ser Ser Xaa Asn Phe Gly Pro Ile Leu Pro Pro Thr His Val
            20                  25                  30

Gly Ser Asn Thr Tyr
        35

<210> SEQ ID NO 264
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid

<400> SEQUENCE: 264

Lys Cys Asn Thr Ala Thr Cys Ala Thr Gln Arg Leu Ala Asn Phe Leu
1               5                   10                  15

Ser His Ser Ser Xaa Asn Phe Gly Pro Ile Leu Pro Pro Thr Pro Val
            20                  25                  30

Gly Ser Asn Thr Tyr
        35

<210> SEQ ID NO 265
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid

<400> SEQUENCE: 265

Lys Cys Asn Thr Ala Thr Cys Ala Thr Gln Arg Leu Ala Asn Phe Leu
1               5                   10                  15

Ser His Ser Ser Xaa Asn Phe Gly Pro Ile Leu Pro Pro Thr Arg Val
            20                  25                  30

Gly Ser Asn Thr Tyr
        35

<210> SEQ ID NO 266
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid

<400> SEQUENCE: 266

Lys Cys Asn Thr Ala Thr Cys Ala Thr Gln Arg Leu Ala Asn Phe Leu
1               5                   10                  15

Ser His Ser Ser Xaa Asn Phe Gly Pro Ile Leu Pro Pro Thr Asn Val
            20                  25                  30

Pro Ser Asn Thr Tyr
        35

<210> SEQ ID NO 267
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid

<400> SEQUENCE: 267

Lys Cys Asn Thr Ala Thr Cys Ala Thr Gln Arg Leu Ala Asn Phe Leu
1               5                   10                  15

Ser His Ser Ser Xaa Asn Phe Gly Pro Ile Leu Pro Pro Thr Asn Val
            20                  25                  30

Gly Ser Pro Thr Tyr
        35

<210> SEQ ID NO 268
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (20)..(20)
<223> OTHER INFORMATION: (S)-2-amino-3-hydroxy-2-methylpropanoic acid

<400> SEQUENCE: 268

Lys Cys Asn Thr Ala Thr Cys Ala Thr Gln Arg Leu Ala Asn Phe Leu
1               5                   10                  15

Val His Ser Xaa Asn Asn Phe Gly Pro Ile Leu Pro Pro Thr Asn Val
            20                  25                  30

Gly Ser Asn Thr Tyr
        35

<210> SEQ ID NO 269
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues

<400> SEQUENCE: 269

Lys Cys Asn Thr Ala Thr Cys Ala Thr Gln Arg Leu Ala Asn Phe Leu
1               5                   10                  15

Val His Ser Pro Pro Asn Phe Pro Ala Ile Leu Ser Pro Thr Asn Val
            20                  25                  30

Gly Ser Asn Thr Tyr
        35

<210> SEQ ID NO 270
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid

<400> SEQUENCE: 270

Lys Cys Asn Thr Ala Thr Cys Ala Thr Gln Arg Leu Ala Asn Phe Leu
1               5                   10                  15

Val His Ser Ser Xaa Asn Phe Gly Pro Ile Leu Pro Pro Thr Asn Val
            20                  25                  30

Gly Ser Asn Thr Tyr
        35

<210> SEQ ID NO 271
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid

<400> SEQUENCE: 271

Lys Cys Asn Thr Ala Thr Cys Ala Thr Gln Arg Leu Ala Asn Phe Leu
1               5                   10                  15

Val His Ser Ser Xaa Asn Phe Pro Ala Ile Leu Ser Pro Thr Asn Val
            20                  25                  30

Gly Ser Asn Thr Tyr
        35

<210> SEQ ID NO 272
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)

<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid
<220> FEATURE:
<221> NAME/KEY: MOD_RES
<222> LOCATION: (31)..(31)
<223> OTHER INFORMATION: 2,4-diaminobutanoic acid (Dab)

<400> SEQUENCE: 272

Lys Cys Asn Thr Ala Thr Cys Ala Thr Gln Arg Leu Ala Asn Phe Leu
1               5                   10                  15

Val His Ser Ser Xaa Asn Phe Pro Ala Ile Leu Ser Pro Thr Xaa Val
            20                  25                  30

Gly Ser Asn Thr Tyr
        35

<210> SEQ ID NO 273
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid
<220> FEATURE:
<221> NAME/KEY: MOD_RES
<222> LOCATION: (35)..(35)
<223> OTHER INFORMATION: 2,4-diaminobutanoic acid (Dab)

<400> SEQUENCE: 273

Lys Cys Asn Thr Ala Thr Cys Ala Thr Gln Arg Leu Ala Asn Phe Leu
1               5                   10                  15

Val His Ser Ser Xaa Asn Phe Pro Ala Ile Leu Ser Pro Thr Asn Val
            20                  25                  30

Gly Ser Xaa Thr Tyr
        35

<210> SEQ ID NO 274
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid
<220> FEATURE:
<221> NAME/KEY: MOD_RES
<222> LOCATION: (26)..(26)
<223> OTHER INFORMATION: D-Ile

<400> SEQUENCE: 274

Lys Cys Asn Thr Ala Thr Cys Ala Thr Gln Arg Leu Ala Asn Phe Leu
1               5                   10                  15

```
Val His Ser Ser Xaa Asn Phe Gly Pro Xaa Leu Pro Pro Thr Asn Val
            20                  25                  30

Gly Ser Asn Thr Tyr
        35

<210> SEQ ID NO 275
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid
<220> FEATURE:
<221> NAME/KEY: MOD_RES
<222> LOCATION: (26)..(26)
<223> OTHER INFORMATION: 2-amino-2-methylpropanoic acid

<400> SEQUENCE: 275

Lys Cys Asn Thr Ala Thr Cys Ala Thr Gln Arg Leu Ala Asn Phe Leu
1               5                   10                  15

Val His Ser Ser Xaa Asn Phe Gly Pro Xaa Leu Pro Pro Thr Asn Val
            20                  25                  30

Gly Ser Asn Thr Tyr
        35

<210> SEQ ID NO 276
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid
<220> FEATURE:
<221> NAME/KEY: MOD_RES
<222> LOCATION: (27)..(27)
<223> OTHER INFORMATION: 2-amino-2-methylpropanoic acid

<400> SEQUENCE: 276

Lys Cys Asn Thr Ala Thr Cys Ala Thr Gln Arg Leu Ala Asn Phe Leu
1               5                   10                  15

Val His Ser Ser Xaa Asn Phe Gly Pro Ile Xaa Pro Pro Thr Asn Val
            20                  25                  30

Gly Ser Asn Thr Tyr
        35

<210> SEQ ID NO 277
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid
<220> FEATURE:
<221> NAME/KEY: MOD_RES
<222> LOCATION: (27)..(27)
<223> OTHER INFORMATION: D-Leu

<400> SEQUENCE: 277

Lys Cys Asn Thr Ala Thr Cys Ala Thr Gln Arg Leu Ala Asn Phe Leu
1               5                   10                  15

Val His Ser Ser Xaa Asn Phe Gly Pro Ile Xaa Pro Pro Thr Asn Val
                20                  25                  30

Gly Ser Asn Thr Tyr
        35

<210> SEQ ID NO 278
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid
<220> FEATURE:
<221> NAME/KEY: MOD_RES
<222> LOCATION: (28)..(28)
<223> OTHER INFORMATION: 2-amino-2-methylpropanoic acid

<400> SEQUENCE: 278

Lys Cys Asn Thr Ala Thr Cys Ala Thr Gln Arg Leu Ala Asn Phe Leu
1               5                   10                  15

Val His Ser Ser Xaa Asn Phe Gly Pro Ile Leu Xaa Pro Thr Asn Val
                20                  25                  30

Gly Ser Asn Thr Tyr
        35

<210> SEQ ID NO 279
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid
<220> FEATURE:
<221> NAME/KEY: MOD_RES
<222> LOCATION: (28)..(28)
<223> OTHER INFORMATION: D-Pro

<400> SEQUENCE: 279

Lys Cys Asn Thr Ala Thr Cys Ala Thr Gln Arg Leu Ala Asn Phe Leu
```

```
1               5                  10                 15
Val His Ser Ser Xaa Asn Phe Gly Pro Ile Leu Xaa Pro Thr Asn Val
            20                 25                 30

Gly Ser Asn Thr Tyr
            35

<210> SEQ ID NO 280
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid
<220> FEATURE:
<221> NAME/KEY: MOD_RES
<222> LOCATION: (31)..(31)
<223> OTHER INFORMATION: 2-amino-2-methylpropanoic acid

<400> SEQUENCE: 280

Lys Cys Asn Thr Ala Thr Cys Ala Thr Gln Arg Leu Ala Asn Phe Leu
1               5                  10                 15

Val His Ser Ser Xaa Asn Phe Gly Pro Ile Leu Pro Pro Thr Xaa Val
            20                 25                 30

Gly Ser Asn Thr Tyr
            35

<210> SEQ ID NO 281
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid

<400> SEQUENCE: 281

Lys Cys Asn Thr Ala Thr Cys Ala Thr Gln Arg Leu Ala Asn Phe Leu
1               5                  10                 15

Val His Ser Ser Xaa Asn Phe Gly Pro Ile Leu Pro Pro Thr Glu Val
            20                 25                 30

Gly Ser Asn Thr Tyr
            35

<210> SEQ ID NO 282
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
```

```
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid

<400> SEQUENCE: 282

Lys Cys Asn Thr Ala Thr Cys Ala Thr Gln Arg Leu Ala Asn Phe Leu
1               5                   10                  15

Val His Ser Ser Xaa Asn Phe Gly Pro Ile Leu Pro Pro Thr His Val
            20                  25                  30

Gly Ser Asn Thr Tyr
        35

<210> SEQ ID NO 283
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid

<400> SEQUENCE: 283

Lys Cys Asn Thr Ala Thr Cys Ala Thr Gln Arg Leu Ala Asn Phe Leu
1               5                   10                  15

Val His Ser Ser Xaa Asn Phe Gly Pro Ile Leu Pro Pro Thr Arg Val
            20                  25                  30

Gly Ser Asn Thr Tyr
        35

<210> SEQ ID NO 284
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid
<220> FEATURE:
<221> NAME/KEY: MOD_RES
<222> LOCATION: (33)..(33)
<223> OTHER INFORMATION: 2-amino-2-methylpropanoic acid

<400> SEQUENCE: 284

Lys Cys Asn Thr Ala Thr Cys Ala Thr Gln Arg Leu Ala Asn Phe Leu
1               5                   10                  15

Val His Ser Ser Xaa Asn Phe Gly Pro Ile Leu Pro Pro Thr Asn Val
            20                  25                  30

Xaa Ser Asn Thr Tyr
        35

<210> SEQ ID NO 285
```

```
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid
<220> FEATURE:
<221> NAME/KEY: MOD_RES
<222> LOCATION: (34)..(34)
<223> OTHER INFORMATION: 2-amino-2-methylpropanoic acid

<400> SEQUENCE: 285

Lys Cys Asn Thr Ala Thr Cys Ala Thr Gln Arg Leu Ala Asn Phe Leu
1               5                   10                  15

Val His Ser Ser Xaa Asn Phe Gly Pro Ile Leu Pro Pro Thr Asn Val
            20                  25                  30

Gly Xaa Asn Thr Tyr
        35

<210> SEQ ID NO 286
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid
<220> FEATURE:
<221> NAME/KEY: MOD_RES
<222> LOCATION: (35)..(35)
<223> OTHER INFORMATION: 2-amino-2-methylpropanoic acid

<400> SEQUENCE: 286

Lys Cys Asn Thr Ala Thr Cys Ala Thr Gln Arg Leu Ala Asn Phe Leu
1               5                   10                  15

Val His Ser Ser Xaa Asn Phe Gly Pro Ile Leu Pro Pro Thr Asn Val
            20                  25                  30

Gly Ser Xaa Thr Tyr
        35

<210> SEQ ID NO 287
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid
```

```
<400> SEQUENCE: 287

Lys Cys Asn Thr Ala Thr Cys Ala Thr Gln Arg Leu Ala Asn Phe Leu
1               5                   10                  15

Val His Ser Ser Xaa Asn Phe Gly Pro Ile Leu Pro Pro Thr Asn Val
                20                  25                  30

Gly Ser Glu Thr Tyr
            35

<210> SEQ ID NO 288
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid

<400> SEQUENCE: 288

Lys Cys Asn Thr Ala Thr Cys Ala Thr Gln Arg Leu Ala Asn Phe Leu
1               5                   10                  15

Val His Ser Ser Xaa Asn Phe Gly Pro Ile Leu Pro Pro Thr Asn Val
                20                  25                  30

Gly Ser Arg Thr Tyr
            35

<210> SEQ ID NO 289
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid
<220> FEATURE:
<221> NAME/KEY: MOD_RES
<222> LOCATION: (36)..(36)
<223> OTHER INFORMATION: 2-amino-2-methylpropanoic acid

<400> SEQUENCE: 289

Lys Cys Asn Thr Ala Thr Cys Ala Thr Gln Arg Leu Ala Asn Phe Leu
1               5                   10                  15

Val His Ser Ser Xaa Asn Phe Gly Pro Ile Leu Pro Pro Thr Asn Val
                20                  25                  30

Gly Ser Asn Xaa Tyr
            35

<210> SEQ ID NO 290
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid
<220> FEATURE:
<221> NAME/KEY: MOD_RES
<222> LOCATION: (37)..(37)
<223> OTHER INFORMATION: 2-amino-2-methylpropanoic acid

<400> SEQUENCE: 290

Lys Cys Asn Thr Ala Thr Cys Ala Thr Gln Arg Leu Ala Asn Phe Leu
1               5                   10                  15

Val His Ser Ser Xaa Asn Phe Gly Pro Ile Leu Pro Pro Thr Asn Val
            20                  25                  30

Gly Ser Asn Thr Xaa
            35

<210> SEQ ID NO 291
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid

<400> SEQUENCE: 291

Lys Cys Asn Thr Ala Thr Cys Ala Thr Gln Arg Leu Ala Asn Phe Leu
1               5                   10                  15

Val His Ser Ser Xaa Asn Phe Gly Pro Ile Leu Pro Pro Thr Asn Val
            20                  25                  30

Gly Ser Asn Thr Pro
            35

<210> SEQ ID NO 292
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2-amino-2-methylpropanoic acid
<220> FEATURE:
<221> NAME/KEY: MOD_RES
<222> LOCATION: (24)..(24)
<223> OTHER INFORMATION: (2S,4R)-4-hydroxypyrrolidine-2-carboxylic acid

<400> SEQUENCE: 292

Lys Cys Asn Thr Ala Thr Cys Ala Thr Gln Arg Leu Ala Asn Phe Leu
1               5                   10                  15

Val His Ser Ser Xaa Asn Phe Xaa Ala Ile Leu Ser Pro Thr Asn Val
```

```
                    20                  25                  30

Gly Ser Asn Thr Tyr
         35

<210> SEQ ID NO 293
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2,4-diaminobutanoic acid (Dab)

<400> SEQUENCE: 293

Lys Cys Asn Thr Ala Thr Cys Ala Thr Gln Arg Leu Ala Asn Phe Leu
 1               5                  10                  15

Val His Ser Ser Xaa Asn Phe Pro Ala Ile Leu Ser Pro Thr Asn Val
                 20                  25                  30

Gly Ser Asn Thr Tyr
         35

<210> SEQ ID NO 294
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (21)..(21)
<223> OTHER INFORMATION: 2,4-diaminobutanoic acid (Dab)
<220> FEATURE:
<221> NAME/KEY: MOD_RES
<222> LOCATION: (25)..(25)
<223> OTHER INFORMATION: 2-amino-2-methylpropanoic acid

<400> SEQUENCE: 294

Lys Cys Asn Thr Ala Thr Cys Ala Thr Gln Arg Leu Ala Asn Phe Leu
 1               5                  10                  15

Val His Ser Ser Xaa Asn Phe Gly Xaa Ile Leu Pro Pro Thr Asn Val
                 20                  25                  30

Gly Ser Asn Thr Tyr
         35

<210> SEQ ID NO 295
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
```

<222> LOCATION: (21)..(21)
<223> OTHER INFORMATION: 2,4-diaminobutanoic acid (Dab)

<400> SEQUENCE: 295

Lys Cys Asn Thr Ala Thr Cys Ala Thr Gln Arg Leu Ala Asn Phe Leu
1               5                   10                  15

Val His Ser Ser Xaa Asn Phe Gly Pro Ile Leu Pro Pro Thr Glu Val
            20                  25                  30

Gly Ser Asn Thr Tyr
        35

<210> SEQ ID NO 296
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues

<400> SEQUENCE: 296

Lys Cys Asn Thr Ala Thr Cys Ala Thr Gln Arg Leu Ala Asn Phe Leu
1               5                   10                  15

Val His Ser Ser Pro Asn Phe Pro Ala Ile Leu Ser Pro Thr Asn Val
            20                  25                  30

Gly Ser Asn Thr Tyr
        35

<210> SEQ ID NO 297
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (22)..(22)
<223> OTHER INFORMATION: 2-amino-2-methylpropanoic acid

<400> SEQUENCE: 297

Lys Cys Asn Thr Ala Thr Cys Ala Thr Gln Arg Leu Ala Asn Phe Leu
1               5                   10                  15

Val His Ser Ser Asn Xaa Phe Gly Pro Ile Leu Pro Pro Thr Asn Val
            20                  25                  30

Gly Ser Asn Thr Tyr
        35

<210> SEQ ID NO 298
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues

```
<400> SEQUENCE: 298

Lys Cys Asn Thr Ala Thr Cys Ala Thr Gln Arg Leu Ala Asn Phe Leu
1               5                   10                  15

Val His Ser Ser Asn His Phe Gly Pro Ile Leu Pro Pro Thr Asn Val
            20                  25                  30

Gly Ser Glu Thr Tyr
        35

<210> SEQ ID NO 299
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (23)..(23)
<223> OTHER INFORMATION: (S)-2-amino-2-methyl-3-phenylpropanoic acid

<400> SEQUENCE: 299

Lys Cys Asn Thr Ala Thr Cys Ala Thr Gln Arg Leu Ala Asn Phe Leu
1               5                   10                  15

Val His Ser Ser Asn Asn Xaa Gly Pro Ile Leu Pro Pro Thr Asn Val
            20                  25                  30

Gly Ser Asn Thr Tyr
        35

<210> SEQ ID NO 300
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (23)..(23)
<223> OTHER INFORMATION: (S)-2-amino-2-methyl-3-phenylpropanoic acid

<400> SEQUENCE: 300

Lys Cys Asn Thr Ala Thr Cys Ala Thr Gln Arg Leu Ala Asn Phe Leu
1               5                   10                  15

Val His Ser Ser Asn Asn Xaa Gly Pro Ile Leu Pro Pro Thr Glu Val
            20                  25                  30

Gly Ser Asn Thr Tyr
        35

<210> SEQ ID NO 301
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
```

```
<220> FEATURE:
<221> NAME/KEY: MOD_RES
<222> LOCATION: (23)..(23)
<223> OTHER INFORMATION: (S)-2-amino-2-methyl-3-phenylpropanoic acid

<400> SEQUENCE: 301

Lys Cys Asn Thr Ala Thr Cys Ala Thr Gln Arg Leu Ala Asn Phe Leu
1               5                   10                  15

Val His Ser Ser Asn Asn Xaa Gly Pro Ile Leu Pro Pro Thr Arg Val
            20                  25                  30

Gly Ser Asn Thr Tyr
            35

<210> SEQ ID NO 302
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (23)..(23)
<223> OTHER INFORMATION: (S)-2-amino-2-methyl-3-phenylpropanoic acid

<400> SEQUENCE: 302

Lys Cys Asn Thr Ala Thr Cys Ala Thr Gln Arg Leu Ala Asn Phe Leu
1               5                   10                  15

Val His Ser Ser Asn Asn Xaa Gly Pro Ile Leu Pro Pro Thr Asn Val
            20                  25                  30

Gly Ser Arg Thr Tyr
            35

<210> SEQ ID NO 303
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (24)..(24)
<223> OTHER INFORMATION: 2-amino-2-methylpropanoic acid

<400> SEQUENCE: 303

Lys Cys Asn Thr Ala Thr Cys Ala Thr Gln Arg Leu Ala Asn Phe Leu
1               5                   10                  15

Val His Ser Ser Asn Asn Phe Xaa Pro Ile Leu Pro Pro Thr Asn Val
            20                  25                  30

Gly Ser Asn Thr Tyr
            35

<210> SEQ ID NO 304
<211> LENGTH: 37
<212> TYPE: PRT
<213> ORGANISM: Artificial Sequence
<220> FEATURE:
<223> OTHER INFORMATION: Description of Artificial Sequence: Synthetic
```

```
         polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (26)..(26)
<223> OTHER INFORMATION: 2-amino-2-methylpropanoic acid

<400> SEQUENCE: 304

Lys Cys Asn Thr Ala Thr Cys Ala Thr Gln Arg Leu Ala Asn Phe Leu
1               5                   10                  15

Val His Ser Ser Asn Asn Phe Gly Pro Xaa Leu Pro Pro Thr Asn Val
            20                  25                  30

Gly Ser Asn Thr Tyr
        35

<210> SEQ ID NO 305
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (27)..(27)
<223> OTHER INFORMATION: 2-amino-2-methylpropanoic acid

<400> SEQUENCE: 305

Lys Cys Asn Thr Ala Thr Cys Ala Thr Gln Arg Leu Ala Asn Phe Leu
1               5                   10                  15

Val His Ser Ser Asn Asn Phe Gly Pro Ile Xaa Pro Pro Thr Asn Val
            20                  25                  30

Gly Ser Asn Thr Tyr
        35

<210> SEQ ID NO 306
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (27)..(27)
<223> OTHER INFORMATION: D-Leu

<400> SEQUENCE: 306

Lys Cys Asn Thr Ala Thr Cys Ala Thr Gln Arg Leu Ala Asn Phe Leu
1               5                   10                  15

Val His Ser Ser Asn Asn Phe Gly Pro Ile Xaa Pro Pro Thr Asn Val
            20                  25                  30

Gly Ser Asn Thr Tyr
        35

<210> SEQ ID NO 307
```

```
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues
<220> FEATURE:
<221> NAME/KEY: MOD_RES
<222> LOCATION: (28)..(28)
<223> OTHER INFORMATION: D-Pro

<400> SEQUENCE: 307

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Xaa Pro Thr Asn Val
            20                  25                  30

Gly Ser Asn Thr Tyr
        35

<210> SEQ ID NO 308
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(7)
<223> OTHER INFORMATION: Disulphide bridge between Cys residues

<400> SEQUENCE: 308

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Pro Thr Asn Val
            20                  25                  30

Gly Ser Arg Thr Tyr
        35

<210> SEQ ID NO 309
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(6)
<223> OTHER INFORMATION: Disulphide bridge between Cys residues
<220> FEATURE:
<221> NAME/KEY: MOD_RES
<222> LOCATION: (20)..(20)
<223> OTHER INFORMATION: 2,4-diaminobutanoic acid (Dab)

<400> SEQUENCE: 309

Cys Asn Ile Ala Thr Cys Ala Thr Gln Arg Leu Ala Asn Phe Leu Val
1               5                   10                  15

His Ser Ser Xaa Asn Phe Gly Pro Ile Leu Pro Pro Thr Asn Val Gly
            20                  25                  30

Ser Arg Thr Tyr
        35
```

```
<210> SEQ ID NO 310
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(6)
<223> OTHER INFORMATION: Disulphide bridge between Cys residues
<220> FEATURE:
<221> NAME/KEY: MOD_RES
<222> LOCATION: (22)..(22)
<223> OTHER INFORMATION: (S)-2-amino-2-methyl-3-phenylpropanoic acid

<400> SEQUENCE: 310

Cys Asn Thr Ala Thr Cys Ala Thr Gln Arg Leu Ala Glu Phe Leu Arg
1               5                   10                  15

His Ser Ser Asn Asn Xaa Gly Pro Ile Leu Pro Pro Thr Asn Val Gly
            20                  25                  30

Ser Asn Thr Tyr
        35

<210> SEQ ID NO 311
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(6)
<223> OTHER INFORMATION: Disulphide bridge between Cys residues
<220> FEATURE:
<221> NAME/KEY: MOD_RES
<222> LOCATION: (20)..(20)
<223> OTHER INFORMATION: 2-amino-2-methylpropanoic acid

<400> SEQUENCE: 311

Cys Asn Thr Ala Thr Cys Ala Thr Gln Arg Leu Ala Asn Phe Leu Val
1               5                   10                  15

His Ser Ser Xaa Asn Phe Gly Pro Ile Leu Pro Pro Thr Arg Val Gly
            20                  25                  30

Ser Asn Thr Tyr
        35
```

POLYPEPTIDES AND USES THEREOF

CROSS-REFERENCE TO RELATED APPLICATIONS

This application claims the benefit under 35 U.S.C. § 119 (e) of U.S. Provisional Patent Application No. 63/125,996, filed on Dec. 16, 2020. This application is incorporated by reference in its entirety for all purposes.

SEQUENCE LISTING

The instant application contains a Sequence Listing which has been submitted electronically in ASCII format and is hereby incorporated by reference in its entirety. Said ASCII copy, created on Sep. 29, 2023, is named 201085-US—NP_SL.txt and is 320,045 bytes in size.

FIELD OF THE INVENTION

The present invention relates to polypeptides which are pramlintide analogues and uses thereof. In particular, the present invention relates to polypeptides which are pramlintide analogues conjugated to half-life extending moieties such as albumin binding moieties and uses thereof.

BACKGROUND

Pramlintide is a synthetic analogue of human amylin with three proline substitutions, at positions 25, 28 and 29. As a result of these substitutions, pramlintide has a reduced propensity to form amyloid fibrils, thereby overcoming a physicochemical liability of native human amylin (Kruger DF, Gloster MA. Pramlintide for the treatment of insulin-requiring diabetes mellitus: rationale and review of clinical data. Drugs. 2004; 64 (13): 1419-32).

Pramlintide is clinically used in amylin replacement therapies and simulates the important glucoregulatory actions of amylin. These glucoregulatory actions complement those of insulin by regulating the rate of appearance of glucose in the circulation, and are achieved through three primary mechanisms: slowing the rate of gastric emptying, suppression of post-meal glucagon secretion and suppression of food intake (Roth JD et. al. GLP-1R and amylin agonism in metabolic disease: complementary mechanisms and future opportunities. Br J Pharmacol. 2012; 166 (1): 121-136). Pramlintide has been used as an adjunct to insulin in patients with diabetes who have failed to reach desired glucose control despite optimal insulin therapy (Pullman J, et. al. Pramlintide is used in the management of insulin-using patients with type 2 and type 1 diabetes. Vasc Health Risk Manag. 2006;2 (3): 203-212).

Pharmacokinetic studies show that the terminal half-life of amylin in rats is around 13 minutes, and the half-life for pramlintide in human is ~20-45 minutes (Roth JD et. al. GLP-1R and amylin agonism in metabolic disease: complementary mechanisms and future opportunities. Br J Pharmacol. 2012; 166 (1): 121-136).

There remains a need for pramlintide analogues which retain amylin agonist activity and provide advantages such as extended half-life and reduced fibrillation tendency.

SUMMARY OF INVENTION

The present invention relates to polypeptides that are pramlintide analogues conjugated to albumin binding moieties (e.g. lipids).

Thus, in one aspect, there is provided a polypeptide, or a pharmaceutically acceptable salt thereof, comprising the amino acid sequence:

Xaa (−4)-Xaa (−3)-Xaa (−2)-Xaa (−1)-Xaa 1-Cys 2-Asn 3-Xaa 4-Ala 5-Thr 6-Cys 7-Ala 8-Thr 9-Gln 10-Arg 11-Leu 12-Ala 13-Xaa 14-Xaa 15-Xaa 16-Xaa 17-His 18-Ser 19-Xaa 20-Xaa 21-Xaa 22-Xaa 23-Xaa 24-Xaa 25-Xaa 26-Xaa 27-Xaa 28-Xaa 29-Thr 30-Xaa 31-Xaa 32-Xaa 33-Xaa 34-Xaa 35-Xaa 36-Xaa 37-amide [SEQ ID NO:2], wherein:

Xaa (−4) is Lys (albumin binding moiety) or is absent;
Xaa (−3) is Gly or is absent;
Xaa (−2) is Gly or is absent;
Xaa (−1) is Gly, (albumin binding moiety), Lys (albumin binding moiety) or is absent;
Xaa 1 is Lys, Lys (albumin binding moiety), (albumin binding moiety) or is absent;
Xaa 4 is Thr, Ile or Ala;
Xaa 14 is Asn, His, Glu, 2,4-diaminobutanoic acid (Dab), or an alpha methyl amino acid;
Xaa 15 is Phe or Trp;
Xaa 16 is Leu or D-Leu (dL);
Xaa 17 is Val, Ser, Glu, Arg, (2S,4R)-4-hydroxypyrrolidine-2-carboxylic acid (Hyp), Dab or an alpha methyl amino acid (e.g. 2-amino-2-methylpropanoic acid [Aib]);
Xaa 20 is Ser, Ile, Pro or an alpha methyl amino acid (e.g. (S)-2-amino-3-hydroxy-2-methylpropanoic acid [aMeSer]);
Xaa 21 is Asn, Dab, His, Pro, Ser, Arg, Lys, Gly, Glu, Ala, Hyp or an alpha methyl amino acid (e.g. Aib);
Xaa 22 is Asn, His, Hyp, Dab or an alpha methyl amino acid (e.g. Aib);
Xaa 23 is Phe, Hyp or an alpha methyl amino acid (e.g. (S)-2-amino-2-methyl-3-phenylpropanoic acid [aMePhe]);
Xaa 24 is Gly, Pro, Hyp or an alpha methyl amino acid (e.g. Aib);
Xaa 25 is Pro, Ala, Hyp or an alpha methyl amino acid (e.g. Aib);
Xaa 26 is Ile, D-Ile (dl), Arg, Hyp or an alpha methyl amino acid (e.g. Aib);
Xaa 27 is Leu, dL, Hyp or an alpha methyl amino acid (e.g. Aib);
Xaa 28 is Pro, D-Pro (dP), Ser, Hyp or an alpha methyl amino acid (e.g. Aib);
Xaa 29 is Pro, Hyp or an alpha methyl amino acid (e.g. Aib);
Xaa 31 is Asn, Glu, His, Arg, Pro, Dab or an alpha methyl amino acid (e.g. Aib);
Xaa 32 is Val, Hyp, Dab or an alpha methyl amino acid (e.g. Aib);
Xaa 33 is Gly, Pro, Hyp or an alpha methyl amino acid (e.g. Aib);
Xaa 34 is Ser, Pro, His, Hyp or an alpha methyl amino acid (e.g. Aib);
Xaa 35 is Asn, Pro, Arg, Glu, Dab, Hyp or an alpha methyl amino acid (e.g. Aib);
Xaa 36 is Thr, Hyp or an alpha methyl amino acid (e.g. Aib); and
Xaa 37 is Tyr, Pro, Hyp or an alpha methyl amino acid (e.g. Aib), and wherein the polypeptide comprises at least one albumin binding moiety.

In another aspect, there is provided a lipidated polypeptide, or a pharmaceutically acceptable salt thereof, comprising the amino acid sequence:

Xaa (−4)-Xaa (−3)-Xaa (−2)-Xaa (−1)-Xaa 1-Cys 2-Asn 3-Xaa 4-Ala 5-Thr 6-Cys 7-Ala 8-Thr 9-Gln 10-Arg 11-Leu 12-Ala 13-Xaa 14-Xaa 15-Xaa 16-Xaa 17-His 18-Ser 19-Xaa 20-Xaa 21-Xaa 22-Xaa 23-Xaa 24-Xaa 25-Xaa 26-Xaa 27-Xaa 28-Xaa 29-Thr 30-Xaa 31-Xaa 32-Xaa 33-Xaa 34-Xaa 35-Xaa 36-Xaa 37-amide [SEQ ID NO: 159], wherein:

Xaa (−4) is Lys (linker-lipid) or is absent;
Xaa (−3) is Gly or is absent;
Xaa (−2) is Gly or is absent;
Xaa (−1) is Gly, (linker-lipid), Lys (linker-lipid) or is absent;
Xaa 1 is Lys, Lys (linker-lipid), (linker-lipid) or is absent;
Xaa 4 is Thr, Ile or Ala;
Xaa 14 is Asn, His, Glu, 2,4-diaminobutanoic acid (Dab), or an alpha methyl amino acid;
Xaa 15 is Phe or Trp;
Xaa 16 is Leu or D-Leu (dL);
Xaa 17 is Val, Ser, Glu, Arg, (2S,4R)-4-hydroxypyrrolidine-2-carboxylic acid (Hyp),
Dab or an alpha methyl amino acid (e.g. 2-amino-2-methylpropanoic acid [Aib]);
Xaa 20 is Ser, Ile, Pro or an alpha methyl amino acid (e.g. (S)-2-amino-3-hydroxy-2-methylpropanoic acid [aMeSer]);
Xaa 21 is Asn, Dab, His, Pro, Ser, Arg, Lys, Gly, Glu, Ala, Hyp or an alpha methyl amino acid (e.g. Aib);
Xaa 22 is Asn, His, Hyp, Dab or an alpha methyl amino acid (e.g. Aib);
Xaa 23 is Phe, Hyp or an alpha methyl amino acid (e.g. (S)-2-amino-2-methyl-3-phenylpropanoic acid [aMePhe]);
Xaa 24 is Gly, Pro, Hyp or an alpha methyl amino acid (e.g. Aib);
Xaa 25 is Pro, Ala, Hyp or an alpha methyl amino acid (e.g. Aib);
Xaa 26 is Ile, D-Ile (dI), Arg, Hyp or an alpha methyl amino acid (e.g. Aib);
Xaa 27 is Leu, dL, Hyp or an alpha methyl amino acid (e.g. Aib);
Xaa 28 is Pro, D-Pro (dP), Ser, Hyp or an alpha methyl amino acid (e.g. Aib);
Xaa 29 is Pro, Hyp or an alpha methyl amino acid (e.g. Aib);
Xaa 31 is Asn, Glu, His, Arg, Pro, Dab or an alpha methyl amino acid (e.g. Aib);
Xaa 32 is Val, Hyp, Dab or an alpha methyl amino acid (e.g. Aib);
Xaa 33 is Gly, Pro, Hyp or an alpha methyl amino acid (e.g. Aib);
Xaa 34 is Ser, Pro, His, Hyp or an alpha methyl amino acid (e.g. Aib);
Xaa 35 is Asn, Pro, Arg, Glu, Dab, Hyp or an alpha methyl amino acid (e.g. Aib);
Xaa 36 is Thr, Hyp or an alpha methyl amino acid (e.g. Aib);
Xaa 37 is Tyr, Pro, Hyp or an alpha methyl amino acid (e.g. Aib).

In yet another aspect, there is provided a polypeptide as set forth in Table 4.

In yet another aspect, there is provided a pharmaceutical composition comprising a polypeptide, a lipidated polypeptide or pharmaceutically acceptable salt of the invention and a pharmaceutically acceptable excipient.

In another aspect, there is provided a method for treating a disease or disorder in a subject comprising administering a polypeptide, a lipidated polypeptide, pharmaceutically acceptable salt or a pharmaceutical composition of the invention.

In a further aspect, there is provided a method for the production of a polypeptide or a lipidated polypeptide described herein.

In a further aspect, there is provided an article of manufacture comprising a polypeptide, a lipidated polypeptide, a pharmaceutically acceptable salt or a pharmaceutical composition of the invention.

In a further aspect, there is provided a kit comprising a polypeptide, a lipidated polypeptide, a pharmaceutically acceptable salt or a pharmaceutical composition of the invention, optionally further comprising instructions for use.

Aspects and embodiments of the invention are set out in the appended claims. These and other aspects and embodiments of the invention are also described herein.

Brief Description of Sequence Listing

TABLE 1

Compound Sequence Listing

| SEQ ID NO. | Full sequence |
|---|---|
| 1 (Pramlintide) | K[CNTATC]ATQRLANFLVHSSNNFGPILPPTNVGSNTY-amide |
| 3 | C18diacid-γE-K[CNTATC]ATQRLANFLVHSSNNFGPILPPTNVGSNTY-amide |
| 4 | C18diacid-γE-γE-GGG-K[CNTATC]ATQRLANFLVHSSNNFGPILPPTNVGSNTY-amide |
| 5 | K(γE-γE-C18diacid)[CNTATC]ATQRLANFLVHSSNNFGPILPPTNVGSNTY-amide |
| 6 | K(O2Oc-O2Oc-γE-C18diacid)[CNTATC]ATQRLANFLVHSSNNFGPILPPTNVGSNTY-amide |
| 7 | K(O2Oc-O2Oc-γE-C18diacid)GGGK[CNTATC]ATQRLANFLVHSSNNFGPILPPTNVGSNTY-amide |
| 8 | K(γE-γE-C18diacid)[CNTATC]ATQRLANFLVHSS(Dab)NFPAILSPTNVGSNTY-amide |
| 9 | K(γE-γE-C18diacid)[CNTATC]ATQRLANFLVHSS(Aib)NFPAILSPTNVGSNTY-amide |
| 10 | C18diacid-γE-[CNTATC]ATQRLAEFLRHSSNN(αMePhe)GPILPPTNVGSNTY-amide |
| 11 | K(γE-γE-C18diacid)[CNTATC]ATQRLAEFLRHSSNN(αMePhe)GPILPPTNVGSNTY-amide |
| 12 | K(γE-C18diacid)K[CNTATC]ATQRLAEFLRHSSNN(αMePhe)GPILPPTNVGSNTY-amide |
| 13 | K(γE-γE-C18diacid)[CNTATC]ATQRLANFLVHSSNN(αMePhe)GPILPPTNVGSNTY-amide |
| 14 | K(γE-C18diacid)K[CNTATC]ATQRLANFLVHSSNN(αMePhe)GPILPPTNVGSNTY-amide |

TABLE 1-continued

Compound Sequence Listing

| SEQ ID NO. | Full sequence |
|---|---|
| 15 | K(γE-C18diacid)K[CNTATC]ATQRLANFLRHSSNN(αMePhe)GPILPPTEVGSNTY-amide |
| 16 | K(γE-C18diacid)[CNTATC]ATQRLANFLRHSSNN(αMePhe)GPILPPTEVGSNTY-amide |
| 17 | K(O2Oc-O2Oc-γE-C18diacid)[CNTATC]ATQRLANFLRHSSNN(αMePhe)GPILPPTEVGSNTY-amide |
| 18 | K(γE-γE-C18diacid)[CNTATC]ATQRLANFLRHSSNN(αMePhe)GPILPPTEVGSNTY-amide |
| 19 | K(γE-C18diacid)[CNTATC]ATQRLANFLRHSSNN(αMePhe)GPILPPTNVGSNTY-amide |
| 20 | K(γE-γE-C18diacid)[CNTATC]ATQRLANFLRHSSNN(αMePhe)GPILPPTNVGSNTY-amide |
| 21 | K(γE-γE-C18diacid)[CNTATC]ATQRLANFLVHSSNN(αMePhe)GPILPPTNVGSRTY-amide |
| 22 | K(γE-γE-C18diacid)[CNTATC]ATQRLANFLVHS(αMeSer)NNFGPILPPTNVGSNTY-amide |
| 23 | K(γE-γE-C18diacid)[CNTATC]ATQRLANFLVHSSNN(αMePhe)GPILPPTEVGSNTY-amide |
| 24 | K(γE-γE-C18diacid)[CNTATC]ATQRLANFLVHSSNN(αMePhe)GPILPPTRVGSNTY-amide |
| 25 | K(γE-C18diacid)[CNTATC]ATQRLANFLVHSSNN(αMePhe)GPILPPTRVGSNTY-amide |
| 26 | K(γE-γE-C18diacid)[CNTATC]ATQRLANFL(Aib)HSSNN(αMePhe)GPILPPTNVGSNTY-amide |
| 27 | K(γE-γE-C18diacid)[CNIATC]ATQRLANFLVHSS(Dab)NFGPILPPTNVGSRTY-amide |
| 28 | K(γE-C18diacid)K[CNTATC]ATQRLANFLVHSS(Dab)NFGPILPPTEVGSNTY-amide |
| 29 | K(γE-C18diacid)K[CNTATC]ATQRLANFLVHSS(Dab)NFGPILPPTNVGSNTY-amide |
| 30 | K(γE-C18diacid)K[CNTATC]ATQRLANFL(Aib)HSS(Dab)NFGPILPPTEVGSNTY-amide |
| 31 | K(γE-C18diacid)K[CNTATC]ATQRLANFLVHSS(Dab)NFG(Aib)ILPPTNVGSNTY-amide |
| 32 | K(γE-C18diacid)K[CNTATC]ATQRLA(Dab)FLVHSSNN(αMePhe)GPILPPTEVGSNTY-amide |
| 33 | K(γE-C18diacid)K[CNTATC]ATQRLA(Dab)FLVHSSNNFGPILPPTNVGSNTY-amide |
| 34 | K(γE-C18diacid)K[CNTATC]ATQRLA(Dab)FLVHSSNNFGPILPPTNVGSNTY-amide |
| 35 | K(γE-C18diacid)K[CNTATC]ATQRLANFLVHSS(Aib)NFGPILPPTNVGSNTY-amide |
| 36 | K(γE-C18diacid)K[CNTATC]ATQRLANFL(Aib)HSS(Aib)NFGPILPPTNVGSNTY-amide |
| 37 | K(γE-C18diacid)K[CNTATC]ATQRLANFLSHSS(Aib)NFGPILPPTNVGSNTY-amide |
| 38 | K(γE-C18diacid)K[CNTATC]ATQRLAEFLVHSS(Aib)NFGPILPPTNVGSNTY-amide |
| 39 | K(γE-C18diacid)K[CNTATC]ATQRLANFLEHSS(Aib)NFGPILPPTNVGSNTY-amide |
| 40 | K(γE-C18diacid)K[CNTATC]ATQRLANFLVHSS(Aib)NFGPILPPTHVGSNTY-amide |
| 41 | K(γE-C18diacid)K[CNTATC]ATQRLANFLVHSS(Aib)NFGPILPPTEVGSNTY-amide |
| 42 | K(γE-C18diacid)K[CNTATC]ATQRLANFLVHSS(Aib)NFGPILPPTNVGSETY-amide |
| 43 | K(γE-C18diacid)K[CNTATC]ATQRLANFLRHSS(Aib)NFGPILPPTEVGSNTY-amide |
| 44 | K(γE-C18diacid)[CNTATC]ATQRLANFLRHSS(Aib)NFGPILPPTEVGSNTY-amide |
| 45 | K(O2Oc-O2Oc-γE-C18diacid)[CNTATC]ATQRLANFLRHSS(Aib)NFGPILPPTEVGSNTY-amide |
| 46 | K(γE-C18diacid)K[CNTATC]ATQRLAHFLVHSS(Aib)NFGPILPPTNVGSNTY-amide |
| 47 | K(γE-C18diacid)K[CNTATC]ATQRLAHFLVHSS(Aib)NFGPILPPTNVGSETY-amide |
| 48 | K(γE-C18diacid)[CNTATC]ATQRLANFLRHSS(Aib)NFGPILPPTNVGSNTY-amide |
| 49 | K(γE-γE-C18diacid)[CNTATC]ATQRLANFLVHSS(Aib)NFGPILPPTEVGSNTY-amide |
| 50 | K(γE-γE-C18diacid)[CNTATC]ATQRLANFLRHSS(Aib)NFGPILPPTEVGSNTY-amide |

TABLE 1-continued

Compound Sequence Listing

| SEQ ID NO. | Full sequence |
|---|---|
| 51 | K(γE-C18diacid)K[CNTATC]ATQRLANFLSHSS(Aib)NFGPILPPTHVGSNTY-amide |
| 52 | K(γE-C18diacid)K[CNTATC]ATQRLANFLSHSS(Aib)NFGPILPPTRVGSNTY-amide |
| 53 | K(γE-C18diacid)K[CNTATC]ATQRLANFLSHSS(Aib)NFGPILPPTPVGSNTY-amide |
| 54 | K(γE-C18diacid)K[CNTATC]ATQRLANFLSHSS(Aib)NFGPILPPTNVPSNTY-amide |
| 55 | K(γE-C18diacid)K[CNTATC]ATQRLANFLSHSS(Aib)NFGPILPPTNVGSPTY-amide |
| 56 | K(γE-C18diacid)[CNTATC]ATQRLANFLVHSS(Aib)NFGPILPPTNVGSNTY-amide |
| 57 | K(γE-γE-C18diacid)K[CNTATC]ATQRLANFLVHSS(Aib)NFGPILPPTNVGSNTY-amide |
| 58 | K(γE-C18diacid)K[CNTATC]ATQRLANFLVHSS(Aib)NFGPILPPTNVGSNTP-amide |
| 59 | K(γE-C18diacid)[CNTATC]ATQRLANFLVHSS(Aib)NFGPI(dL)PPTNVGSNTY-amide |
| 60 | K(γE-C18diacid)[CNTATC]ATQRLANFLVHSS(Aib)NFGPIL(dP)PTNVGSNTY-amide |
| 61 | K(γE-C18diacid)[CNTATC]ATQRLANFLVHSS(Aib)NFGP(dI)LPPTNVGSNTY-amide |
| 62 | K(γE-C18diacid)[CNTATC]ATQRLANF(dL)VHSS(Aib)NFGPILPPTNVGSNTY-amide |
| 63 | K(γE-C18diacid)[CNTATC]ATQRLANFLVHSS(Aib)NFGPILPPTRVGSNTY-amide |
| 64 | K(γE-C18diacid)[CNTATC]ATQRLANFLVHSS(Aib)NFGPILPPTNVGSRTY-amide |
| 65 | K(γE-C18diacid)K[CNTATC]ATQRLANFLRHSS(Aib)NFGPILPPTNVGSNTY-amide |
| 66 | K(γE-γE-C18diacid)K[CNTATC]ATQRLANFLRHSS(Aib)NFGPILPPTNVGSNTY-amide |
| 67 | K(γE-γE-C18diacid)[CNTATC]ATQRLANFLVHSS(Aib)NFGPILPPTRVGSNTY-amide |
| 68 | (C18diacid-γE-[CNTATC]ATQRLANFLVHSS(Aib)NFGPILPPTRVGSNTY-amide |
| 69 | K(γE-C18diacid)K[CNTATC]ATQRLANFLVHSS(Aib)NFGPILPPTRVGSNTY-amide |
| 70 | K(γE-γE-C18diacid)K[CNTATC]ATQRLANFLVHSS(Aib)NFGPILPPTRVGSNTY-amide |
| 71 | C18diacid-γE-K[CNTATC]ATQRLANFLVHSS(Aib)NFGPILPPTRVGSNTY-amide |
| 72 | K(γE-γE-C18diacid)[CNTATC]ATQRLANFLVHSS(Aib)NFGPILPPTNVGSRTY-amide |
| 73 | K(γE-C18diacid)K[CNTATC]ATQRLANFLVHSS(Aib)NFGPILPPTNVGSRTY-amide |
| 74 | K(γE-γE-C18diacid)K[CNTATC]ATQRLANFLVHSS(Aib)NFGPILPPTNVGSRTY-amide |
| 75 | K(γE-γE-C18diacid)[CNTATC]ATQRLANFLRHSS(Aib)NFGPILPPTNVGSNTY-amide |
| 76 | K(γE-C18diacid)[CNTATC]ATQRLANFLRHSS(Aib)NFGPILPPTRVGSNTY-amide |
| 77 | K(γE-γE-C18diacid)[CNTATC]ATQRLANFLRHSS(Aib)NFGPILPPTRVGSNTY-amide |
| 78 | K(γE-C18diacid)K[CNTATC]ATQRLANFLVHSS(Aib)NFGP(Aib)LPPTNVGSNTY-amide |
| 79 | K(γE-C18diacid)K[CNTATC]ATQRLANFLVHSS(Aib)NFGPI(Aib)PPTNVGSNTY-amide |
| 80 | K(γE-C18diacid)K[CNTATC]ATQRLANFLVHSS(Aib)NFGPILPPT(Aib)VGSNTY-amide |
| 81 | K(γE-C18diacid)K[CNTATC]ATQRLANFLVHSS(Aib)NFGPILPPTNV(Aib)SNTY-amide |
| 82 | K(γE-C18diacid)K[CNTATC]ATQRLANFLVHSS(Aib)NFGPILPPTNVGS(Aib)TY-amide |
| 83 | K(γE-C18diacid)K[CNTATC]ATQRLANFLVHSS(Aib)NFGPILPPTNVGSN(Aib)Y-amide |
| 84 | K(γE-C18diacid)K[CNTATC]ATQRLANFLVHSS(Aib)NFGPILPPTNVG(Aib)NTY-amide |
| 85 | K(γE-C18diacid)K[CNTATC]ATQRLANFLVHSS(Aib)NFGPILPPTNVGSNT(Aib)-amide |
| 86 | K(γE-C18diacid)K[CNTATC]ATQRLAHFL(Aib)HSS(Aib)NFGPILPPTEVGSNTY-amide |

TABLE 1-continued

Compound Sequence Listing

| SEQ ID NO. | Full sequence |
|---|---|
| 87 | K(γE-C18diacid)K[CNTATC]ATQRLANFL(Aib)HSS(Aib)NFGPILPPTNVGSNTP-amide |
| 88 | K(γE-C18diacid)K[CNTATC]ATQRLANFLVHSS(Aib)NFGPIL(Aib)PTNVGSNTY-amide |
| 89 | K(γE-γE-C18diacid)[CNTATC]ATQRLANFLVHSS(Aib)NFGPILPPT(Aib)VGSNTY-amide |
| 90 | K(γE-γE-C18diacid)[CNTATC]ATQRLANFLRHSS(Aib)NFGPILPPT(Aib)VGSNTY-amide |
| 91 | K(γE-γE-C18diacid)[CNTATC]ATQRLANFLVHSS(Aib)NFGPILPPTNVGS(Aib)TY-amide |
| 92 | K(γE-γE-C18diacid)[CNTATC]ATQRLANFLRHSS(Aib)NFGPILPPTNVGS(Aib)TY-amide |
| 93 | K(γE-C18diacid)K[CNTATC]ATQRLANFL(Aib)HSS(Dab)NFG(Aib)ILPPTNVGSNTY-amide |
| 94 | K(γE-C18diacid)K[CNTATC]ATQRLANFL(Aib)HSSNNFGP(Aib)LPPTNVGSNTY-amide |
| 95 | K(γE-C18diacid)K[CNTATC]ATQRLANFL(Aib)HSSNNFGPI(Aib)PPTNVGSNTY-amide |
| 96 | K(γE-C18diacid)K[CNTATC]ATQRLANFL(Aib)HSSNNFGPIL(Aib)PTNVGSNTY-amide |
| 97 | K(γE-C18diacid)K[CNTATC]ATQRLANFL(Aib)HSSNNFGPILP(Aib)TNVGSNTY-amide |
| 98 | K(γE-C18diacid)K[CNTATC]ATQRLANFL(Aib)HSSNNFGPILPPT(Aib)VGSNTY-amide |
| 99 | K(γE-C18diacid)K[CNTATC]ATQRLANFL(Aib)HSSNNFGPILPPTN(Aib)GSNTY-amide |
| 100 | K(γE-C18diacid)K[CNTATC]ATQRLANFL(Aib)HSSNNFGPILPPTNV(Aib)SNTY-amide |
| 101 | K(γE-C18diacid)K[CNTATC]ATQRLANFL(Aib)HSSNNFGPILPPTNVG(Aib)NTY-amide |
| 102 | K(γE-C18diacid)K[CNTATC]ATQRLANFL(Aib)HSSNNFGPILPPTNVGS(Aib)TY-amide |
| 103 | K(γE-C18diacid)[CNTATC]ATQRLANFLVHSSNNFGPI(dL)PPTNVGSNTY-amide |
| 104 | K(γE-C18diacid)[CNTATC]ATQRLANFLVHSSNNFGPIL(dP)PTNVGSNTY-amide |
| 105 | K(γE-C18diacid)K[CNTATC]ATQRLANFLSHSS(Dab)NFG(Aib)ILPPTNVGSNTY-amide |
| 106 | K(γE-C18diacid)K[CNTATC]ATQRLANFLVHSSNNFGP(Aib)LPPTNVGSNTY-amide |
| 107 | K(γE-C18diacid)K[CNTATC]ATQRLANFLRHSSNNFGP(Aib)LPPTNVGSNTY-amide |
| 108 | K(γE-C18diacid)K[CNTATC]ATQRLANFLVHSSNNFGPI(Aib)PPTNVGSNTY-amide |
| 109 | K(γE-C18diacid)K[CNTATC]ATQRLANFLVHSSN(Aib)FGPILPPTNVGSNTY-amide |
| 110 | K(γE-C18diacid)K[CNTATC]ATQRLANFLVHSSNNF(Aib)PILPPTNVGSNTY-amide |
| 111 | K(γE-C18diacid)K[CNTATC]ATQRLANFLVHSSNHFGPILPPTNVGSETY-amide |
| 112 | C20diacid-γE-K[CNTATC]ATQRLANFLVHSSNNFGPILPPTNVGSNTY-amide |
| 113 | C20diacid-γE-O2Oc-O2Oc-K[CNTATC]ATQRLANFLVHSSNNFGPILPPTNVGSNTY-amide |
| 114 | K(γE-γE-C20diacid)[CNTATC]ATQRLANFLVHSSNNFGPILPPTNVGSRTY-amide |
| 115 | K(γE-γE-C20diacid)[CNTATC]ATQRLANFLVHSSPNFPAILSPTNVGSNTY-amide |
| 116 | K(γE-γE-C20diacid)[CNTATC]ATQRLAEFLRHSSNNFGPILPPTNVGSNTY-amide |
| 117 | K(γE-γE-C20diacid)[CNTATC]ATQRLANFLVHSS(Aib)NFPAILSPTNVGSNTY-amide |
| 118 | K(γE-γE-C20diacid)[CNIATC]ATQRLANFLVHSIANFGPILPPTNVGSRTY-amide |
| 119 | K(γE-γE-C20diacid)[CNTATC]ATQRLANFLVHSPPNFPAILSPTNVGSNTY-amide |
| 120 | K(γE-γE-C20diacid)[CNAATC]ATQRLANWLVHSSPNFPAILSPTNVGSNTY-amide |
| 121 | K(γE-γE-C20diacid)[CNTATC]ATQRLANFLVHSS(Aib)NF(Hyp)AILSPTNVGSNTY-amide |
| 122 | K(γE-γE-C18diacid)[CNTATC]ATQRLANFLVHSS(Aib)NFPAILSPT(Dab)VGSNTY-amide |
| 123 | K(γE-γE-C20diacid)[CNTATC]ATQRLANFLVHSS(Aib)NFPAILSPT(Dab)VGSNTY-amide |

TABLE 1-continued

Compound Sequence Listing

| SEQ ID NO. | Full sequence |
|---|---|
| 124 | K(γE-γE-C18diacid)[CNTATC]ATQRLANFLVHSS(Aib)NFPAILSPTNVGS(Dab)TY-amide |
| 125 | K(γE-γE-C20diacid)[CNTATC]ATQRLANFLVHSS(Aib)NFPAILSPTNVGS(Dab)TY-amide |
| 126 | K(γE-C18diacid)K[CNTATC]ATQRLANFL(Aib)HSS(Dab)NFGPILPPTNVGSNTY-amide |
| 127 | K(γE-γE-C18diacid)[CNTATC]ATQRLANFL(Aib)HSSNNFGPILPPTNVGSNTY-amide |
| 128 | K(γE-C18diacid)K[CNTATC]ATQRLAEFL(Aib)HSSNNFGPILPPTNVGSNTY-amide |
| 129 | K(γE-C18diacid)K[CNTATC]ATQRLANFL(Aib)HSSNNFGPILPPTNVGSNTY-amide |
| 130 | K(γE-C18diacid)K[CNTATC]ATQRLAEFL(Aib)HSSHNFGPILPPTNVGSNTY-amide |
| 131 | K(γE-C18diacid)K[CNTATC]ATQRLANFL(Aib)HSSHNFGPILPPTNVGSNTY-amide |
| 132 | K(γE-C18diacid)K[CNTATC]ATQRLANFL(Aib)HSSPNFGPILPPTNVGSNTY-amide |
| 133 | K(γE-C18diacid)K[CNTATC]ATQRLANFL(Aib)HSSSNFGPILPPTNVGSNTY-amide |
| 134 | K(γE-C18diacid)K[CNTATC]ATQRLANFL(Aib)HSSNNFGPILPPTPVGSNTY-amide |
| 135 | K(γE-C18diacid)K[CNTATC]ATQRLANFL(Aib)HSSNHFGPILPPTNVGSNTY-amide |
| 136 | K(γE-C18diacid)K[CNTATC]ATQRLANFL(Aib)HSSNNFGPILPPTNVGSNTP-amide |
| 137 | K(γE-C18diacid)K[CNTATC]ATQRLANFL(Aib)HSSRNFGPILPPTNVGSNTY-amide |
| 138 | K(γE-C18diacid)K[CNTATC]ATQRLANFL(Aib)HSSPNFGPILPPTEVGSNTY-amide |
| 139 | K(γE-C18diacid)K[CNTATC]ATQRLANFL(Aib)HSSPNFGPILPPTNVGSETY-amide |
| 140 | K(γE-C18diacid)K[CNTATC]ATQRLANFL(Aib)HSSNNFGPILPPTEVGSNTY-amide |
| 141 | K(γE-C18diacid)K[CNTATC]ATQRLANFL(Aib)HSSNNFGPILPPTNVGSRTY-amide |
| 142 | K(γE-C18diacid)K[CNTATC]ATQRLANFL(Aib)HSSNNFGPILPPTNVGSETY-amide |
| 143 | K(γE-C18diacid)GGK[CNTATC]ATQRLANFL(Aib)HSSNNFGPILPPTNVGSNTY-amide |
| 144 | K(γE-C18diacid)[CNTATC]ATQRLAHFL(Aib)HSSNNFGPILPPTNVGSNTY-amide |
| 145 | K(γE-C18diacid)K[CNTATC]ATQRLANFL(Aib)HSSNNFGPILPPTNVGHNTY-amide |
| 146 | K(γE-C18diacid)K[CNTATC]ATQRLANFL(Aib)HSSNNFGPILPPTHVGSETY-amide |
| 147 | K(γE-C18diacid)K[CNTATC]ATQRLANFL(Aib)HSSNHFGPILPPTNVGSETY-amide |
| 148 | K(γE-C18diacid)K[CNTATC]ATQRLANFL(Aib)HSSNNFGPILPPTNVGPNTY-amide |
| 149 | K(γE-C18diacid)[CNTATC]ATQRLANFL(Aib)HSSNNFGPILPPTNVGSNTY-amide |
| 150 | K(γE-C18diacid)[CNTATC]ATQRLANFL(Aib)HSS(Dab)NFGPILPPTNVGSNTY-amide |
| 151 | K(γE-C18diacid)[CNTATC]ATQRLANFL(Aib)HSSNNFGPI(dL)PPTNVGSNTY-amide |
| 152 | K(γE-C18diacid)K[CNTATC]ATQRLANFL(Aib)HSSNNFGPRLPPTNVGSNTY-amide |
| 153 | K(γE-C18diacid)K[CNTATC]ATQRLANFL(Aib)HSSKNFGPILPPTNVGSNTY-amide |
| 154 | K(γE-C18diacid)K[CNTATC]ATQRLANFL(Aib)HSSGNFGPILPPTNVGSNTY-amide |
| 155 | K(γE-C18diacid)[CNTATC]ATQRLANFL(Aib)HSSNNFGPILPPTRVGSNTY-amide |
| 156 | K(γE-C18diacid)K[CNTATC]ATQRLA(Dab)FL(Aib)HSSNNFGPILPPTEVGSNTY-amide |
| 157 | (C18diacid)K[CNTATC]ATQRLANFLVHSS(Aib)NFGPILPPT(Aib)VGSNTY-amide |
| 158 | K(C18diacid)[CNTATC]ATQRLANFLVHSS(Aib)NFGPILPPT(Aib)VGSNTY-amide |

Table 1: The square bracket [] between the two cysteine residues (cys 2 and cys 7) indicate the presence of an intramolecular disulphide bridge.

DETAILED DESCRIPTION

The present inventors have observed that pramlintide conjugated to an albumin binding moiety, such as a lipid, has poor stability (e.g. the fibril-forming tendency of pramlintide is increased) under conditions required for drug product formulation. The present invention is based, at least in part, on the finding that the polypeptides (e.g. lipidated polypeptides) described herein may exhibit improved stability (e.g. reduced or no fibrillation tendency) as compared to such pramlintide conjugates.

For example, the present inventors have found that when pramlintide is conjugated to a lipid to increase the half-life, the fibril-forming tendency also increases. Accordingly, the polypeptides (e.g. lipidated polypeptides) described herein may bring the benefit of extended half-life compared to pramlintide but without the fibril-forming tendency of alternative lipidated pramlintide analogues. Peptides disclosed here can be formulated in or chemically conjugated to e.g. a protein, polymeric drug carrier or advance drug delivery system that enhances the chemical stability and or physical stability and or the circulatory exposure of the therapeutic moiety. The present inventors have further found that the polypeptides (e.g. lipidated polypeptides) described herein may exhibit improved physical and/or chemical stability as compared to human amylin or pramlintide. Furthermore, the polypeptides (e.g. lipidated polypeptides) described herein may have similar or improved selectivity to human amylin (hAMYR) compared to pramlintide.

Throughout this specification, amino acid positions of the polypeptides (e.g. lipidated polypeptides) are numbered according to the corresponding position in pramlintide having the sequence set forth in SEQ ID NO. 1.

Throughout this specification, amino acids are referred to by their conventional three-letter or single-letter abbreviations (e.g. Ala or A for alanine, Arg or R for arginine, etc.). In the case of certain less common or non-naturally occurring amino acids (i.e. amino acids other than the 20 encoded by the standard mammalian genetic code), unless they are referred to by their full name, frequently employed three- or four-character codes are employed for residues thereof, including aMeSer ((S)-2-amino-2-methyl-3-phenylpropanoic acid), aMePhe ((S)-2-amino-2-methyl-3-phenylpropanoic acid), Aib (2-amino-2-methylpropanoic acid), Dab (2,4-diaminobutanoic acid) and γ-Glu (γ-glutamic acid).

In embodiments of any aspect of the invention, the polypeptides (e.g. lipidated polypeptides) of the invention are isolated polypeptides (e.g. isolated lipidated polypeptides).

Albumin Binding Moiety

The polypeptides of the invention comprise at least one albumin binding moiety. Without being bound by theory, it is thought that the albumin binding moiety protects the polypeptide against clearance and degradation, thereby extending the half-life of the polypeptide. As used herein, "albumin binding moiety" refers to a compound that binds to albumin. Exemplary albumin binding moieties suitable for use in the polypeptides of the invention include lipids (e.g. a fatty acid derivative), albumin-binding peptides, albumin-binding proteins, or small molecule ligands that bind to albumin. Optionally, the albumin binding moiety is a lipid, e.g. a lipid described herein.

The polypeptides of the invention may comprise one or more albumin binding moiety (e.g. lipid), e.g. one, two or three albumin binding moieties. In preferred embodiments, the polypeptides of the invention comprise only one albumin binding moiety (e.g. lipid).

The albumin binding moiety (e.g. lipid) may be attached to an amino acid residue of the polypeptide. In some embodiments, the albumin binding moiety (e.g. lipid) is attached to the amino acid residue through a linker. In alternative embodiments, the albumin binding moiety (e.g. lipid) is directly attached to the amino acid residue without an intervening linker. The albumin binding moiety (e.g. lipid) may be attached to the amino acid residue via an ester, a sulfonyl ester, a thioester, an amide, an amine or a sulphonamide. Accordingly, it will be understood that the albumin binding moiety (e.g. lipid) or the linker includes an acyl group, a sulphonyl group, an N atom, an O atom or an S atom which forms part of the ester, sulphonyl ester, thioester, amide, amine or sulphonamide.

Optionally, an acyl group in the albumin binding moiety (e.g. lipid) or the linker forms part of an amide or ester with the amino acid residue. Accordingly, in preferred embodiments the albumin binding moiety (e.g. lipid) is attached to an acylation site on the amino acid residue.

The albumin binding moiety (e.g. lipid) may be attached to any residue at position Xaa-4 to Xaa 37 (e.g. to the EN of a lysine residue) of the polypeptide. In some embodiments, the albumin binding moiety (e.g. lipid) is attached to the side chain of an amino acid residue in the polypeptide, for example to the EN of a lysine residue. In some embodiments, the albumin binding moiety (e.g. lipid) is attached to the N-terminus of the polypeptide, (e.g. to a lysine at the N-terminus of the polypeptide).

In some embodiments, the albumin binding moiety (e.g. lipid) is attached to the N-terminus of the polypeptide, (e.g. to a lysine at the N-terminus of the polypeptide). In some embodiments, the albumin binding moiety (e.g. lipid) is attached to the amino acid residue at Xaa −4, Xaa −3, Xaa −2, Xaa −1 or Xaa 1 (e.g. to the EN of a lysine residue at Xaa −4, Xaa −3, Xaa −2, Xaa −1 or Xaa 1). In preferred embodiments, the albumin binding moiety (e.g. lipid) is attached to Xaa −4, Xaa −1 or Xaa 1 (either to the N-terminus or to the side chain of Xaa −4, Xaa −1 or Xaa 1).

Lipid

In preferred embodiments, the albumin binding moiety is a lipid. Accordingly, the polypeptides of the invention may comprise at least one lipid (referred to herein as "lipidated polypeptide"). Without being bound by theory, it is thought that the lipid acts as an albumin binding moiety and protects the polypeptide against clearance and degradation, thereby extending the half-life of the polypeptide. The lipid may also modulate the potency of the compound as an agonist to the amylin (calcitonin) receptor.

In some embodiments, the polypeptide comprises at least one lipidated amino acid residue. In some embodiments, the polypeptide comprises at least two lipidated amino acid residues. In preferred embodiments, the polypeptide contains only one lipidated amino acid residue. The lipid may be attached to an amino acid residue of the polypeptide. In some embodiments, the lipid is attached to the amino acid residue through a linker (referred to herein as "linker-lipid"). In alternative embodiments, the lipid is directly attached to the amino acid residue without an intervening linker. The lipid may be attached to the amino acid residue via an ester, a sulfonyl ester, a thioester, an amide, an amine or a sulphonamide. Accordingly, it will be understood that the lipid or the linker includes an acyl group, a sulphonyl group, an N atom, an O atom or an S atom which forms part of the ester, sulphonyl ester, thioester, amide, amine or sulphonamide. Optionally, an acyl group in the lipid or linker forms part of an amide or ester with the amino acid residue.

Accordingly, in preferred embodiments the lipid is attached to an acylation site on the amino acid residue.

The lipid may be attached to any residue at position Xaa-4 to Xaa 37 (e.g. to the εN of a lysine residue) of the polypeptide. In some embodiments, the lipid is attached to the side chain of an amino acid residue in the polypeptide, for example to the εN of a lysine residue. In some embodiments, the lipid is attached to the N-terminus of the polypeptide, (e.g. to a lysine at the N-terminus of the polypeptide).

In some embodiments, the lipid is attached to the N-terminus of the polypeptide, (e.g. to a lysine at the N-terminus of the polypeptide). In some embodiments, the lipid is attached to the amino acid residue at Xaa-4, Xaa-3, Xaa-2, Xaa-1 or Xaa 1 (e.g. to the εN of a lysine residue at Xaa-4, Xaa-3, Xaa-2, Xaa-1 or Xaa 1). In preferred embodiments, the lipid is attached to Xaa-4, Xaa-1 or Xaa 1 (either to the N-terminus or to the side chain of Xaa-4, Xaa-1 or Xaa 1).

In embodiments of any aspect of the invention, the lipid may comprise a hydrocarbon chain having from 10 to 26 C atoms, e.g. from 14 to 24 C atoms, e.g. from 16 to 22 C atoms. For example, the hydrocarbon chain may contain 14, 15, 16, 17, 18, 19, 20, 21, 22, 23 or 24 C atoms. In preferred embodiments, the lipid has 18 to 20 C atoms. In particular, the lipid may have 18 C atoms or 20 C atoms. The hydrocarbon chain may be linear or branched, and may be saturated or unsaturated. Furthermore, it can include a functional group at the end of the lipophilic chain, e.g. a carboxylic acid group which may or may not be protected during synthesis.

Optionally, the lipid comprises a dicarboxylic acid. For example, the lipid may comprise C12diacid, C14diacid, C16diacid, C17diacid, C18diacid, C19diacid or C20diacid. In preferred embodiments, the lipid comprises C18diacid or C20diacid.

Linker

The albumin binding moiety (e.g. lipid) may be attached to the polypeptide through a linker. In embodiments of any aspect of the invention, the linker may comprise one or more residues of any naturally occurring or non-naturally occurring amino acid. The linker may comprise a combination of residues, as single or repeating units. For example, the linker may comprise multiple combinations of residues, as single or repeating units, each of which may independently be a residue of Glu, γ-Glu, Lys, ε-Lys, Asp, β-Asp, Gaba, β-Ala (3-aminopropanoyl), O2Oc (2-(2-(2-aminoethoxy) ethoxy) acetic acid), PEG2 (3-(2-(2-aminoethoxy) ethoxy) propanoic acid), PEG4 (1-amino-3,6,9,12-tetraoxapentadecan-15-oic acid), PEG8 (1-amino-3,6,9,12, 15, 18,21,24-octaoxaheptacosan-27-oic acid, PEG12 (1-amino-3,6,9,12,15, 18,21,24,27,30,33,36-dodecaoxanonatriacontan-39-oic acid). γ-Glu and β-Asp refer to amino acids where the alpha-amino group and the side chain carboxyl group participate in peptide bond formation. ε-Lys refers to an amino acid where the epsilon-amino and carboxyl group of lysine participate in peptide bond formation.

In some embodiments, the linker comprises a residue of γ-Glu, e.g. γGlu, γGlu-γGlu, γGlu-(O2Oc)-(O2Oc) or γGlu-(PEG2)-(PEG2). In some embodiments, the linker consists of γGlu, γGlu-γGlu, γGlu-(O2Oc)-(O2Oc) or γGlu-(PEG2)-(PEG2).

In some embodiments of any aspect of the invention, the polypeptide comprises any one of the linker and lipid combinations set forth in any one of the rows in Table 2.

The linker may be attached to the amino acid residue via an ester, a sulfonyl ester, a thioester, an amide, an amine or a sulphonamide. Accordingly it will be understood that optionally the linker includes an acyl group, a sulphonyl group, an N atom, an O atom or an S atom which forms part of the ester, sulphonyl ester, thioester, amide, amine or sulphonamide. Optionally, an acyl group in the linker forms part of an amide or ester with the amino acid residue. Accordingly, in preferred embodiments the linker is attached to an acylation site on the amino acid residue.

The linker may be attached to a site (e.g. an acylation site) at the N-terminus of the lipidated polypeptide or to the ε amino group "εN" of a residue in the lipidated polypeptide, e.g. to εN of a lysine residue.

In some embodiments, the polypeptide comprises a combination of linker, lipid and acylation site set forth in any one of the rows of Table 2.

TABLE 2

Combinations of linker, lipid and polypeptide acylation site

| Lipid | Linker | Acylation site | Formula |
|---|---|---|---|
| C18diacid | γE-γE | N-terminal | |
| C18diacid | γE | (εN)K | |
| C18diacid | γE-(O2Oc)-(O2Oc) | (εN)K | |

TABLE 2-continued

Combinations of linker, lipid and polypeptide acylation site

| Lipid | Linker | Acylation site | Formula |
|---|---|---|---|
| C18diacid | γE-γE | (εN)K | |
| C20diacid | γE-γE | N-terminal | |
| C20diacid | γE | N-terminal | |
| C20diacid | γE-(O2oc)-(O2oc) | N-terminal | |

TABLE 2-continued

Combinations of linker, lipid and polypeptide acylation site

| Lipid | Linker | Acylation site | Formula |
|---|---|---|---|
| C20diacid | γE-γE | (εN)K | |
| C18diacid | Nil | (εN)K | |
| C18diacid | Nil | N-terminal | |

The linker may be attached to any residue at position Xaa −4 to Xaa 37 (e.g. to the EN of a lysine residue) of the polypeptide. In some embodiments, the linker is attached to the side chain of an amino acid residue in the polypeptide, for example to the EN of a lysine residue. In some embodiments, the linker is attached to the N-terminus of the polypeptide, (e.g. to a lysine at the N-terminus of the polypeptide).

In some embodiments, the linker is attached to the N-terminus of the polypeptide, (e.g. to a lysine at the N-terminus of the polypeptide). In some embodiments, the linker is attached to the amino acid residue at Xaa −4, Xaa −3, Xaa −2, Xaa −1 or Xaa 1 (e.g. to the EN of a lysine residue at Xaa −4, Xaa −3, Xaa −2, Xaa −1 or Xaa 1). In preferred embodiments, the linker is attached to Xaa −4, Xaa −1 or Xaa 1 (either to the N-terminus or to the side chain of Xaa −4, Xaa −1 or Xaa 1).

In some embodiments, the linker is attached to a site (e.g. an acylation site) selected from the N-terminus of the polypeptide, EN of a lysine at position Xaa (1) "1K", the EN of a lysine at position Xaa (−1) "−1K", or the EN of a lysine at position Xaa (−4) "−4K".

Amino Acid Substitutions and Modifications

The polypeptides (e.g. lipidated polypeptides) of the invention may comprise one or more amino acid modifications or substitutions compared to the pramlintide sequence [SEQ ID NO: 1].

In some embodiments, the polypeptides (e.g. lipidated polypeptides) comprises one or more non-proteinogenic amino acids. Non-proteinogenic amino acids may include alpha methyl amino acids, D-enantiomers of naturally occurring amino acids, 2,4-diaminobutanoic acid (Dab), and (2S,4R)-4-hydroxypyrrolidine-2-carboxylic acid (Hyp). In some embodiments, the polypeptide (e.g. lipidated polypeptide) comprises one or more non-proteinogenic amino acids between positions 14-37, optionally at one or more of 14, 17 or 20-37.n some embodiments, the polypeptide (e.g. lipidated polypeptide) comprises one or more alpha methyl amino acids between positions 14-37, optionally at one or more of alpha methyl amino acids at positions 14, 17 or 20-37. Polypeptides (e.g. lipidated polypeptides) comprising one or more alpha methyl amino acids at positions 17, 21 or 23 are particularly preferred. Representative examples of alpha methyl amino acids include 2-amino-2-methylpropanoic acid (Aib), alpha-methyl glutamine (αMeGlu), alpha methyl phenylalanine (αMePhe or αMeF), alpha-methyl leucine (αMeLeu) and alpha-methyl serine (αMeSer). Thus, in certain embodiments, the alpha methyl amino acid can be Aib, αMeGlu, αMePhe, αMeLeu or αMeSer, or any combination thereof. In preferred embodiments, the polypeptide (e.g. lipidated polypeptide) comprises at least one alpha methyl amino acid, optionally selected from Aib, αMePhe and αMeSer. The reference to αMePhe and αMeF herein refers to(S)-2-amino-2-methyl-3-phenylpropanoic acid. The reference to αMeSer herein refers to(S)-2-amino-3-hydroxy-2-methylpropanoic acid. In preferred embodiments, the alpha methyl amino acid is Aib, αMePhe or αMeSer.

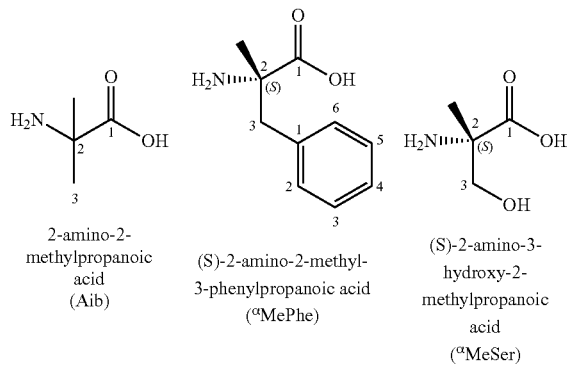

2-amino-2-methylpropanoic acid (Aib)

(S)-2-amino-2-methyl-3-phenylpropanoic acid (αMePhe)

(S)-2-amino-3-hydroxy-2-methylpropanoic acid (αMeSer)

In some embodiments, the polypeptide (e.g. lipidated polypeptide) comprises one or more non-proteinogenic amino acids between positions 14-37 selected from the group consisting of: 2,4-diaminobutanoic acid (Dab), (2S, 4R)-4-hydroxypyrrolidine-2-carboxylic acid (Hyp), D-leucine (dL), D-isoleucine (dI) and D-proline (dP).

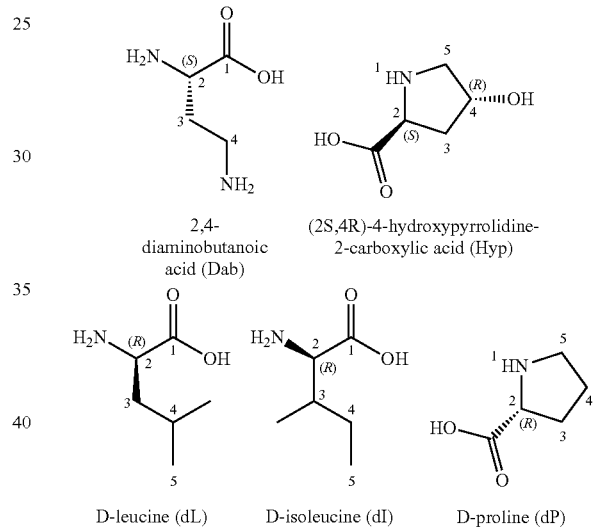

2,4-diaminobutanoic acid (Dab)

(2S,4R)-4-hydroxypyrrolidine-2-carboxylic acid (Hyp)

D-leucine (dL)

D-isoleucine (dI)

D-proline (dP)

In some embodiments, the polypeptide (e.g. lipidated polypeptide) does not comprise (2S)-2-aminohexanedioic acid) (Aad) and/or does not comprise Aad at positions 14-37.

In some embodiments, the polypeptide (e.g. lipidated polypeptide) does not comprise Aib at one or more of positions 15, 16, 17, 19 or 20. In alternative embodiments, the polypeptide (e.g. lipidated polypeptide) comprises Aib at one or more of positions 15, 16, 17, 19 or 20 and at least one different non-proteinogenic amino acid (e.g. an alpha methyl amino acid that is not Aib) at positions 14-37.

In some embodiments, the polypeptide (e.g. lipidated polypeptide) comprises one or more natural amino acid substitutions or modifications compared to the pramlintide sequence [SEQ ID NO: 1].

In preferred embodiments, the polypeptide (e.g. lipidated polypeptide) comprises one or more of the following natural amino acid substitutions or modifications: deleted 1K (Δ1K), Ile 4, Ala 4, Glu 14, His 14, Trp 15, Arg 17, Ser 17, Glu 17,, Pro 20, Ile 20, His 21, Ala 21, Glu 21, Gly 21, Lys 21, Pro 21, Arg 21, Ser 21, His 22, Pro 24, Ala 25, Arg 26, Ser 28, His 31, Glu 31, Pro 31, Arg 31, His 34, Pro 33, Pro 34, Glu 35, Arg 35, Pro 35 and Pro 37 (SEQ ID NO: 160).

It will be understood that the polypeptide (e.g. lipidated polypeptides) may comprise a combination of non-proteinogenic amino acids and natural amino acid substitutions or modifications compared to the pramlintide sequence [SEQ ID NO: 1].

In some aspects, there is provided a polypeptide (e.g. lipidated polypeptide) that is a pramlintide analogue, or a pharmaceutically acceptable salt thereof, comprising any of the amino acid sequence modification combinations set forth in Table 3.

TABLE 3

Amino acid modifications to pramlintide sequence

| Sequence modification with respect to pramlintide | SEQ ID NO: |
|---|---|
| −1G, −2G, 17Aib | 199 |
| 4A, 15W, 21P, 24P, 25A, 28S | 200 |
| 4I, 20I, 21A, 35R | 201 |
| 4I, 21Dab, 35R | 202 |
| 14Dab | 203 |
| 14Dab, 17Aib, 31E | 204 |
| 14Dab, 23αMePhe, 31E | 205 |
| 14Dab, 31E | 206 |
| 14E, 17Aib | 207 |
| 14E, 17Aib, 21H | 208 |
| 14E, 17R | 209 |
| 14E, 17R, 23αMePhe | 210 |
| 14E, 21Aib | 211 |
| 14H, 17Aib | 212 |
| 14H, 17Aib, 21Aib, 31E | 213 |
| 14H, 21Aib | 214 |
| 14H, 21Aib, 35E | 215 |
| 16dL, 21Aib | 216 |
| 17Aib | 217 |
| 17Aib, 37P | 218 |
| 17Aib, 21Aib | 219 |
| 17Aib, 21Aib, 37P | 220 |
| 17Aib, 21G | 221 |
| 17Aib, 21H | 222 |
| 17Aib, 21K | 223 |
| 17Aib, 21P | 224 |
| 17Aib, 21P, 31E | 225 |
| 17Aib, 21P, 35E | 226 |
| 17Aib, 21R | 227 |
| 17Aib, 21S | 228 |
| 17Aib, 21Dab | 229 |
| 17Aib, 21Dab, 31E | 230 |
| 17Aib, 22H | 231 |
| 17Aib, 22H, 35E | 232 |
| 17Aib, 23αMePhe | 233 |
| 17Aib, 26Aib | 234 |
| 17Aib, 26R | 235 |
| 17Aib, 27Aib | 236 |
| 17Aib, 27dL | 237 |
| 17Aib, 28Aib | 238 |
| 17Aib, 29Aib | 239 |
| 17Aib, 31Aib | 240 |
| 17Aib, 31E | 241 |
| 17Aib, 31H, 35E | 242 |
| 17Aib, 31P | 243 |
| 17Aib, 31R | 244 |
| 17Aib, 32Aib | 245 |
| 17Aib, 33Aib | 246 |
| 17Aib, 34Aib | 247 |
| 17Aib, 34H | 248 |
| 17Aib, 34P | 249 |
| 17Aib, 35Aib | 250 |
| 17Aib, 35E | 251 |
| 17Aib, 35R | 252 |
| 17E, 21Aib | 253 |
| 17R, 21Aib | 254 |
| 17R, 21Aib, 31Aib | 255 |
| 17R, 21Aib, 31E | 256 |
| 17R, 21Aib, 31R | 257 |
| 17R, 21Aib, 35Aib | 258 |
| 17R, 23αMePhe | 259 |

TABLE 3-continued

Amino acid modifications to pramlintide sequence

| Sequence modification with respect to pramlintide | SEQ ID NO: |
|---|---|
| 17R, 23αMePhe, 31E | 260 |
| 17R, 26Aib | 261 |
| 17S, 21Aib | 262 |
| 17S, 21Aib, 31H | 263 |
| 17S, 21Aib, 31P | 264 |
| 17S, 21Aib, 31R | 265 |
| 17S, 21Aib, 33P | 266 |
| 17S, 21Aib, 35P | 267 |
| 20αMeSer | 268 |
| 20P, 21P, 24P, 25A, 28S | 269 |
| 21Aib | 270 |
| 21Aib, 24P, 25A, 28S | 271 |
| 21Aib, 24P, 25A, 28S, 31Dab | 272 |
| 21Aib, 24P, 25A, 28S, 35Dab | 273 |
| 21Aib, 26dl | 274 |
| 21Aib, 26Aib | 275 |
| 21Aib, 27Aib | 276 |
| 21Aib, 27dL | 277 |
| 21Aib, 28Aib | 278 |
| 21Aib, 28dP | 279 |
| 21Aib, 31Aib | 280 |
| 21Aib, 31E | 281 |
| 21Aib, 31H | 282 |
| 21Aib, 31R | 283 |
| 21Aib, 33Aib | 284 |
| 21Aib, 34Aib | 285 |
| 21Aib, 35Aib | 286 |
| 21Aib, 35E | 287 |
| 21Aib, 35R | 288 |
| 21Aib, 36Aib | 289 |
| 21Aib, 37Aib | 290 |
| 21Aib, 37P | 291 |
| 21Aib, 24Hyp, 25A, 28S | 292 |
| 21Dab, 24P, 25A, 28S | 293 |
| 21Dab, 25Aib | 294 |
| 21Dab, 31E | 295 |
| 21P, 24P, 25A, 28S | 296 |
| 22Aib | 297 |
| 22H, 35E | 298 |
| 23αMePhe | 299 |
| 23αMePhe, 31E | 300 |
| 23aMePhe, 31R | 301 |
| 23αMePhe, 35R | 302 |
| 24Aib | 303 |
| 26Aib | 304 |
| 27Aib | 305 |
| 27dL | 306 |
| 28dP | 307 |
| 35R | 308 |
| Δ1K, 4I, 21Dab, 35R | 309 |
| Δ1K, 14E, 17R, 23αMePhe | 310 |
| Δ1K, 21Aib, 31R, | 311 |

In one aspect, there is provided a polypeptide (e.g. lipidated polypeptide) that is a pramlintide analogue, or a pharmaceutically acceptable salt thereof, having an alpha methyl amino acid at position 23. In preferred embodiments, the alpha methyl amino acid is αMePhe.

In preferred embodiments of any aspect in which the polypeptide (e.g. lipidated polypeptide) comprises an alpha methyl amino acid (e.g. αMePhe) at position 23, the polypeptide (e.g. lipidated polypeptide) comprises any one of the following combinations of modifications:

14E, 17R, 23αMePhe (SEQ ID NO: 210);
Δ1K, 14E, 17R, 23αMePhe (SEQ ID NO: 310);
14Dab, 23αMePhe, 31E (SEQ ID NO: 205);
17Aib, 23αMePhe (SEQ ID NO: 233);
17R, 23αMePhe, 31E (SEQ ID NO: 260);
23αMePhe, 31E (SEQ ID NO: 300);
23αMePhe, 31R (SEQ ID NO: 301); or
23αMePhe, 35R (SEQ ID NO: 302).

In one aspect, there is provided a polypeptide (e.g. lipidated polypeptide) that is a pramlintide analogue, or a pharmaceutically acceptable salt thereof having at least two Aib residues. In preferred embodiments, the polypeptide (e.g. lipidated polypeptide) comprises Aib at at least two of positions 17 and 20-37. In particularly preferred embodiments, the polypeptide (e.g. lipidated polypeptide) comprises Aib at positions 21, 26, 27, 28, 29, 31, 32, 33, 34 and 35.

In preferred embodiments of any aspect in which the polypeptide (e.g. lipidated polypeptide) comprises at least two Aib residues, the polypeptide (e.g. lipidated polypeptide) comprises any one of the following combinations of modifications:

14H, 17Aib, 21Aib, 31E (SEQ ID NO: 213);
17Aib, 21Aib (SEQ ID NO: 219);
17Aib, 21Aib, 37P (SEQ ID NO: 220);
17Aib, 26Aib (SEQ ID NO: 234);
17Aib, 27Aib (SEQ ID NO: 236);
17Aib, 28Aib (SEQ ID NO: 238);
17Aib, 29Aib (SEQ ID NO: 239);
17Aib, 31Aib (SEQ ID NO: 240);
17Aib, 32Aib (SEQ ID NO: 245);
17Aib, 33Aib (SEQ ID NO: 246);
17Aib, 34Aib (SEQ ID NO: 247);
17Aib, 35Aib (SEQ ID NO: 250);
17R, 21Aib, 31Aib (SEQ ID NO: 255);
17R, 21Aib, 35Aib (SEQ ID NO: 258);
21Aib, 26Aib (SEQ ID NO: 275);
21Aib, 27Aib (SEQ ID NO: 276);
21Aib, 28Aib (SEQ ID NO: 278);
21Aib, 31Aib (SEQ ID NO: 280);
21Aib, 33Aib (SEQ ID NO: 284);
21Aib, 34Aib (SEQ ID NO: 285);
21Aib, 35Aib (SEQ ID NO: 286);
21Aib, 36Aib (SEQ ID NO: 289); or
21Aib, 37Aib (SEQ ID NO: 290).

In one aspect, there is provided a polypeptide (e.g. lipidated polypeptide) that is a pramlintide analogue, or a pharmaceutically acceptable salt thereof, having an alpha methyl amino acid at position 21. In preferred embodiments, the alpha methyl amino acid is Aib.

In preferred embodiments of any aspect in which the polypeptide (e.g. lipidated polypeptide) comprises an alpha methyl amino acid (e.g. Aib) at position 21, the polypeptide (e.g. lipidated polypeptide) comprises any one of the following combinations of modifications:

14E, 21Aib (SEQ ID NO: 211);
14H, 17Aib, 21Aib, 31E (SEQ ID NO: 213);
14H, 21Aib, 35E (SEQ ID NO: 215);
14H, 21Aib (SEQ ID NO: 214);
16dL, 21Aib (SEQ ID NO: 216);
17Aib, 21Aib, 37P (SEQ ID NO: 220);
17Aib, 21Aib (SEQ ID NO: 219);
17E, 21Aib (SEQ ID NO: 253);
17R, 21Aib, 31Aib (SEQ ID NO: 255);
17R, 21Aib, 31E (SEQ ID NO: 256);
17R, 21Aib, 31R (SEQ ID NO: 257);
17R, 21Aib, 35Aib (SEQ ID NO: 258);
17R, 21Aib (SEQ ID NO: 254);
17S, 21Aib, 31H (SEQ ID NO: 263);
17S, 21Aib, 31P (SEQ ID NO: 264);
17S, 21Aib, 31R (SEQ ID NO: 265);
17S, 21Aib, 33P (SEQ ID NO: 266);
17S, 21Aib, 35P (SEQ ID NO: 267);
17S, 21Aib (SEQ ID NO: 262);
21Aib, 24Hyp, 25A, 28S (SEQ ID NO: 292)
21Aib, 24P, 25A, 28S, 31Dab (SEQ ID NO: 272);
21Aib, 24P, 25A, 28S, 35Dab (SEQ ID NO: 273).
21Aib, 24P, 25A, 28S (SEQ ID NO: 271);
21Aib, 26Aib (SEQ ID NO: 275);
21Aib, 26dl (SEQ ID NO: 274);
21Aib, 27Aib (SEQ ID NO: 276);
21Aib, 27dL (SEQ ID NO: 277);
21Aib, 28Aib (SEQ ID NO: 278);
21Aib, 28dP (SEQ ID NO: 279);
21Aib, 31Aib (SEQ ID NO: 280);
21Aib, 31E (SEQ ID NO: 281);
21Aib, 31H (SEQ ID NO: 282);
21Aib, 31R; Δ1K (SEQ ID NO: 311)
21Aib, 33Aib (SEQ ID NO: 284);
21Aib, 34Aib (SEQ ID NO: 285);
21Aib, 35Aib (SEQ ID NO: 286);
21Aib, 35E (SEQ ID NO: 287);
21Aib, 35R (SEQ ID NO: 288);
21Aib, 36Aib (SEQ ID NO: 289);
21Aib, 37Aib (SEQ ID NO: 290);
21Aib, 37P (SEQ ID NO: 291); or
21Aib (SEQ ID NO: 270).

In one aspect, there is provided a polypeptide (e.g. lipidated polypeptide) that is a pramlintide analogue, or a pharmaceutically acceptable salt thereof, having an alpha methyl amino acid at position 17. In preferred embodiments, the alpha methyl amino acid is Aib.

In preferred embodiments of any aspect in which the polypeptide (e.g. lipidated polypeptide) comprises an alpha methyl amino acid (e.g. Aib) at position 17, the polypeptide (e.g. lipidated polypeptide) comprises any one of the following combinations of modifications:

14H, 17Aib (SEQ ID NO: 212);
−1G, −2G, 17Aib (SEQ ID NO: 199);
17Aib, 23αMePhe (SEQ ID NO: 233);
17Aib, 21Dab, 31E (SEQ ID NO: 230);
17Aib, 21Dab (SEQ ID NO: 229);
17Aib, 21Aib (SEQ ID NO: 219);
14H, 17Aib, 21Aib, 31E (SEQ ID NO: 213);
17Aib, 21Aib, 37P (SEQ ID NO: 220);
17Aib, 26Aib (SEQ ID NO: 234);
17Aib, 27Aib (SEQ ID NO: 236);
17Aib, 28Aib (SEQ ID NO: 238);
17Aib, 29Aib (SEQ ID NO: 239);
17Aib, 31Aib (SEQ ID NO: 240);
17Aib, 32Aib (SEQ ID NO: 245);
17Aib, 33Aib (SEQ ID NO: 246);
17Aib, 34Aib (SEQ ID NO: 247); or
17Aib, 35Aib (SEQ ID NO: 250).

Pharmacokinetics

The polypeptides (e.g. lipidated polypeptides) of the invention may exhibit favourable pharmacokinetic properties as compared to pramlintide. For example, the polypeptides (e.g. lipidated polypeptides) of the invention may have an extended half-life as compared to pramlintide.

As used herein, the term "half-life" is used to refer to the time taken for the concentration of isolated polypeptide in plasma to decline to 50% of its original level. Methods to determine the half-life of proteins are known in the art and are described in Example 4.

It will be recognised that an extended half-life is advantageous, as it permits the therapeutic proteins to be administered according to a safe and convenient dosing schedule, e.g. lower doses that can be administered less frequently. Moreover, the achievement of lower doses may provide further advantages such as the provision of an improved safety profile. To the contrary, pramlintide requires frequent and inconvenient administration.

The present inventors have shown that the polypeptides (e.g. lipidated polypeptides) of the invention may have a half-life of at least 4 hours in rat models (see Example 4). In embodiments, the polypeptide (e.g. lipidated polypeptide) has a half-life of at least 1 hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours or at least 14 hours in rat models. In preferred embodiments, the polypeptide (e.g. lipidated polypeptide) has a half-life of at least 14 hours.

Reduced Fibrillation

The polypeptides (e.g. lipidated polypeptides) of the invention may exhibit reduced tendency to undergo fibrillation in pharmaceutically relevant aqueous media, especially at pH values in the range from 4 to 7, as compared to lipidated pramlintide. In some embodiments, the polypeptide (e.g. lipidated polypeptide) exhibits reduced tendency to undergo fibrillation in pharmaceutically relevant aqueous media, especially at pH values in the range from 4 to 7, as compared to pramlintide which is lipidated in a similar manner e.g. the same lipid is attached, the lipid is attached through the same linker and/or the lipid is attached at the same position. Exemplary lipidated pramlintide molecules are given in Table 1, for example SEQ ID NO. 3, 4, 5, 6, 7, 112 and 113.

Accordingly, the polypeptides (e.g. lipidated polypeptides) of the invention may be suited for formulation in acidic media (e.g. pH 4) and in neutral or near-neutral media (e.g. pH 7 or 7.4). Such polypeptides (e.g. lipidated polypeptides) may be well suited for co-formulation with, for example, insulin, various insulin analogues and/or other therapeutic (e.g. anti-diabetic or anti-obesity) agents that require a neutral or near-neutral formulation pH.

In some embodiments, the polypeptide (e.g. lipidated polypeptide) shows no detectable fibrillation after about 5 hours, after about 7 hours, after about 9 hours, after about 11 hours, after about 13 hours, after about 15 hours, after about 17 hours or after about 20 hours at pH 4 and 37° C., e.g. under the conditions described in Example 3.

In preferred embodiments, the polypeptide (e.g. lipidated polypeptide) shows no detectable fibrillation after about 48 hours, after about 72 hours, after about 96 hours, after about 108 hours, after about 120 hours, after 132 about hours or after about 144 hours at pH 4 and 37° C., e.g. under the conditions described in Example 3. In particularly preferred embodiments, the polypeptide (e.g. lipidated polypeptide) shows no detectable fibrillation after 144 hours at pH 4 and 37° C., e.g. under the conditions described in Example 3.

In some embodiments, the formation of fibrils is detected by an increase in fluorescence intensity in a Thioflavin T fibrillation assay, e.g. as described in Example 3.

In preferred embodiments, the polypeptides (e.g. lipidated polypeptides) of the invention are soluble at concentrations required for therapeutic efficacy. In some embodiments, the lipidated polypeptides of the invention are soluble at a concentration of at least 1 mg/ml under the conditions described in Example 3.

Efficacy

The polypeptides (e.g. lipidated polypeptides) of the invention are amylin receptor agonists, i.e. they are capable of binding to, and inducing signalling by, one or more receptors or receptor complexes regarded as physiological receptors for human amylin. These include the human calcitonin receptor hCTR, as well as complexes comprising the human calcitonin receptor hCTR and at least one of the human receptor activity modifying proteins designated hRAMP1, hRAMP2 and hRAMP3. Complexes between hCTR and hRAMP1, hRAMP2 and hRAMP3 are designated hAMYR1, hAMYR2 and hAMYR3 (i.e. human amylin receptors 1, 2 and 3) respectively. In some embodiments, a compound is considered an amylin receptor agonist if it has agonist activity at one or more of hAMYR1, hAMYR2 and hAMYR3. For example, a compound may be considered an amylin receptor agonist if it has agonist activity at hAMYR3.

The ability to induce CAMP formation as a result of binding to the relevant receptor or receptor complex is typically regarded as indicative of agonist activity. Other intracellular signaling pathways or events may also be used as readouts for amylin receptor agonist activity. These may include calcium release, arrestin recruitment, receptor internalization, kinase activation or inactivation, lipase activation, inositol phosphate release, diacylglycerol release or nuclear transcription factor translocation.

EC50 values may be used as a measure of agonist potency at a given receptor. An EC50 value is a measure of the concentration of a compound required to achieve half of that compound's maximal activity in a particular assay, for example a CAMP assay as described in Example 2. In Example 2, the present inventors have shown that certain polypeptides (e.g. lipidated polypeptides) disclosed herein exhibit greater or similar selectivity to hAMYR over hCTR as pramlintide, as measured using CAMP release from binding to hAMYR and hCTR. Pramlintide exhibits at least 10-fold selectivity to hAMYR as compared to hCTR.

The polypeptides (e.g. lipidated polypeptides) of the invention may exhibit improved efficacy, e.g. as amylin receptor agonists, as compared to lipidated pramlintide.

In some embodiments, the polypeptide (e.g. lipidated polypeptide) has at least about 1-fold selectivity to hAMYR over hCTR, optionally at least about 2-fold, at least about 4-fold, at least about 6-fold, at least about 8-fold, at least about 10-fold, at least about 12-fold, at least about 14-fold, at least about 16-fold, at least about 18-fold, at least about 20-fold, at least about 50-fold, at least about 75-fold, or at least about 100-fold selectivity to hAMYR over hCTR. In preferred embodiments, the polypeptide (e.g. lipidated polypeptide) has at least about 10-fold selectivity to hAMYR over hCTR.

In some embodiments, the polypeptide (e.g. lipidated polypeptide) has around 12-20 fold, around 14-18 fold, optionally around 16-fold selectivity to hAMYR over hCTR.

n some embodiments, the isolated polypeptide has an EC50 measured under the conditions described in Example 2 (i.e. containing 0.1% bovine serum albumin (BSA)) of below about 1.4 nM, below about 1.2 nM, below about 1 nM, below about 0.8 nM, below about 0.6 nM, below about 0.4 nM, below about 0.3 nM, or below about 0.2 nM.

Chemical Stability

The polypeptides (e.g. lipidated polypeptides) of the invention may be chemically stable, e.g. they may form in a formulation an acceptable percentage of degradation products produced over a defined period of time by chemical pathways, such as deamidation, aggregation, or oxidation.

The polypeptides (e.g. lipidated polypeptides) of the invention may be chemically conjugated to a protein or polymeric drug carrier, or formulated in an advance drug delivery system, that enhances the chemical stability and/or physical stability and/or the circulatory exposure of the polypeptide.

In some aspects, there is provided a polypeptide or a pharmaceutically acceptable salt thereof, wherein the polypeptide comprises any one of the lipid linkers as set forth in Table 2 and any one of the sequence modifications as set forth in Table 3.

In some aspects, there is provided a polypeptide or a pharmaceutically acceptable salt thereof, wherein the polypeptide comprises the lipid linker and amino acid sequence modification combinations set forth in Table 4.

TABLE 4

Lipidated polypeptides

| SEQ ID NO: | Lipid | Linker | Acylation site | Sequence modification with respect to pramlintide |
|---|---|---|---|---|
| 8 | C18diacid | γE-γE | 1K | 21Dab, 24P, 25A, 28S |
| 9 | C18diacid | γE-γE | 1K | 21Aib, 24P, 25A, 28S |
| 10 | C18diacid | γE | N-terminal | 14E, 17R, 23αMePhe, an dΔ1K |
| 11 | C18diacid | γE-γE | 1K | 14E, 17R, 23αMePhe |
| 12 | C18diacid | γE | -1K | 14E, 17R, 23αMePhe |
| 13 | C18diacid | γE-γE | 1K | 23αMePhe |
| 14 | C18diacid | γE | -1K | 23αMePhe |
| 15 | C18diacid | γE | -1K | 17R, 23αMePhe, 31E |
| 16 | C18diacid | γE | 1K | 17R, 23αMePhe, 31E |
| 17 | C18diacid | γE-(O2Oc)-(O2Oc) | 1K | 17R, 23αMePhe, 31E |
| 18 | C18diacid | γE-γE | 1K | 17R, 23αMePhe, 31E |
| 19 | C18diacid | γE | 1K | 17R, 23αMePhe |
| 20 | C18diacid | γE-γE | 1K | 17R, 23αMePhe |
| 21 | C18diacid | γE-γE | 1K | 23αMePhe, 35R |
| 22 | C18diacid | γE-γE | 1K | 20αMeS |
| 23 | C18diacid | γE-γE | 1K | 23αMePhe, 31E |
| 24 | C18diacid | γE-γE | 1K | 23αMePhe, 31R |
| 25 | C18diacid | γE | 1K | 23αMePhe, 31R |
| 26 | C18diacid | γE-γE | 1K | 17Aib, 23αMePhe |
| 27 | C18diacid | γE-γE | 1K | 4I, 21Dab, 35R |
| 28 | C18diacid | γE | -1K | 21Dab, 31E |
| 29 | C18diacid | γE | -1K | 21Dab |
| 30 | C18diacid | γE | -1K | 17Aib, 21Dab, 31E |
| 31 | C18diacid | γE | -1K | 21Dab, 25Aib |
| 32 | C18diacid | γE | -1K | 14Dab, 23αMePhe, 31E |
| 33 | C18diacid | γE | -1K | 14Dab |
| 34 | C18diacid | γE | -1K | 14Dab, 31E |
| 35 | C18diacid | γE | -1K | 21Aib |
| 36 | C18diacid | γE | -1K | 17Aib, 21Aib |
| 37 | C18diacid | γE | -1K | 17S, 21Aib |
| 38 | C18diacid | γE | -1K | 14E, 21Aib |
| 39 | C18diacid | γE | -1K | 17E, 21Aib |
| 40 | C18diacid | γE | -1K | 21Aib, 31H |
| 41 | C18diacid | γE | -1K | 21Aib, 31E |
| 42 | C18diacid | γE | -1K | 21Aib, 35E |
| 43 | C18diacid | γE | -1K | 17R, 21Aib, 31E |
| 44 | C18diacid | γE | 1K | 17R, 21Aib, 31E |
| 45 | C18diacid | γE-(O2Oc)-(O2Oc) | 1K | 17R, 21Aib, 31E |
| 46 | C18diacid | γE | -1K | 14H, 21Aib |
| 47 | C18diacid | γE | -1K | 14H, 21Aib, 35E |
| 48 | C18diacid | γE | -1K | 17R, 21Aib |
| 49 | C18diacid | γE-γE | 1K | 21Aib, 31E |
| 50 | C18diacid | γE-γE | 1K | 17R, 21Aib, 31E |
| 51 | C18diacid | γE | -1K | 17S, 21Aib, 31H |
| 52 | C18diacid | γE | -1K | 17S, 21Aib, 31R |
| 53 | C18diacid | γE | -1K | 17S, 21Aib, 31P |
| 54 | C18diacid | γE | -1K | 17S, 21Aib, 33P |
| 55 | C18diacid | γE | -1K | 17S, 21Aib, 35P |
| 56 | C18diacid | γE | 1K | 21Aib |
| 58 | C18diacid | γE | -1K | 21Aib, 37P |
| 59 | C18diacid | γE | 1K | 21Aib, 27dL |
| 60 | C18diacid | γE | 1K | 21Aib, 28dP |
| 61 | C18diacid | γE | 1K | 21Aib, 26dI |
| 62 | C18diacid | γE | 1K | 16dL, 21Aib |
| 63 | C18diacid | γE | 1K | 21Aib, 31R |
| 64 | C18diacid | γE | 1K | 21Aib, 35R |
| 65 | C18diacid | γE | -1K | 17R, 21Aib |
| 66 | C18diacid | γE-γE | -1K | 17R, 21Aib |
| 67 | C18diacid | γE-γE | 1K | 21Aib, 31R |
| 68 | C18diacid | γE | N-terminal | 21Aib, 31R, Δ1K |
| 69 | C18diacid | γE | -1K | 21Aib, 31R |
| 70 | C18diacid | γE-γE | -1K | 21Aib, 31R |
| 71 | C18diacid | γE | -1K | 21Aib, 31R |
| 72 | C18diacid | γE-γE | 1K | 21Aib, 35R |
| 73 | C18diacid | γE | -1K | 21Aib, 35R |
| 74 | C18diacid | γE-γE | -1K | 21Aib, 35R |
| 75 | C18diacid | γE-γE | 1K | 17R, 21Aib |
| 76 | C18diacid | γE | 1K | 17R, 21Aib, 31R |
| 77 | C18diacid | γE-γE | 1K | 17R, 21Aib, 31R |
| 78 | C18diacid | γE | -1K | 21Aib, 26Aib |
| 79 | C18diacid | γE | -1K | 21Aib, 27Aib |
| 80 | C18diacid | γE | -1K | 21Aib, 31Aib |
| 81 | C18diacid | γE | -1K | 21Aib, 33Aib |
| 82 | C18diacid | γE | -1K | 21Aib, 35Aib |
| 83 | C18diacid | γE | -1K | 21Aib, 36Aib |
| 84 | C18diacid | γE | -1K | 21Aib, 34Aib |
| 85 | C18diacid | γE | -1K | 21Aib, 37Aib |
| 86 | C18diacid | γE | -1K | 14H, 17Aib, 21Aib, 31E |
| 87 | C18diacid | γE | -1K | 17Aib, 21Aib, 37P |
| 88 | C18diacid | γE | -1K | 21Aib, 28Aib |
| 89 | C18diacid | γE-γE | 1K | 21Aib, 31Aib |
| 90 | C18diacid | γE-γE | 1K | 17R, 21Aib, 31Aib |
| 91 | C18diacid | γE-γE | 1K | 21Aib, 35Aib |
| 92 | C18diacid | γE-γE | 1K | 17R, 21Aib, 35Aib |
| 94 | C18diacid | γE | -1K | 17Aib, 26Aib |
| 95 | C18diacid | γE | -1K | 17Aib, 27Aib |
| 96 | C18diacid | γE | -1K | 17Aib, 28Aib |
| 97 | C18diacid | γE | -1K | 17Aib, 29Aib |
| 98 | C18diacid | γE | -1K | 17Aib, 31Aib |
| 99 | C18diacid | γE | -1K | 17Aib, 32Aib |
| 100 | C18diacid | γE | -1K | 17Aib, 33Aib |
| 101 | C18diacid | γE | -1K | 17Aib, 34Aib |
| 102 | C18diacid | γE | -1K | 17Aib, 35Aib |
| 103 | C18diacid | γE | 1K | 27dL |
| 104 | C18diacid | γE | 1K | 28dP |
| 106 | C18diacid | γE | -1K | 26Aib |
| 107 | C18diacid | γE | -1K | 17R, 26Aib |
| 108 | C18diacid | γE | -1K | 27Aib |
| 109 | C18diacid | γE | -1K | 22Aib |
| 110 | C18diacid | γE | -1K | 24Aib |
| 111 | C18diacid | γE | -1K | 22H, 35E |
| 114 | C20diacid | γE-γE | 1K | 35R |
| 115 | C20diacid | γE-γE | 1K | 21P, 24P, 25A, 28S |
| 116 | C20diacid | γE-γE | 1K | 14E, 17R |
| 117 | C20diacid | γE-γE | 1K | 21Aib, 24P, 25A, 28S |
| 118 | C20diacid | γE-γE | 1K | 4I, 20I, 21A, 35R |
| 119 | C20diacid | γE-γE | 1K | 20P, 21P, 24P, 25A, 28S |
| 120 | C20diacid | γE-γE | 1K | 4A, 15W, 21P, 24P, 25A, 28S |
| 121 | C20diacid | γE-γE | 1K | 21Dab, 24Hyp, 25A, 28S |
| 122 | C18diacid | γE-γE | 1K | 21Aib, 24P, 25A, 28S, 31Dab |
| 123 | C20diacid | γE-γE | 1K | 21Aib, 24P, 25A, 28S, 31Dab |
| 124 | C18diacid | γE-γE | 1K | 21Aib, 24P, 25A, 28S, 35Dab |
| 125 | C20diacid | γE-γE | 1K | 21Aib, 24P, 25A, 28S, 35Dab |
| 126 | C18diacid | γE | -1K | 17Aib, 21Dab |
| 127 | C18diacid | γE-γE | 1K | 17Aib |
| 128 | C18diacid | γE | -1K | 14E, 17Aib |
| 129 | C18diacid | γE | -1K | 17Aib |
| 130 | C18diacid | γE | -1K | 14E, 17Aib, 21H |
| 131 | C18diacid | γE | -1K | 17Aib, 21H |
| 132 | C18diacid | γE | -1K | 17Aib, 21P |
| 133 | C18diacid | γE | -1K | 17Aib, 21S |
| 134 | C18diacid | γE | -1K | 17Aib, 31P |
| 135 | C18diacid | γE | -1K | 17Aib, 22H |
| 136 | C18diacid | γE | -1K | 17Aib, 37P |
| 137 | C18diacid | γE | -1K | 17Aib, 21R |

TABLE 4-continued

Lipidated polypeptides

| SEQ ID NO: | Lipid | Linker | Acylation site | Sequence modification with respect to pramlintide |
|---|---|---|---|---|
| 138 | C18diacid | γE | −1K | 17Aib, 21P, 31E |
| 139 | C18diacid | γE | −1K | 17Aib, 21P, 35E |
| 140 | C18diacid | γE | −1K | 17Aib, 31E |
| 141 | C18diacid | γE | −1K | 17Aib, 35R |
| 142 | C18diacid | γE | −1K | 17Aib, 35E |
| 143 | C18diacid | γE | −3K | −1G, −2G, 17Aib |
| 144 | C18diacid | γE | 1K | 14H, 17Aib |
| 145 | C18diacid | γE | −1K | 17Aib, 34H |
| 146 | C18diacid | γE | −1K | 17Aib, 31H, 35E |
| 147 | C18diacid | γE | −1K | 17Aib, 22H, 35E |
| 148 | C18diacid | γE | −1K | 17Aib, 34P |
| 149 | C18diacid | γE | 1K | 17Aib |
| 150 | C18diacid | γE | 1K | 17Aib, 21Dab |
| 151 | C18diacid | γE | 1K | 17Aib, 27dL |
| 152 | C18diacid | γE | −1K | 17Aib, 26R |
| 153 | C18diacid | γE | −1K | 17Aib, 21K |
| 154 | C18diacid | γE | −1K | 17Aib, 21G |
| 155 | C18diacid | γE | 1K | 17Aib, 31R |
| 156 | C18diacid | γE | −1K | 14Dab, 17Aib, 31E |
| 157 | C18diacid | Nil | N-terminal | 21Aib, 31Aib |
| 158 | C18diacid | Nil | 1K | 21Aib, 31Aib |

Process

The polypeptides (e.g. lipidated polypeptides) of the invention may be produced by any method known in the art. The production of polypeptides such as amylin or analogues thereof is well known in the art. The polypeptide (e.g. lipidated polypeptides) of the invention can thus be produced by chemical synthesis, e.g. solid phase polypeptide synthesis using t-Boc or Fmoc chemistry, or other well-established techniques. They may alternatively be produced by recombinant expression of a nucleic acid molecule encoding a fusion polypeptide in a host cell. Following synthesis, the polypeptides (e.g. lipidated polypeptides) of the invention may optionally be isolated or purified.

Therapeutic Methods

In further aspects, the polypeptides (e.g. lipidated polypeptides) of the invention are provided in a pharmaceutical composition.

The pharmaceutical compositions of the invention may comprise one or more excipient(s). Pharmaceutically acceptable excipients are known in the art, see for instance Remington's Pharmaceutical Sciences (by Joseph P. Remington, 18th ed., Mack Publishing Co., Easton, PA), which is incorporated herein in its entirety.

The present invention encompasses therapies which involve administering the polypeptides (e.g. lipidated polypeptides) of the invention to an animal, in particular a mammal, for instance a human, for preventing, treating, or ameliorating symptoms associated with a disease, disorder, or infection.

Accordingly, the polypeptides (e.g. lipidated polypeptides) or pharmaceutical compositions of the invention may be used in therapy, for example for treating a disease or disorder. Also provided is a method of treating a disease or disorder comprising administering to a subject or patient in need thereof a therapeutically effective amount of the polypeptides (e.g. lipidated polypeptides) or pharmaceutical compositions of the invention. The use or method may comprise administering a therapeutically effective schedule that has less frequent doses of the polypeptides (e.g. lipidated polypeptides) of the invention than the therapeutically effective dosing schedule of pramlintide.

It will be understood that the polypeptides (e.g. lipidated polypeptides) of the invention may be used in the treatment and/or prevention of obesity, metabolic diseases such as diabetes (e.g. type 1 or type 2 diabetes), and/or obesity-related conditions.

Accordingly, the polypeptides (e.g. lipidated polypeptides) of the invention may be used in a method of treating obesity, overweight, morbid obesity, obesity prior to surgery, obesity-linked inflammation, obesity-linked gallbladder disease, sleep apnea and respiratory problems, hyperlipidemia, degeneration of cartilage, osteoarthritis, or reproductive health complications of obesity or overweight such as infertility in a subject, the method comprising administering a therapeutically effective amount of the polypeptide (e.g. lipidated polypeptide) to the subject.

This is also provided a method of inhibiting or reducing weight gain, promoting weight loss, reducing food intake, and/or reducing excess body weight, the method comprising administering the polypeptide (e.g. lipidated polypeptide) of the invention to the subject.

Metabolic diseases that may be treated by the polypeptide (e.g. lipidated polypeptide) of the invention include diabetes, type 1 diabetes, type 2 diabetes, gestational diabetes, pre-diabetes, insulin resistance, impaired glucose tolerance (IGI), disease states associated with elevated blood glucose levels, metabolic disease including metabolic syndrome, or hyperglycemia e.g. abnormal postprandial hyperglycemia . . .

In preferred embodiments, the polypeptides (e.g. lipidated polypeptides) of the invention are used for the treatment of type 1 diabetes or type 2 diabetes.

The polypeptides (e.g. lipidated polypeptides) or pharmaceutical compositions of the invention may be used for treating, inhibiting or reducing weight gain, promoting weight loss, reducing food intake, and/or reducing excess body weight.

The polypeptides (e.g. lipidated polypeptides) or pharmaceutical compositions of the invention may be used in the treatment and/or prevention of an eating disorder, Alzheimer's disease, hepatic steatosis ("fatty liver"), kidney failure, arteriosclerosis (e.g. atherosclerosis), cardiovascular disease, macrovascular disease, microvascular disease, diabetic heart (including diabetic cardiomyopathy and heart failure as a diabetic complication), coronary heart disease, peripheral artery disease or stroke, cancer, dumping syndrome, hypertension e.g. pulmonary hypertension, or dyslipidemia e.g. atherogenic dyslipidemia, cholescystitis, or short bowel syndrome.

The route of administration of polypeptides (e.g. lipidated polypeptides) of the invention, or pharmaceutical compositions thereof, can be, for example, oral, parenteral, by inhalation or topical. In preferred embodiments, the polypeptide (e.g. lipidated polypeptide) or pharmaceutical composition thereof is administered by parenteral administration to a subject or patient. The term "parenteral" as used herein includes, e.g., intravenous, intraarterial, intraperitoneal, intramuscular, subcutaneous, rectal, or vaginal administration. In preferred embodiments, the polypeptide (e.g. lipidated polypeptide) or pharmaceutical composition thereof is administered by injection, such as by intravenous, subcutaneous or intramuscular injection, to a subject or patient. In particularly preferred embodiments, the polypeptide (e.g. lipidated polypeptide) or pharmaceutical composition thereof is administered by subcutaneous injection. Administration by injection, such as by subcutaneous injection, offers the advantage of better comfort for the subject or patient and the opportunity to administer to a subject or patient outside of a hospital setting. In some embodiments, the polypeptide (e.g. lipidated polypeptide) or pharmaceutical composition thereof is administered by self-administration.

In some embodiments the subject or patient is a mammal, in particular a human.

In some embodiments, the polypeptide or pharmaceutical composition is administered to the subject in combination with insulin.

Articles of Manufacture and Kits

In other aspects, the present invention provides an article of manufacture comprising the polypeptides (e.g. lipidated polypeptides) or pharmaceutical compositions of the invention.

In yet other aspects, the present invention provides a kit comprising the polypeptides (e.g. lipidated polypeptides) or pharmaceutical compositions of the invention. The kit may comprise a package containing the polypeptide (e.g. lipidated polypeptide) or pharmaceutical composition, optionally with instructions. In some embodiments, the polypeptides (e.g. lipidated polypeptides) or pharmaceutical compositions of the invention are formulated in single dose vials or a container closure system (e.g. pre-filled syringe).

Optionally associated with such container(s) can be a notice in the form prescribed by a governmental agency regulating the manufacture, use or sale of pharmaceuticals or biological products, which notice reflects approval by the agency of manufacture, use or sale for human administration.

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide the skilled person with a general dictionary of many of the terms used in this disclosure.

This disclosure is not limited by the exemplary methods and materials disclosed herein, and any methods and materials similar or equivalent to those described herein can be used in the practice or testing of embodiments of this disclosure.

Unless otherwise indicated, any nucleic acid sequences are written left to right in 5' to 3' orientation; amino acid sequences are written left to right in amino to carboxy orientation, respectively.

It must be noted that as used herein and in the appended claims, the singular forms "a", "an", and "the" include plural referents unless the context clearly dictates otherwise. Thus, for example, reference to "an agent" includes a plurality of such agents and reference to "the agent" includes reference to one or more agents and equivalents thereof known to those skilled in the art, and so forth.

"About" may generally mean an acceptable degree of error for the quantity measured given the nature or precision of the measurements. Exemplary degrees of error are within 20 percent (%), typically, within 10%, and more typically, within 5% of a given value or range of values. Optionally, the term "about" shall be understood herein as plus or minus (±) 5%, optionally ±4%, ±3%, ±2%, ±1%, ±0.5%, ±0.1%, of the numerical value of the number with which it is being used.

Embodiments described herein as "comprising" one or more features may also be considered as disclosure of the corresponding embodiments "consisting of" such features.

The term "pharmaceutically acceptable" as used herein means approved by a regulatory agency of the Federal or a state government, or listed in the U.S. Pharmacopeia, European Pharmacopeia or other generally recognized pharmacopeia for use in animals, and more particularly in humans.

Concentrations, amounts, volumes, percentages and other numerical values may be presented herein in a range format. It is also to be understood that such range format is used merely for convenience and brevity and should be interpreted flexibly to include not only the numerical values explicitly recited as the limits of the range but also to include all the individual numerical values or sub-ranges encompassed within that range as if each numerical value and sub-range is explicitly recited.

The above embodiments are to be understood as illustrative examples. Further embodiments are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

In the context of the present disclosure other examples and variations of the polypeptides (e.g. lipidated polypeptides) and methods described herein will be apparent to a person of skill in the art.

Other examples and variations are within the scope of the disclosure, as set out in the appended claims.

All documents cited herein are each entirely incorporated by reference herein, including all data, tables, figures, and text presented in the cited documents.

EXAMPLES

Example 1: Generation of Lipidated Pramlintide Analogue Peptides

Lipidated pramlintide analogue peptides were synthesized as C-terminal carboxamides using rink amide MBHA resin (100-200 mesh). All peptides were prepared by automated synthesis using a Liberty Blue™ microwave solid phase peptide synthesizer (CEM Corporation, NC, USA) using the Fmoc/tBu protocol. Manufacturer-supplied protocols were applied for coupling of amino acids in DMF and deprotection of Fmoc protecting group using piperidine in DMF (20% v/v). Asparagine, cysteine, glutamine and histidine were incorporated as their sidechain trityl (Trt) derivatives. Lysine was incorporated as the sidechain tert-butyloxycarbonyl (Boc) derivative. Serine, threonine and tyrosine were incorporated as sidechain tert-butyl (tBu) ethers, and aspartate and glutamate as their sidechain OtBu esters. Arginine was incorporated as the sidechain 2,2,4,6,7-pentamethyldihydrobenzofuran-5-sulfonyl (Pbf) derivative.

Boc-Lys (Fmoc) was incorporated when a subsequent chemical modification of the N-terminal lysine side chain was required. Upon completion of the peptide chain elongation, coupling of an albumin binding moiety, such as a lipid, was performed manually using HATU as a coupling reagent in the presence of DIPEA.

Peptides were cleaved from the solid support by treatment with a mixture of TFA:TIS:EDT:thioanisole:water (90:2.5:2.5:2.5:2.5 v/v) for 4 h with agitation at room temperature. Thereafter, the cleavage mixtures were filtered, concentrated in vacuo, precipitated and washed with diethyl ether and solids were isolated by centrifugation. The linear crude peptides were dried under a flow of nitrogen and dissolved in 20% MeCN in water (v/V) with 1% TFA (v/v) and filtered. The crude linear peptides were purified using a preparative RP-HPLC on a Varian SD-1 Prep Star binary pump system, monitoring by UV absorption at 210 nm using an Xbridge C18-A stationary phase (19.0× 250 mm, 5 micron) column eluting a linear solvent gradient of 25-70% MeCN (0.1% TFA v/v) in water (0.1% TFA v/v) over 25 min.

The linear purified peptides were cyclised by treatment with iodine (1% w/v in methanol) for 10 min at room temperature and excess iodine was reduced by treatment with ascorbic acid (1% w/v in water). The cyclic crude peptides were re-purified as described above. The purified fractions were pooled, frozen and lyophilised.

LC/MS characterisation of purified peptides were performed on a Waters MassLynx 3100 platform using a XBridge C18 stationary phase (4.6×100 mm, 3 micron) eluting a linear binary gradient of 10-90% MeCN (0.1% TFA v/V) in water (0.1% TFA v/V) over 10 minutes at 1.5 mL/min at ambient temperature. Analytes were detected by both UV absorption at 210 nm and ionization using a Waters 3100 mass detector (ESI+ mode). Analytical RP-HPLC characterisation was performed on an Agilent 1260 Infinity system using an Agilent Polaris C8-A stationary phase (4.6×100 mm, 3 micron) eluting a linear binary gradient of 10-90% MeCN (0.1% TFA v/v) in water (0.1% TFA v/v) at 1.5 mL/min over 15 minutes at 40° C.

Example 2: In Vitro Potency of Lipidated Pramlintide Analogue Peptides in Human or Rat Amylin or Calcitonin Receptor Cells The functional activities of lipidated pramlintide analogue peptides, such as cAMP production, were tested in 1321N1 cell line with stable recombinant expression of human calcitonin receptor (hCTR) or human amylin receptor (calcitonin receptor co-expressed with receptor activity modifying protein, RAMP3) (hAMYR3) or HEK cells with stable recombinant expression of rat calcitonin receptor (rat CTR) or rat amylin receptor (calcitonin receptor co-expressed with receptor activity modifying protein, RAMP3) (Rat AMYR3).

Cryopreserved cell stock was thawed rapidly in a water-bath, suspended in assay buffer (0.1% BSA (Sigma #A3059) in HBSS (Sigma #H8264) with 25 mM HEPES, pH 7.4 and containing 0.5 mM IB MX (Sigma #I7018)) and spun at 240×g for 5 minutes. Cells were re-suspended in assay buffer at a batch-dependent optimized concentration (e.g. hCTR cells at $0.125 \times 10^5$ cells/mL, hAMYR3 cells at $0.125 \times 10^5$ cells/mL, rat CTR cells at at $1 \times 10^5$ cells/mL, rat AMYR3 at $2 \times 10^5$ cells/mL).

The test peptide stock was prepared in DMSO and diluted in assay buffer to reach stated concentrations and transferred in duplicates into a 384-black shallow well microtitre assay plate (Corning #3676). Cells were added to the assay plate, incubated at room temperature for 30 minutes and the CAMP level measured using CAMP dynamic 2 HTRF kit (Cisbio, Cat #62AM4PEJ), following the two step protocol as per manufacturer's recommendations. The plates were read on an Envision (Perkin Elmer) using excitation wavelength of 320 nm and emission wavelengths of 620 nm & 665 nm.

Data was transformed to % Delta F as described in the manufacturer's guidelines and analyzed as percent activation of maximal amylin or calcitonin effect by 4-parameter logistic fit to determine EC50 values. The selectivity of a peptide to hAMYR vs hCTR is defined as a ratio of EC50 values at the two receptors.

All tested compounds show measurable potency in hAMYR and hCTR. Analogues that show >10 fold selectivity for hAMYR over hCTR are preferred.

TABLE 5 in vitro potency of lipidated pramlintide analogues at human amylin3 and calcitonin receptors

| Peptide | EC50 (pM) hAMYR3 | hCTR | Ratio |
|---|---|---|---|
| 1 | 10 | 160 | 16 |
| 3 | 246 | 1353 | 5 |
| 4 | 248 | 7532 | 30 |
| 5 | 174 | 3605 | 21 |
| 6 | 68 | 310 | 5 |
| 7 | 173 | 2159 | 12 |
| 8 | 375 | 20228 | 54 |
| 9 | 320 | 13521 | 42 |
| 10 | 183 | 2728 | 15 |
| 11 | 177 | 3640 | 21 |
| 12 | 158 | 1224 | 8 |
| 13 | 196 | 2043 | 10 |
| 14 | 220 | 1350 | 6 |
| 15 | 522 | 5461 | 10 |
| 16 | 221 | 2018 | 9 |
| 17 | 365 | 7083 | 19 |
| 18 | 319 | 4686 | 15 |
| 19 | 278 | 4041 | 15 |
| 20 | 174 | 4593 | 26 |
| 21 | 136 | 3408 | 25 |
| 22 | 162 | 6539 | 40 |
| 23 | 238 | 589 | 2 |
| 24 | 127 | 1857 | 15 |
| 25 | 105 | 1248 | 12 |
| 26 | 409 | 2797 | 7 |
| 27 | 134 | 731 | 5 |
| 28 | 390 | 9142 | 23 |
| 29 | 243 | 8211 | 34 |
| 30 | 873 | 10549 | 12 |
| 31 | 349 | 1280 | 4 |
| 32 | 742 | 11149 | 15 |
| 33 | 598 | 15830 | 26 |
| 34 | 877 | 17733 | 20 |
| 35 | 259 | 14153 | 55 |
| 36 | 331 | 6394 | 19 |
| 37 | 249 | 1962 | 8 |
| 38 | 190 | 1049 | 6 |
| 39 | 1048 | 10362 | 10 |
| 40 | 228 | 3329 | 15 |
| 41 | 178 | 1184 | 7 |
| 42 | 470 | 2954 | 6 |
| 43 | 647 | 19046 | 29 |
| 44 | 284 | 6262 | 22 |
| 45 | 588 | 16891 | 29 |
| 46 | 109 | 362 | 3 |
| 47 | 218 | 468 | 2 |
| 48 | 126 | 5273 | 42 |
| 49 | 334 | 4142 | 12 |
| 50 | 349 | 18927 | 54 |
| 51 | 126 | 1645 | 13 |
| 52 | 89 | 1104 | 12 |
| 53 | 98 | 235 | 2 |
| 54 | 7587 | 1507 | 0.2 |
| 55 | 678 | 1874 | 3 |
| 56 | 70 | 493 | 7 |
| 58 | 71 | 65 | 1 |
| 59 | 157 | 809 | 5 |
| 60 | 96 | 1027 | 11 |
| 61 | 99 | 654 | 7 |
| 62 | 167 | 7249 | 43 |
| 63 | 76 | 375 | 5 |
| 64 | 149 | 1278 | 9 |
| 65 | 207 | 6400 | 31 |
| 66 | 418 | 7011 | 17 |

TABLE 5-continued in vitro potency of lipidated pramlintide analogues at human amylin3 and calcitonin receptors

| Peptide | EC50 (pM) hAMYR3 | hCTR | Ratio |
|---|---|---|---|
| 67 | 132 | 4006 | 30 |
| 68 | 192 | 1774 | 9 |
| 69 | 164 | 1572 | 10 |
| 70 | 235 | 5405 | 23 |
| 71 | 211 | 1385 | 7 |
| 72 | 227 | 4004 | 18 |
| 73 | 256 | 1821 | 7 |
| 74 | 356 | 4574 | 13 |
| 75 | 161 | 15998 | 99 |
| 76 | 209 | 22291 | 107 |
| 77 | 231 | 2520 | 11 |
| 78 | 288 | 3147 | 11 |
| 79 | 659 | 4799 | 7 |
| 80 | 407 | 2970 | 7 |
| 81 | 404 | 2764 | 7 |
| 82 | 514 | 4277 | 8 |
| 83 | 599 | 6342 | 11 |
| 84 | 118 | 401 | 3 |
| 85 | 806 | 3104 | 4 |
| 86 | 119 | 311 | 3 |
| 87 | 71 | 74 | 1 |
| 88 | 281 | 1172 | 4 |
| 89 | 447 | 8239 | 18 |
| 90 | 1056 | 15595 | 15 |
| 91 | 200 | 2357 | 12 |
| 92 | 341 | 44414 | 130 |
| 94 | 322 | 1903 | 6 |
| 95 | 691 | 1172 | 2 |
| 96 | 556 | 859 | 2 |
| 97 | 684 | 944 | 1 |
| 98 | 942 | 972 | 1 |
| 99 | 3798 | 1825 | 0.5 |
| 100 | 364 | 459 | 1 |
| 101 | 177 | 441 | 2 |
| 102 | 479 | 1630 | 3 |
| 103 | 161 | 1881 | 12 |
| 104 | 79 | 1816 | 23 |
| 106 | 473 | 3420 | 7 |
| 107 | 1071 | 26264 | 25 |
| 108 | 801 | 6808 | 8 |
| 109 | 82 | 176 | 2 |
| 110 | 204 | 541 | 3 |
| 111 | 403 | 1875 | 5 |
| 112 | 861 | 1335 | 2 |
| 113 | 1173 | 18495 | 16 |
| 114 | 1317 | 15796 | 12 |
| 115 | 703 | 7645 | 11 |
| 116 | 1207 | 9557 | 8 |
| 117 | 770 | 3190 | 4 |
| 118 | 417 | 792 | 2 |
| 119 | 1461 | 34657 | 24 |
| 120 | 1769 | 10717 | 6 |
| 121 | 1328 | 6074 | 5 |
| 122 | 655 | 6181 | 9 |
| 123 | 873 | 4793 | 5 |
| 124 | 1129 | 6633 | 6 |
| 125 | 1201 | 10197 | 8 |
| 126 | 445 | 8453 | 19 |
| 127 | 364 | 7127 | 19.6 |
| 128 | 118 | 568 | 4.8 |
| 129 | 553 | 5750 | 10.4 |
| 130 | 446 | 6686 | 15 |
| 131 | 737 | 15143 | 20.5 |
| 132 | 416 | 3848 | 9.3 |
| 133 | 378 | 2578 | 6.8 |
| 134 | 281 | 2223 | 7.9 |
| 135 | 296 | 345 | 1.2 |
| 136 | 122 | 101 | 0.8 |
| 137 | 238 | 1504 | 6.3 |
| 138 | 612 | 2506 | 4.1 |
| 139 | 285 | 1043 | 3.7 |
| 140 | 656 | 6046 | 9.2 |
| 141 | 414 | 3950 | 9.5 |
| 142 | 730 | 2270 | 3.1 |
| 143 | 592 | 6937 | 11.7 |
| 144 | 138 | 725 | 5.3 |
| 145 | 417 | 1876 | 4.5 |
| 146 | 2533 | 4874 | 1.9 |
| 147 | 802 | 1508 | 1.9 |
| 148 | 191 | 728 | 3.8 |
| 149 | 130 | 1200 | 9.2 |
| 150 | 179 | 4181 | 23.4 |
| 151 | 61 | 898 | 14.7 |
| 154 | 574 | 1540 | 2.7 |
| 155 | 329 | 3930 | 11.9 |
| 156 | 3749 | 83771 | 22.3 |

TABLE 6 in vitro potency of lipidated pramlintide analogues at rat amylin3 and calcitonin receptors

| Peptide | EC50 (pM) Rat AMYR3 | Rat CTR |
|---|---|---|
| 1 | 0.4 | 70.0 |
| 3 | 2.9 | 186.0 |
| 8 | 25.6 | 19856.1 |
| 9 | 17.8 | 9724.4 |
| 10 | 12.1 | 2781.5 |
| 12 | 5.0 | 106.8 |
| 15 | 10.3 | 1821.8 |
| 18 | 16.5 | 3086.9 |
| 20 | 10.4 | 1854.2 |
| 24 | 17.7 | 754.9 |
| 35 | 5.9 | 514.1 |
| 38 | 5.1 | 20.3 |
| 40 | 12.0 | 782.1 |
| 41 | 8.2 | 924.8 |
| 43 | 14.5 | 3650.9 |
| 44 | 18.5 | 2237.3 |
| 48 | 4.8 | 2431.0 |
| 112 | 16.0 | 258.5 |
| 113 | 32.6 | 10375.7 |
| 114 | 12.2 | 4873.7 |
| 115 | 22.6 | 22552.0 |
| 116 | 23.7 | 9052.7 |
| 129 | 11.2 | 2869.2 |
| 140 | 19.5 | 1218.4 |
| 149 | 5.6 | 521.8 |

Example 3: Thioflavin T Fibrillation Assay

Peptide aggregation that form fibrils is an indication of physical instability. Fibril formation in solution poses a significant risk for the stability of injectable peptide drug products. Thioflavin T (ThT) fibrillation assay is a useful tool to assess the aggregation kinetics of a peptide or protein under accelerated and stressed conditions that can be used to forecast the long-term viability of a compound in solution.

ThT can selectively bind amyloid fibrils and the resultant complex emits strong fluorescence signal at 482 nm when excited at 450 nm (Anal Biochem. 1989 March; 177 (2): 244-9). Monitoring of the change in fluorescence signal is an established method to study the fibril forming potential of peptides and proteins.

ThT (purchased from Sigma Aldrich) stock solution is prepared by dissolving the ThT powder in Milli-Q water and filtered to obtain a 0.25 mM solution. The concentration of the solution is measured at 412 nm using an extinction coefficient of 36 mM-1 cm-1. Test peptides were dissolved at 1 mg/mL in 25 mM sodium acetate buffer pH 4.0.

100 µL aliquot of peptide solution and 5 µL aliquot of ThT solution were placed in a clear bottom black fluorescence 96-well plate. 5 replicates of each test samples were placed in the same row of the plate. Buffer was placed in control wells for baseline correction. All empty wells were filled with water to prevent evaporation. The plate was sealed with aluminium seal and placed in fluorescence plate reader and incubated for 6 days at 37° C. with intermittent orbital shaking at 500 to 750 rpm. The fluorescence intensity was measured every 30 min using excitation at 444 nm and emission at 480 nm.

The fibril forming potential of the test peptides was determined by measuring the average time taken to detect an increase in baseline corrected fluorescence intensity. A time >144 h indicates no increase in fluorescence intensity, relative to baseline, during the course of the experiment.

Conjugating pramlintide to a lipid (for example, as in SEQ ID NO. 3, 4, 5, 6, 112, 113, increases the fibril-forming tendency as seen in Table 7.

TABLE 7

Tht fibrillation assay of lipidated pramlintide analogues

| Peptide | Time taken to detect increase in fluorescence intensity (h) |
|---|---|
| 3 | <5 |
| 4 | <5 |
| 5 | 7 |
| 6 | 15 |
| 8 | 7 |
| 9 | 7 |
| 10 | >144 |
| 11 | >144 |
| 12 | >144 |
| 13 | 25 |
| 15 | >144 |
| 17 | >144 |
| 18 | >144 |
| 19 | >144 |
| 20 | >144 |
| 21 | >144 |
| 24 | >144 |
| 25 | >144 |
| 28 | 45 |
| 33 | >144 |
| 40 | >144 |
| 44 | >144 |
| 48 | >144 |
| 66 | >144 |
| 70 | >144 |
| 80 | >144 |
| 103 | <5 |
| 104 | <5 |
| 112 | <5 |
| 113 | <5 |
| 114 | <5 |
| 115 | <5 |
| 129 | >144 |
| 156 | >144 |

Example 4: Pharmacokinetic Determination Via IV and SC Administration in Sprague Dawley Rats The objective of the pharmacokinetic (PK) studies were to determine the plasma pharmacokinetic profile of lipidated pramlintide analogue peptides in fasted male SD rats after single intravenous (IV) and subcutaneous (SC) administration. PK studies were performed to determine the half-life ($T_{1/2}$) of test peptides. $T_{1/2}$ describes the time taken for the maximum plasma concentration (Cmax) of a test substance to halve its steady-state concentration when in circulation.

Male SD rats were purchased from Si Bei Fu Laboratory Animal Technology Co. Ltd (China). The animals were 6-8 weeks old with body weights of 200-300 g on the dosing date. The animals were housed in a 12-hour light/12-hour dark cycle environment and were fasted overnight before dosing. The body weight of the animals were recorded before dosing, 24 h and 48 h post dosing. Animals had free access to food and drinks, and the food consumption was quantified every day.

Test articles were administered at 20 nmol/kg. Blood samples were collected from each animal via Jugular vein. The sampling timepoints are as below.
Blood Samples Per Test Article;

| Group | Route | Animals | | | Time points |
|---|---|---|---|---|---|
| 1 | IV | 1 | 2 | 3 | 0, 0.033, 0.1, 0.167, 0.25, 0.5, 1, 2, 4, 6, 8, 12, 24, 48 h |
| 2 | SC | 4 | 5 | 6 | 0, 0.033, 0.1, 0.167, 0.25, 0.5, 1, 2, 4 6, 8, 12, 24, 36, 48 h |

The blood samples were transferred into eppendorf low binding tube containing $K_2$EDTA. Above 0.150 mL blood were collected at each time point. Blood samples were centrifuged at 4,000 g for 5 minutes at 4° C. to obtain plasma. The plasma samples were stored frozen at −75±15° C. until analysis.

Concentrations of the test articles in the plasma samples were analyzed using a LC-MS/MS method. Data acquisition was performed by LabSolution version 5.89 software (Shimadzu, Kyoto, Japan). Data statistics were performed using Excel 97-2003 software. The pharmacokinetic parameters of test articles were calculated using a non-compartmental approach with Phoenix™ WinNonlin®6.1.

The following pharmacokinetic parameters were calculated, whenever possible from the plasma concentration versus time data:

IV administration: $T_{1/2}$, $C_0$, $AUC_{last}$, $AUC_{inf}$, $MRT_{inf}$, CI, Vss, Number of Points for Regression.

SC administration: $T_{max}$, $C_{max}$, $AUC_{last}$, $AUC_{inf}$, $MRT_{inf}$, F, Number of Points for Regression.

TABLE 8

Half-life of lipidated pramlintide analogues in rats

| | Rat $T_{1/2}$ (h) | |
|---|---|---|
| ID | IV | SC |
| 3 | 14 | — |
| 4 | 12 | 12 |
| 5 | 10.5 | 9.4 |
| 6 | 9.5 | 17.6 |
| 8 | 4.2 | 6.2 |
| 9 | 5.9 | 7.8 |
| 10 | 10.1 | 8.8 |
| 12 | 9.2 | 9.7 |
| 15 | 10.4 | 11.5 |
| 18 | 12 | 13.6 |
| 19 | 6.6 | 9.3 |
| 20 | 10 | 10.8 |
| 21 | 8 | 8.1 |
| 24 | 9.4 | 10.5 |
| 25 | 6.9 | 8 |
| 35 | 5.4 | 8.1 |

TABLE 8-continued

Half-life of lipidated pramlintide analogues in rats

| | Rat T$_{1/2}$ (h) | |
|---|---|---|
| ID | IV | SC |
| 36 | 7.2 | 11.6 |
| 38 | 6.6 | 9 |
| 40 | 7.4 | 8.1 |
| 41 | 8.3 | 10.1 |
| 43 | 9.3 | 10 |
| 44 | 8.9 | 11 |
| 48 | 5.6 | 8.1 |
| 64 | 6 | 5 |
| 65 | 6 | 9.3 |
| 66 | 9.4 | 12.2 |
| 69 | 6.3 | 8.5 |
| 70 | 10.3 | 12.5 |
| 80 | 9.7 | 9.9 |
| 112 | 11.8 | 19 |
| 113 | 11.2 | 18.2 |
| 114 | 13 | 21.6 |
| 115 | 14.9 | 20.3 |
| 117 | 9.8 | 12.9 |
| 129 | 10.3 | 9 |
| 140 | 10.6 | 12.9 |
| 149 | 6.9 | 9.3 |
| 155 | 7.7 | 8.9 |

Pharmacokinetic studies show that the terminal half-life of amylin in rats is around 13 minutes, and the half-life for pramlintide in human is ~20-45 minutes (Roth JD et. al. GLP-1R and amylin agonism in metabolic disease: complementary mechanisms and future opportunities. Br J Pharmacol. 2012; 166 (1): 121-136). The lipidated polypeptides show marked improvement in prolonging circulatory T$_{1/2}$ compared to pramlintide.

Example 6: Rat Acute Food Intake Study

Male Sprague Dawley rats were obtained from Taconic Denmark, ApS at approximately 7 weeks of age. . . . Rats were implanted with a microchip for identification, housed 4/cage with enrichment, free access to food and water, and allowed one week acclimatisation while non-invasive characterization was performed. Rats were on a 12:12 light:dark cycle that switches at 1 pm:1 am. Food intake was monitored via the HM2 system (Lafayette Instrument) that allows for monitoring in a home cage. As each rat enters an access tunnel to feed, an IR beam is broken, and the implanted microchip is read. Resulting changes to food weight is then assigned to the specific animal. Social order has shown no impact to overall feeding patterns and amounts.

Rats were sorted into groups based on Day-1 body weight and 24-hour accumulated food intake (n=7 per group). On Day 0 rats were weighed, then fasted for 6 hours. Thirty (30) minutes prior to the reintroduction of food, rats were dosed subcutaneously (5 ml/kg) with 20 nmol/kg of test compound or 60 nmol/kg peptide 1 (pramlintide) diluted in an appropriate vehicle, after which food was returned, and lights went out. Automated food intake was monitored for the following 3 days, and rats were weighed once per day.

Food intake per rat was batched into 1-hour intervals and integrated into Gubra's GubraView data management system. Discrete food intake data was exported into MS Excel from which cumulative food intake data was generated. Cumulative food intake data was then transposed into GraphPad Prism (v8.0.1) for analysis of dark period feeding The lipidated polypeptides show marked suppression of food intake compared to pramlintide.

TABLE 9

Effect of lipidated pramlintide analogues on food uptake in lean rats

| | Cummulative food intake (% vehicle treated intake) ) | | |
|---|---|---|---|
| Peptide | At 12 h | At 24 h | At 48 h |
| 1 | 71.6 | 85.6 | 98.7 |
| 3 | 13.4 | 14.4 | 30.3 |
| 8 | 28.1 | 42.7 | 68.8 |
| 9 | 21.9 | 30.8 | 56.5 |
| 10 | 18.8 | 24.6 | 46.6 |
| 12 | 9.4 | 7.5 | 23.6 |
| 15 | 45.2 | 49.1 | 51 |
| 18 | 45.8 | 46.9 | 68.8 |
| 20 | 27 | 26.2 | 49.7 |
| 24 | 18.7 | 19.4 | 40.6 |
| 35 | 49.8 | 44.8 | 72 |
| 38 | 6.9 | 5.5 | 13.7 |
| 40 | 60.7 | 51.8 | 72.4 |
| 41 | 44.6 | 38.5 | 58.8 |
| 43 | 60.8 | 55.6 | 46.6 |
| 44 | 33.5 | 39.2 | 60.7 |
| 48 | 27.5 | 32.6 | 57.1 |
| 112 | 15.8 | 15.9 | 22.1 |
| 113 | 69.5 | 65.8 | 77.9 |
| 114 | 42.3 | 45.1 | 53.8 |
| 115 | 42.4 | 41.3 | 52.2 |
| 116 | 51.7 | 43.1 | 50.2 |
| 129 | 29 | 32.4 | 51 |
| 140 | 62.4 | 54.4 | 56.5 |
| 149 | 31 | 31.8 | 17.5 |

The invention claimed is:

1. A polypeptide, or a pharmaceutically acceptable salt thereof, comprising the amino acid sequence selected from the group consisting of:

(SEQ ID NO: 15)
K(γE-C18diacid)K[CNTATC]ATQRLANFLRHSSNN(αMePhe)GP
ILPPTEVGSNTY-amide, (SEQ ID NO: 16)
K(γE-C18diacid)[CNTATC]ATQRLANFLRHSSNN(αMePhe)GPI
LPPTEVGSNTY-amide, (SEQ ID NO: 17)
K(O2Oc-O2Oc-γE-C18diacid)[CNTATC]ATQRLANFLRHSSNN
(αMePhe)GPILPPTEVGSNTY-amide, and (SEQ ID NO: 18)
K(γE-γE-C18diacid)[CNTATC]ATQRLANFLRHSSNN(αMePhe)
GPILPPTEVGSNTY-amide.

2. The polypeptide, or pharmaceutically acceptable salt thereof, comprising the amino acid sequence (SEQ ID NO: 15)
K(γE-C18diacid)K[CNTATC]ATQRLANFLRHSSNN(αMePhe)GP
ILPPTEVGSNTY-amide.

3. The polypeptide, or pharmaceutically acceptable salt thereof, comprising the amino acid sequence (SEQ ID NO: 16)
K(γE-C18diacid)[CNTATC]ATQRLANFLRHSSNN(αMePhe)GPI
LPPTEVGSNTY-amide.

4. The polypeptide, or pharmaceutically acceptable salt thereof, comprising the amino acid sequence K(O2Oc-O2Oc-γE-C18diacid)[CNTATC]ATQRLANFLRHSSNN (SEQ ID NO: 17)
(αMePhe)GPILPPTEVGSNTY-amide.

5. The polypeptide, or pharmaceutically acceptable salt thereof, comprising the amino acid sequence K(γE-γE-C18diacid)[CNTATC]ATQRLANFLRHSSNN(αMePhe) (SEQ ID NO: 18)
GPILPPTEVGSNTY-amide.

6. A pharmaceutical composition comprising the polypeptide or pharmaceutically acceptable salt of claim 1 and a pharmaceutically acceptable excipient.

7. A kit comprising the polypeptide or pharmaceutically acceptable salt of claim 1, optionally further comprising instructions for use.

\* \* \* \* \*